(12) United States Patent
Higuchi et al.

(10) Patent No.: US 8,999,922 B2
(45) Date of Patent: Apr. 7, 2015

(54) LINEAR PEPTIDE ANTIBIOTICS

(71) Applicant: RQX Pharmaceuticals, Inc., La Jolla, CA (US)

(72) Inventors: Robert I. Higuchi, Solana Beach, CA (US); Tucker Curran Roberts, San Diego, CA (US); Peter Andrew Smith, La Jolla, CA (US); David Campbell, San Diego, CA (US); Prasuna Paraselli, San Diego, CA (US)

(73) Assignee: RQX Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/769,130

(22) Filed: Feb. 15, 2013

(65) Prior Publication Data

US 2013/0217619 A1 Aug. 22, 2013

Related U.S. Application Data

(60) Provisional application No. 61/730,928, filed on Nov. 28, 2012, provisional application No. 61/599,851, filed on Feb. 16, 2012.

(51) Int. Cl.

| | |
|---|---|
| *A61K 38/08* | (2006.01) |
| *C07K 5/06* | (2006.01) |
| *C07K 5/08* | (2006.01) |
| *C07K 5/10* | (2006.01) |
| *C07K 7/06* | (2006.01) |
| *C07K 5/11* | (2006.01) |
| *A61K 45/06* | (2006.01) |
| *A61K 38/07* | (2006.01) |
| *C07K 5/113* | (2006.01) |
| *C07K 5/103* | (2006.01) |
| *C07K 5/117* | (2006.01) |

(52) U.S. Cl.
CPC ............... *C07K 7/06* (2013.01); *C07K 5/1019* (2013.01); *A61K 45/06* (2013.01); *A61K 38/08* (2013.01); *A61K 38/07* (2013.01); *C07K 5/1021* (2013.01); *C07K 5/1013* (2013.01); *C07K 5/1024* (2013.01)

(58) Field of Classification Search
None
See application file for complete search history.

(56) References Cited

U.S. PATENT DOCUMENTS

| | | | | |
|---|---|---|---|---|
| 4,499,082 | A * | 2/1985 | Shenvi et al. | 514/20.4 |
| 6,265,380 | B1 * | 7/2001 | Tung et al. | 514/4.3 |
| 2004/0024178 | A1 | 2/2004 | Ashman et al. | |
| 2008/0039612 | A1* | 2/2008 | Gutheil | 530/333 |

FOREIGN PATENT DOCUMENTS

WO WO-02-095007 11/2002

OTHER PUBLICATIONS

Buzder-Lantos et al. Substrate based peptide aldehyde inhibits bacterial type I signal peptidase. Bioorganic & Medicinal Chemistry Letters. 2009, vol. 19, pp. 2880-2883.*
Ede et al. Solid Phase Synthesis of Peptide Aldehyde Protease Inhibitors . . . Journal of Peptide Science. 2000, vol. 6, pp. 11-18.*
Sorg et al. Progress in the preparation of peptide aldehydes . . . Journal of Peptide Science. 2005, vol. 11, pp. 142-152.*
STN Registry No. 1177859-76-5 (Aug. 30, 2009).*
Lelievre et al. Simple and Efficient Solid-Phase Synthesis of Unprotected Peptide Aldehyde for Peptide Segment Ligation. Tetrahedron Letters. 1998, vol. 39, pp. 9675-9678.*
Bruton et al. Lipopeptide substrates for SpsB, the *Staphylococcus aureus* type I signal peptidase: design, conformation and conversion to α-ketoamide inhibitors. European Journal of Medicinal Chemistry 38:351-356. (2003).
Butler et al. Natural Products—The Future Scaffold for Novel Antibotics. Biochemical Pharmacology, 2006; 71: 919-929.
Crauste et al., Asymmetric Synthesis of New β-Lactam Lipopeptides as Bacterial Signal Peptidase I Inhibitors. Eur. J. Org. Chem. 2011. 3437-3449.
Liu et al. Synthesis and Characterization of the Arylomycin Lipoglycopeptide Antibiotics and the Crytallographic Analysis of Their Complex with Signal Peptidase. J. Am. Chem. Soc. 2011. 133:17869-17877.
Marquette et al. Aggregation and Membrane Permeabilizing Properties of Designed Histidine-Containing Cationic Linear Peptide Antibiotics. Journal of Peptide Science. 2007. 14:488-495.
PCT/US2013/026520 International Search Report and Written Opinion mailed Jun. 18, 2013.
Smith et al. Broad Spectrum Antibiotic activity of the Arylomycin National Products is Masked by Natural Target Mutations. Chemistry & Biology. 2010. 17:1223-1231.

\* cited by examiner

*Primary Examiner* — Jeffrey E Russel
(74) *Attorney, Agent, or Firm* — Wilson Sonsini Goodrich & Rosati

(57) ABSTRACT

Provided herein are antibacterial compounds, wherein the compounds in some embodiments have broad spectrum bioactivity. The compounds provided herein can in other embodiments overcome the resistance conferred by single amino acid mutations at defined positions of bacterial Signal Peptidases (SPases) and in other embodiments provide for a broad spectrum of antibiotic bioactivity. Pharmaceutical compositions and methods for treatment using the compounds described herein are also provided.

25 Claims, No Drawings

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal decanoyl
<220> FEATURE:
<221> NAME/KEY: VARIANT
<222> LOCATION: (6)..(6)
<223> OTHER INFORMATION: Fluorescence acceptor 3-nitrotyrosine
<220> FEATURE:
<221> NAME/KEY: MISC_FEATURE
<222> LOCATION: (7)..(8)
<223> OTHER INFORMATION: Cleavage site between residues 7 and 8
<220> FEATURE:
<221> NAME/KEY: VARIANT
<222> LOCATION: (11)..(11)
<223> OTHER INFORMATION: Fluorescence donor 2-aminobenzamide

<400> SEQUENCE: 1

Leu Ser Ser Pro Ala Xaa Ala Ala Asp Lys Xaa Pro Asp
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: N-terminal decanoyl
<220> FEATURE:
<221> NAME/KEY: VARIANT
<222> LOCATION: (6)..(6)
<223> OTHER INFORMATION: Fluorescence acceptor 3-nitrotyrosine
<220> FEATURE:
<221> NAME/KEY: MISC_FEATURE
<222> LOCATION: (7)..(8)
<223> OTHER INFORMATION: Cleavage site between residues 7 and 8
<220> FEATURE:
<221> NAME/KEY: VARIANT
<222> LOCATION: (12)..(12)
<223> OTHER INFORMATION: Fluorescence donor 2-aminobenzamide

<400> SEQUENCE: 2

Leu Thr Pro Thr Ala Xaa Ala Ala Ser Lys Lys Xaa Asp Asp
1               5                   10
```

LINEAR PEPTIDE ANTIBIOTICS

CROSS-REFERENCE

This application claims the benefit of U.S. provisional application Ser. No. 61/730,928, filed Nov. 28, 2012, and U.S. provisional application Ser. No. 61/599,851, filed Feb. 16, 2012; both of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 28, 2014, is named 40681-702-201SEQ.txt and is 1,583 bytes in size.

BACKGROUND OF THE INVENTION

Since the appearance of the first antibiotic-resistant bacterial strains in the 1940's, at least thirteen strains that are impervious to many antibiotics have been discovered. According to the Infectious Disease Society of America, bacteria that are resistant to one or more drugs are responsible for some 100,000 U.S. hospital deaths a year, and cost the health care system more than $34 billion. The discovery of new antibiotics, especially those that act via the inhibition of a novel target, is an urgent need.

SUMMARY OF THE INVENTION

Described herein are linear peptides for the treatment of microbial infections, such as for the treatment of bacterial infections. In various embodiments, the present disclosure provides lipopeptide compounds for the treatment of bacterial infections. In various embodiments, the lipopeptide compounds act by inhibition of bacterial type 1 signal peptidase (SpsB), an essential protein in bacteria.

In one aspect described herein are compounds of Formula (I):

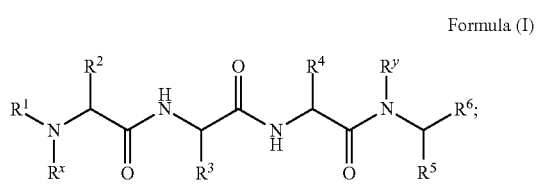

Formula (I)

wherein:

$R^1$ is selected from:

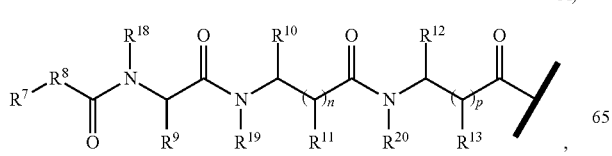

A)

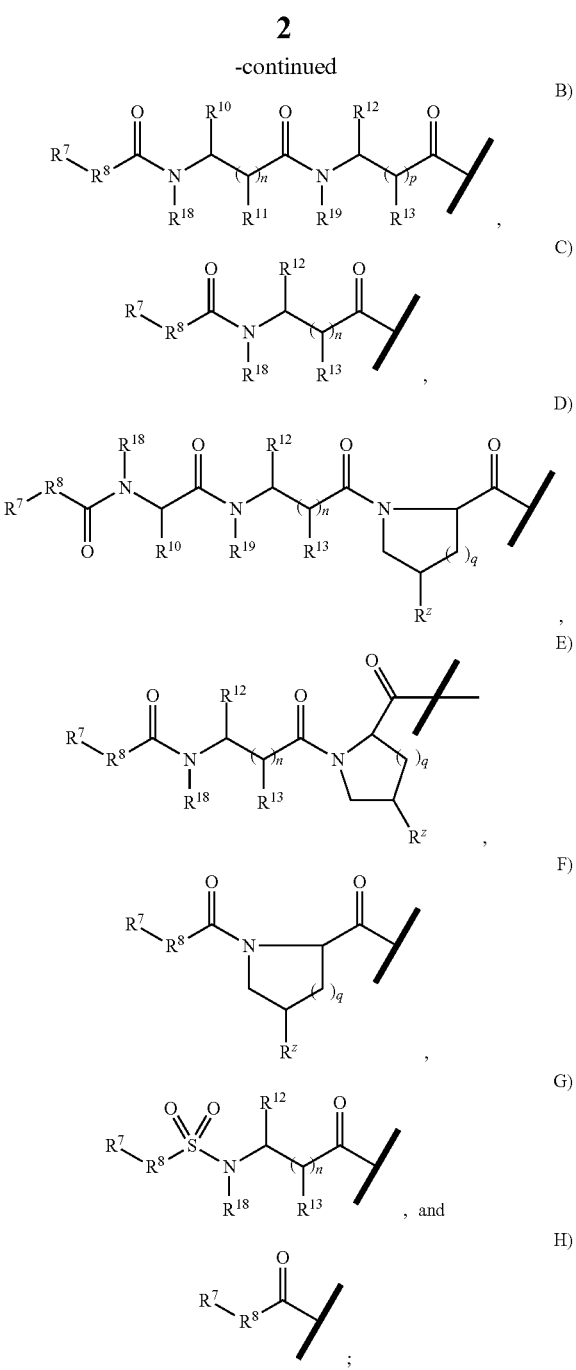

$R^2$, $R^4$, $R^{10}$, $R^{11}$, $R^{12}$, and $R^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$C(O)OR$^{25}$, —CH$_2$CH$_2$C(O)OH, —CH$_2$CH$_2$C(O)OR$^{25}$, —CH$_2$C(O)NH$_2$, —CH$_2$CH$_2$C(O)NH$_2$, —CH$_2$CH$_2$C(O)N(H)C(H)(CH$_3$)CO$_2$H, —CH$_2$CH$_2$C(O)N(H)C(H)(CO$_2$H)CH$_2$CO$_2$H, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, —(CH$_2$)$_4$N(R$^{25}$)$_3$, —(CH$_2$)$_4$N(H)C(O)(2,3-dihydroxybenzene), optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl,

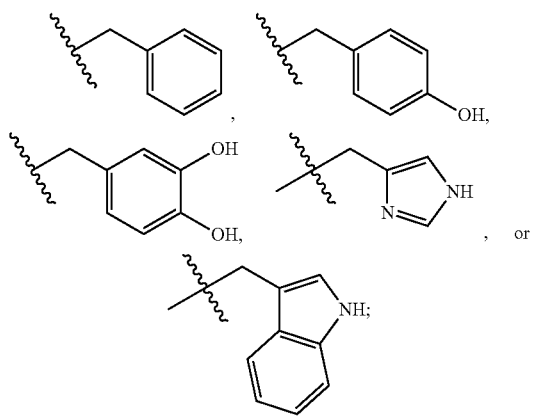

R³ is methyl, ethyl, isopropyl, or cyclopropyl;

R⁵ is H, methyl, ethyl, or —CH₂OH; or R⁵ and R²⁴ together with the boron atom form a 5- or 6-membered boron containing ring;

R⁶ is —C(=O)H, —CH₂C(=O)H, —C(=O)NHCH₂C(=O)H, —C(=O)C(=O)N(R¹⁴)₂, —B(OR²³)(OR²⁴), or

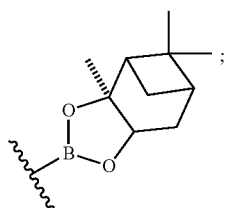 [SMILES: *B1OC2CC3CC(C3(C)C)[C@]2(C)O1]

or R⁵ and R⁶ together with the carbon atom form

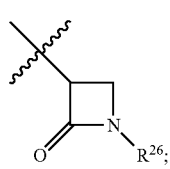

R$^x$ is H, optionally substituted C₁-C₆alkyl, optionally substituted C₁-C₆heteroalkyl, or optionally substituted C₃-C₈cycloalkyl; or R$^x$ and R² together with the nitrogen atom form an optionally substituted nitrogen containing ring;

R$^y$ is H or methyl; or R$^y$ and R⁵ together with the nitrogen atom form an optionally substituted nitrogen containing ring;

R$^z$ is —NR¹⁵R¹⁶, —CH₂—NR¹⁵R¹⁶, or —(CH₂)₂—NR¹⁵R¹⁶;

R⁷ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

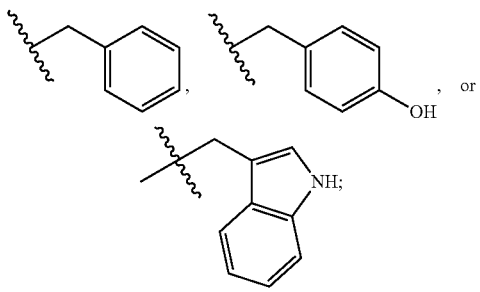

wherein Z is a bond, O, S, NH, CH₂, NHCH₂, or C≡C;

R⁸ is a bond, —O—, or —N(R¹⁷)—, optionally substituted aryl, or optionally substituted heteroaryl;

R⁹ is —CH₂OH, —CH₂CH(CH₃)₂,

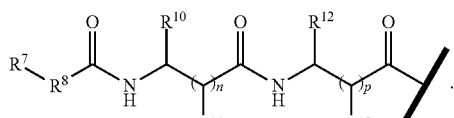

R¹⁴, R¹⁵, and R¹⁶ are each independently H, or C₁-C₄alkyl;

R¹⁷ is H, methyl, ethyl, isopropyl, or cyclopropyl;

R¹⁸, R¹⁹, and R²⁰ are each independently H, or methyl;

each R²¹ is independently H, or C₁-C₄alkyl;

each R²² is independently H, C₁-C₄alkyl, —C(=NH)(NH₂), or —CH(=NH);

R²³ and R²⁴ are each independently H, or C₁-C₄alkyl; or R²³ and R²⁴ together with the boron atom form an optionally substituted 5- or 6-membered boron containing ring;

each R²⁵ is independently C₁-C₆alkyl;

R²⁶ is H, C₁-C₄alkyl, C₁-C₄alkoxy, —CH₂C(O)OR²⁵, or —OCH₂C(O)OR²⁵;

n is 0 or 1;

p is 0 or 1; and q is 0 or 1;

or a pharmaceutically acceptable salt, solvate, or prodrug thereof.

In one embodiment is a compound of Formula (I) wherein R¹ is

In another embodiment is a compound of Formula (I) wherein R⁸ is a bond. In another embodiment is a compound of Formula (I) wherein R², R⁴, R¹⁰, R¹¹, R¹², and R¹³ are each independently —H, —CH₃, —CH(CH₃)₂, —C(CH₃)₃, —CH(CH₃)(CH₂CH₃), —CH₂CH(CH₃)₂, —CH₂OH, —CH(OH)(CH₃), —CH₂CF₃, —CH₂C(O)OH, —CH₂CH₂C(O)OH, —CH₂C(O)NH₂, —CH₂CH₂C(O)NH₂, —CH₂NH₂, —(CH₂)₂NH₂, —(CH₂)₃NH₂, —(CH₂)₄NH₂,

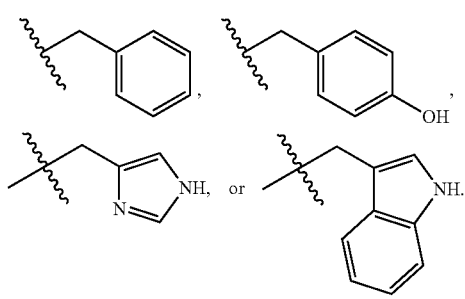

In another embodiment is a compound of Formula (I) wherein R$^2$, R$^4$, R$^{10}$, R$^{11}$, R$^{12}$, and R$^{13}$ are each independently —H, —CH$_3$, —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$, or

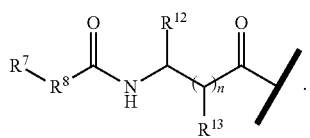

In another embodiment is a compound of Formula (I) wherein n is 1 and p is 0.

In another embodiment is a compound of Formula (I) having the structure of Formula (Ib):

Formula Ib

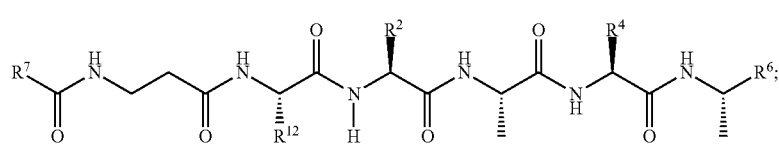

wherein R$^2$, R$^4$, and R$^{12}$ are each independently —CH$_2$CH(CH$_3$)$_2$, —(CH$_2$)$_3$NH$_2$, or —(CH$_2$)$_4$NH$_2$.

In another embodiment is a compound of Formula (I) wherein R$^1$ is

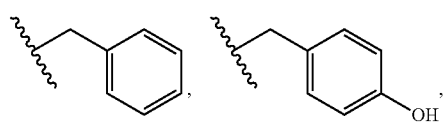

In a further embodiment is a compound of Formula (I) wherein R$^2$, R$^4$, R$^{12}$, and R$^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

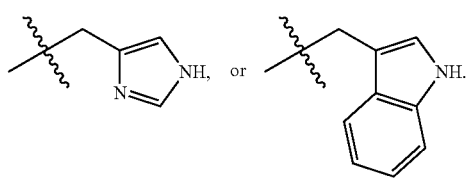

In yet a further embodiment is a compound of Formula (I) wherein R$^2$, R$^4$, R$^{12}$, and R$^{13}$ are each independently —H, —CH$_3$, —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

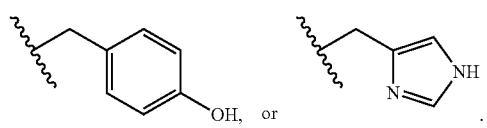 [SMILES: *Cc1ccc(O)cc1 ; "or" ; *Cc1c[nH]cn1]

In a further embodiment is a compound of Formula (I) wherein n is 0. In yet a further embodiment is a compound of Formula (I) wherein R$^8$ is a bond.

In another embodiment is a compound of Formula (I) having the structure of Formula (Ic):

Formula (Ic)

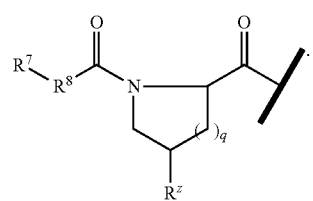

wherein R$^2$, R$^4$, and R$^{12}$ are each independently —CH$_2$CH(CH$_3$)$_2$, —CH(OH)(CH$_3$), —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, or —(CH$_2$)$_4$NH$_2$.

In another embodiment is a compound of Formula (I) wherein R$^1$ is

In a further embodiment is a compound of Formula (I) wherein $R^2$ and $R^4$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

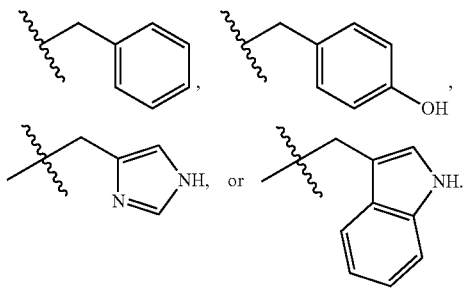

In a further embodiment is a compound of Formula (I) wherein q is 1; and $R^8$ is a bond.

In another embodiment is a compound of Formula (I) having the structure of Formula (Id):

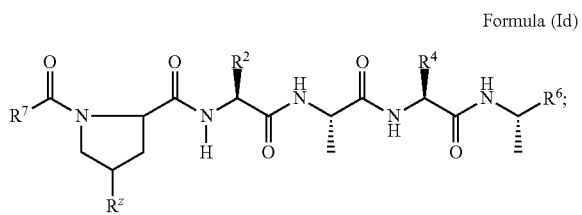

Formula (Id)

wherein $R^z$ is NH$_2$; and $R^2$ and $R^4$ are each independently —CH$_2$CH(CH$_3$)$_2$, —CH(OH)(CH$_3$), —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, or —(CH$_2$)$_4$NH$_2$.

In another aspect is a hydrate or metabolite of a compound of Formula (I).

In another aspect is a pharmaceutical composition comprising a compound of Formula (I) and a pharmaceutically acceptable excipient.

In another aspect is the use of a compound of Formula (I) or a pharmaceutically acceptable salt, pharmaceutically acceptable solvate, or pharmaceutically acceptable prodrug thereof, for the preparation of a medicament for the treatment of a bacterial infection in a patient.

In one aspect is a method for treating a bacterial infection in a mammal comprising administering to the mammal a compound of Formula (I) or a pharmaceutically acceptable salt or prodrug thereof at a frequency and for a duration sufficient to provide a beneficial effect to the mammal. In another embodiment, the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In another embodiment the bacterial infection is an infection involving a Gram-negative bacteria. In another embodiment, administering comprises a topical administration.

In a further embodiment are methods of treating a mammal in need of such treatment comprising administering to the mammal a second therapeutic agent. In another embodiment, the second therapeutic agent is not an SpsB inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid. In another embodiment, the second therapeutic agent is a β-lactam antibiotic. In another embodiment, the β-lactam antibiotic is selected from penicillins, monobactams, cephalosporins, and carbapenems. A further embodiment comprises administering β-lactamase inhibitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

The expression "effective amount", when used to describe therapy to an individual suffering from a disorder, refers to the amount of a compound described herein that is effective to inhibit or otherwise act on SPase in the individual's tissues wherein SPase involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds described herein are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^3H$ can be prepared using neutrons generated in a nuclear reactor. Following nuclear transformation, $^{14}C$ and $^3H$ are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

The term "alkyl" refers to a straight or branched hydrocarbon chain radical group consisting solely of carbon and hydrogen atoms from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups. A description herein that a group is an alkyl chain "optionally comprising within the alkyl chain or at an alkyl chain terminus", signifies that a moiety can be disposed between two subunits of the alkyl chain, or can be disposed at an unsubstituted end of the chain, or can be disposed between the chain and a point of attachment of the chain, for example to a carbonyl, NR, or O group. For example, an alkylbenzoyl group is an alkyl chain with a phenyl group disposed between the alkyl and a carbonyl, fitting the above description; an N-alkylphenylcarboxamido is an alkyl chain with a phenyl group disposed between the alkyl and the aminocarbonyl group, filling within the above description.

The term "alkylene" means a linear saturated divalent hydrocarbon radical of one to six carbon atoms or a branched saturated divalent hydrocarbon radical of one to six carbon atoms unless otherwise stated, such as methylene, ethylene, propylene, 1-methylpropylene, 2-methylpropylene, butylene, pentylene, and the like.

The term "carbonyl" means CO=O.

The terms "carboxy" and "hydroxycarbonyl" mean COOH.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring or "heterocycloalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b] furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo [b]thiophenyl, 6-benzo[b]thiophenyl, 7-benzo[b] thiophenyl), 2,3-dihydro-benzo[b]thiophenyl, (2-(2,3-dihydro-benzo[b]thiophenyl), 3-(2,3-dihydro-benzo[b] thiophenyl), 4-(2,3-dihydro-benzo[b]thiophenyl), 5-(2,3-dihydro-benzo[b]thiophenyl), 6-(2,3-dihydro-benzo[b] thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "thioalkoxy" refers to an alkyl group previously defined attached to the parent molecular moiety through a sulfur atom.

The term "glycosyloxyoxy" refers to a glycoside attached to the parent molecular moiety through an oxygen atom.

The term "alkoxycarbonyl" represents as ester group; i.e. an alkoxy group, attached to the parent molecular moiety through a carbonyl group such as methoxycarbonyl, ethoxycarbonyl, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x\text{-}C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkyl, more preferred is —$(C_1\text{-}C_3)$perfluoroalkyl, most preferred is —$CF_3$.

The term "$(C_x\text{-}C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkylene, more preferred is —$(C_1\text{-}C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like.

In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" or "aminocarbonyl" group is a group of the formula C(O)NR$_2$, wherein R can be H, alkyl, aryl, etc.

The term "azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds described herein may take the form of salts. The term "salts" embraces addition salts of free acids or free bases which are compounds described herein. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the present disclosure.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the present disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the present disclosure are described in terms of Markush groups, those skilled in the art will recognize that the presently described compounds is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the present disclosure are described in terms of Markush groups, those skilled in the art will recognize that the present disclosure is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present disclosure further embraces isolated compounds according to Formula (I). The expression "isolated compound" refers to a preparation of a compound of Formula (I), or a mixture of compounds according to Formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of Formula (I) or a mixture of compounds according to Formula (I), which contains the named compound or mixture of compounds according to Formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds described herein and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds Described Herein

Tautomerism

Within the present disclosure it is to be understood that a compound of the Formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the present disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

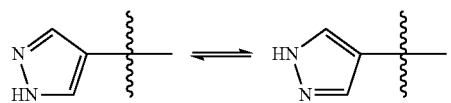

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

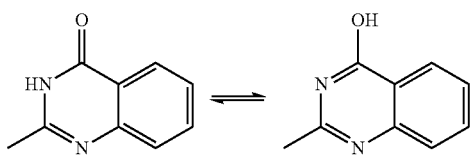

is an example of tautomerism. Accordingly, a structure depicted herein as one tautomer is intended to also include the other tautomer.

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

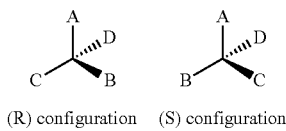

(R) configuration      (S) configuration

The present disclosure is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present disclosure therefore includes any possible stable rotamers of Formula (I) which are biologically active in the treatment of cancer or other proliferative disease states.

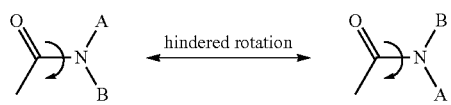

Regioisomerism

In some embodiments, the compounds described herein have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

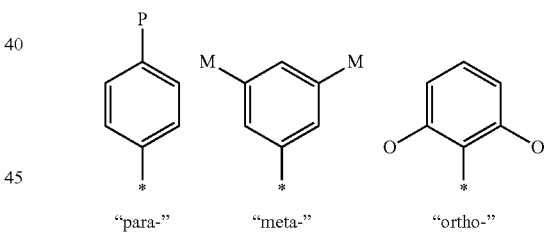

"para-"      "meta-"      "ortho-"

In various embodiments, the compound or set of compounds, such as are among the inventive compounds or are used in the inventive methods, can be any one of any of the combinations and/or sub-combinations of the above-listed embodiments.

Compounds

In one aspect described herein are compounds of Formula (I):

Formula (I)

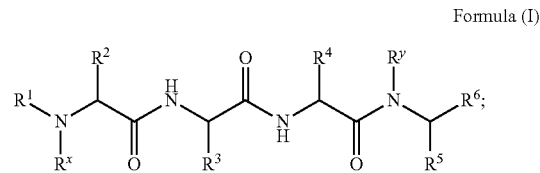

wherein:
R¹ is selected from:

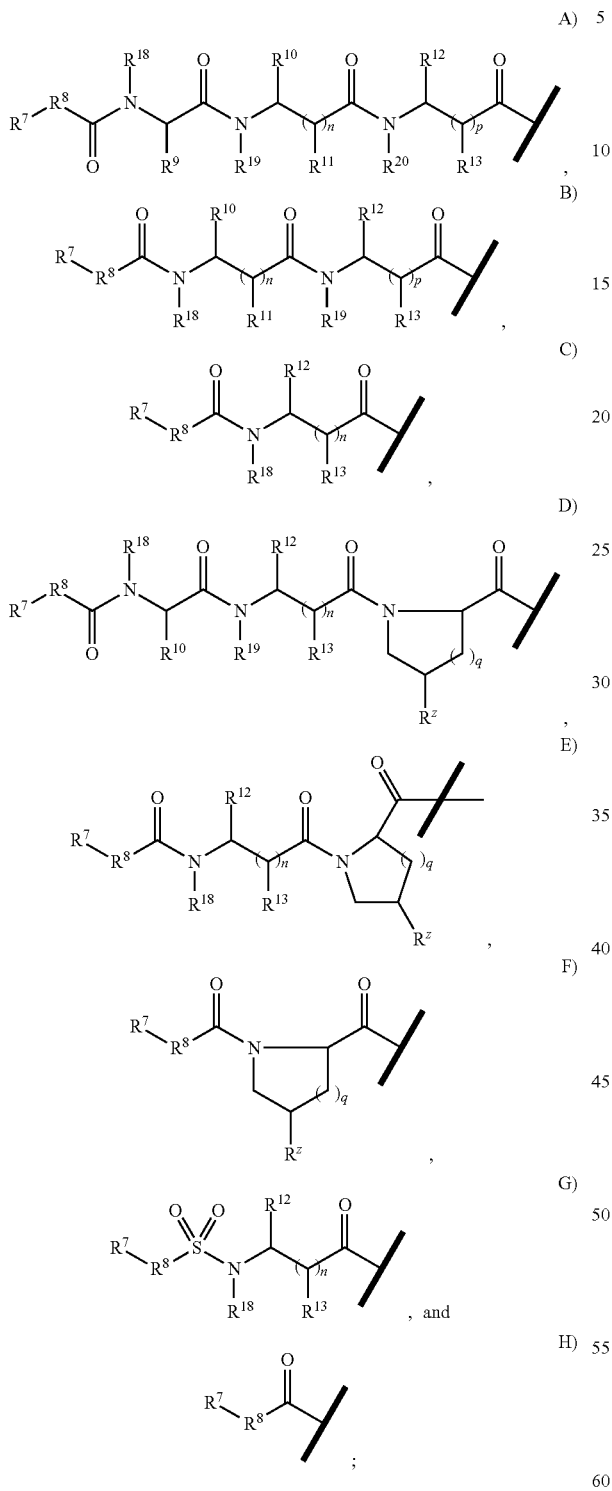

R², R⁴, R¹⁰, R¹¹, R¹², and R¹³ are each independently —H, —CH₃, —CH(CH₃)₂, —C(CH₃)₃, —CH(CH₃)(CH₂CH₃), —CH₂CH(CH₃)₂, —CH₂OH, —CH(OH)(CH₃), —CH₂CF₃, —CH₂C(O)OH, —CH₂C(O)OR²⁵, —CH₂CH₂C(O)OH, —CH₂CH₂C(O)OR²⁵, —CH₂C(O)NH₂, —CH₂CH₂C(O)NH₂, —CH₂CH₂C(O)N(H)C(H)(CH₃)CO₂H, —CH₂CH₂C(O)N(H)C(H)(CO₂H)CH₂CO₂H, —CH₂NR²¹R²², —(CH₂)₂NR²¹R²², —(CH₂)₃NR²¹R²², —(CH₂)₄NR²¹R²², —(CH₂)₄N(R²⁵)₃, —(CH₂)₄N(H)C(O)(2,3-dihydroxybenzene), optionally substituted C₁-C₈alkyl, optionally substituted C₁-C₈heteroalkyl, optionally substituted C₃-C₈cycloalkyl, optionally substituted —CH₂—C₃-C₈cycloalkyl, optionally substituted heterocycloalkyl, optionally substituted aryl, optionally substituted heteroaryl,

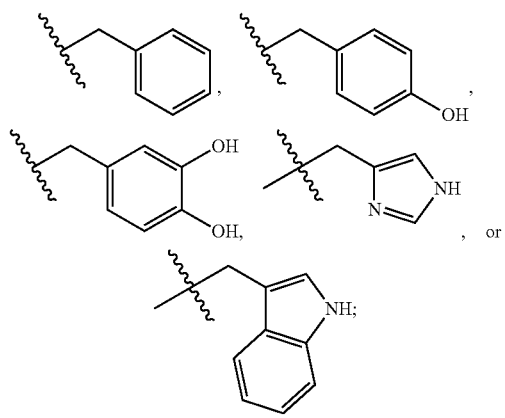

R³ is methyl, ethyl, isopropyl, or cyclopropyl;
R⁵ is H, methyl, ethyl, or —CH₂OH; or R⁵ and R²⁴ together with the boron atom form a 5- or 6-membered boron containing ring;
R⁶ is —C(=O)H, —CH₂C(=O)H, —C(=O)NHCH₂C(=O)H, —C(=O)C(=O)N(R¹⁴)₂, —B(OR²³)(OR²⁴), or

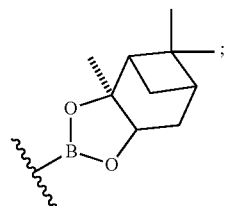 [SMILES: *B1OC2CC3CC(C3(C)C)[C@]2(C)O1]

or R⁵ and R⁶ together with the carbon atom form

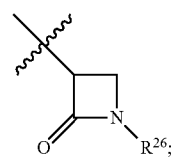

Rˣ is H, optionally substituted C₁-C₆alkyl, optionally substituted C₁-C₆heteroalkyl, or optionally substituted C₃-C₈cycloalkyl; or Rˣ and R² together with the nitrogen atom form an optionally substituted nitrogen containing ring;
Rʸ is H or methyl; or Rʸ and R⁵ together with the nitrogen atom form an optionally substituted nitrogen containing ring;
Rᶻ is —NR¹⁵R¹⁶, —CH₂—NR¹⁵R¹⁶, or —(CH₂)₂—NR¹⁵R¹⁶;

$R^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

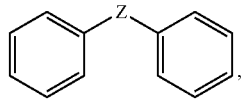

wherein Z is a bond, O, S, NH, CH$_2$, NHCH$_2$, or C≡C;

$R^8$ is a bond, —O—, or —N($R^{17}$)—, optionally substituted aryl, or optionally substituted heteroaryl;

$R^9$ is —CH$_2$OH, —CH$_2$CH(CH$_3$)$_2$,

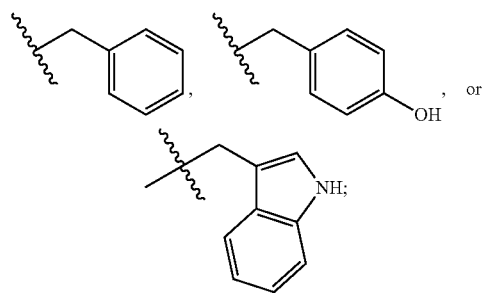

$R^{14}$, $R^{15}$, and $R^{16}$ are each independently H, or C$_1$-C$_4$alkyl;
$R^{17}$ is H, methyl, ethyl, isopropyl, or cyclopropyl;
$R^{18}$, $R^{19}$, and $R^{20}$ are each independently H, or methyl;
each $R^{21}$ is independently H, or C$_1$-C$_4$alkyl;
each $R^{22}$ is independently H, C$_1$-C$_4$alkyl, —C(=NH)(NH$_2$), or —CH(=NH);
$R^{23}$ and $R^{24}$ are each independently H, or C$_1$-C$_4$alkyl; or $R^{23}$ and $R^{24}$ together with the boron atom form an optionally substituted 5- or 6-membered boron containing ring;
each $R^{25}$ is independently C$_1$-C$_6$alkyl;
$R^{26}$ is H, C$_1$-C$_4$alkyl, C$_1$-C$_4$alkoxy, —CH$_2$C(O)OR$^{25}$, or —OCH$_2$C(O)OR$^{25}$;
n is 0 or 1;
p is 0 or 1; and
q is 0 or 1;
or a pharmaceutically acceptable salt, solvate, or prodrug thereof.

In one embodiment is a compound of Formula (I) having the structure of Formula (I'):

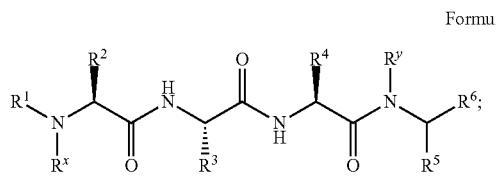

Formula (I')

wherein:
$R^1$ is selected from:

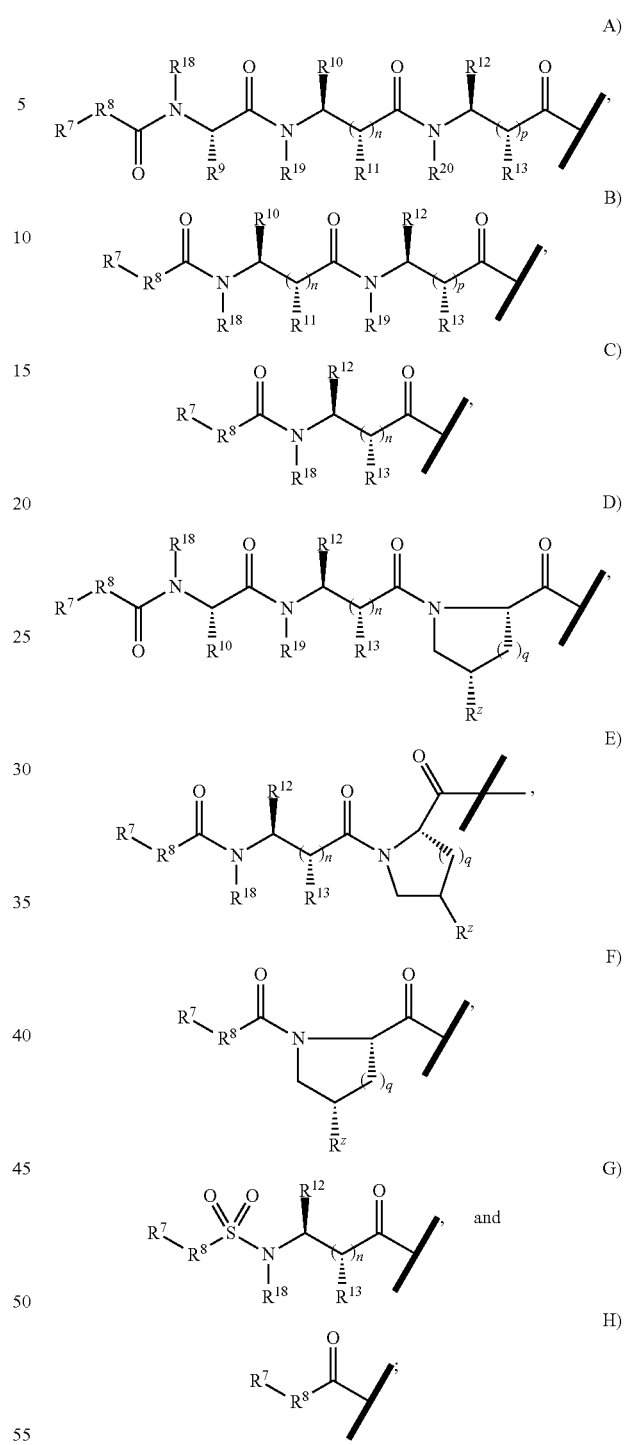

$R^2$, $R^4$, $R^{10}$, $R^{11}$, $R^{12}$, and $R^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$C(O)OR$^{25}$, —CH$_2$CH$_2$C(O)OH, —CH$_2$CH$_2$C(O)OR$^{25}$, —CH$_2$C(O)NH$_2$, —CH$_2$CH$_2$C(O)NH$_2$, —CH$_2$CH$_2$C(O)N(H)C(H)(CH$_3$)CO$_2$H, —CH$_2$CH$_2$C(O)N(H)C(H)(CO$_2$H)CH$_2$CO$_2$H, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, —(CH$_2$)$_4$N(R$^{25}$)$_3$, —(CH$_2$)$_4$N(H)C(O)(2,3-dihydroxybenzene), optionally substituted $C_1$-$C_8$alkyl, optionally substituted $C_1$-$C_8$heteroalkyl, optionally substituted $C_3$-$C_8$cycloalkyl, optionally substituted —$CH_2$—$C_3$-$C_8$cycloalkyl, optionally substituted heterocycloalkyl, optionally substituted aryl, optionally substituted heteroaryl,

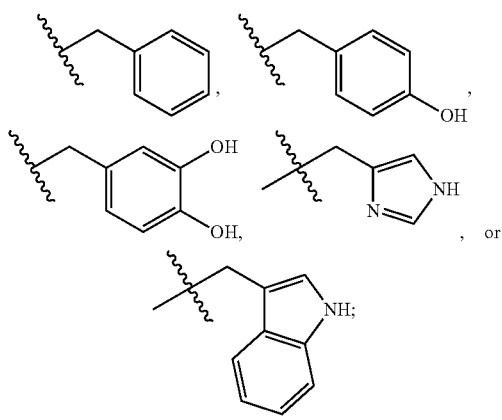

$R^3$ is methyl, ethyl, isopropyl, or cyclopropyl;
$R^5$ is H, methyl, ethyl, or —$CH_2OH$; or $R^5$ and $R^{24}$ together with the boron atom form a 5- or 6-membered boron containing ring;
$R^6$ is —C(=O)H, —$CH_2$C(=O)H, —C(=O)NHCH$_2$C(=O)H, —C(=O)C(=O)N($R^{14}$)$_2$, —B(O$R^{23}$)(O$R^{24}$), or

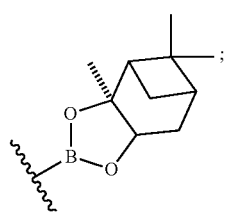 [SMILES: *B1OC2CC3CC(C3(C)C)[C@]2(C)O1]

or $R^5$ and $R^6$ together with the carbon atom form

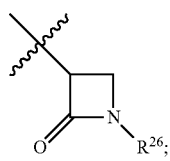

$R^x$ is H, optionally substituted $C_1$-$C_6$alkyl, optionally substituted $C_1$-$C_6$heteroalkyl, or optionally substituted $C_3$-$C_8$cycloalkyl; or $R^x$ and $R^2$ together with the nitrogen atom form an optionally substituted nitrogen containing ring;
$R^y$ is H or methyl; or $R^y$ and $R^5$ together with the nitrogen atom form an optionally substituted nitrogen containing ring;
$R^z$ is —NR$^{15}$R$^{16}$, —CH$_2$—NR$^{15}$R$^{16}$, or —(CH$_2$)$_2$—NR$^{15}$R$^{16}$;
$R^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

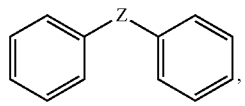

wherein Z is a bond, O, S, NH, CH$_2$, NHCH$_2$, or C≡C;
$R^8$ is a bond, —O—, or —N($R^{17}$)—, optionally substituted aryl, or optionally substituted heteroaryl;
$R^9$ is —CH$_2$OH, —CH$_2$CH(CH$_3$)$_2$,

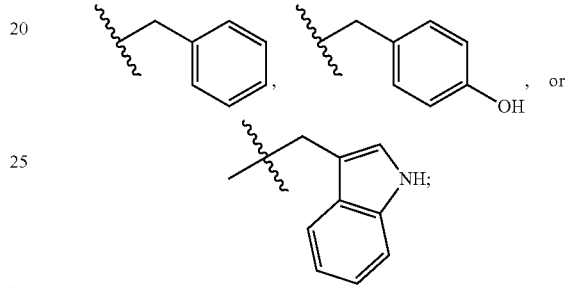

$R^{14}$, $R^{15}$, and $R^{16}$ are each independently H, or $C_1$-$C_4$alkyl;
$R^{17}$ is H, methyl, ethyl, isopropyl, or cyclopropyl;
$R^{18}$, $R^{19}$, and $R^{20}$ are each independently H, or methyl;
each $R^{21}$ is independently H, or $C_1$-$C_4$alkyl;
each $R^{22}$ is independently H, $C_1$-$C_4$alkyl, —C(=NH)(NH$_2$), or —CH(=NH);
$R^{23}$ and $R^{24}$ are each independently H, or $C_1$-$C_4$alkyl; or $R^{23}$ and $R^{24}$ together with the boron atom form an optionally substituted 5- or 6-membered boron containing ring;
each $R^{25}$ is independently $C_1$-$C_6$alkyl;
$R^{26}$ is H, $C_1$-$C_4$alkyl, $C_1$-$C_4$alkoxy, —CH$_2$C(O)OR$^{25}$, or —OCH$_2$C(O)OR$^{25}$;
n is 0 or 1;
p is 0 or 1; and
q is 0 or 1;
or a pharmaceutically acceptable salt, solvate, or prodrug thereof.

In one embodiment is a compound of Formula (I) or Formula (I') wherein $R^1$ is

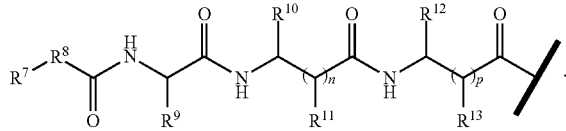

In a further embodiment, $R^8$ is a bond. In another embodiment, $R^2$, $R^4$, $R^{10}$, $R^{11}$, $R^{12}$, and $R^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)$_4$NH$_2$,

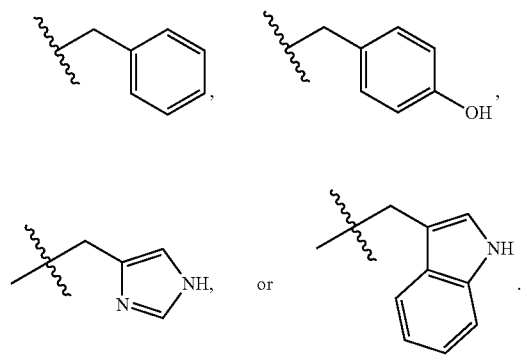 [SMILES: *Cc1ccccc1 ; *Cc1ccc(O)cc1 ; *Cc1c[nH]cn1 ; *Cc1c[nH]c2ccccc12]

In a further embodiment, $R^2$, $R^4$, $R^{10}$, $R^{11}$, $R^{12}$, and $R^{13}$ are each independently —H, —CH$_3$, —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)$_4$NH$_2$,

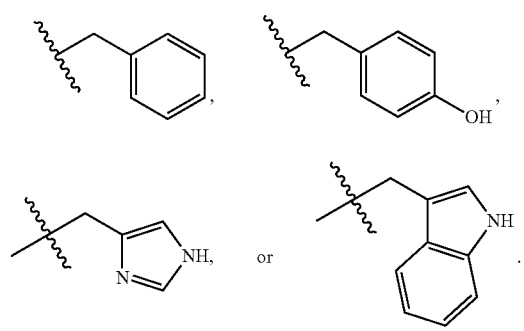

In yet a further embodiment, $R^2$, $R^4$, $R^{10}$, $R^{11}$, $R^{12}$, and $R^{13}$ are each independently —H, —CH$_3$, —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)$_4$NH$_2$,

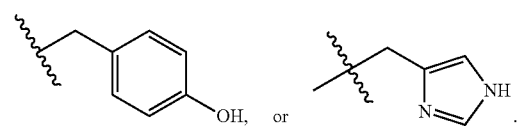 [SMILES: *Cc1ccc(O)cc1 ; *Cc1c[nH]cn1]

In a further embodiment of the aforementioned embodiments is a compound of Formula (I) or Formula (I') wherein n is 0 and p is 0. In another embodiment, n is 0 and p is 1. In yet a further embodiment, n is 1 and p is 0.

In a further embodiment is a compound of Formula (I') having the structure of Formula (Ia):

In another embodiment is a compound of Formula (Ia) wherein $R^2$ is —CH(OH)(CH$_3$), —CH$_2$CH$_2$C(O)OH, or —(CH$_2$)$_4$NH$_2$. In some embodiments, $R^2$ is —CH(OH)(CH$_3$). In some embodiments, $R^2$ is —CH$_2$CH$_2$C(O)OH. In some embodiments, $R^2$ is —(CH$_2$)$_4$NH$_2$. In a further embodiment is a compound of Formula (Ia) wherein $R^4$ is CH$_2$CH(CH$_3$)$_2$ or —CH$_2$C(O)NH$_2$. In some embodiments, $R^4$ is CH$_2$CH(CH$_3$)$_2$. In some embodiments, $R^4$ is —CH$_2$C(O)NH$_2$. In yet a further embodiment is a compound of Formula (Ia) wherein $R^5$ is H or —CH$_3$. In some embodiments, $R^4$ is H. In some embodiments, $R^4$ is —CH$_3$.

In another embodiment is a compound of Formula (I) or Formula (I') wherein $R^1$ is

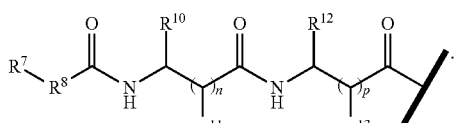

In a further embodiment, $R^8$ is a bond. In another embodiment, $R^2$, $R^4$, $R^{10}$, $R^{11}$, $R^{12}$, and $R^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

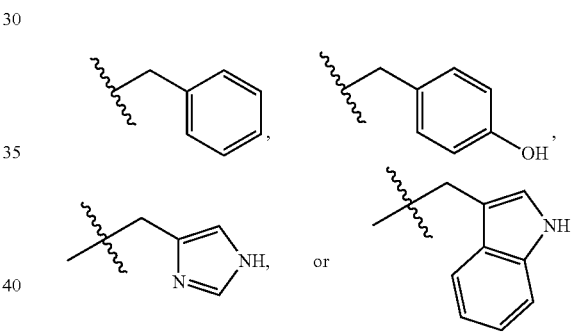

In a further embodiment, $R^2$, $R^4$, $R^{10}$, $R^{11}$, $R^{12}$, and $R^{13}$ are each independently —H, —CH$_3$, —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)NH$_2$,

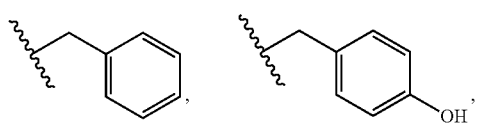

Formula (Ia)

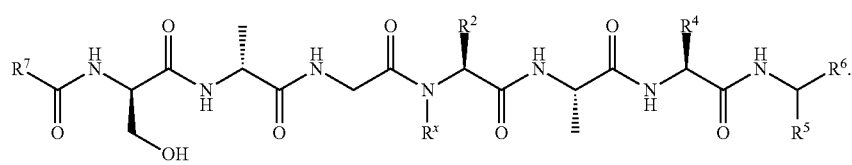

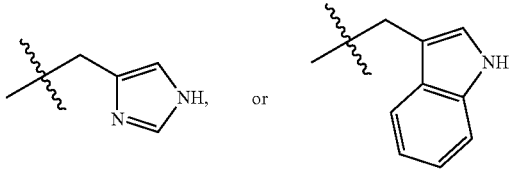 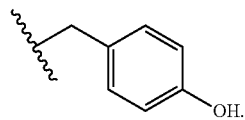 [SMILES: *Cc1ccc(O)cc1]

In yet a further embodiment, $R^2$, $R^4$, $R^{10}$, $R^{11}$, $R^{12}$, and $R^{13}$ are each independently —H, —$CH_3$, —$CH_2CH(CH_3)_2$, —$CH_2OH$, —$CH(OH)(CH_3)$, —$CH_2CH_2C(O)OH$, —$CH_2C(O)NH_2$, —$CH_2CH_2C(O)NH_2$, —$CH_2NH_2$, —$(CH_2)_2NH_2$, —$(CH_2)_3NH_2$, —$(CH_2)_4NH_2$, or In a further embodiment of the aforementioned embodiments is a compound of Formula (I) or Formula (I') wherein n is 0 and p is 0. In another embodiment, n is 0 and p is 1. In yet a further embodiment, n is 1 and p is 0.

In a further embodiment is a compound of Formula (I') having the structure of Formula (Ib):

Formula (Ib)

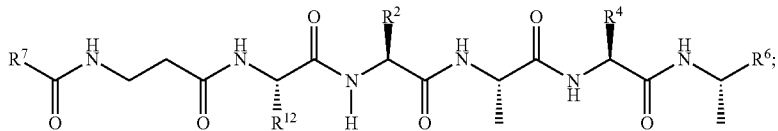

wherein $R^2$, $R^4$, and $R^{12}$, are each independently —$CH_2CH(CH_3)_2$, —$(CH_2)_3NH_2$, or —$(CH_2)_4NH_2$.

In another embodiment is a compound of Formula (Ib) wherein $R^2$, $R^4$, and $R^{12}$ are each —$(CH_2)_4NH_2$. In another embodiment is a compound of Formula (Ib) wherein $R^2$, $R^4$, and $R^{12}$ are each —$(CH_2)_3NH_2$. In another embodiment is a compound of Formula (Ib) wherein $R^4$ is —$CH_2CH(CH_3)_2$, $R^2$ is —$(CH_2)_3NH_2$, and $R^{12}$ is —$(CH_2)_4NH_2$. In another embodiment is a compound of Formula (Ib) wherein $R^4$ is —$CH_2CH(CH_3)_2$, $R^2$ is —$(CH_2)_4NH_2$, and $R^{12}$ is —$(CH_2)_4NH_2$.

In a further embodiment is a compound of Formula (I') having the structure of Formula (Ibb):

Formula (Ibb)

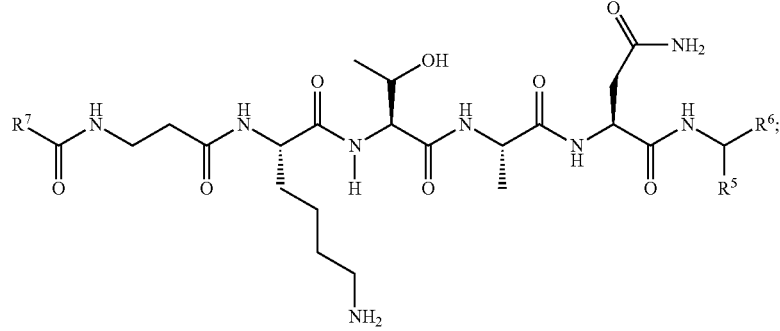

wherein $R^5$ is —H, or —$CH_3$.

In a further embodiment is a compound of Formula (I') having the structure of Formula (Ibbb):

Formula (Ibbb)

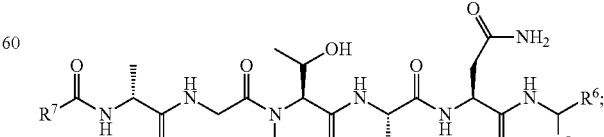

wherein $R^5$ is —H, or —$CH_3$.

In another embodiment is a compound of Formula (I) or Formula (I') wherein $R^1$ is

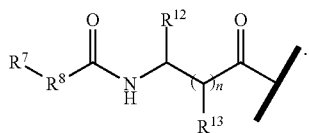

In a further embodiment, $R^8$ is a bond. In another embodiment, $R^2$, $R^4$, $R^{12}$, and $R^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

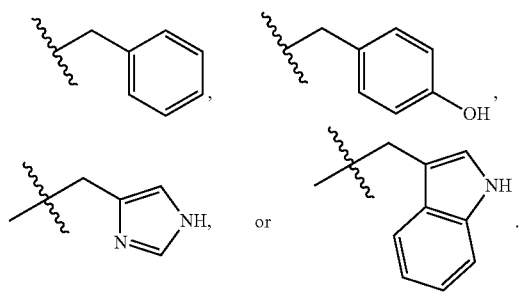

In a further embodiment, $R^2$, $R^4$, $R^{12}$, and $R^{13}$ are each independently —H, —CH$_3$, —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

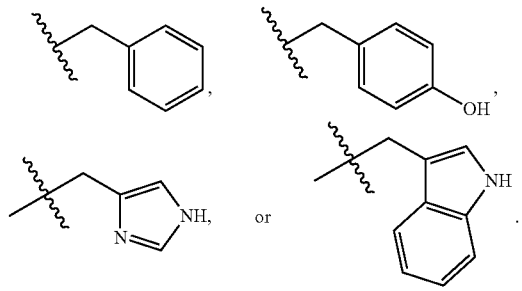

In yet a further embodiment, $R^2$, $R^4$, $R^{12}$, and $R^{13}$ are each independently —H, —CH$_3$, —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

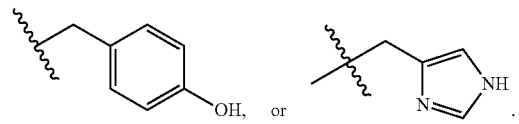 [SMILES: *Cc1ccc(O)cc1 ; *Cc1c[nH]cn1]

In a further embodiment of the aforementioned embodiments is a compound of Formula (I) or Formula (I') wherein n is 0. In yet a further embodiment, n is 1.

In a further embodiment is a compound of Formula (I') having the structure of Formula (Ic):

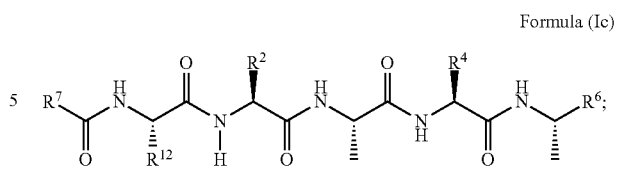

Formula (Ic)

wherein $R^2$, $R^4$, and $R^{12}$, are each independently —CH$_2$CH(CH$_3$)$_2$, —CH(OH)(CH$_3$), —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, or —(CH$_2$)$_4$NH$_2$.

In another embodiment is a compound of Formula (Ic) wherein $R^4$ is —(CH$_2$)$_4$NH$_2$, $R^2$ is —CH(OH)(CH$_3$), and $R^{12}$ is —(CH$_2$)$_2$NH$_2$. In another embodiment is a compound of Formula (Ic) wherein $R^4$ is —(CH$_2$)$_4$NH$_2$, $R^2$ is —CH(OH)(CH$_3$), and $R^{12}$ is —CH$_2$NH$_2$. In another embodiment is a compound of Formula (Ic) wherein $R^4$ is —CH$_2$C(O)NH$_2$, $R^2$ is —CH(OH)(CH$_3$), and $R^{12}$ is —(CH$_2$)$_4$NH$_2$. In another embodiment is a compound of Formula (Ic) wherein $R^4$ is —(CH$_2$)$_4$NH$_2$, $R^2$ is —(CH$_2$)$_4$NH$_2$, and $R^{12}$ is —CH$_2$NH$_2$. In another embodiment is a compound of Formula (Ic) wherein $R^4$ is —CH$_2$C(O)NH$_2$, $R^2$ is —(CH$_2$)$_4$NH$_2$, and $R^{12}$ is —CH$_2$NH$_2$. In another embodiment is a compound of Formula (Ic) wherein $R^4$ is —CH$_2$CH(CH$_3$)$_2$, $R^2$ is —(CH$_2$)$_2$NH$_2$, and $R^{12}$ is —(CH$_2$)$_2$NH$_2$.

In a further embodiment is a compound of Formula (I') having the structure of Formula (Icc):

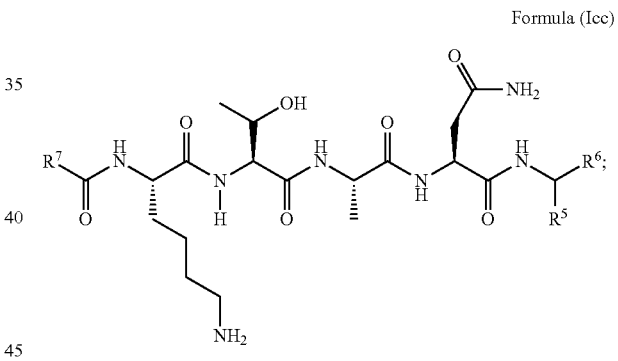

Formula (Icc)

wherein $R^5$ is —H, or —CH$_3$.

In another embodiment is a compound of Formula (I) or Formula (I') wherein $R^1$ is

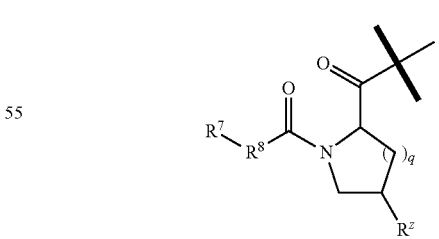

In a further embodiment, $R^2$ and $R^4$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

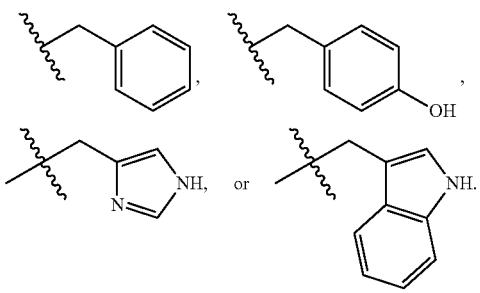

In a further embodiment, q is 1 and $R^8$ is a bond.

In a further embodiment is a compound of Formula (I') having the structure of Formula (Id):

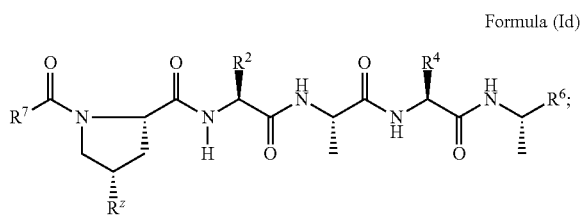

Formula (Id)

wherein $R^z$ is $NH_2$; and $R^2$ and $R^4$ are each independently $—CH_2CH(CH_3)_2$, $—CH(OH)(CH_3)$, $—CH_2C(O)NH_2$, $—CH_2CH_2C(O)NH_2$, $—CH_2NH_2$, $—(CH_2)_2NH_2$, $—(CH_2)_3NH_2$, or $—(CH_2)_4NH_2$.

In another embodiment is a compound of Formula (Id) wherein $R^2$ is $—CH(OH)(CH_3)$, and $R^4$ is $—CH_2C(O)NH_2$. In another embodiment is a compound of Formula (Id) wherein $R^2$ is $—CH(OH)(CH_3)$, and $R^4$ is $—(CH_2)_2NH_2$. In another embodiment is a compound of Formula (Id) wherein $R^2$ is $—CH(OH)(CH_3)$, and $R^4$ is $—(CH_2)_3NH_2$. In another embodiment is a compound of Formula (Id) wherein $R^2$ is $—CH(OH)(CH_3)$, and $R^4$ is $—(CH_2)_4NH_2$. In another embodiment is a compound of Formula (Id) wherein $R^2$ is $—(CH_2)_4NH_2$ and $R^4$ is $—CH_2CH(CH_3)_2$. In another embodiment is a compound of Formula (Id) wherein $R^2$ is $—(CH_2)_4NH_2$ and $R^4$ is $—CH_2C(O)NH_2$. In another embodiment is a compound of Formula (Id) wherein $R^2$ is $—(CH_2)_4NH_2$ and $R^4$ is $—(CH_2)_4NH_2$.

In another embodiment is a compound of Formula (I) or Formula (I') wherein $R^1$ is

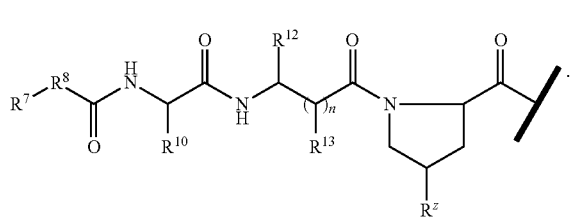

In a further embodiment, $R^8$ is a bond. In another embodiment, $R^2$, $R^4$, $R^{10}$, $R^{12}$, and $R^{13}$ are each independently —H, $—CH_3$, $—CH(CH_3)_2$, $—C(CH_3)_3$, $—CH(CH_3)(CH_2CH_3)$, $—CH_2CH(CH_3)_2$, $—CH_2OH$, $—CH(OH)(CH_3)$, $—CH_2CF_3$, $—CH_2C(O)OH$, $—CH_2CH_2C(O)OH$, $—CH_2C(O)NH_2$, $—CH_2CH_2C(O)NH_2$, $—(CH_2)_2NH_2$, $—(CH_2)_3NH_2$, $—(CH_2)_4NH_2$,

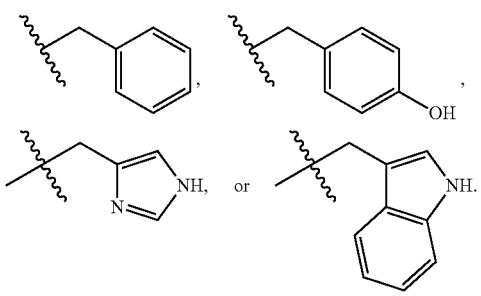

In a further embodiment, $R^2$, $R^4$, $R^{10}$, $R^{12}$, and $R^{13}$ are each independently —H, $—CH_3$, $—CH(CH_3)_2$, $—CH(CH_3)(CH_2CH_3)$, $—CH_2CH(CH_3)_2$, $—CH_2OH$, $—CH(OH)(CH_3)$, $—CH_2CH_2C(O)OH$, $—CH_2C(O)NH_2$, $—CH_2CH_2C(O)NH_2$, $—(CH_2)_2NH_2$, $—(CH_2)_3NH_2$, $—(CH_2)_4NH_2$,

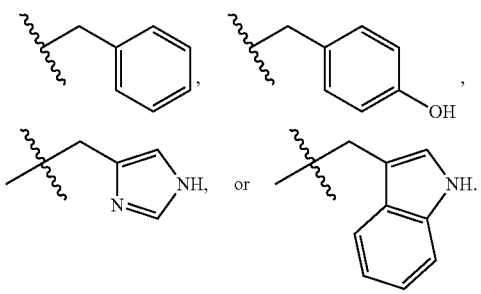

In yet a further embodiment, $R^2$, $R^4$, $R^{10}$, $R^{12}$, and $R^{13}$ are each independently —H, $—CH_3$, $—CH_2CH(CH_3)_2$, $—CH_2OH$, $—CH(OH)(CH_3)$, $—CH_2CH_2C(O)OH$, $—CH_2C(O)NH_2$, $—CH_2CH_2C(O)NH_2$, $—(CH_2)_2NH_2$, $—(CH_2)_3NH_2$, $—(CH_2)_4NH_2$,

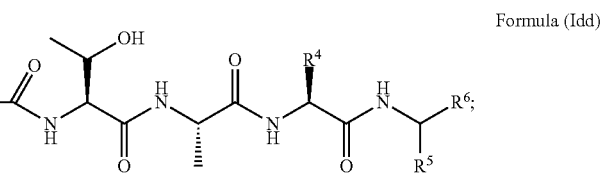

In a further embodiment of the aforementioned embodiments is a compound of Formula (I) or Formula (I') wherein n is 0. In yet a further embodiment, n is 1.

In a further embodiment is a compound of Formula (I') having the structure of Formula (Idd):

Formula (Idd)

wherein $R^5$ is —H, or —$CH_3$.

In another embodiment is a compound of Formula (Idd) wherein $R^{10}$ is —$CH_2OH$, and $R^{12}$ is —$CH_3$. In another embodiment is a compound of Formula (Idd) wherein $R^{10}$ is —$CH_2CH(CH_3)_2$, and $R^{12}$ is —$CH(OH)(CH_3)$. In another embodiment of the aforementioned compounds of Formula (Id) is a compound wherein $R^4$ is —$CH_2C(O)NH_2$. In yet another embodiment of the aforementioned compounds of Formula (Idd) is a compound wherein $R^4$ is

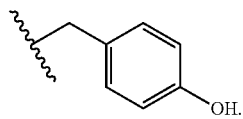 [SMILES: *Cc1ccc(O)cc1]

In another embodiment is a compound of Formula (I) or Formula (I') wherein $R^1$ is

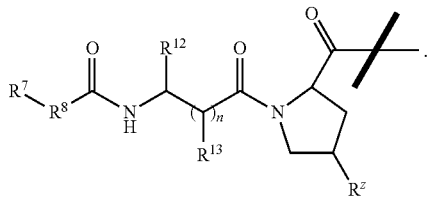

In a further embodiment, $R^8$ is a bond. In another embodiment, $R^2$, $R^4$, $R^{12}$, and $R^{13}$ are each independently —H, —$CH_3$, —$CH(CH_3)_2$, —$C(CH_3)_3$, —$CH(CH_3)(CH_2CH_3)$, —$CH_2CH(CH_3)_2$, —$CH_2OH$, —$CH(OH)(CH_3)$, —$CH_2CF_3$, —$CH_2C(O)OH$, —$CH_2CH_2C(O)OH$, —$CH_2C(O)NH_2$, —$CH_2CH_2C(O)NH_2$, —$CH_2NH_2$, —$(CH_2)_2NH_2$, —$(CH_2)_3NH_2$, —$(CH_2)_4NH_2$,

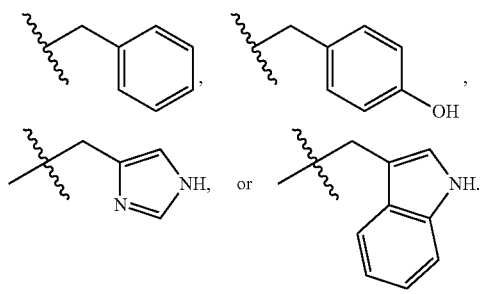

In a further embodiment, $R^2$, $R^4$, $R^{12}$, and $R^{13}$ are each independently —H, —$CH_3$, —$CH(CH_3)_2$, —$CH(CH_3)(CH_2CH_3)$, —$CH_2CH(CH_3)_2$, —$CH_2OH$, —$CH(OH)(CH_3)$, —$CH_2CH_2C(O)OH$, —$CH_2C(O)NH_2$, —$CH_2CH_2C(O)NH_2$, —$CH_2NH_2$, —$(CH_2)_2NH_2$, —$(CH_2)_3NH_2$, —$(CH_2)_4NH_2$,

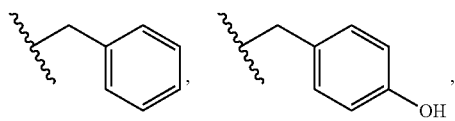

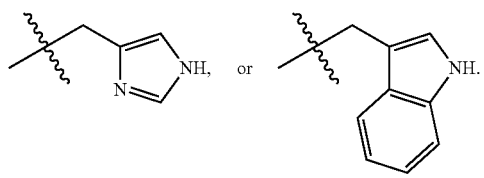

In yet a further embodiment, $R^2$, $R^4$, $R^{12}$, and $R^{13}$ are each independently —H, —$CH_3$, —$CH_2CH(CH_3)_2$, —$CH_2OH$, —$CH(OH)(CH_3)$, —$CH_2CH_2C(O)OH$, —$CH_2C(O)NH_2$, —$CH_2NH_2$, —$CH_2CH_2C(O)NH_2$, —$(CH_2)_2NH_2$, —$(CH_2)_3NH_2$, —$(CH_2)_4NH_2$,

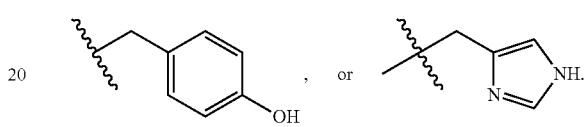

In a further embodiment of the aforementioned embodiments is a compound of Formula (I) or Formula (I') wherein n is 0. In yet a further embodiment, n is 1.

In another embodiment is a compound of Formula (I) or Formula (I') wherein $R^1$ is

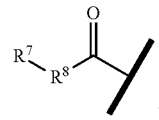

In a further embodiment, $R^8$ is a bond. In another embodiment, $R^2$ and $R^4$ are each independently —H, —$CH_3$, —$CH(CH_3)_2$, —$C(CH_3)_3$, —$CH(CH_3)(CH_2CH_3)$, —$CH_2CH(CH_3)_2$, —$CH_2OH$, —$CH(OH)(CH_3)$, —$CH_2CF_3$, —$CH_2C(O)OH$, —$CH_2CH_2C(O)OH$, —$CH_2C(O)NH_2$, —$CH_2CH_2C(O)NH_2$, —$(CH_2)_2NH_2$, —$(CH_2)_3NH_2$, —$(CH_2)_4NH_2$,

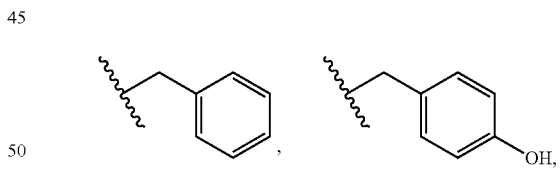

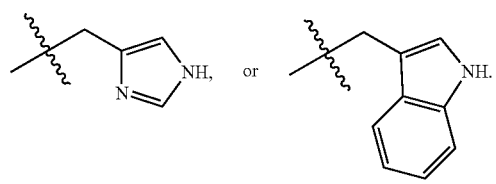

In a further embodiment, $R^2$ and $R^4$ are each independently —H, —$CH_3$, —$CH(CH_3)_2$, —$CH(CH_3)(CH_2CH_3)$, —$CH_2CH(CH_3)_2$, —$CH_2OH$, —$CH(OH)(CH_3)$, —$CH_2CH_2C(O)OH$, —$CH_2C(O)NH_2$, —$CH_2CH_2C(O)$ $NH_2$, —$(CH_2)_2NH_2$, —$(CH_2)_3NH_2$, —$(CH_2)_4NH_2$,

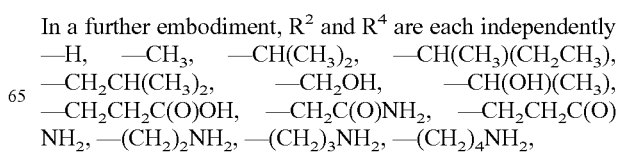

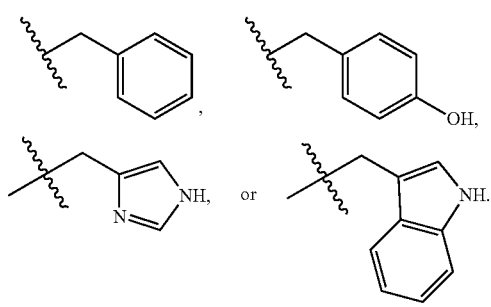

In yet a further embodiment, $R^2$ and $R^4$ are each independently —H, —CH$_3$, —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)$_4$NH$_2$,

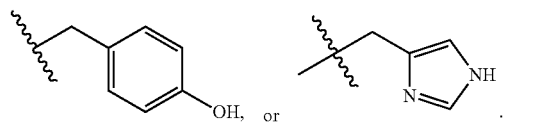 [SMILES: *Cc1ccc(O)cc1 ; *Cc1c[nH]cn1 ; "or"]

In another embodiment is a compound of Formula (I) or Formula (I') wherein $R^x$ and $R^2$ together with the nitrogen atom form an optionally substituted nitrogen containing ring. In a further embodiment is a compound of Formula (I') having the structure of Formula (Ie):

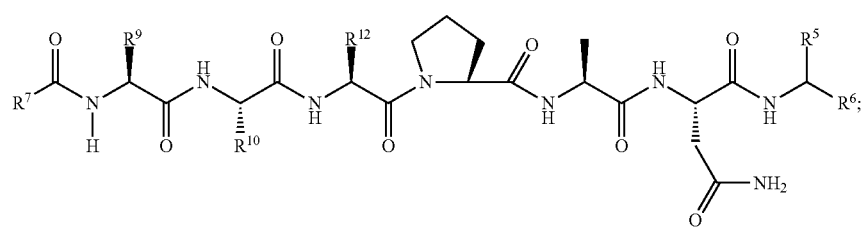

Formula (Ie)

wherein $R^5$ is —H, or —CH$_3$.

In another embodiment is a compound of Formula (Ie) wherein $R^{16}$ and $R^{12}$ are each independently —H, —CH$_3$, —CH$_2$CH(CH$_3$)$_2$, —CH$_2$OH, or —CH(OH)(CH$_3$).

In another embodiment of any of the aforementioned embodiments of Formula (I) or Formula (I') is a compound wherein $R^6$ is —C(=O)H.

In another aspect described herein are compounds of Formula (II):

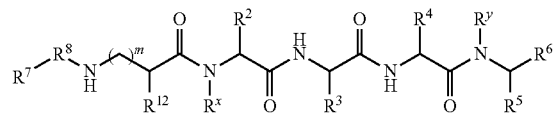

Formula (II)

wherein:
$R^2$, $R^4$, and $R^{12}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl,

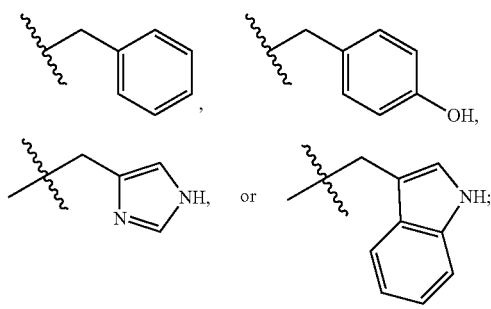

$R^3$ is methyl, ethyl, isopropyl, or cyclopropyl;
$R^5$ is H, methyl, ethyl, or —CH$_2$OH; or $R^5$ and $R^{24}$ together with the boron atom form a 5- or 6-membered boron containing ring;
$R^6$ is —CH$_2$C(=O)H, —C(=O)NHCH$_2$C(=O)H, —C(=O)C(=O)N(R$^{14}$)$_2$, —B(OR$^{23}$)(OR$^{24}$), or

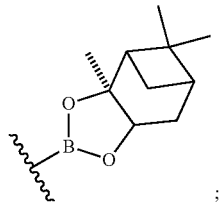 [SMILES: *B1OC2CC3CC(C3(C)C)[C@]2(C)O1]

$R^x$ is H, optionally substituted C$_1$-C$_6$alkyl, optionally substituted C$_1$-C$_6$heteroalkyl, or optionally substituted C$_3$-C$_8$cycloalkyl; or IV and $R^2$ together with the nitrogen atom form an optionally substituted nitrogen containing ring;
$R^y$ is H or methyl; or $R^y$ and $R^5$ together with the nitrogen atom form an optionally substituted nitrogen containing ring;
$R^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

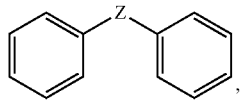, wherein Z is a bond, O, S, NH, $CH_2$, $NHCH_2$, or $C\equiv C$;

$R^8$ is bond, optionally substituted aryl, optionally substituted heteroaryl, or optionally substituted heterocycloalkyl;

$R^{14}$ is each independently H, or $C_1$-$C_4$alkyl;

each $R^{21}$ is independently H, or $C_1$-$C_4$alkyl;

each $R^{22}$ is independently H, $C_1$-$C_4$alkyl, —C(=NH)($NH_2$), or —CH(=NH);

$R^{23}$ and $R^{24}$ are each independently H, or $C_1$-$C_4$alkyl; or $R^{23}$ and $R^{24}$ together with the boron atom form an optionally substituted 5- or 6-membered boron containing ring; and m is 0-4;

or a pharmaceutically acceptable salt, solvate, or prodrug thereof.

In another embodiment is a compound of Formula (II) having the structure of Formula (II'):

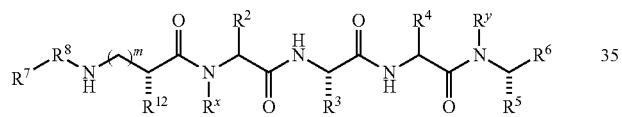

Formula (II')

wherein:

$R^2$, $R^4$, and $R^{12}$ are each independently —H, —$CH_3$, —CH($CH_3$)$_2$, —C($CH_3$)$_3$, —CH($CH_3$)($CH_2CH_3$), —$CH_2$CH($CH_3$)$_2$, —$CH_2$OH, —CH(OH)($CH_3$), —$CH_2CF_3$, —$CH_2$C(O)OH, —$CH_2CH_2$C(O)OH, —$CH_2$C(O)$NH_2$, —$CH_2CH_2$C(O)$NH_2$, —$CH_2$$NR^{21}R^{22}$, —($CH_2$)$_2$$NR^{21}R^{22}$, —($CH_2$)$_3$$NR^{21}R^{22}$, —($CH_2$)$_4$$NR^{21}R^{22}$, optionally substituted $C_1$-$C_8$alkyl, optionally substituted $C_1$-$C_8$heteroalkyl, optionally substituted $C_3$-$C_8$cycloalkyl, optionally substituted —$CH_2$—$C_3$-$C_8$cycloalkyl, optionally substituted heterocycloalkyl, optionally substituted aryl, optionally substituted heteroaryl,

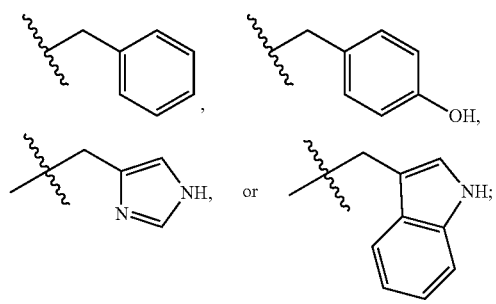

$R^3$ is methyl, ethyl, isopropyl, or cyclopropyl;

$R^5$ is H, methyl, ethyl, or —$CH_2$OH; or $R^5$ and $R^{24}$ together with the boron atom form a 5- or 6-membered boron containing ring;

$R^6$ is —$CH_2$C(=O)H, —C(=O)$NHCH_2$C(=O)H, —C(=O)C(=O)N($R^{14}$)$_2$, —B($OR^{23}$)($OR^{24}$), or

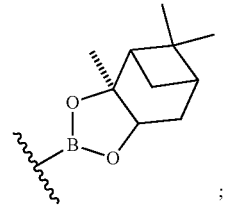 [SMILES: *B1OC2CC3CC(C3(C)C)[C@]2(C)O1];

$R^x$ is H, optionally substituted $C_1$-$C_6$alkyl, optionally substituted $C_1$-$C_6$heteroalkyl, or optionally substituted $C_3$-$C_8$cycloalkyl; or $R^x$ and $R^2$ together with the nitrogen atom form an optionally substituted nitrogen containing ring;

$R^y$ is H or methyl; or $R^y$ and $R^5$ together with the nitrogen atom form an optionally substituted nitrogen containing ring;

$R^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

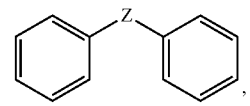, wherein Z is a bond, O, S, NH, $CH_2$, $NHCH_2$, or $C\equiv C$;

$R^8$ is bond, optionally substituted aryl, optionally substituted heteroaryl, or optionally substituted heterocycloalkyl;

$R^{14}$ is each independently H, or $C_1$-$C_4$alkyl;

each $R^{21}$ is independently H, or $C_1$-$C_4$alkyl;

each $R^{22}$ is independently H, $C_1$-$C_4$alkyl, —C(=NH)($NH_2$), or —CH(=NH);

$R^{23}$ and $R^{24}$ are each independently H, or $C_1$-$C_4$alkyl; or $R^{23}$ and $R^{24}$ together with the boron atom form an optionally substituted 5- or 6-membered boron containing ring; and m is 0-4;

or a pharmaceutically acceptable salt, solvate, or prodrug thereof.

In a further embodiment is a compound of Formula (II) or Formula (II') wherein $R^8$ is a bond. In another embodiment of Formula (II) or Formula (II'), $R^2$ and $R^4$ are each independently —H, —$CH_3$, —CH($CH_3$)$_2$, —C($CH_3$)$_3$, —CH($CH_3$)($CH_2CH_3$), —$CH_2$CH($CH_3$)$_2$, —$CH_2$OH, —CH(OH)($CH_3$), —$CH_2CF_3$, —$CH_2$C(O)OH, —$CH_2CH_2$C(O)OH, —$CH_2$C(O)$NH_2$, —$CH_2CH_2$C(O)$NH_2$, —($CH_2$)$_2$$NH_2$, —($CH_2$)$_3$$NH_2$, —($CH_2$)$_4$$NH_2$,

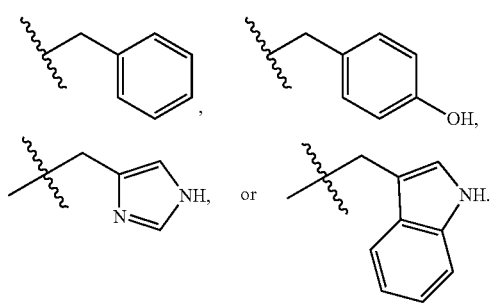

In a further embodiment, $R^2$ and $R^4$ are each independently —H, —CH$_3$, —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)$_4$NH$_2$,

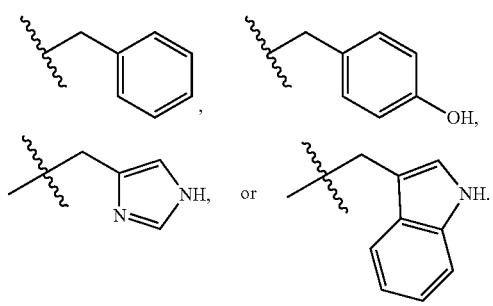

In yet a further embodiment, $R^2$ and $R^4$ are each independently —H, —CH$_3$, —CH$_2$CH(CH$_3$)$_2$, —CH$_2$OH, —CH(OH)(CH$_3$), —CH$_2$CH$_2$C(O)OH, —CH$_2$C(O)NH$_2$, —CH$_2$CH$_2$C(O)NH$_2$, —(CH$_2$)$_2$NH$_2$, —(CH$_2$)$_3$NH$_2$, —(CH$_2$)$_4$NH$_2$,

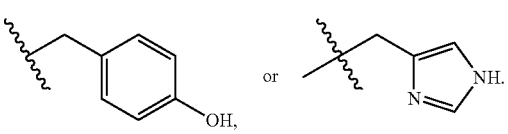 [SMILES: *Cc1ccc(O)cc1 ; "or" ; *Cc1c[nH]cn1]

In another aspect described herein are compounds of Formula (III):

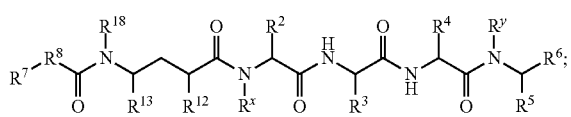

Formula (III)

wherein:
$R^2$ and $R^4$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl,

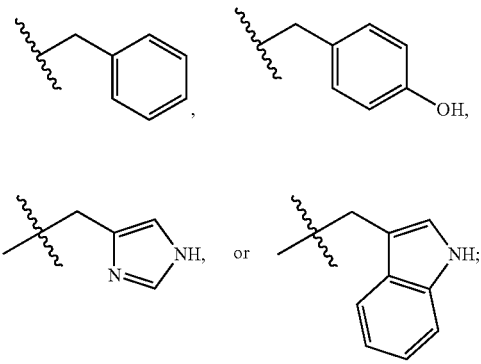

$R^{12}$ and $R^{13}$ are each independently —H, —NR$^{21}$R$^{22}$, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, optionally substituted C$_1$-C$_8$alkyl, or optionally substituted C$_1$-C$_8$heteroalkyl; or $R^{12}$ and $R^{13}$ together with the carbon atoms to which they are attached form a heterocycloalkyl ring;

$R^3$ is methyl, ethyl, isopropyl, or cyclopropyl;

$R^5$ is H, methyl, ethyl, or —CH$_2$OH; or $R^5$ and $R^{24}$ together with the boron atom form a 5- or 6-membered boron containing ring;

$R^6$ is —CH$_2$C(=O)H, —C(=O)NHCH$_2$C(=O)H, —C(=O)C(=O)N(R$^{14}$)$_2$, —B(OR$^{23}$)(OR$^{24}$), or

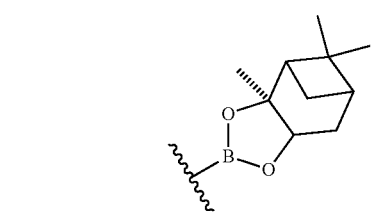

;

$R^x$ is H, optionally substituted C$_1$-C$_6$alkyl, optionally substituted C$_1$-C$_6$heteroalkyl, or optionally substituted C$_3$-C$_8$cycloalkyl; or $R^x$ and $R^2$ together with the nitrogen atom form an optionally substituted nitrogen containing ring;

$R^y$ is H or methyl; or $R^y$ and $R^5$ together with the nitrogen atom form an optionally substituted nitrogen containing ring;

$R^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

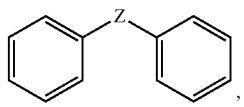, wherein Z is a bond, O, S, NH, CH$_2$, NHCH$_2$, or C≡C;
R$^8$ is bond, optionally substituted aryl, optionally substituted heteroaryl, or optionally substituted heterocycloalkyl;
R$^{14}$ is each independently H, or C$_1$-C$_4$alkyl;
R$^{18}$ is H, or methyl; or R$^{18}$ and R$^{12}$ together with the atoms to which they are attached form a heterocycloalkyl ring;
each R$^{21}$ is independently H, or C$_1$-C$_4$alkyl;
each R$^{22}$ is independently H, C$_1$-C$_4$alkyl, —C(=NH)(NH$_2$), or —CH(=NH);
R$^{23}$ and R$^{24}$ are each independently H, or C$_1$-C$_4$alkyl; or R$^{23}$ and R$^{24}$ together with the boron atom form an optionally substituted 5- or 6-membered boron containing ring; and
m is 0-4;
or a pharmaceutically acceptable salt, solvate, or prodrug thereof.

In another embodiment is a compound of Formula (III) having the structure of Formula (III'):

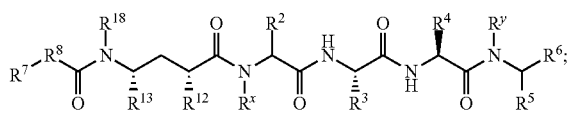

Formula (III')

wherein:
R$^2$ and R$^4$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl,

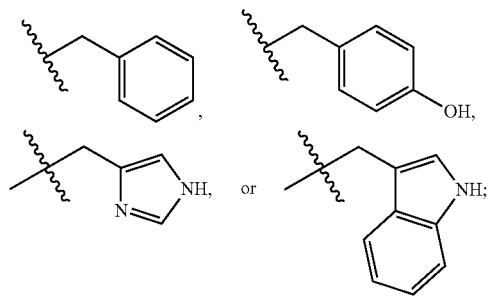

R$^{12}$ and R$^{13}$ are each independently —H, —NR$^{21}$R$^{22}$, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, optionally substituted C$_1$-C$_8$alkyl, or optionally substituted C$_1$-C$_8$heteroalkyl; or R$^{12}$ and R$^{13}$ together with the carbon atoms to which they are attached form a heterocycloalkyl ring;
R$^3$ is methyl, ethyl, isopropyl, or cyclopropyl;
R$^5$ is H, methyl, ethyl, or —CH$_2$OH; or R$^5$ and R$^{24}$ together with the boron atom form a 5- or 6-membered boron containing ring;
R$^6$ is —CH$_2$C(=O)H, —C(=O)NHCH$_2$C(=O)H, —C(=O)C(=O)N(R$^{14}$)$_2$, —B(OR$^{23}$)(OR$^{24}$), or

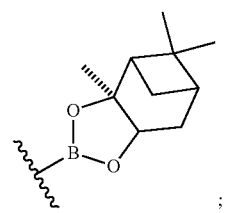 [SMILES: *B1OC2CC3CC(C3(C)C)[C@]2(C)O1]

;

R$^x$ is H, optionally substituted C$_1$-C$_6$alkyl, optionally substituted C$_1$-C$_6$heteroalkyl, or optionally substituted C$_3$-C$_8$cycloalkyl; or R$^x$ and R$^2$ together with the nitrogen atom form an optionally substituted nitrogen containing ring;
R$^y$ is H or methyl; or R$^y$ and R$^5$ together with the nitrogen atom form an optionally substituted nitrogen containing ring;
R$^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

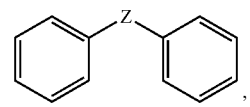, wherein Z is a bond, O, S, NH, CH$_2$, NHCH$_2$, or C≡C;
R$^8$ is bond, optionally substituted aryl, optionally substituted heteroaryl, or optionally substituted heterocycloalkyl;
R$^{14}$ is each independently H, or C$_1$-C$_4$alkyl;
R$^{18}$ is H, or methyl; or R$^{18}$ and R$^{12}$ together with the atoms to which they are attached form a heterocycloalkyl ring;
each R$^{21}$ is independently H, or C$_1$-C$_4$alkyl;
each R$^{22}$ is independently H, C$_1$-C$_4$alkyl, —C(=NH)(NH$_2$), or —CH(=NH);
R$^{23}$ and R$^{24}$ are each independently H, or C$_1$-C$_4$alkyl; or R$^{23}$ and R$^{24}$ together with the boron atom form an optionally substituted 5- or 6-membered boron containing ring; and
m is 0-4;
or a pharmaceutically acceptable salt, solvate, or prodrug thereof.

In some embodiments is a compound of Formula (III) or Formula (III') wherein R$^8$ is a bond. In a further embodiment is a compound of Formula (III) or Formula (III') wherein R$^2$ and R$^4$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, or —(CH$_2$)$_4$NR$^{21}$R$^{22}$. In yet a further embodiment is a compound of Formula (III) or Formula (III') wherein R$^2$ and R$^4$ are each independently —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$C(O)OH, —CH$_2$CH$_2$C(O)OH, —CH$_2$C(O)NH$_2$, —CH$_2$CH$_2$C(O)NH$_2$, —CH$_2$NR$^{21}$R$^{22}$, (CH$_2$)$_2$NR$^{21}$R$^{22}$, —(CH$_2$)$_3$NR$^{21}$R$^{22}$, or —(CH$_2$)$_4$NR$^{21}$R$^{22}$.

In another embodiment is a compound of Formula (III) or Formula (III') wherein R$^{12}$ and R$^{13}$ together with the carbon atoms to which they are attached form a heterocycloalkyl ring. In a further embodiment is a compound of Formula (III) or Formula (III') wherein R$^{12}$ and R$^{13}$ together with the carbon atoms to which they are attached form a pyrrolidine ring. In yet a further embodiment is a compound of Formula (III) or Formula (III') wherein R$^2$ and R$^4$ are each independently —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, or —(CH$_2$)$_4$NR$^{21}$R$^{22}$.

In another embodiment is a compound of Formula (III) or Formula (III') wherein R$^{18}$ and R$^{12}$ together with the atoms to which they are attached form a heterocycloalkyl ring. In a further embodiment is a compound of Formula (III) or Formula (III') wherein R$^{18}$ and R$^{12}$ together with the atoms to which they are attached form a piperidine ring In yet a further embodiment is a compound of Formula (III) or Formula (III') wherein R$^{13}$ is H and R$^2$ and R$^4$ are each independently —CH(CH$_3$)$_2$, —CH(CH$_3$)(CH$_2$CH$_3$), —CH$_2$CH(CH$_3$)$_2$, —CH$_2$OH, —CH(OH)(CH$_3$), —CH$_2$C(O)NH$_2$, —CH$_2$CH$_2$C(O)NH$_2$, —CH$_2$NR$^{21}$R$^{22}$, —(CH$_2$)$_2$NR$^{21}$R$^{22}$, —(CH$_2$)$_3$NR$^{21}$R$^{22}$, or (CH$_2$)$_4$NR$^{21}$R$^{22}$.

In another embodiment of the aforementioned embodiments of Formula (I), (II), or (III) is a compound wherein R$^7$ is a linear or branched alkyl chain of about 1-22 carbon atoms. In another embodiment of the aforementioned embodiments of Formula (I), (II), or (III) is a compound wherein R$^7$ is

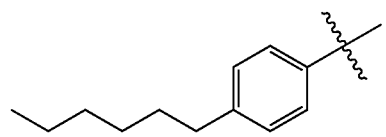

In another embodiment of the aforementioned embodiments of Formula (I), (II), or (III) is a compound wherein R$^7$ is

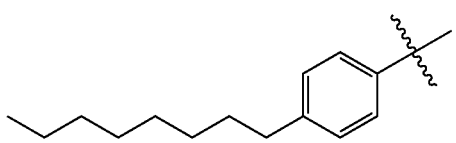

In another embodiment of the aforementioned embodiments of Formula (I), (II), or (III) is a compound wherein R$^7$ is

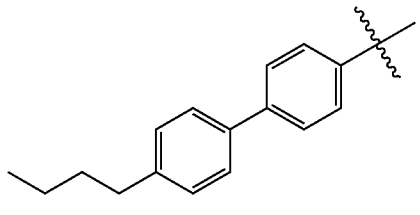

In another embodiment of the aforementioned embodiments of Formula (I), (II), or (III) is a compound wherein R$^5$ is H. In another embodiment of the aforementioned embodiments of Formula (I), (II), or (III) is a compound wherein R$^5$ is methyl. In another embodiment of the aforementioned embodiments of Formula (I), (II), or (III) is a compound wherein R$^5$ is —CH$_2$OH. In another embodiment of the aforementioned embodiments of Formula (I), (II), or (III) is a compound wherein R$^6$ is —B(OH)$_2$. In another embodiment of the aforementioned embodiments of Formula (I), (II), or (III) is a compound wherein R$^6$ is —B(OR$^{23}$)(OR$^{24}$) wherein R$^{23}$ and R$^{24}$ together with the boron atom form an optionally substituted 5- or 6-membered boron containing ring. In another embodiment of the aforementioned embodiments of Formula (I), (II), or (III) is a compound wherein R$^6$ is

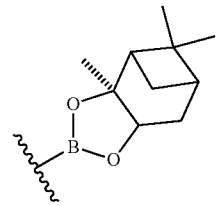

In another embodiment of the aforementioned embodiments of Formula (I) is a compound wherein R$^5$ is methyl, R$^6$ is

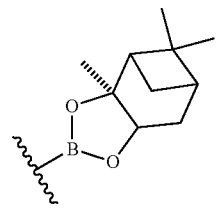

,

R$^8$ is a bond, and R$^7$ is

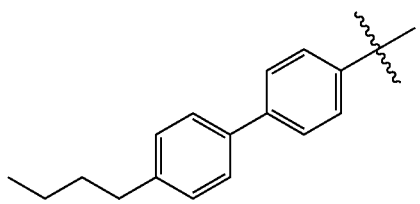

In another embodiment of the aforementioned embodiments of Formula (I) is a compound wherein R$^5$ is methyl, R$^6$ is —B(OH)$_2$, R$^8$ is a bond, and R$^7$ is

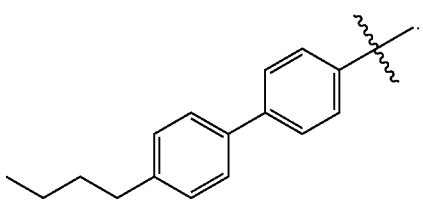 [SMILES: *c1ccc(-c2ccc(CCCC)cc2)cc1]

In another embodiment of the aforementioned embodiments of Formula (I) is a compound wherein $R^5$ is methyl, $R^6$ is

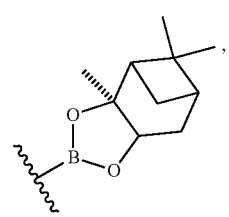 [SMILES: *B1OC2CC3CC(C3(C)C)[C@]2(C)O1]

$R^8$ is a bond, and $R^7$ is

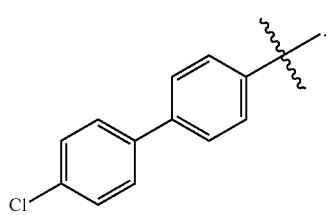 [SMILES: *c1ccc(-c2ccc(Cl)cc2)cc1]

In another embodiment of the aforementioned embodiments of Formula (I) is a compound wherein $R^5$ is methyl, $R^6$ is —B(OH)$_2$, $R^8$ is a bond, and $R^7$ is

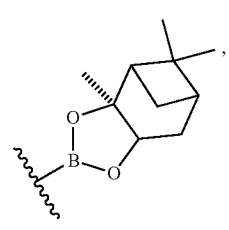 [SMILES: *B1OC2CC3CC(C3(C)C)[C@]2(C)O1]

$R^8$ is a bond, and $R^7$ is

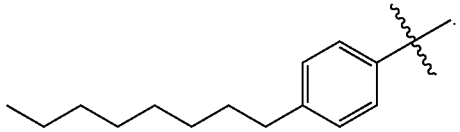 [SMILES: *c1ccc(CCCCCCCC)cc1]

In another embodiment of the aforementioned embodiments of Formula (I) is a compound wherein $R^5$ is methyl, $R^6$ is —B(OH)$_2$, $R^8$ is a bond, and $R^7$ is

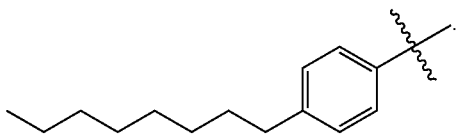 [SMILES: *c1ccc(CCCCCCCC)cc1]

In another embodiment of the aforementioned embodiments of Formula (I) is a compound wherein $R^5$ is methyl, $R^6$ is

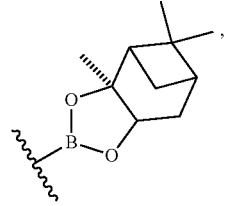 [SMILES: *B1OC2CC3CC(C3(C)C)[C@]2(C)O1]

$R^8$ is heteroaryl, and $R^7$ is

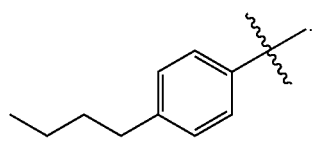 [SMILES: *c1ccc(CCCC)cc1]

In another embodiment of the aforementioned embodiments of Formula (I) is a compound wherein $R^5$ is methyl, $R^6$ is —B(OH)$_2$, $R^8$ is heteroaryl, and $R^7$ is

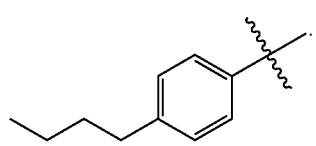 [SMILES: *c1ccc(CCCC)cc1]

In another embodiment of the aforementioned embodiments of Formula (I'), (II'), or (III') is a compound wherein $R^7$ is a linear or branched alkyl chain of about 1-22 carbon atoms. In another embodiment of the aforementioned embodiments of Formula (I'), (II'), or (III') is a compound wherein $R^7$ is

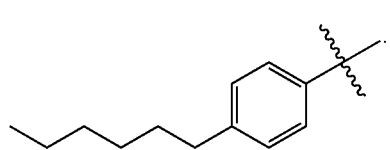 [SMILES: *c1ccc(CCCCCC)cc1]

In another embodiment of the aforementioned embodiments of Formula (I'), (II'), or (III') is a compound wherein R⁷ is

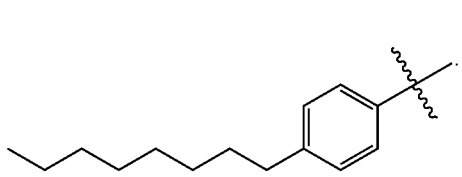 [SMILES: *c1ccc(CCCCCCCC)cc1]

In another embodiment of the aforementioned embodiments of Formula (I'), (II'), or (III') is a compound wherein R⁷ is

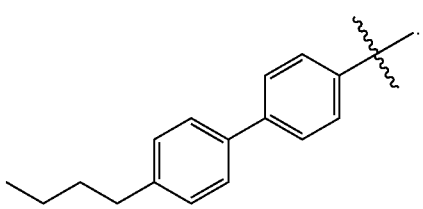 [SMILES: *c1ccc(-c2ccc(CCCC)cc2)cc1]

In another embodiment of the aforementioned embodiments of Formula (I'), (II'), or (III') is a compound wherein R⁵ is H. In another embodiment of the aforementioned embodiments of Formula (I'), (II'), or (III') is a compound wherein R⁵ is methyl. In another embodiment of the aforementioned embodiments of Formula (I'), (II'), or (III') is a compound wherein R⁵ is —CH₂OH. In another embodiment of the aforementioned embodiments of Formula (I'), (II'), or (III') is a compound wherein R⁶ is —B(OH)₂. In another embodiment of the aforementioned embodiments of Formula (I'), (II'), or (III') is a compound wherein R⁶ is —B(OR²³)(OR²⁴) wherein R²³ and R²⁴ together with the boron atom form an optionally substituted 5- or 6-membered boron containing ring. In another embodiment of the aforementioned embodiments of Formula (I'), (II'), or (III') is a compound wherein R⁶ is

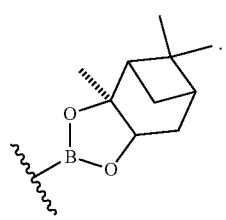 [SMILES: *B1OC2CC3CC(C3(C)C)[C@]2(C)O1]

In another embodiment of the aforementioned embodiments of Formula (I') is a compound wherein R⁵ is methyl, R⁶ is

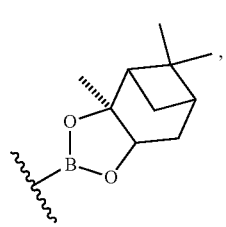 [SMILES: *B1OC2CC3CC(C3(C)C)[C@]2(C)O1]

R⁸ is a bond, and R⁷ is

In another embodiment of the aforementioned embodiments of Formula (I') is a compound wherein R⁵ is methyl, R⁶ is

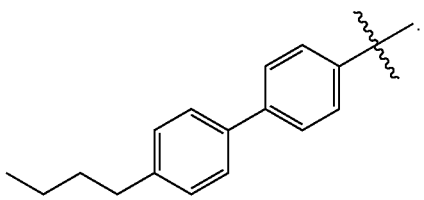

In another embodiment of the aforementioned embodiments of Formula (I') is a compound wherein R⁵ is methyl, R⁶ is —B(OH)₂, R⁸ is a bond, and R⁷ is

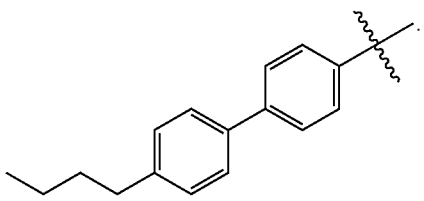 [SMILES: *c1ccc(-c2ccc(CCCC)cc2)cc1]

In another embodiment of the aforementioned embodiments of Formula (I') is a compound wherein R⁵ is methyl, R⁶ is

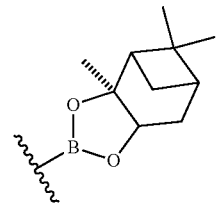

R⁸ is a bond, and R⁷ is

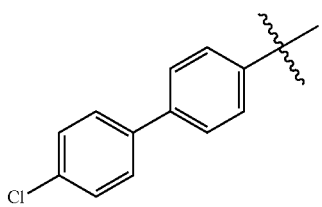

In another embodiment of the aforementioned embodiments of Formula (I') is a compound wherein R⁵ is methyl, R⁶ is —B(OH)₂, R⁸ is a bond, and R⁷ is

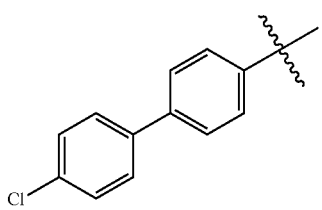

In another embodiment of the aforementioned embodiments of Formula (I') is a compound wherein R⁵ is methyl, R⁶ is

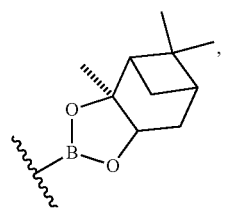 [SMILES: *B1OC2CC3CC(C3(C)C)[C@]2(C)O1]

R[8] is a bond, and R[7] is

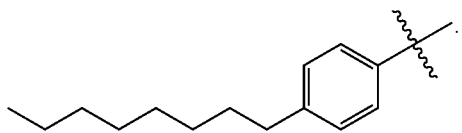 [SMILES: *c1ccc(CCCCCCCC)cc1]

In another embodiment of the aforementioned embodiments of Formula (I') is a compound wherein R[5] is methyl, R[6] is —B(OH)$_2$, R[8] is a bond, and R[7] is

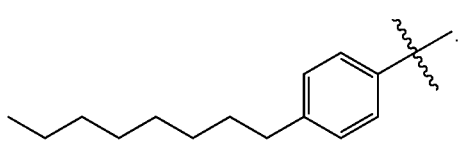 [SMILES: *c1ccc(CCCCCCCC)cc1]

In another embodiment of the aforementioned embodiments of Formula (I') is a compound wherein R[5] is methyl, R[6] is

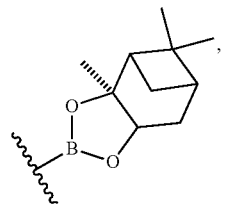 [SMILES: *B1OC2CC3CC(C3(C)C)[C@]2(C)O1]

R[8] is heteroaryl, and R[7] is

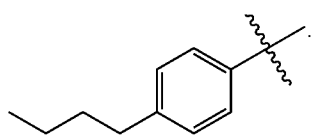 [SMILES: *c1ccc(CCCC)cc1]

In another embodiment of the aforementioned embodiments of Formula (I') is a compound wherein R[5] is methyl, R[6] is —B(OH)$_2$, R[8] is heteroaryl, and R[7] is

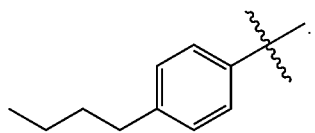 [SMILES: *c1ccc(CCCC)cc1]

In another aspect described herein are compounds of Formula (IV):

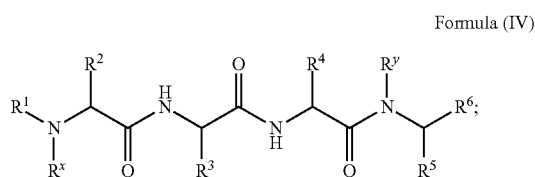

wherein:

R[1] is selected from:

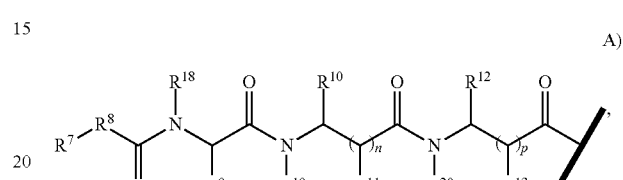

A)

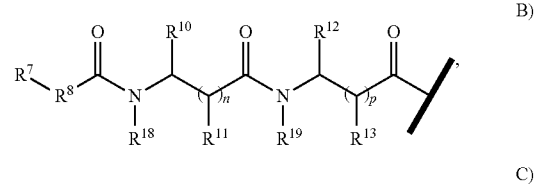

B)

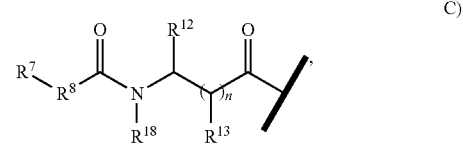

C)

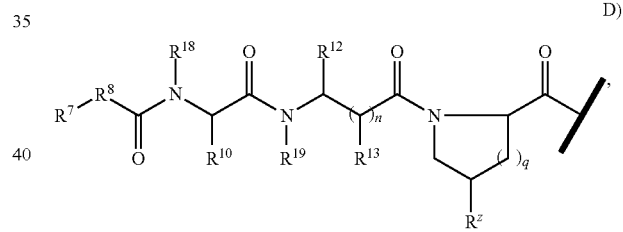

D)

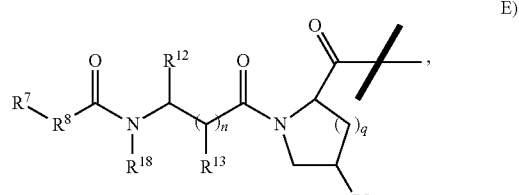

E)

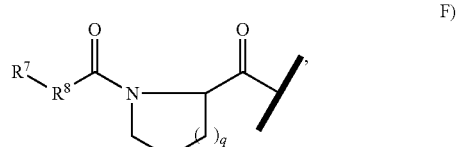

F)

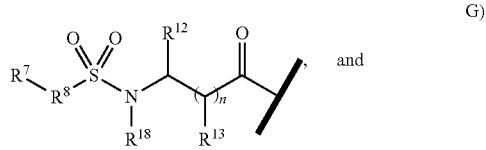

G)

and

-continued

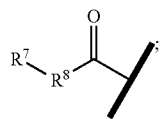
H)

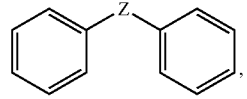

wherein Z is a bond, O, S, NH, CH$_2$, NHCH$_2$, or C≡C;

R$^8$ is a bond, —O—, or —N(R$^{17}$)—, optionally substituted aryl, or optionally substituted heteroaryl;

R$^9$ is —CH$_2$OH, —CH$_2$CH(CH$_3$)$_2$,

R$^2$, R$^4$, R$^{10}$, R$^{11}$, R$^{12}$, and R$^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$C(O)OR$^{25}$, —CH$_2$CH$_2$C(O)OH, —CH$_2$CH$_2$C(O)OR$^{25}$, —CH$_2$C(O)NH$_2$, —CH$_2$CH$_2$C(O)NH$_2$, —CH$_2$CH$_2$C(O)N(H)C(H)(CH$_3$)CO$_2$H, —CH$_2$CH$_2$C(O)N(H)C(H)(CO$_2$H)CH$_2$CO$_2$H, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, —(CH$_2$)$_4$N(R$^{25}$)$_3$, —(CH$_2$)$_4$N(H)C(O)(2,3-dihydroxybenzene), optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl,

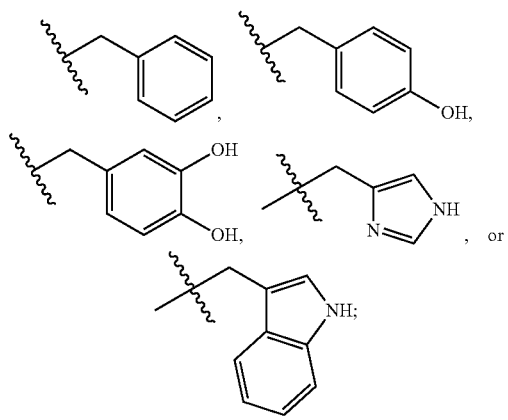

R$^3$ is methyl, ethyl, isopropyl, or cyclopropyl;

R$^5$ is H, methyl, ethyl, or —CH$_2$OH;

R$^6$ is —C(═O)OH;

R$^x$ is H, optionally substituted C$_1$-C$_6$alkyl, optionally substituted C$_1$-C$_6$heteroalkyl, or optionally substituted C$_3$-C$_8$cycloalkyl; or R$^x$ and R$^2$ together with the nitrogen atom form an optionally substituted nitrogen containing ring;

R$^y$ is H or methyl; or R$^y$ and R$^5$ together with the nitrogen atom form an optionally substituted nitrogen containing ring;

R$^z$ is —NR$^{15}$R$^{16}$, —CH$_2$—NR$^{15}$R$^{16}$, or —(CH$_2$)$_2$—NR$^{15}$R$^{16}$;

R$^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted R$^{15}$ and R$^{16}$ are each independently H, or C$_1$-C$_4$alkyl;

R$^{17}$ is H, methyl, ethyl, isopropyl, or cyclopropyl;

R$^{18}$, R$^{19}$, and R$^{20}$ are each independently H, or methyl;

each R$^{21}$ is independently H, or C$_1$-C$_4$alkyl;

each R$^{22}$ is independently H, C$_1$-C$_4$alkyl, —C(═NH)(NH$_2$), or —CH(═NH);

each R$^{25}$ is independently C$_1$-C$_6$alkyl;

n is 0 or 1;

p is 0 or 1; and q is 0 or 1;

or a pharmaceutically acceptable salt, solvate, or prodrug thereof.

In another embodiment is a compound of Formula (IV) having the structure of Formula (IV'):

Formula (IV')

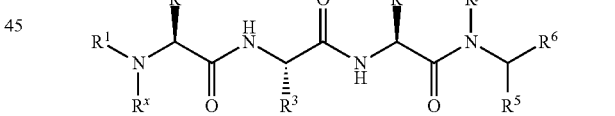

wherein:

R$^1$ is selected from:

A)

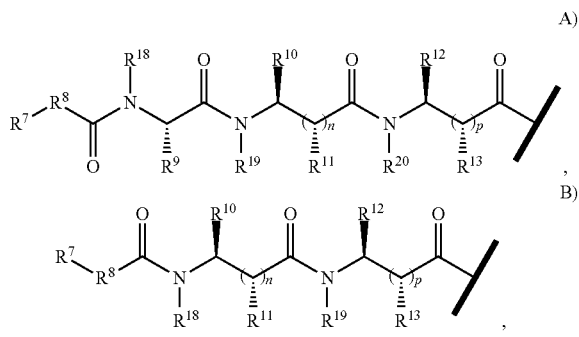

B)

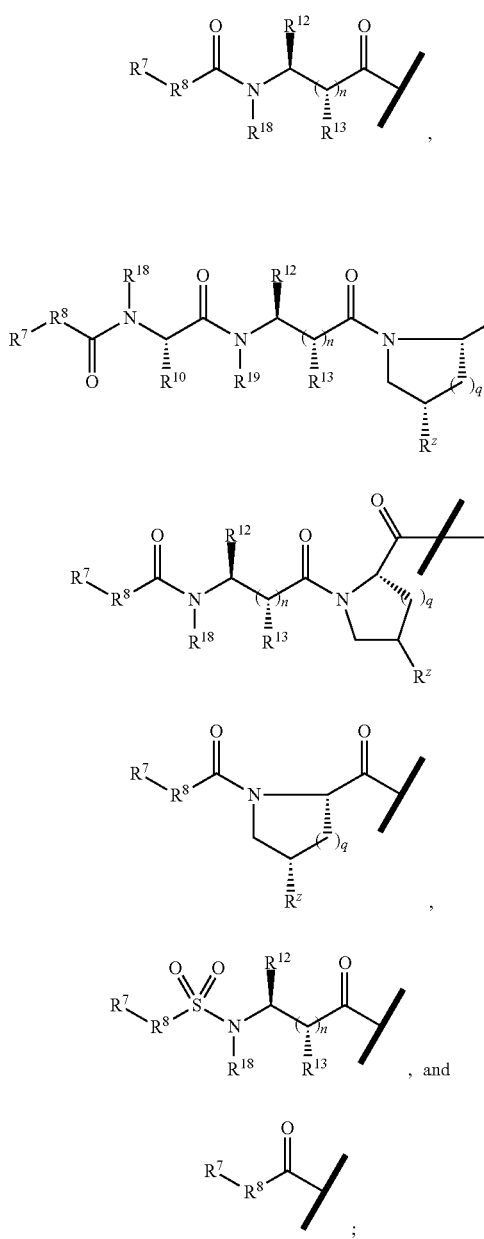

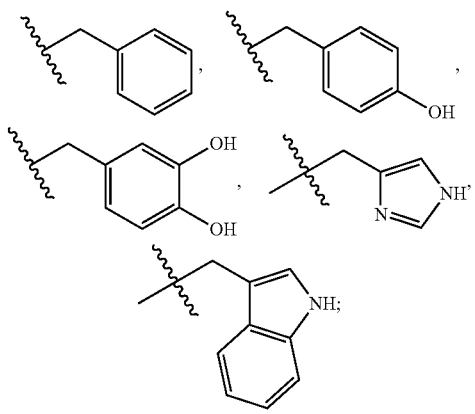

$R^3$ is methyl, ethyl, isopropyl, or cyclopropyl;
$R^5$ is H, methyl, ethyl, or —CH$_2$OH;
$R^6$ is —C(=O)OH;
$R^x$ is H, optionally substituted C$_1$-C$_6$alkyl, optionally substituted C$_1$-C$_6$heteroalkyl, or optionally substituted C$_3$-C$_8$cycloalkyl; or R$^x$ and R$^2$ together with the nitrogen atom form an optionally substituted nitrogen containing ring;
$R^y$ is H or methyl; or R$^y$ and R$^5$ together with the nitrogen atom form an optionally substituted nitrogen containing ring;
$R^z$ is —NR$^{15}$R$^{16}$, —CH$_2$—NR$^{15}$R$^{16}$, or —(CH$_2$)$_2$—NR$^{15}$R$^{16}$;
$R^7$ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

[structure: phenyl-Z-phenyl], wherein Z is a bond, O, S, NH, CH$_2$, NHCH$_2$, or C≡C;
$R^8$ is a bond, —O—, or —N(R$^{17}$)—, optionally substituted aryl, or optionally substituted heteroaryl;
$R^9$ is —CH$_2$OH, —CH$_2$CH(CH$_3$)$_2$,

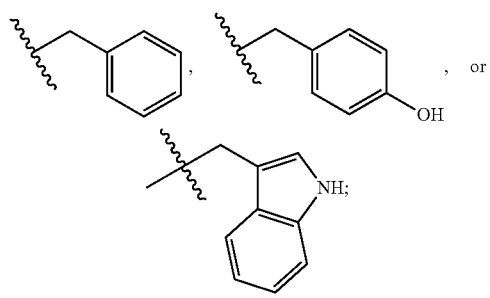

$R^{15}$ and $R^{16}$ are each independently H, or C$_1$-C$_4$alkyl;
$R^{17}$ is H, methyl, ethyl, isopropyl, or cyclopropyl;

R$^2$, R$^4$, R$^{10}$, R$^{11}$, R$^{12}$, and R$^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$C(O)OR$^{25}$, —CH$_2$CH$_2$C(O)OH, —CH$_2$CH$_2$C(O)OR$^{25}$, —CH$_2$C(O)NH$_2$, —CH$_2$CH$_2$C(O)NH$_2$, —CH$_2$CH$_2$C(O)N(H)C(H)(CH$_3$)CO$_2$H, —CH$_2$CH$_2$C(O)N(H)C(H)(CO$_2$H)CH$_2$CO$_2$H, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, —(CH$_2$)$_4$N(R$^{25}$)$_3$, —(CH$_2$)$_4$N(H)C(O)(2,3-dihydroxybenzene), optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl, $R^{18}$, $R^{19}$, and $R^{20}$ are each independently H, or methyl;
each $R^{21}$ is independently H, or $C_1$-$C_4$alkyl;
each $R^{22}$ is independently H, $C_1$-$C_4$alkyl, —C(═NH)(NH$_2$), or —CH(═NH);
each $R^{25}$ is independently $C_1$-$C_6$alkyl;
n is 0 or 1;
p is 0 or 1; and
q is 0 or 1;
or a pharmaceutically acceptable salt, solvate, or prodrug thereof.
In another aspect is a compound selected from:
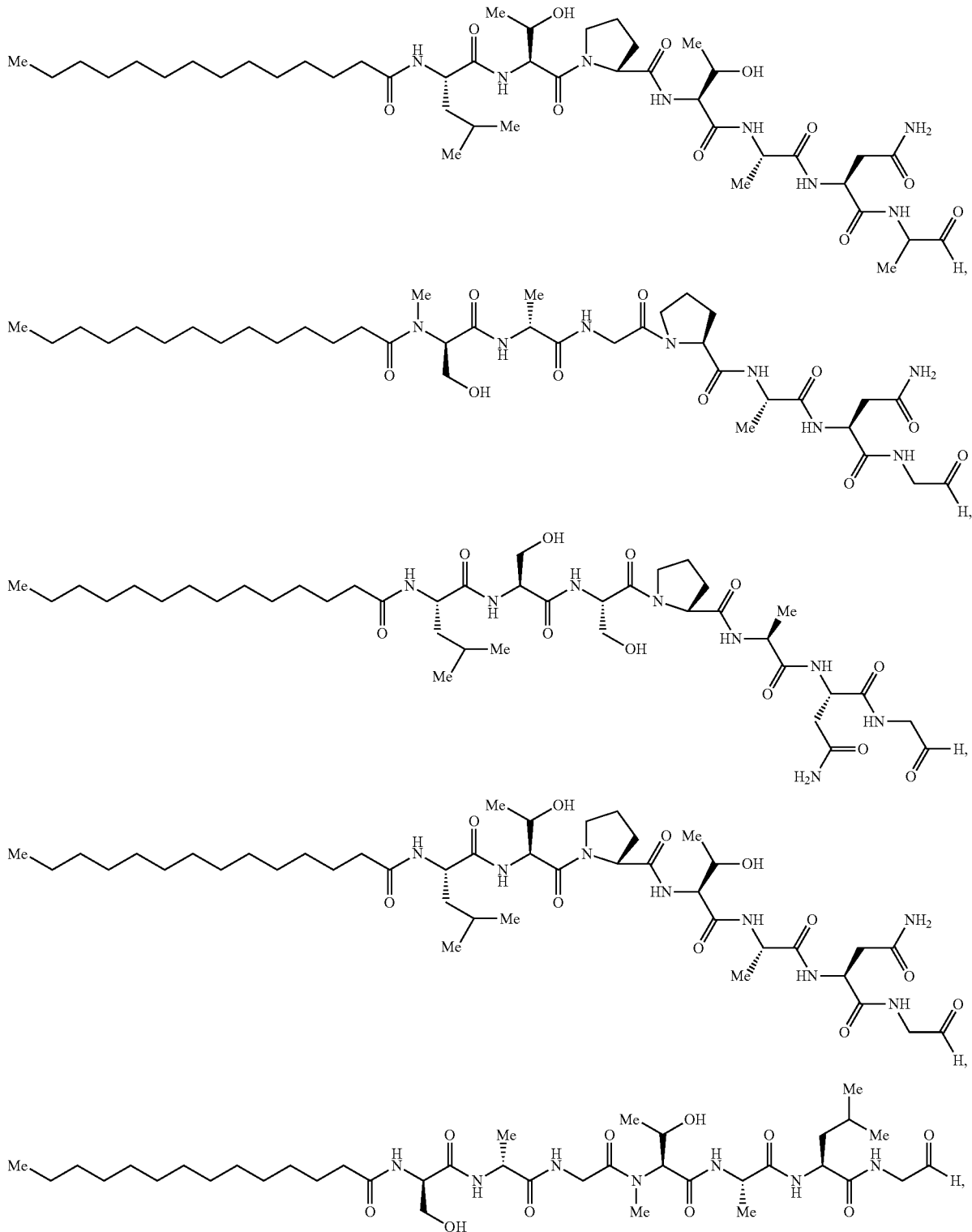

-continued
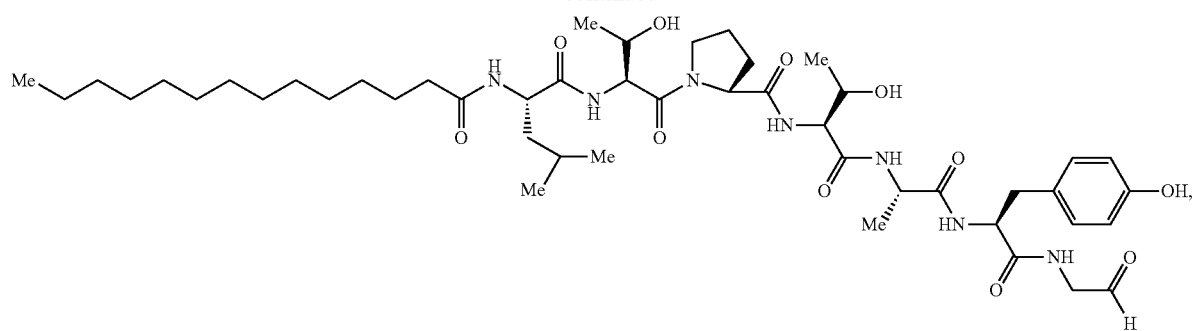
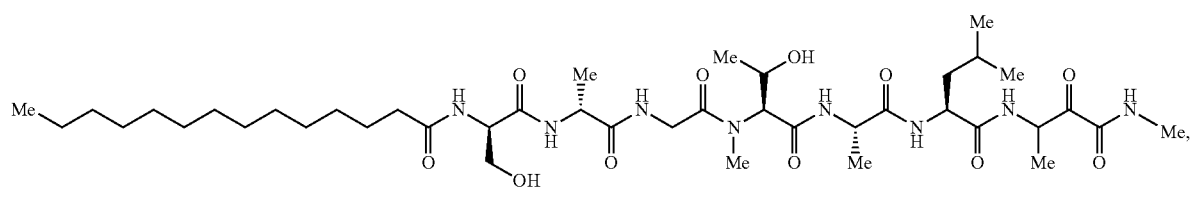
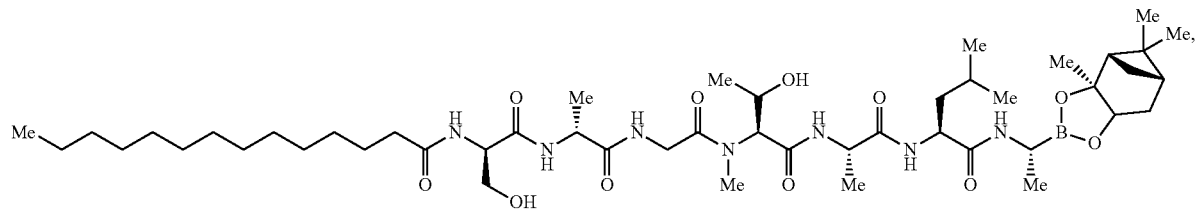
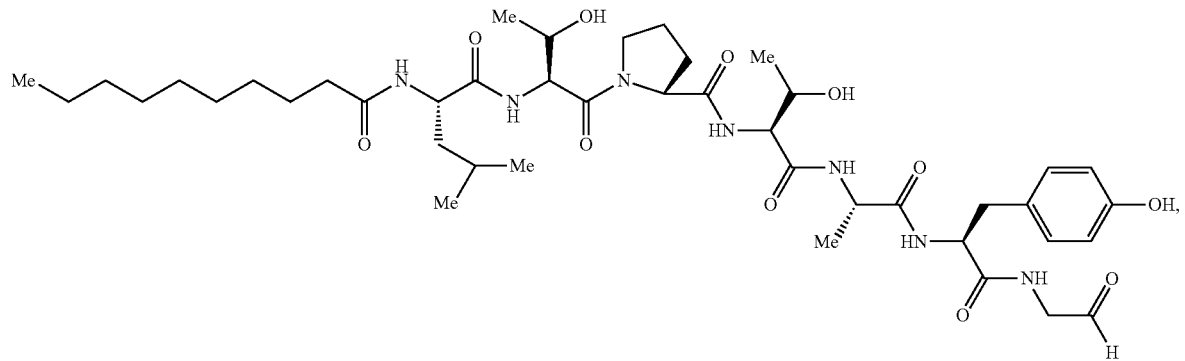
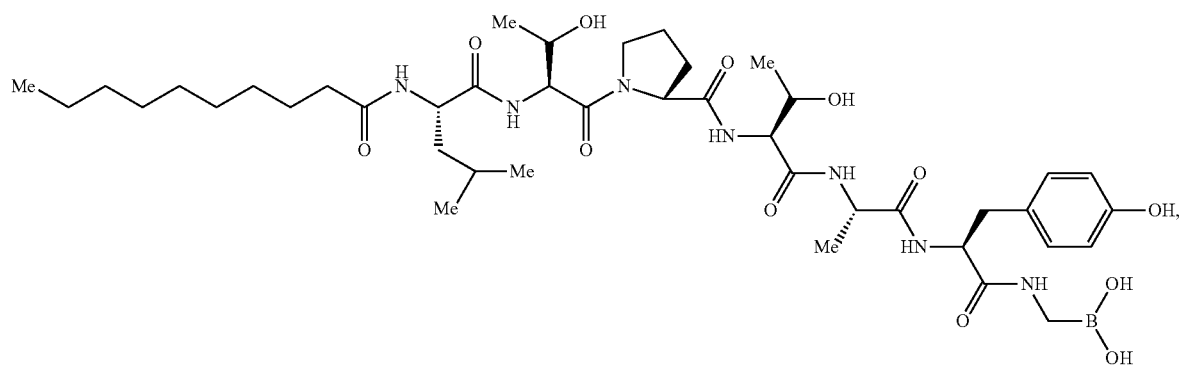

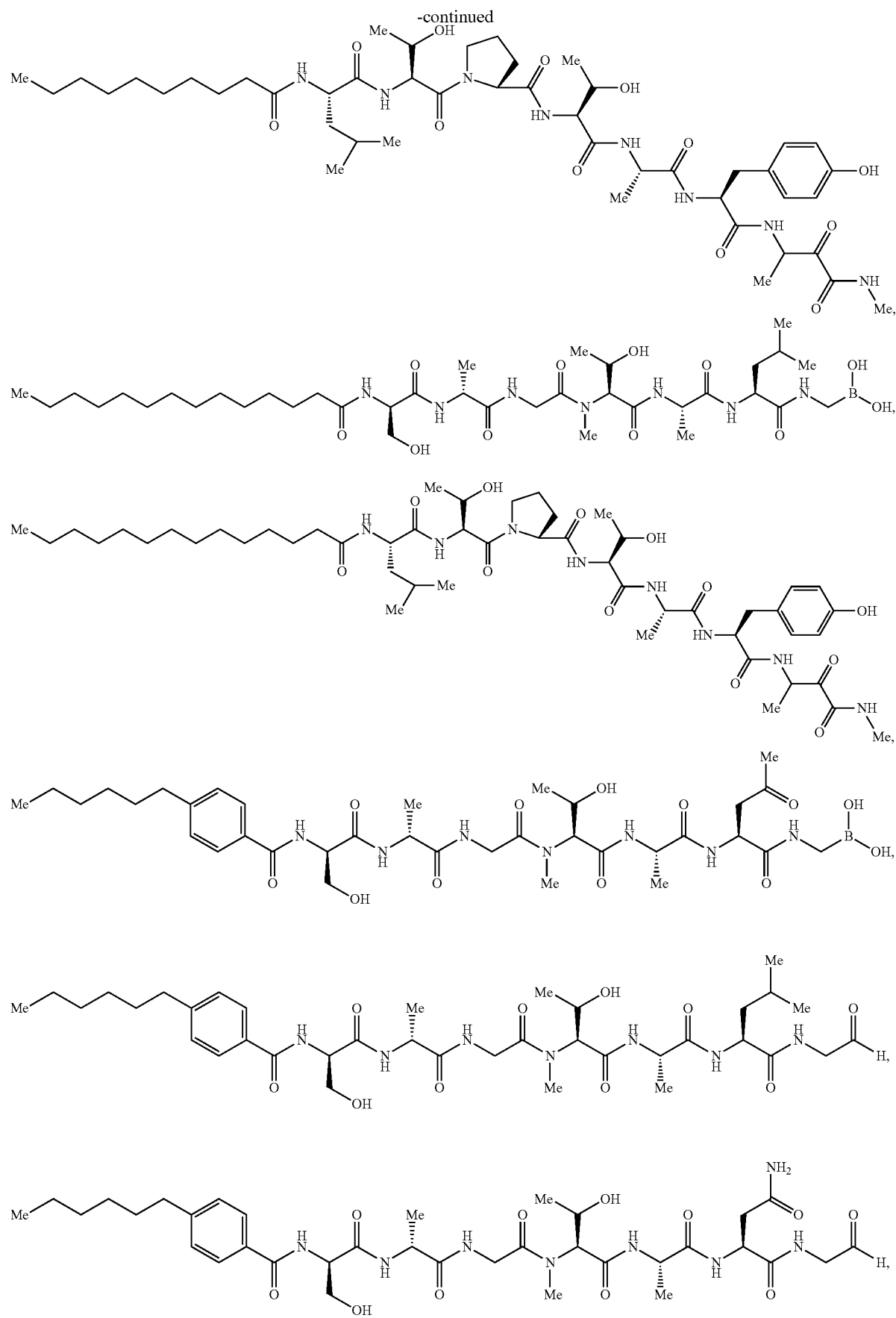

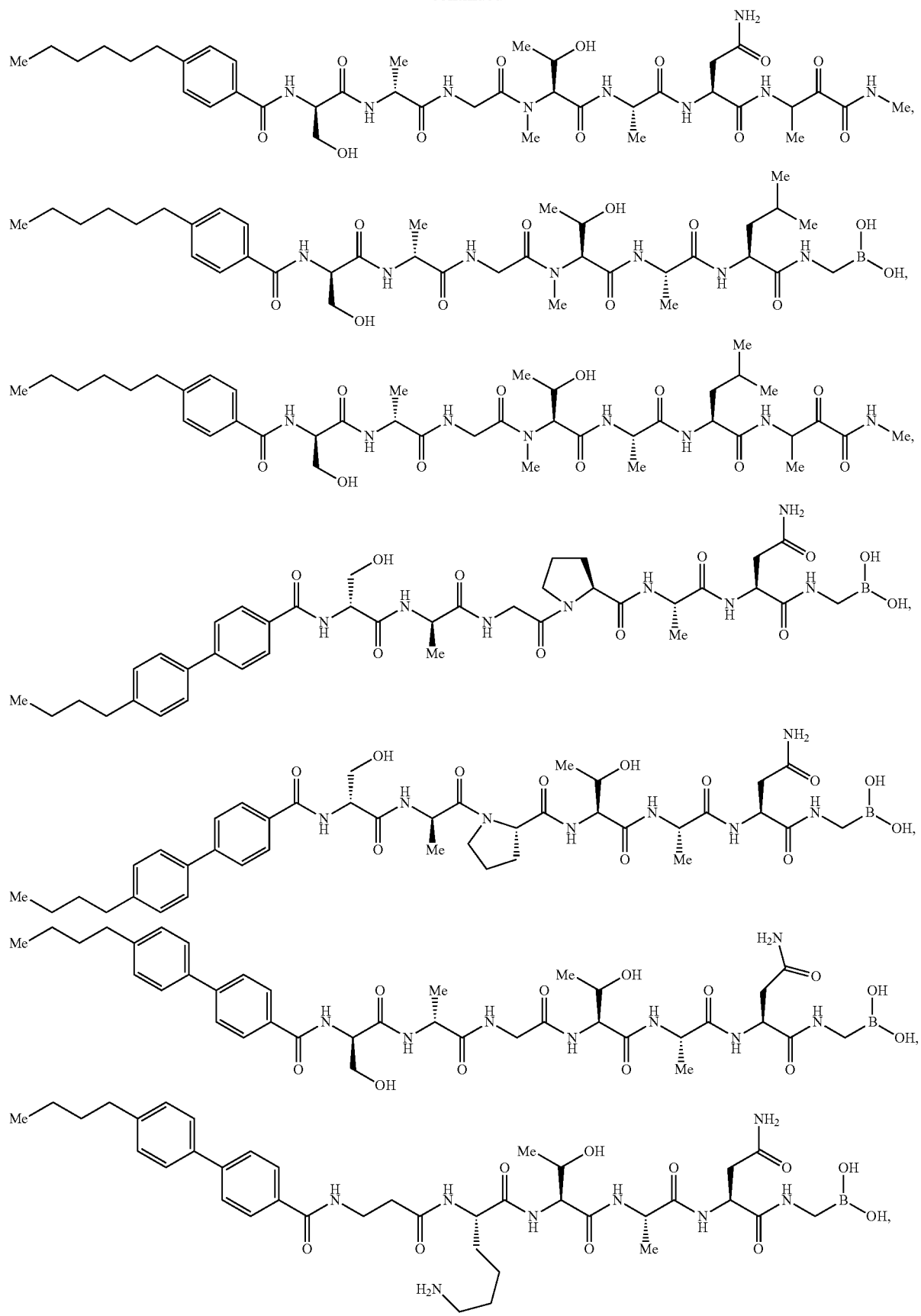

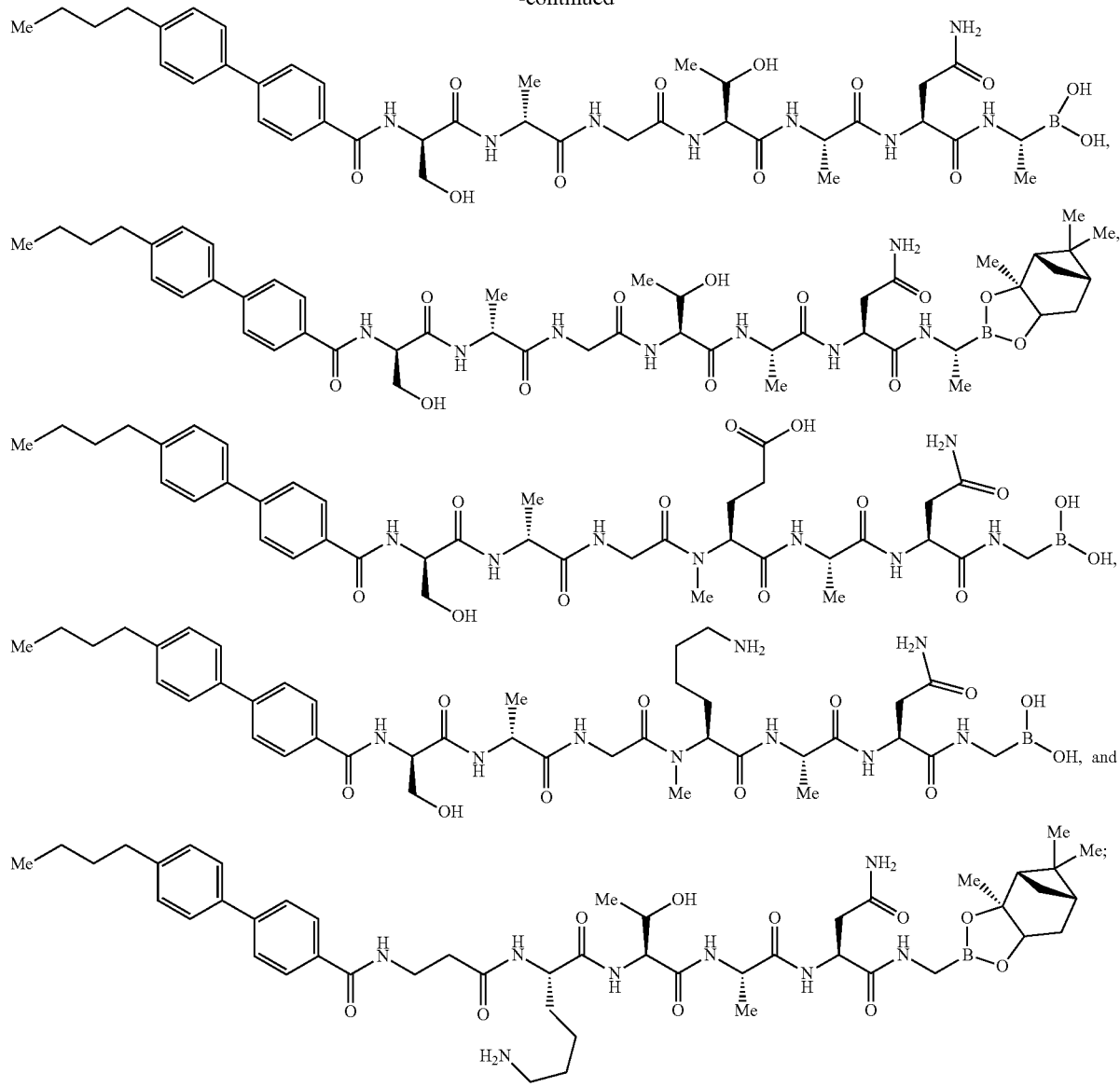
or a pharmaceutically acceptable salt, solvate, or prodrug thereof.
In another embodiment is a compound selected from:
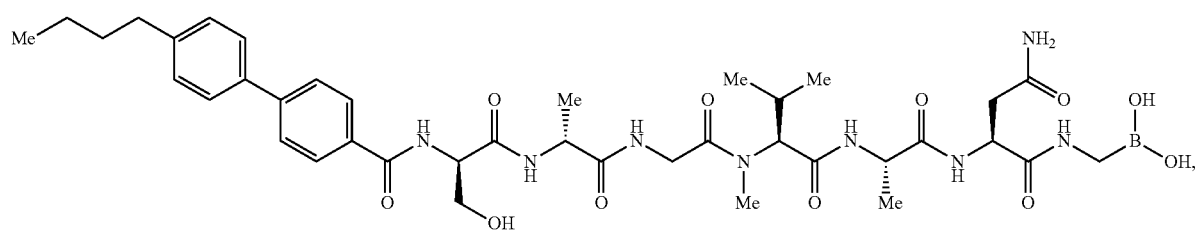

-continued
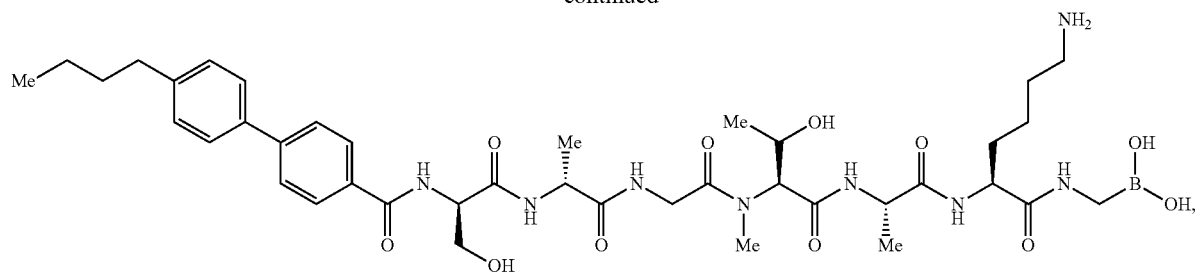
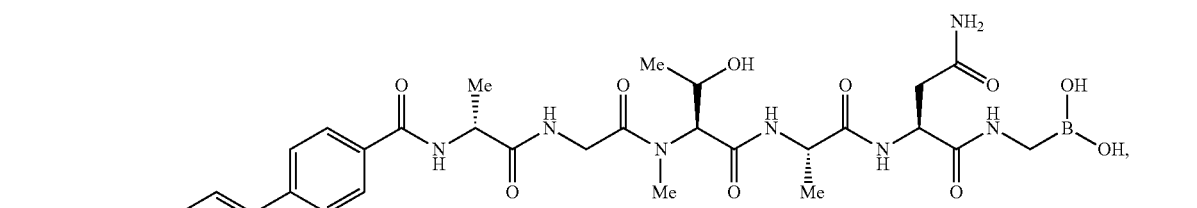
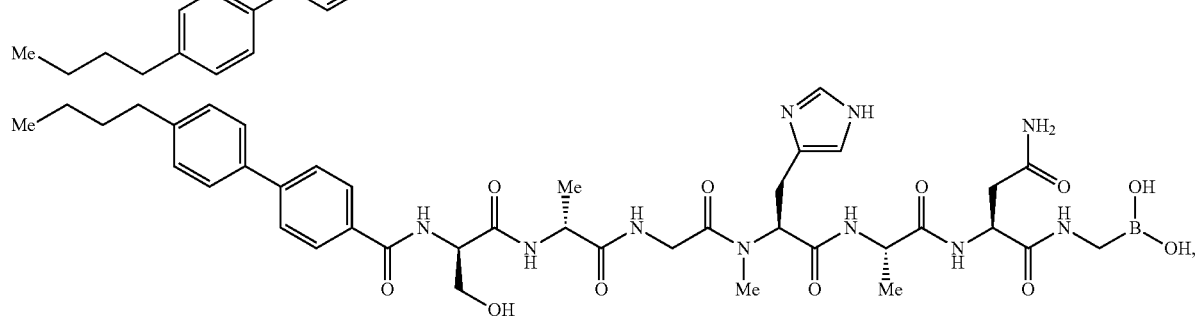
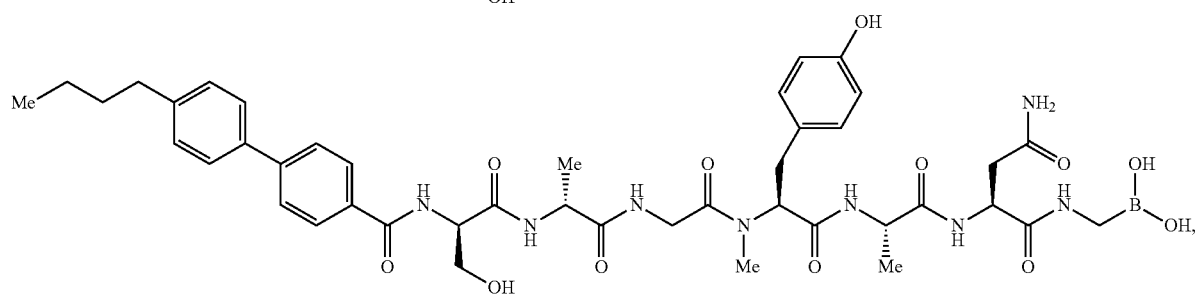
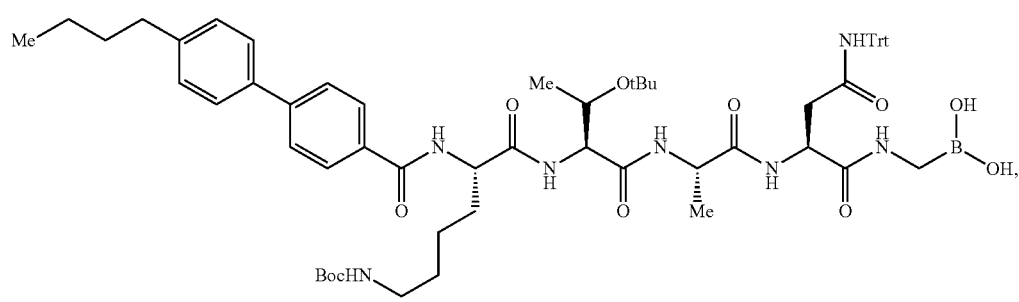
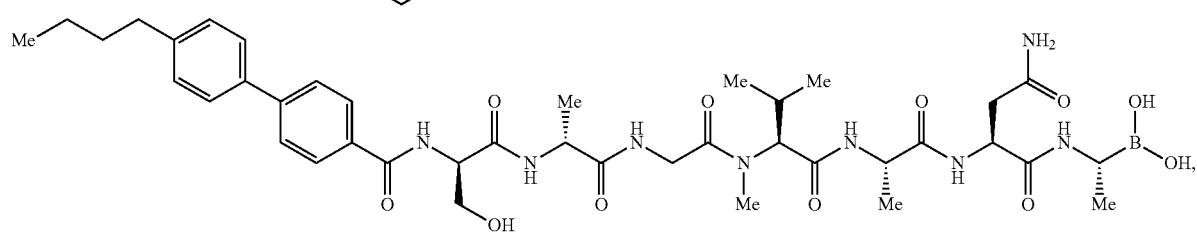

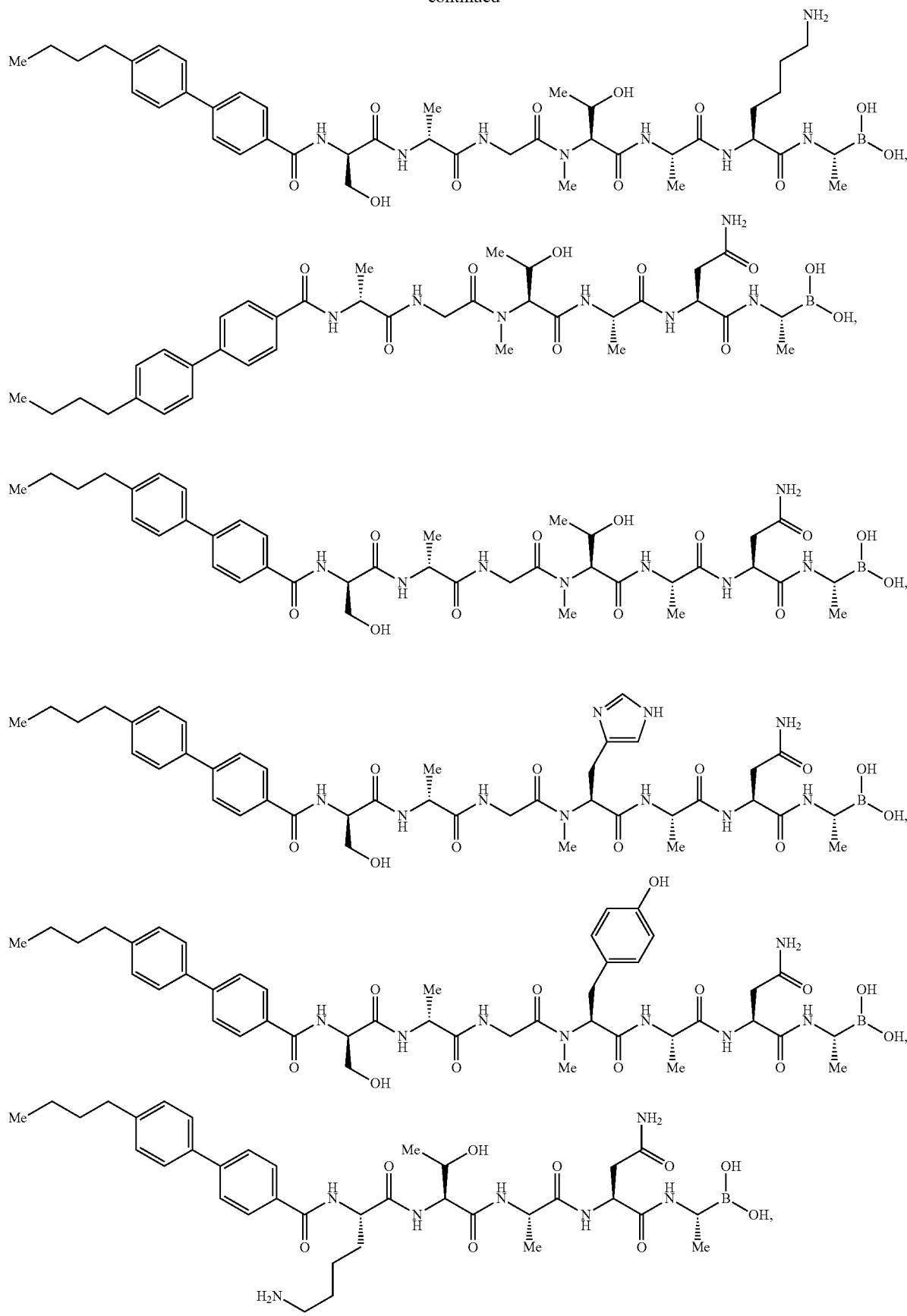

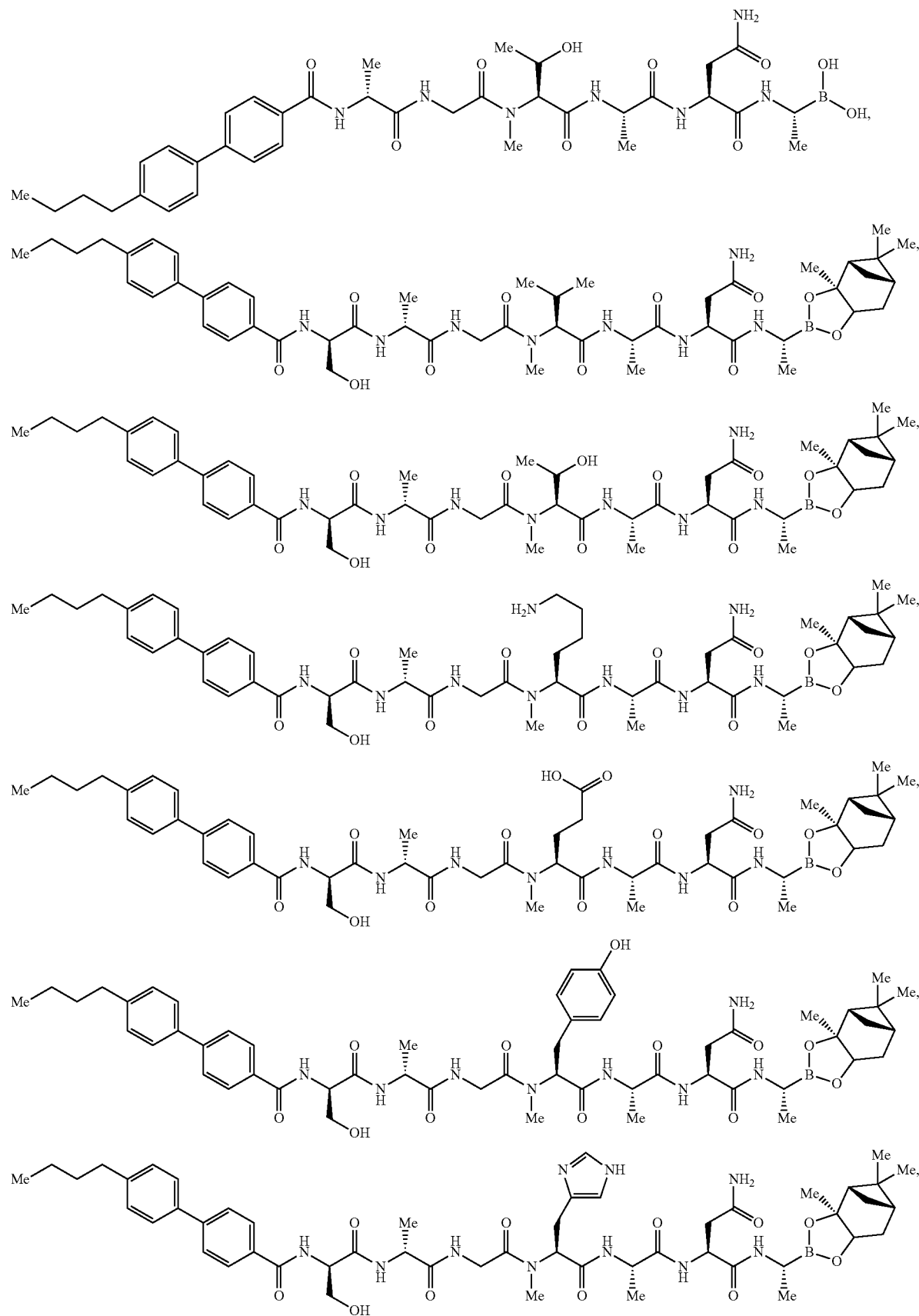

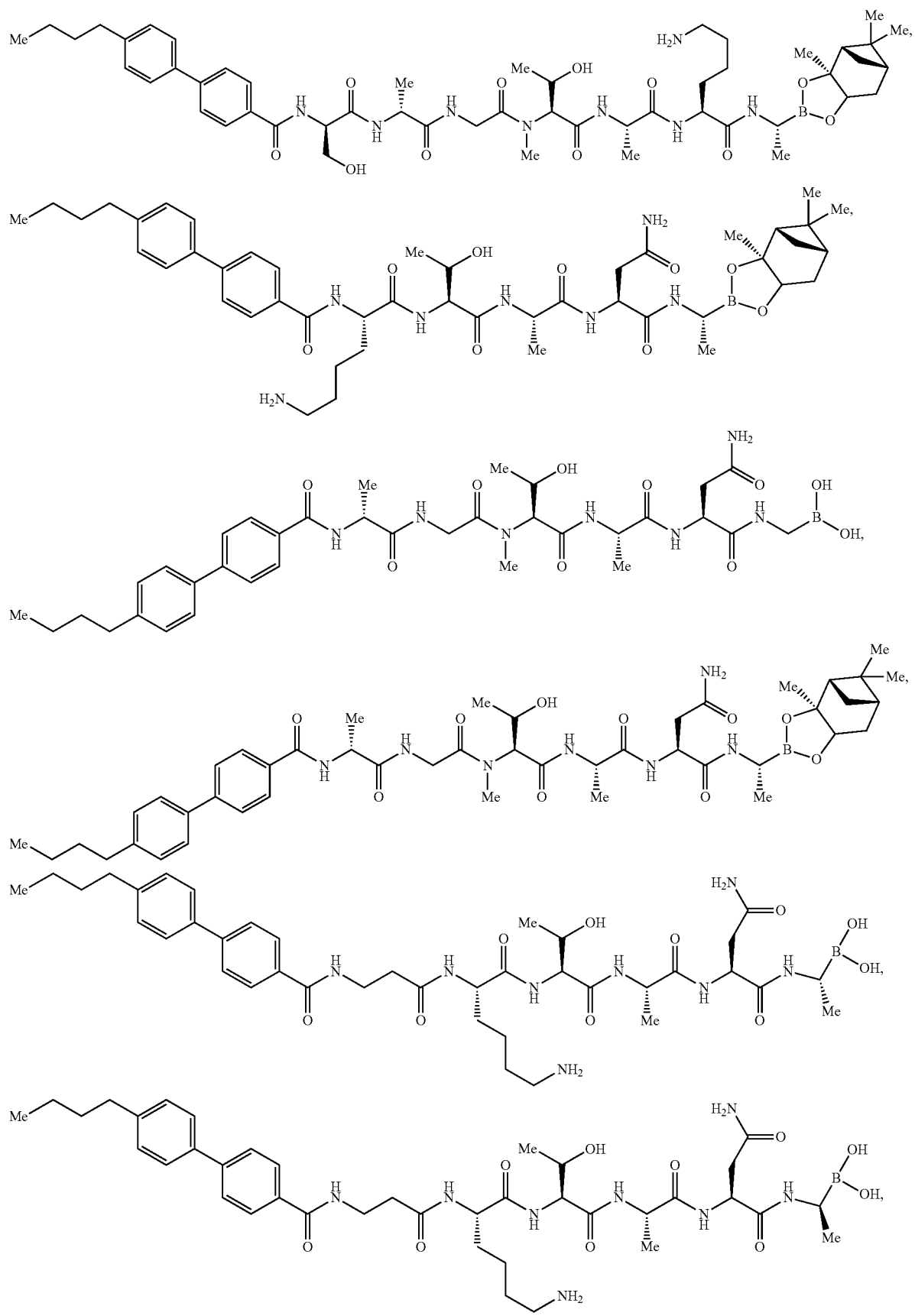

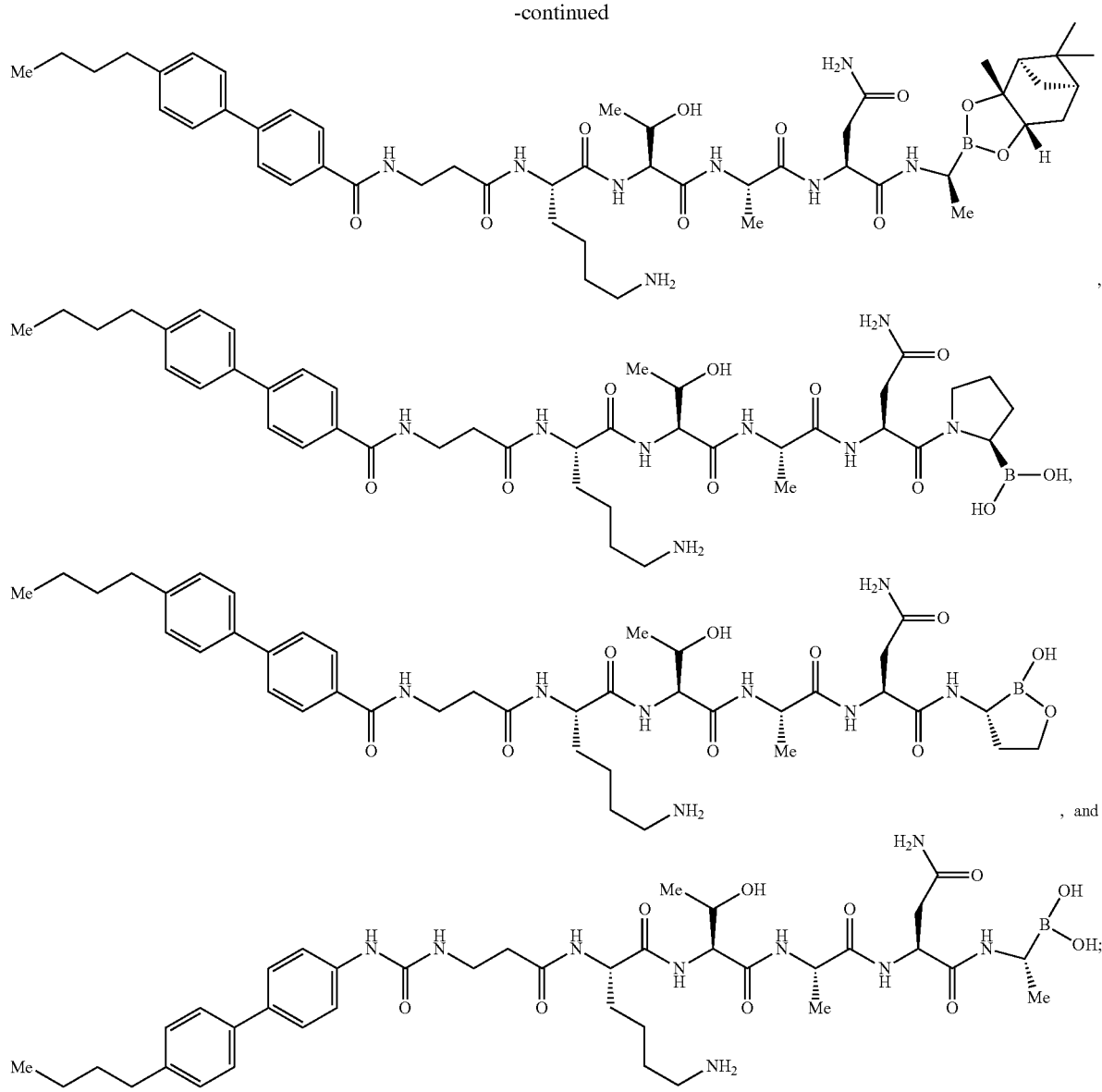
or a pharmaceutically acceptable salt, solvate, or prodrug thereof.
In another embodiment is a compound selected from:
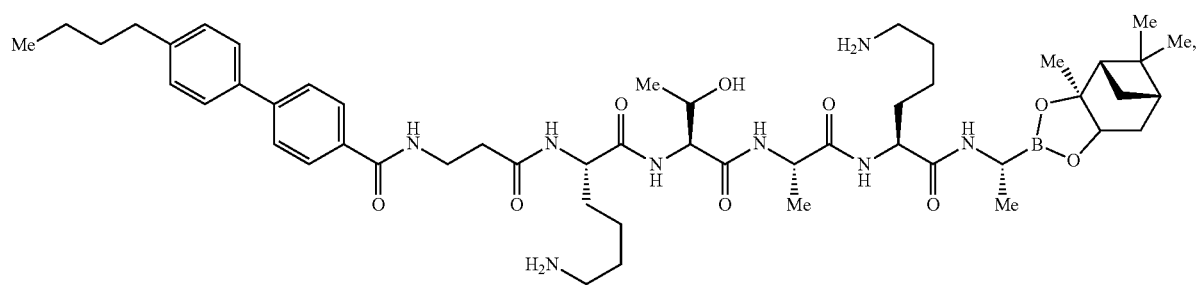

-continued
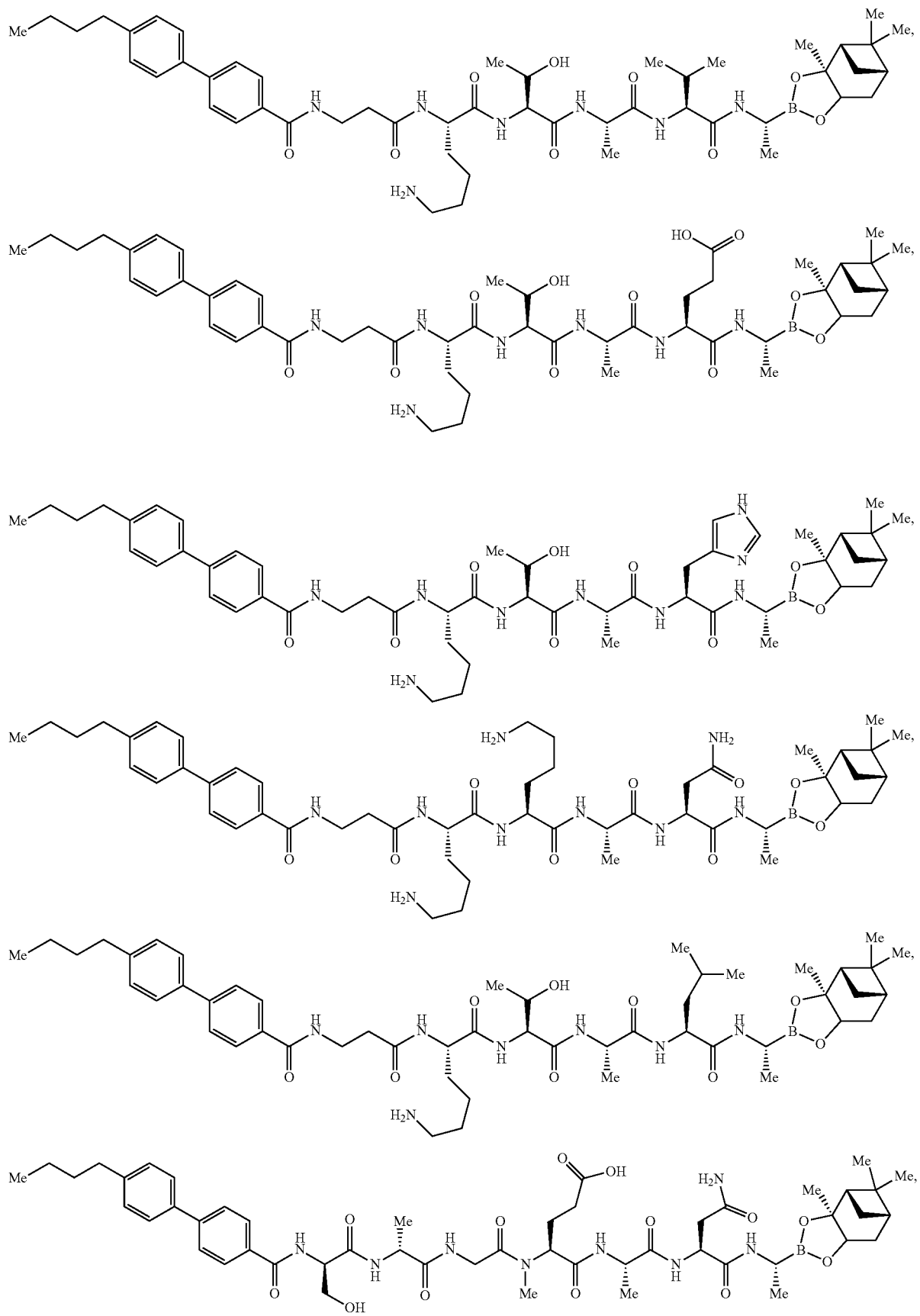

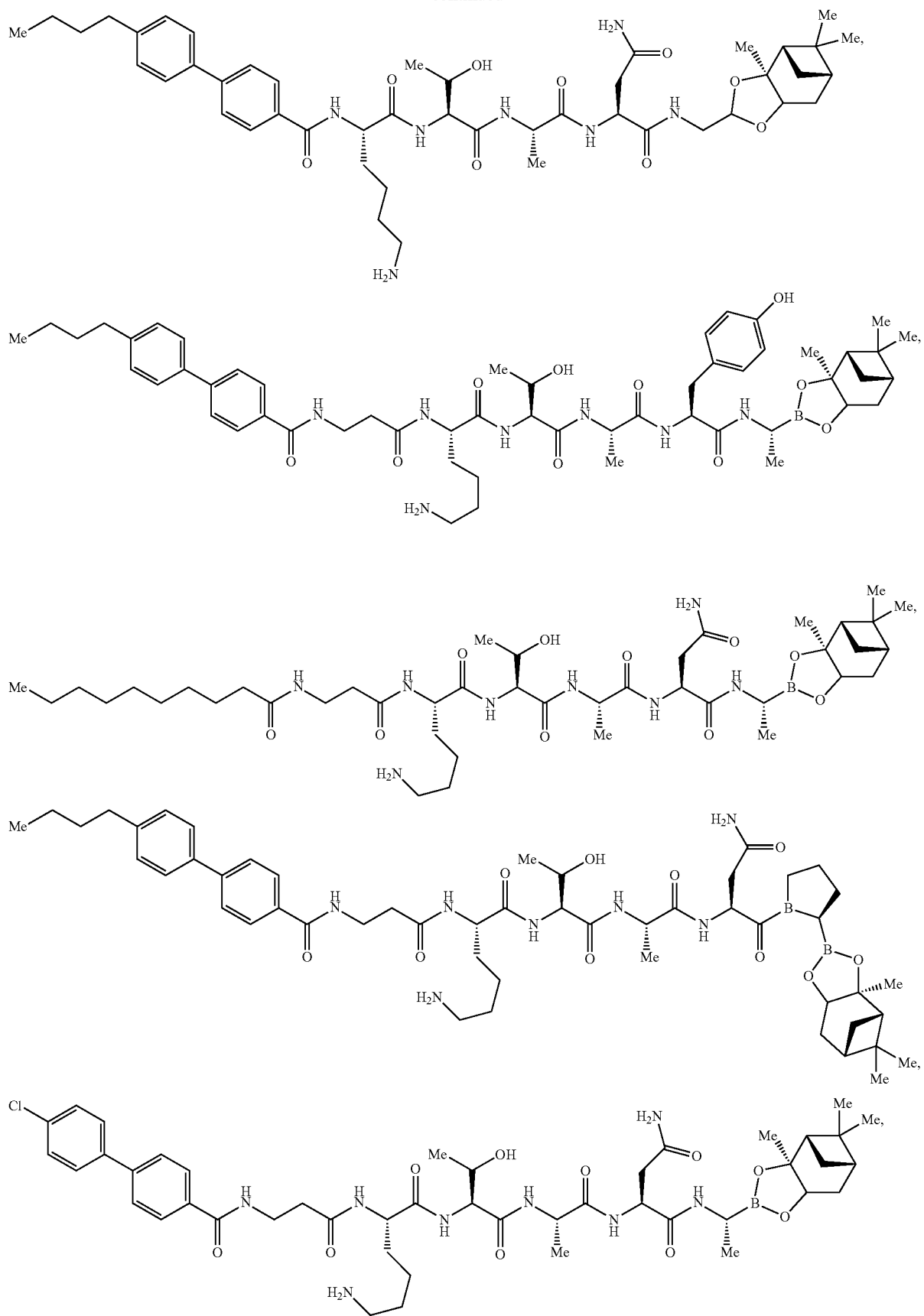
-continued

-continued
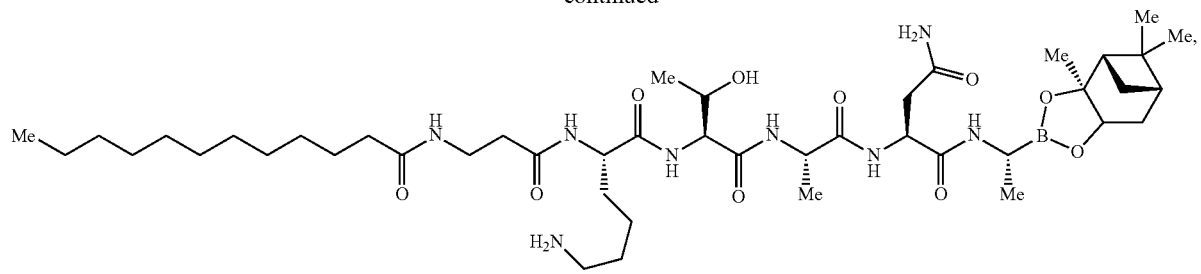
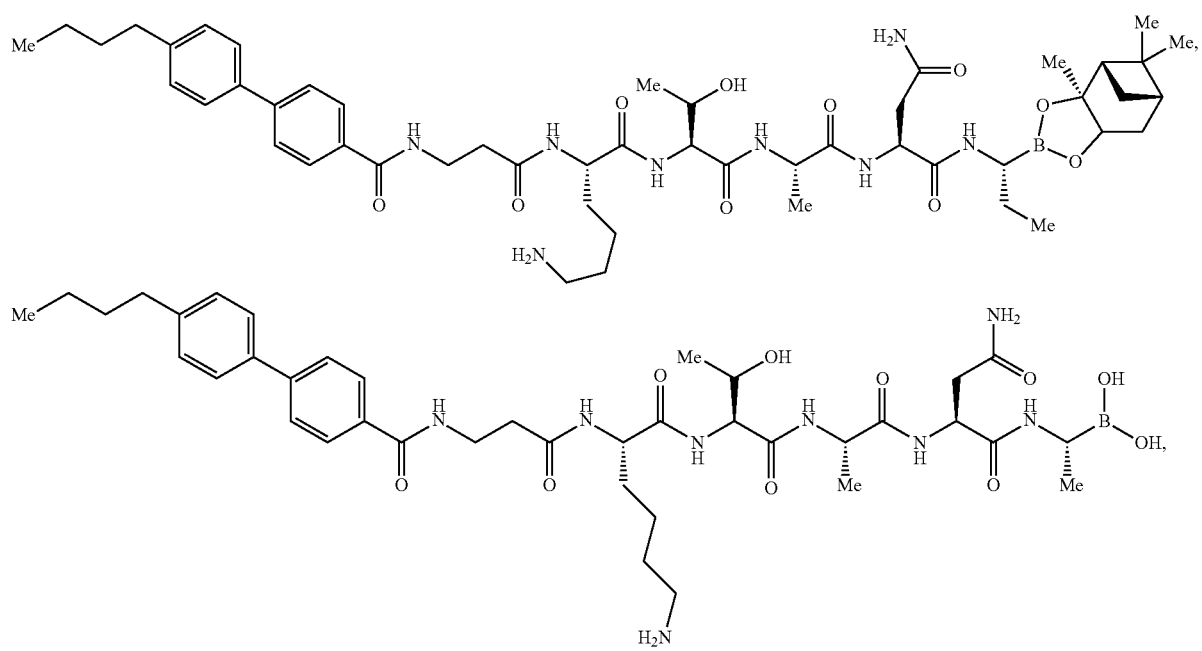
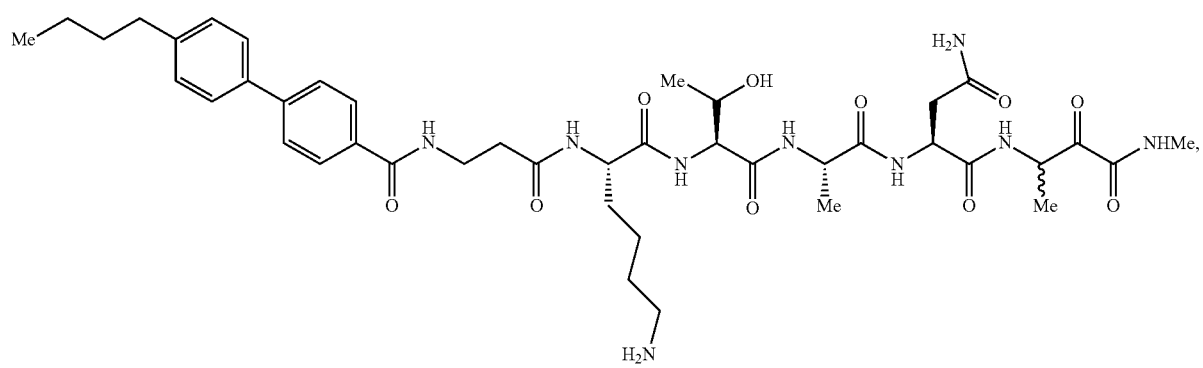
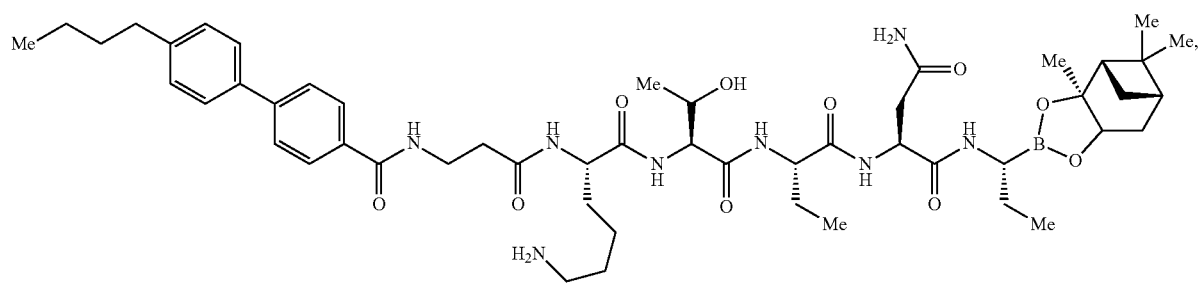

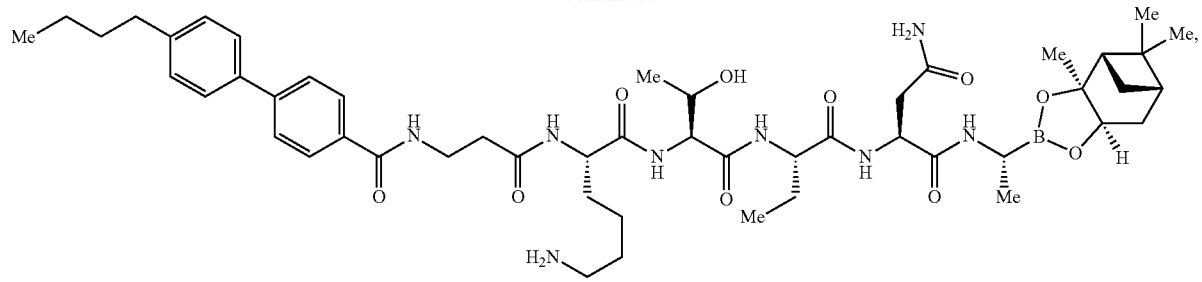
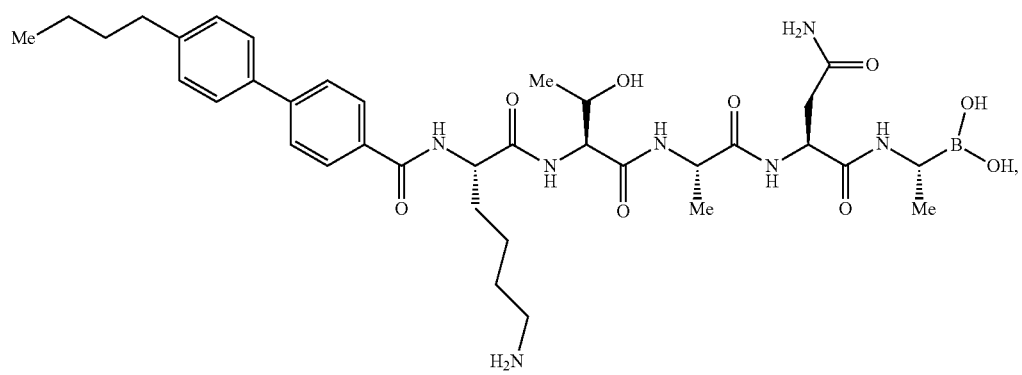
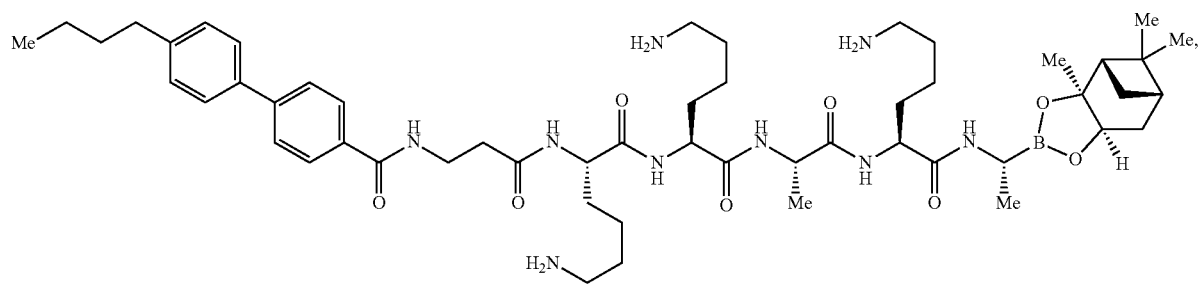
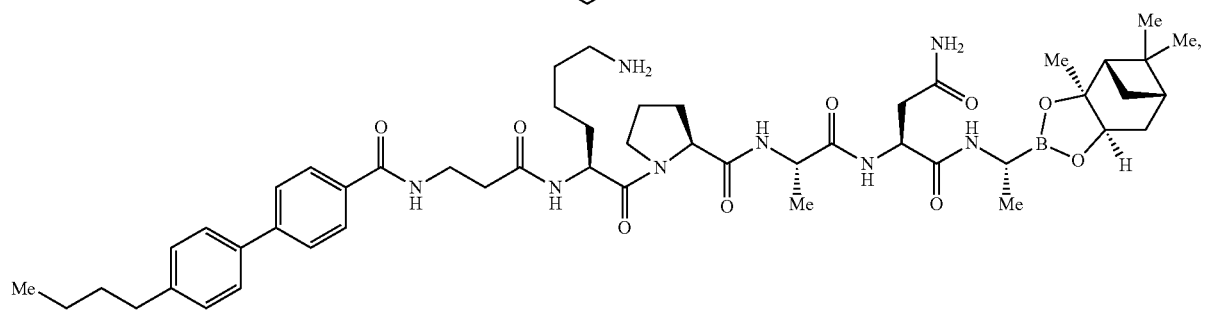
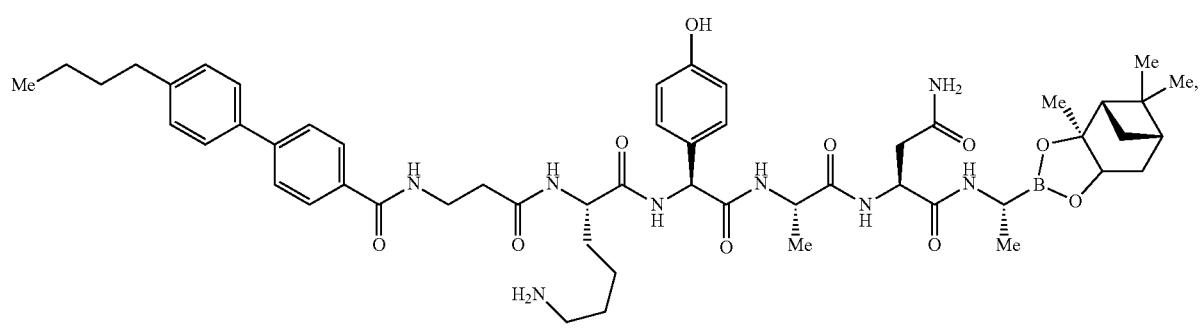

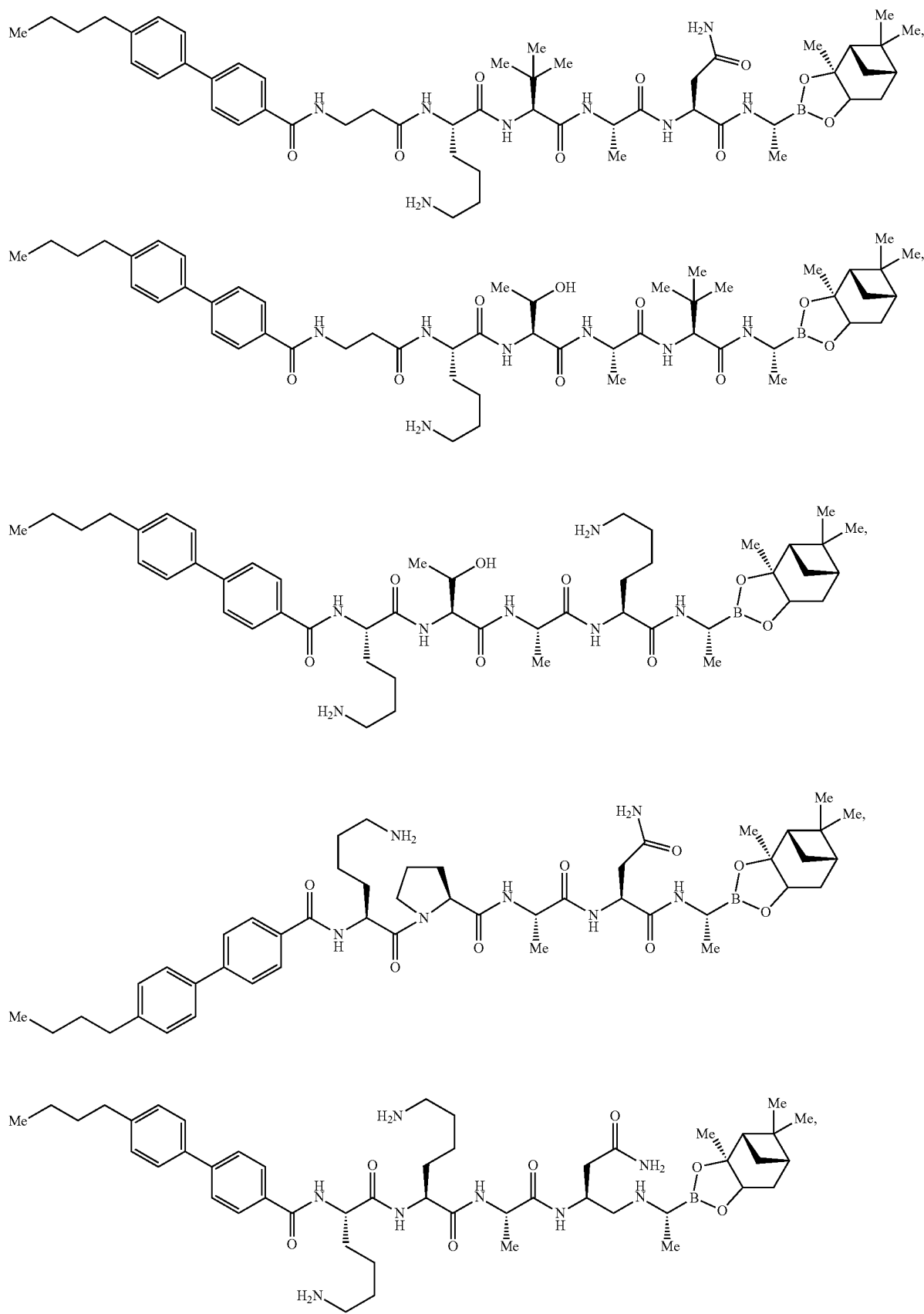

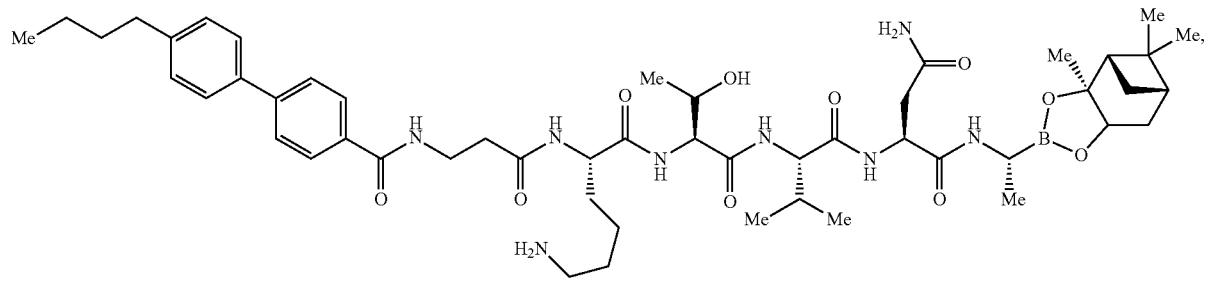
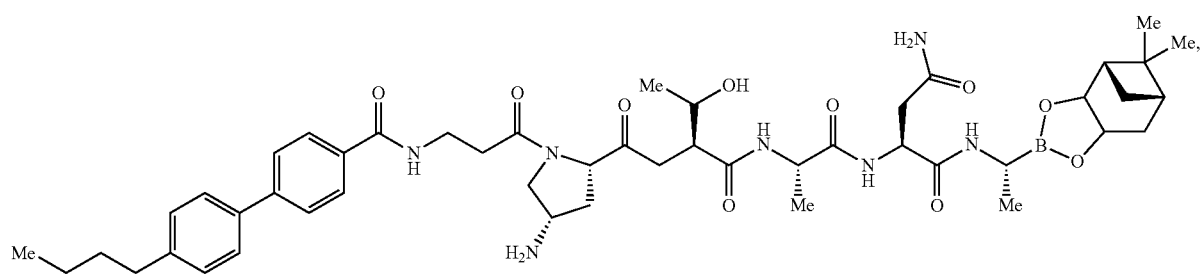
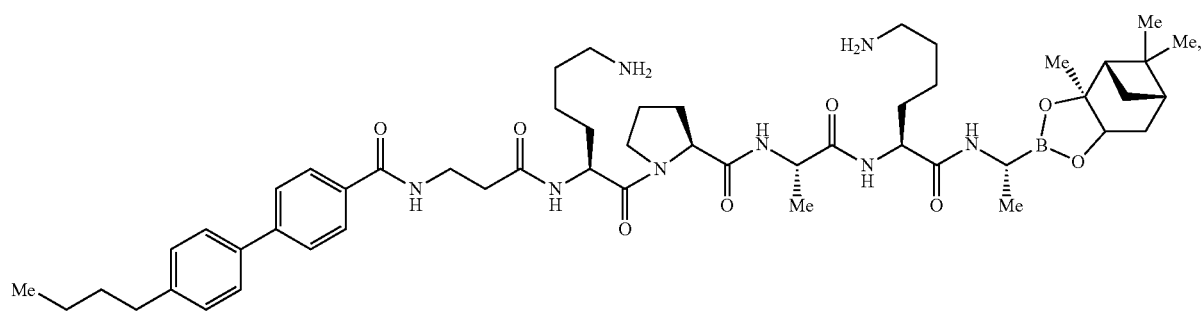
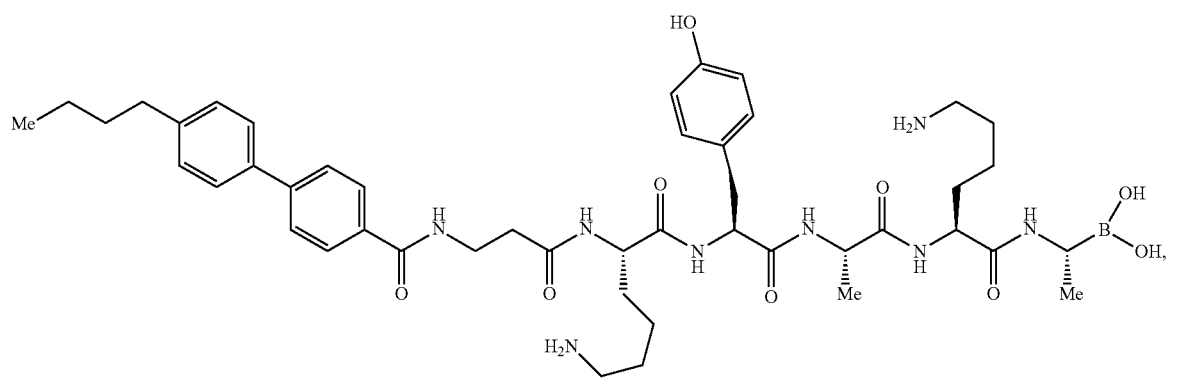
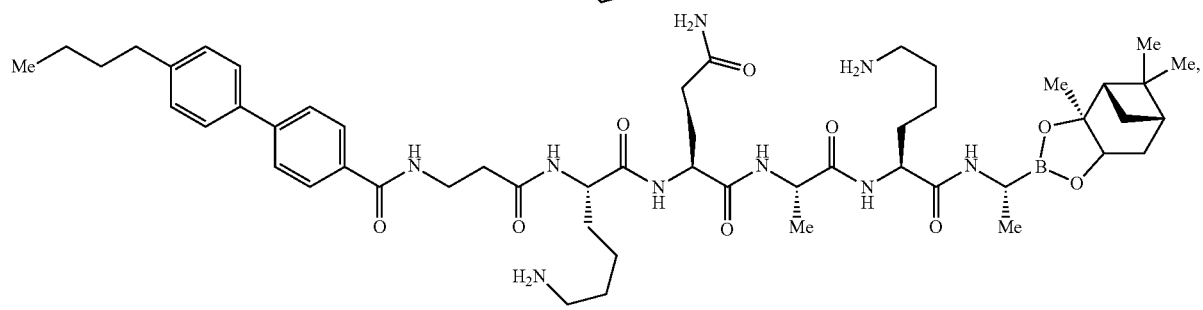

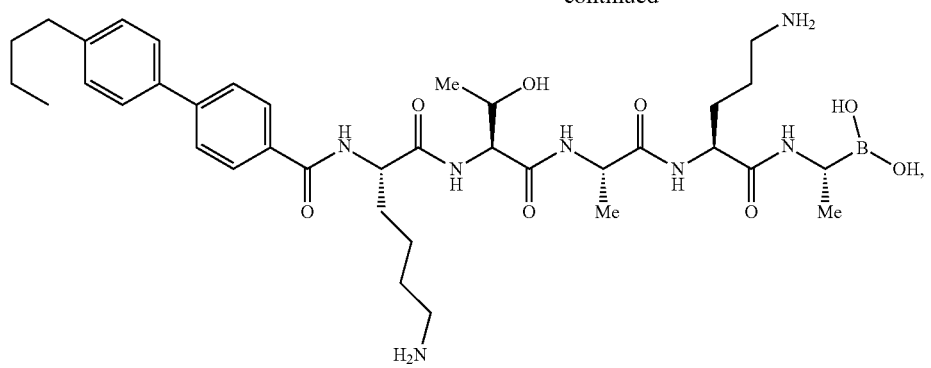
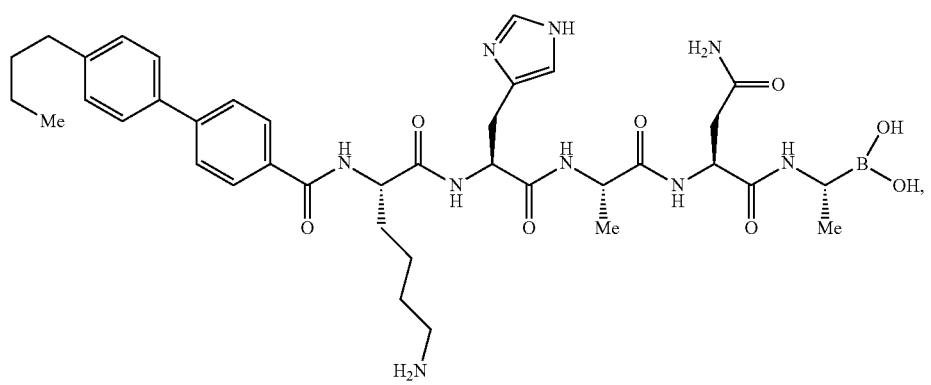
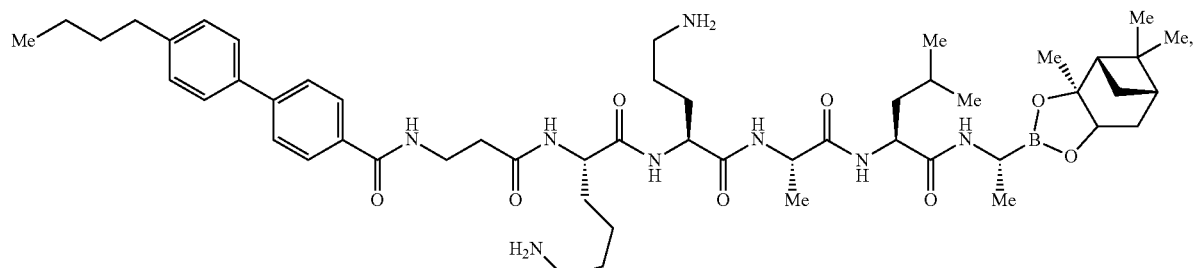
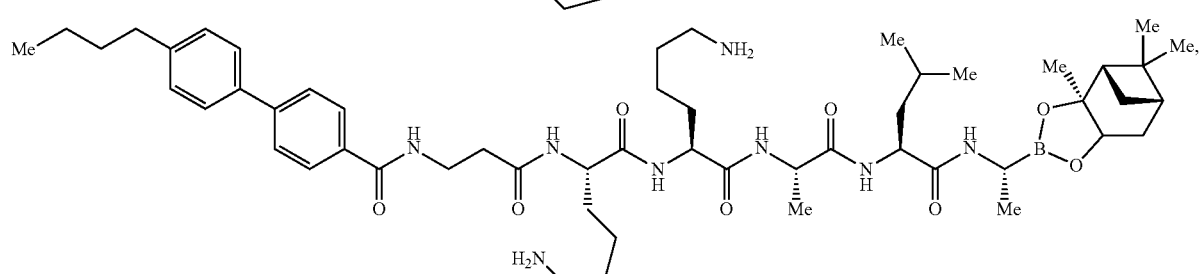
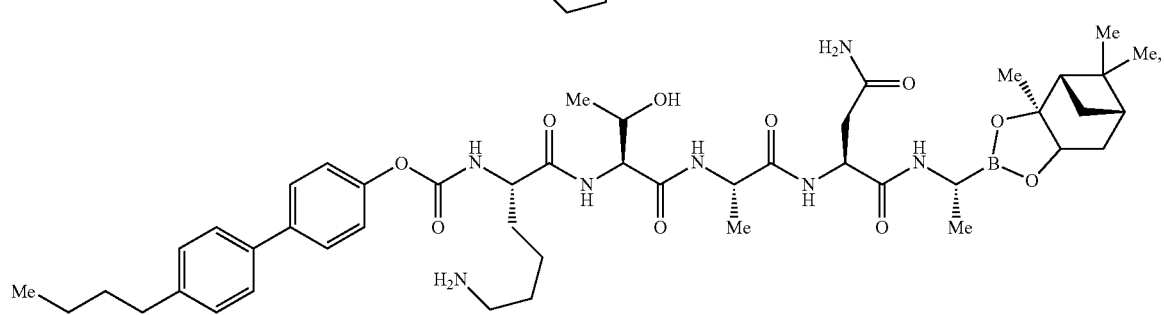

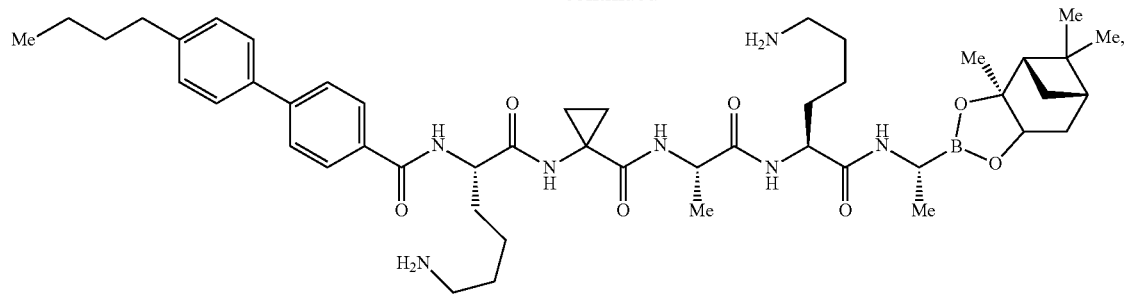
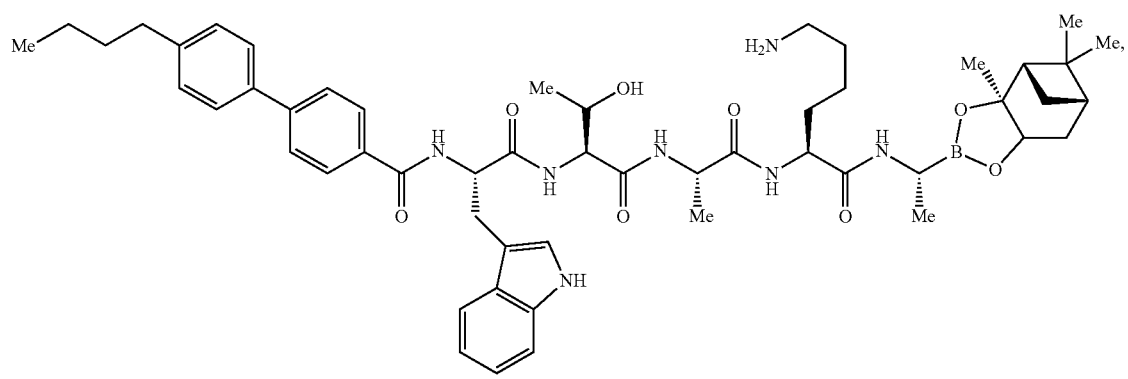
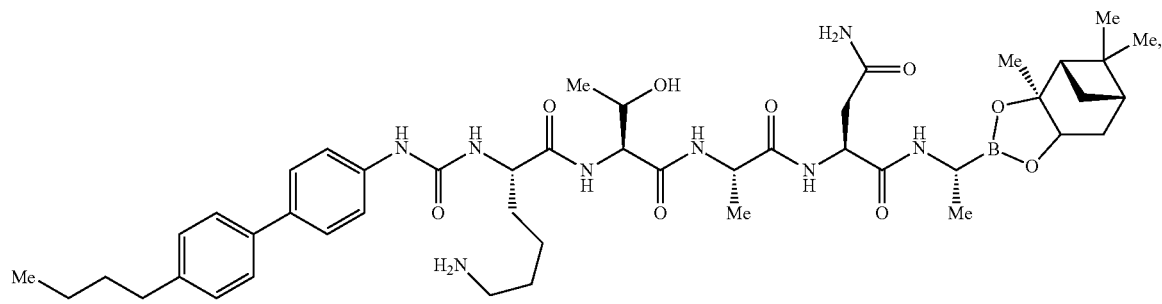
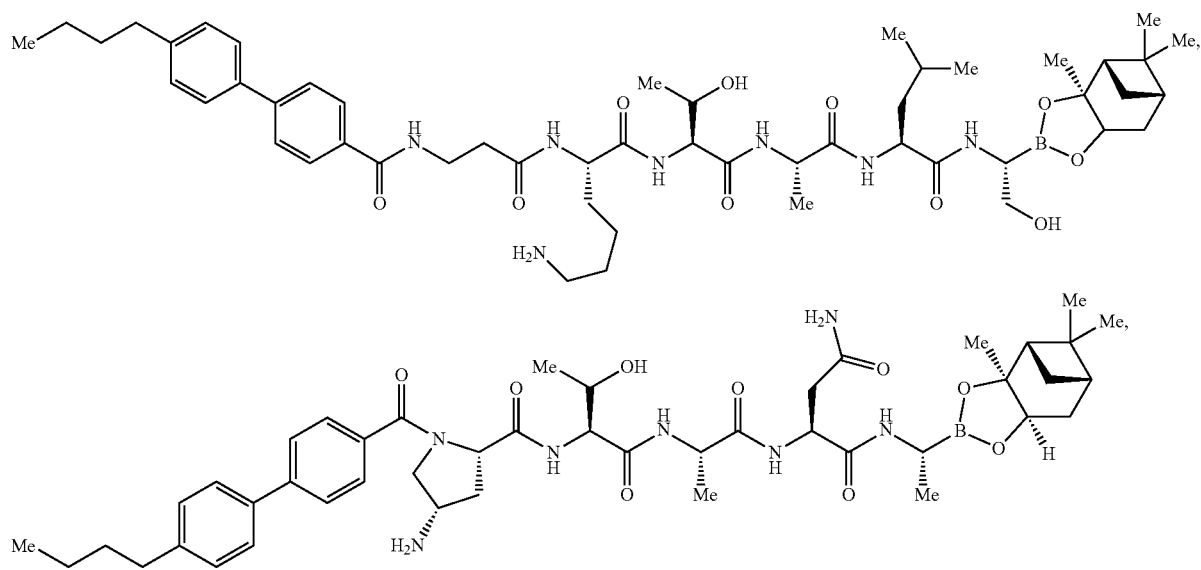

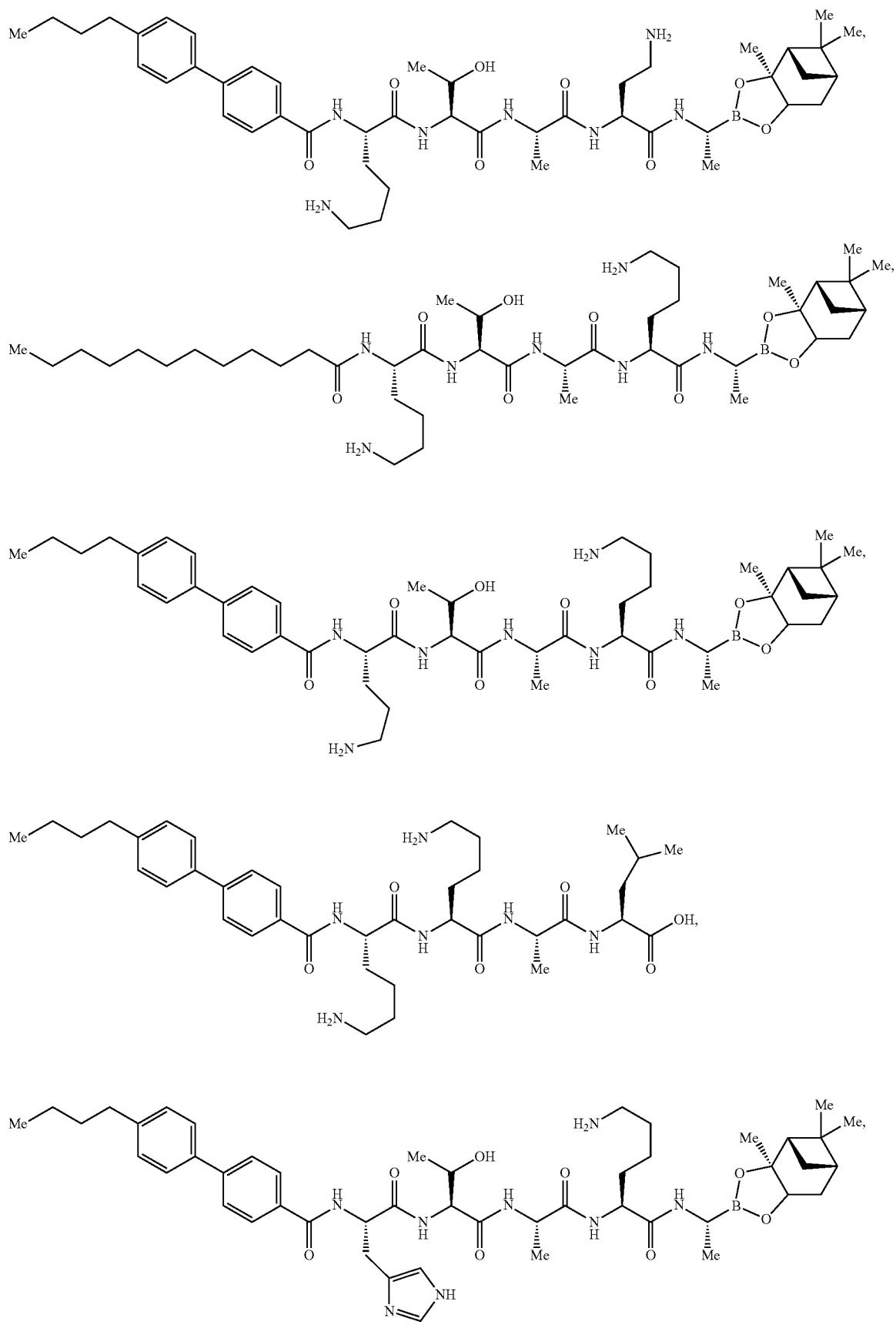

-continued
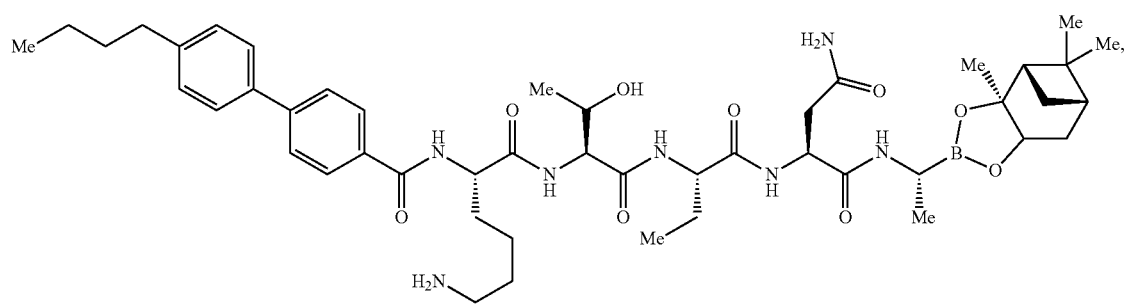
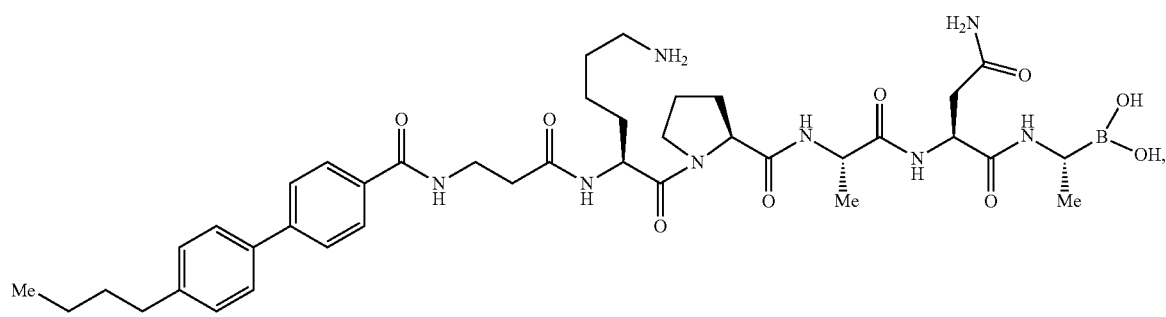
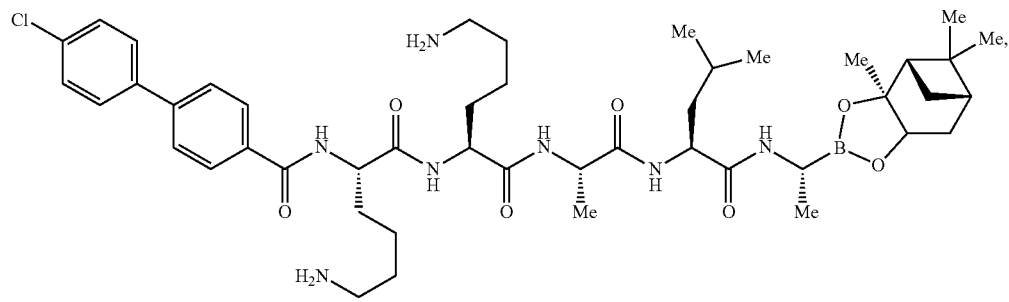
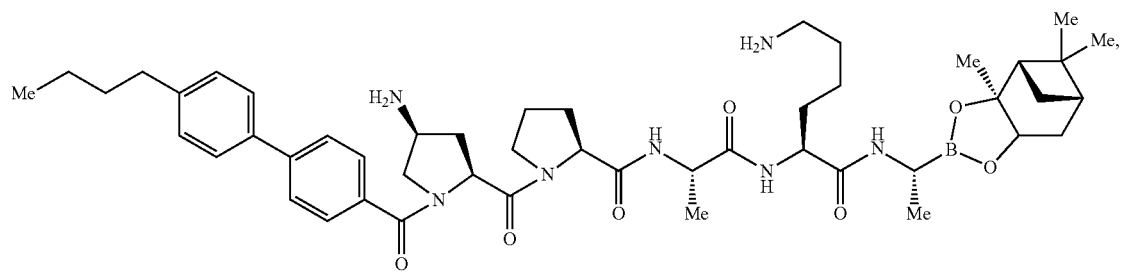
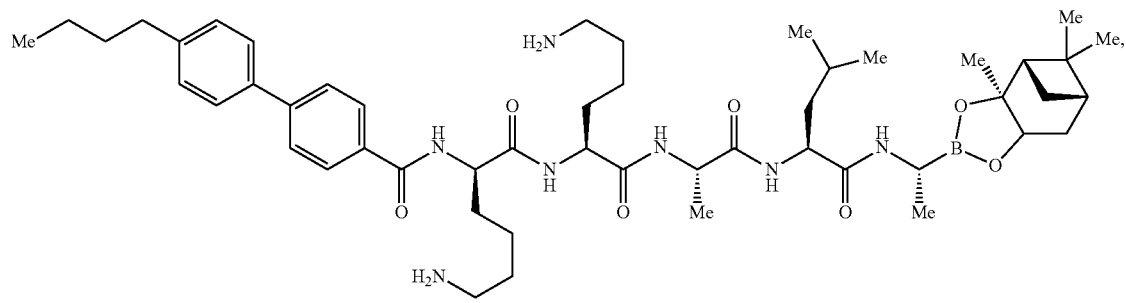

-continued
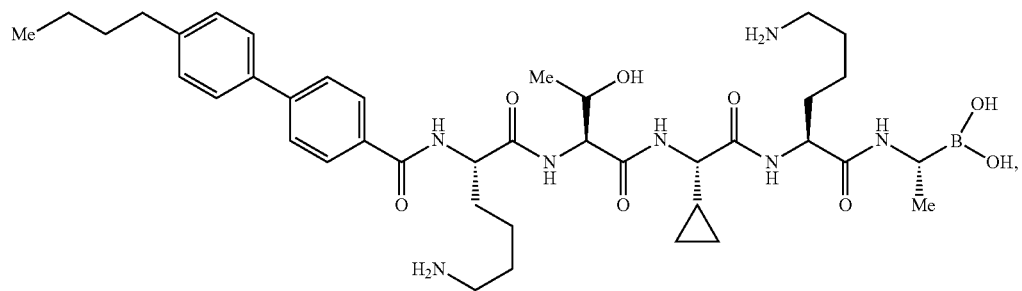
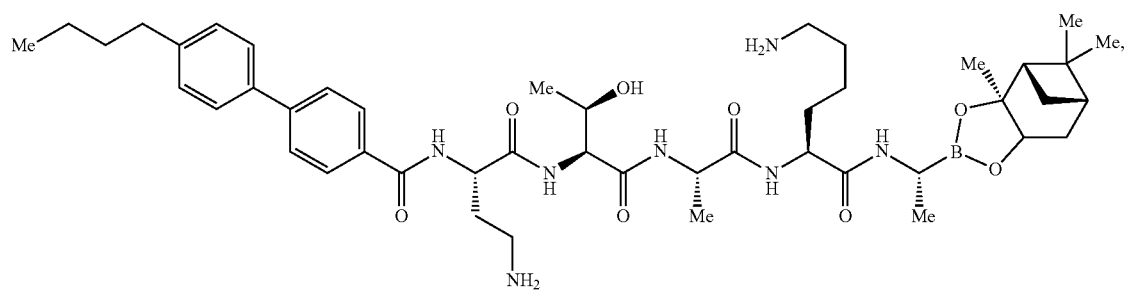
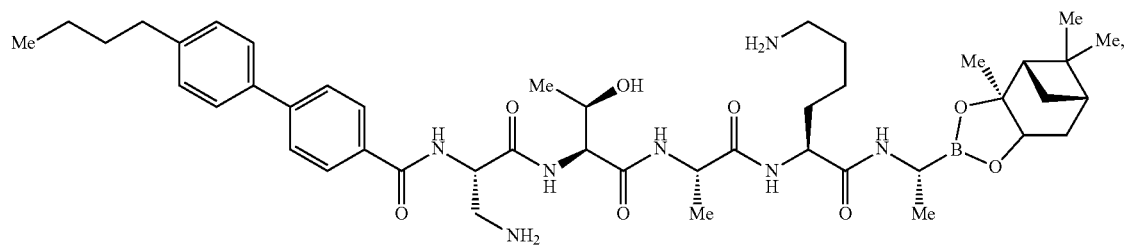
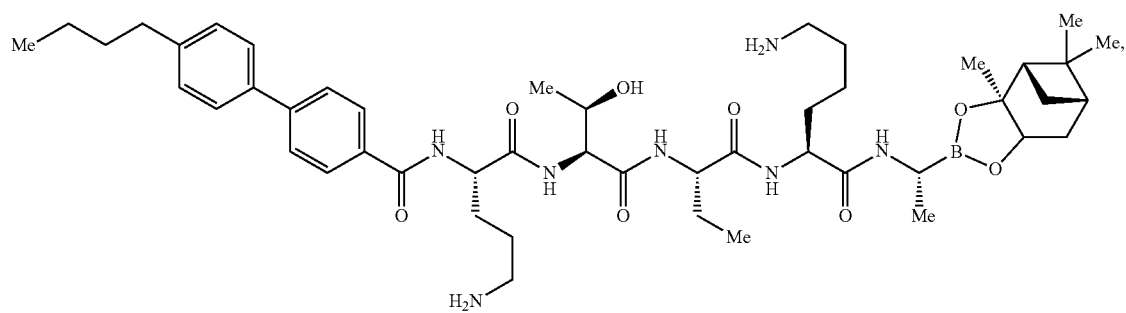
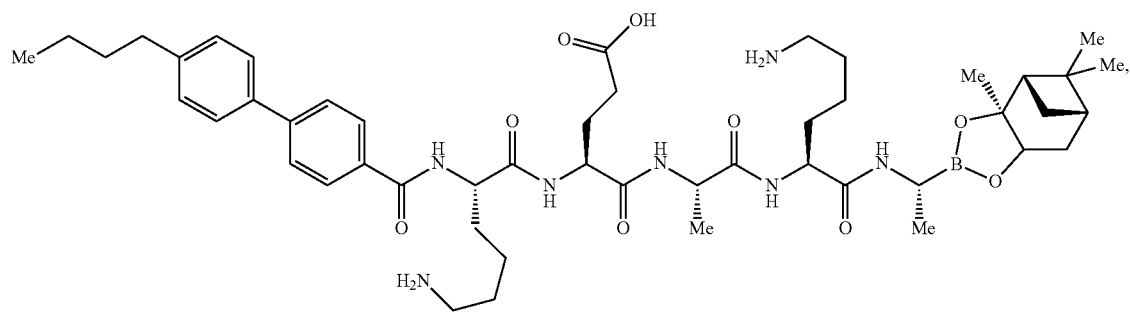

-continued
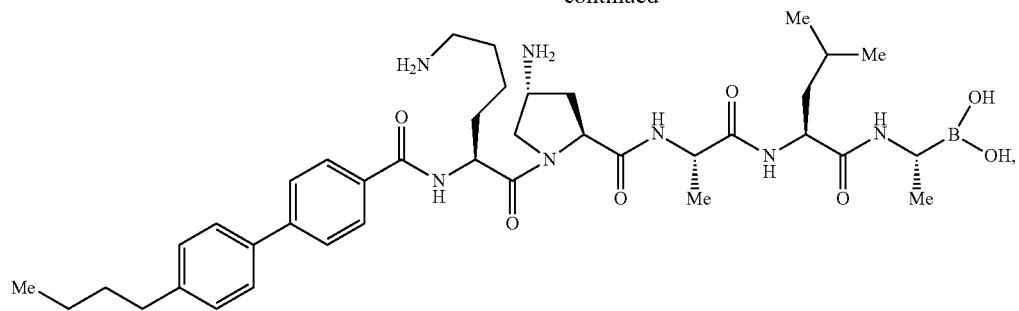
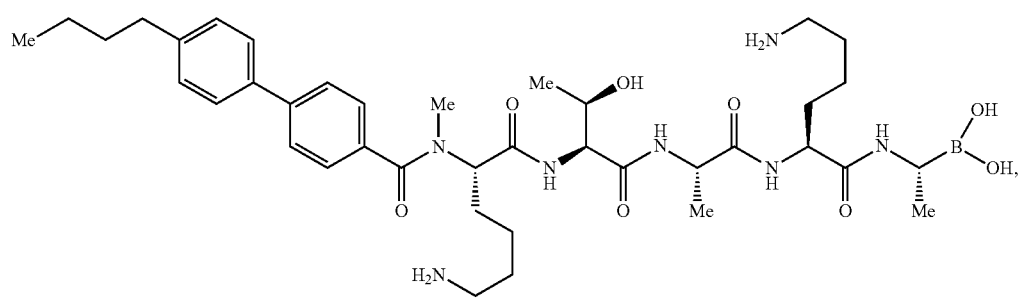
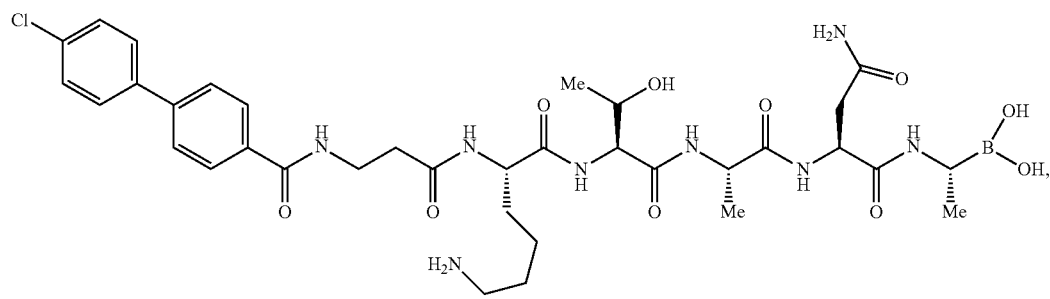
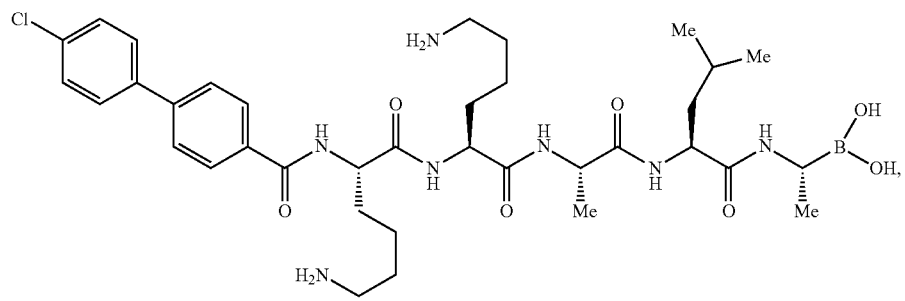
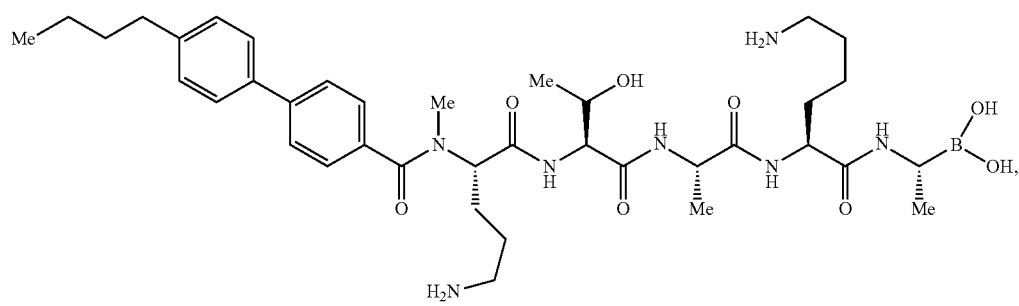

-continued
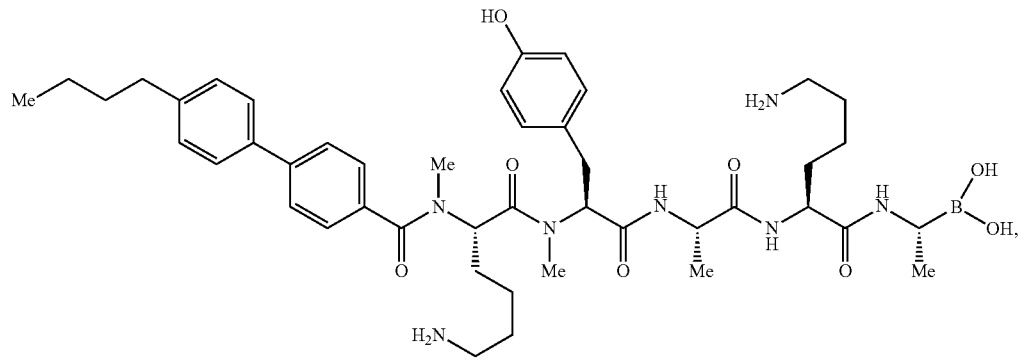
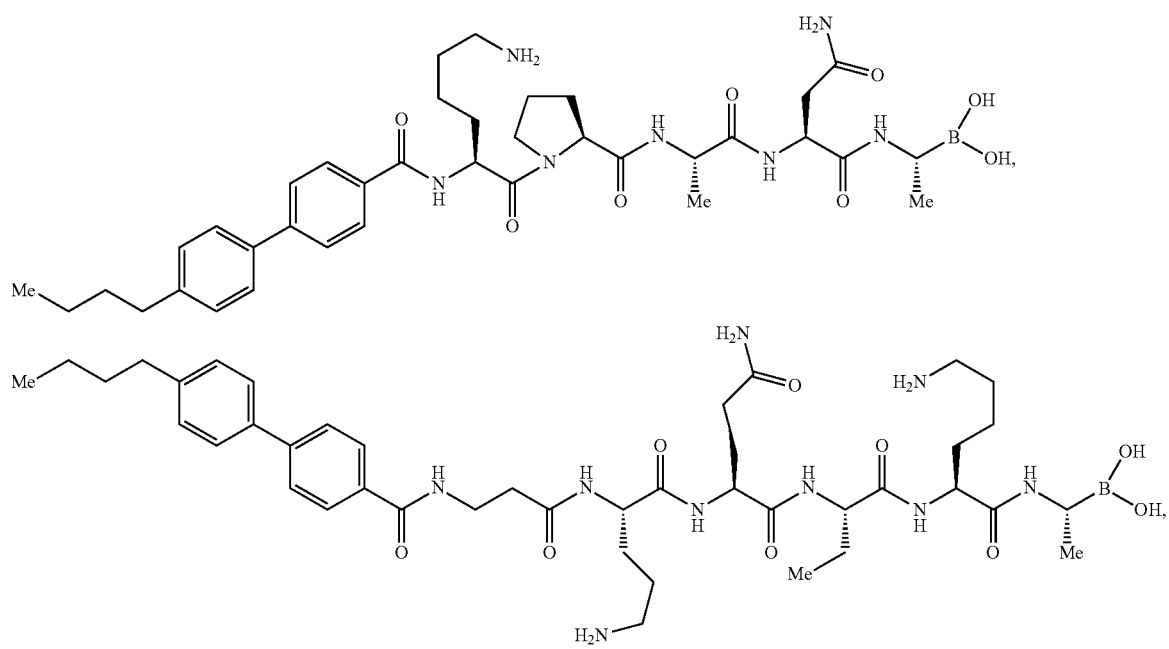
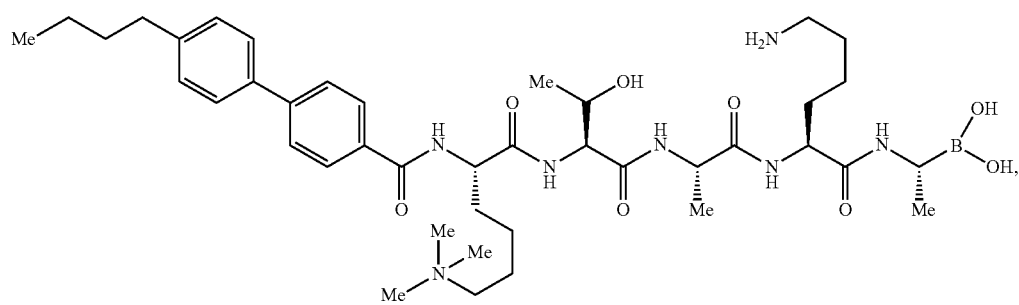
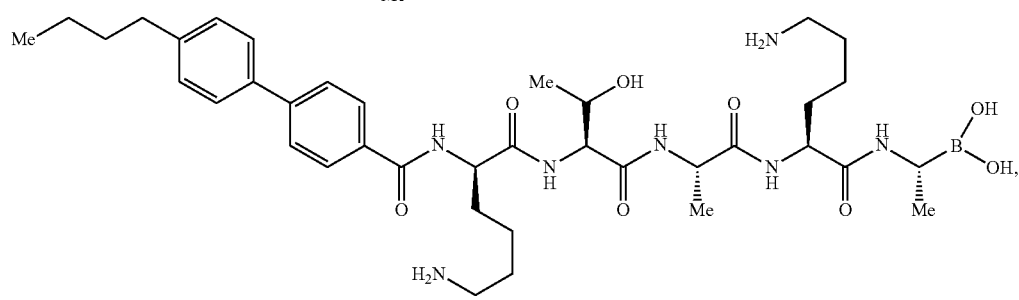

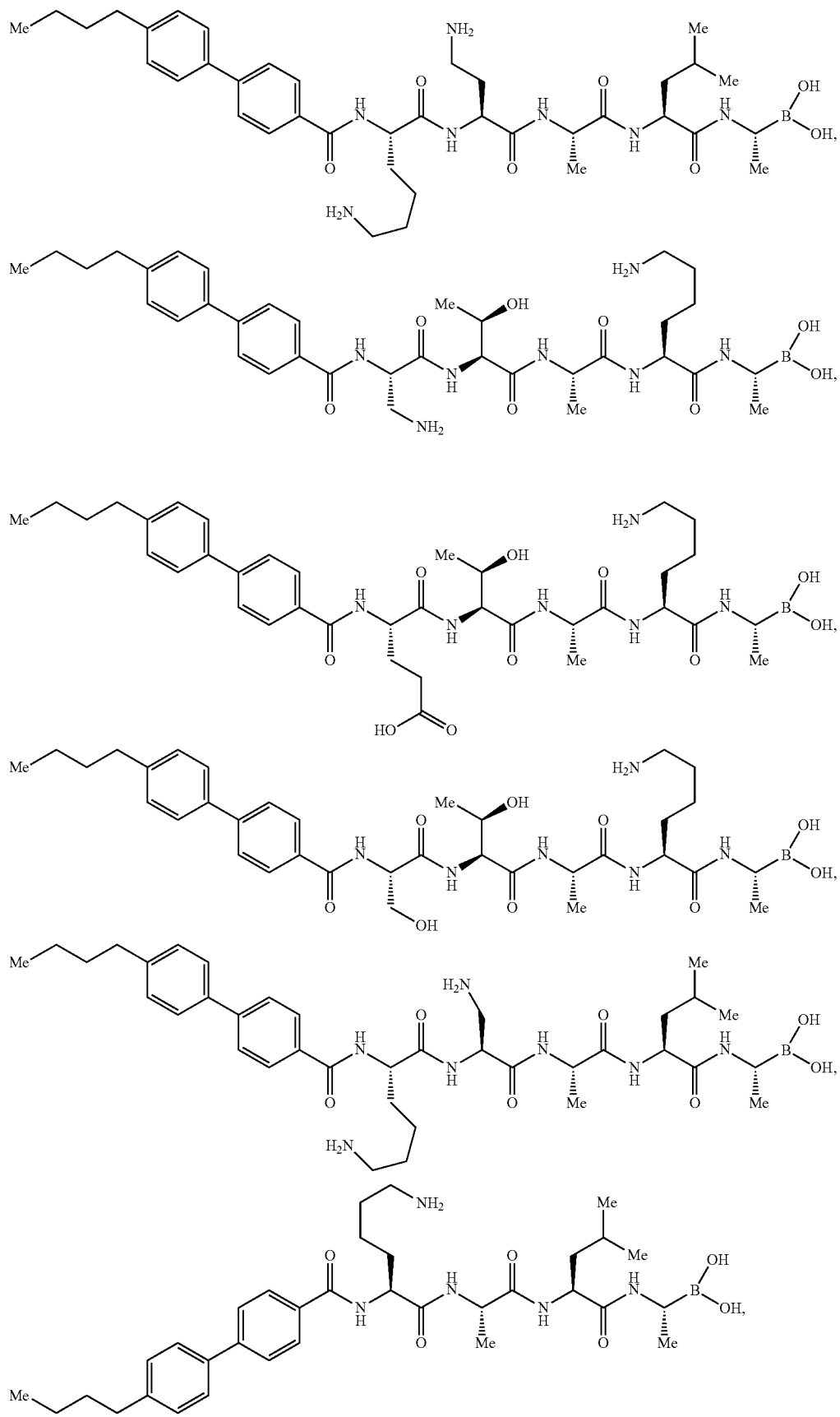

-continued
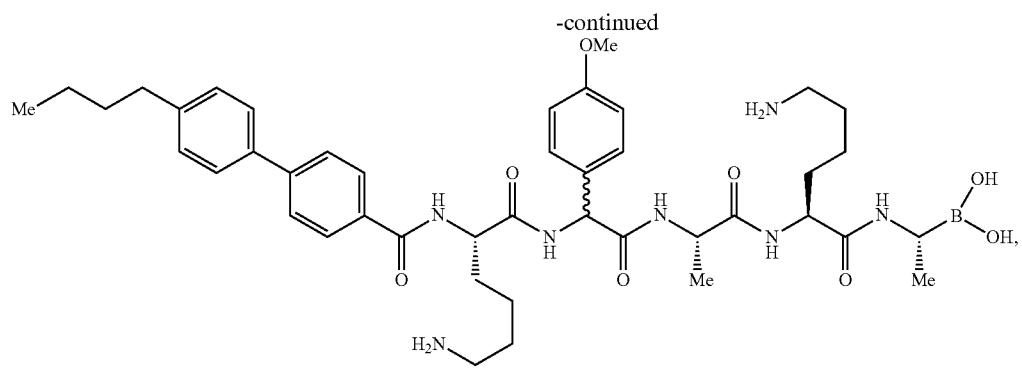
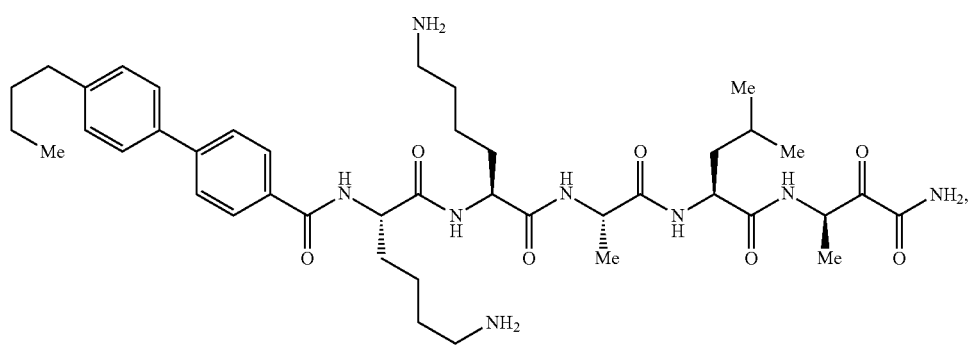
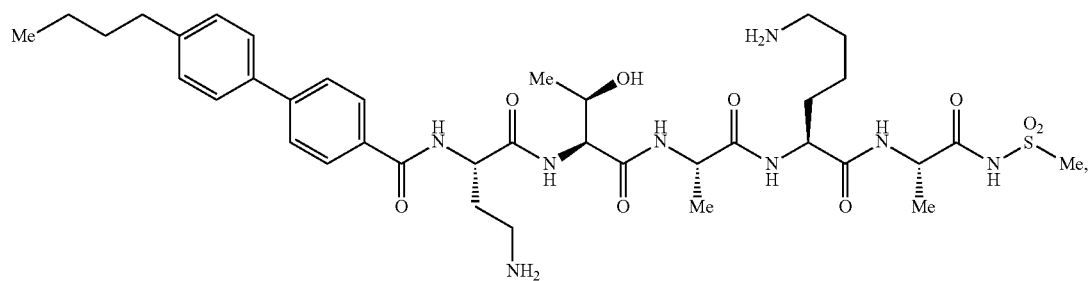
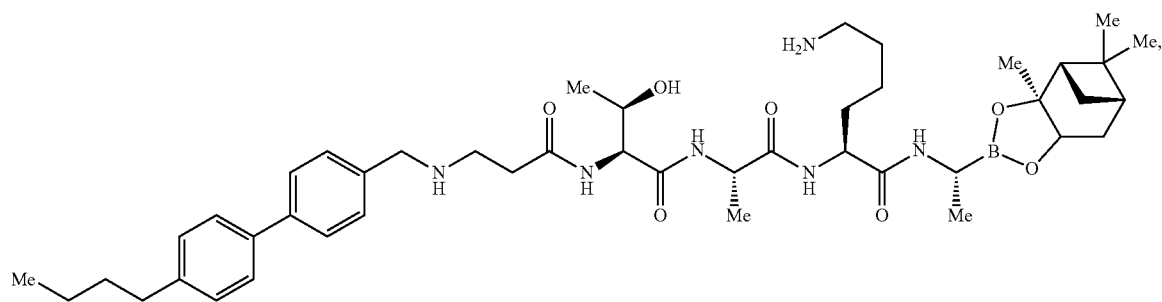
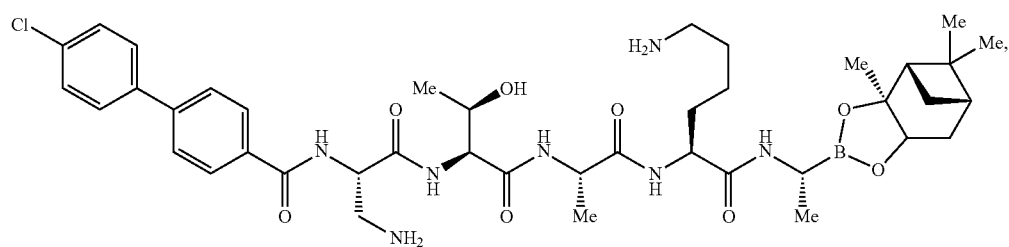

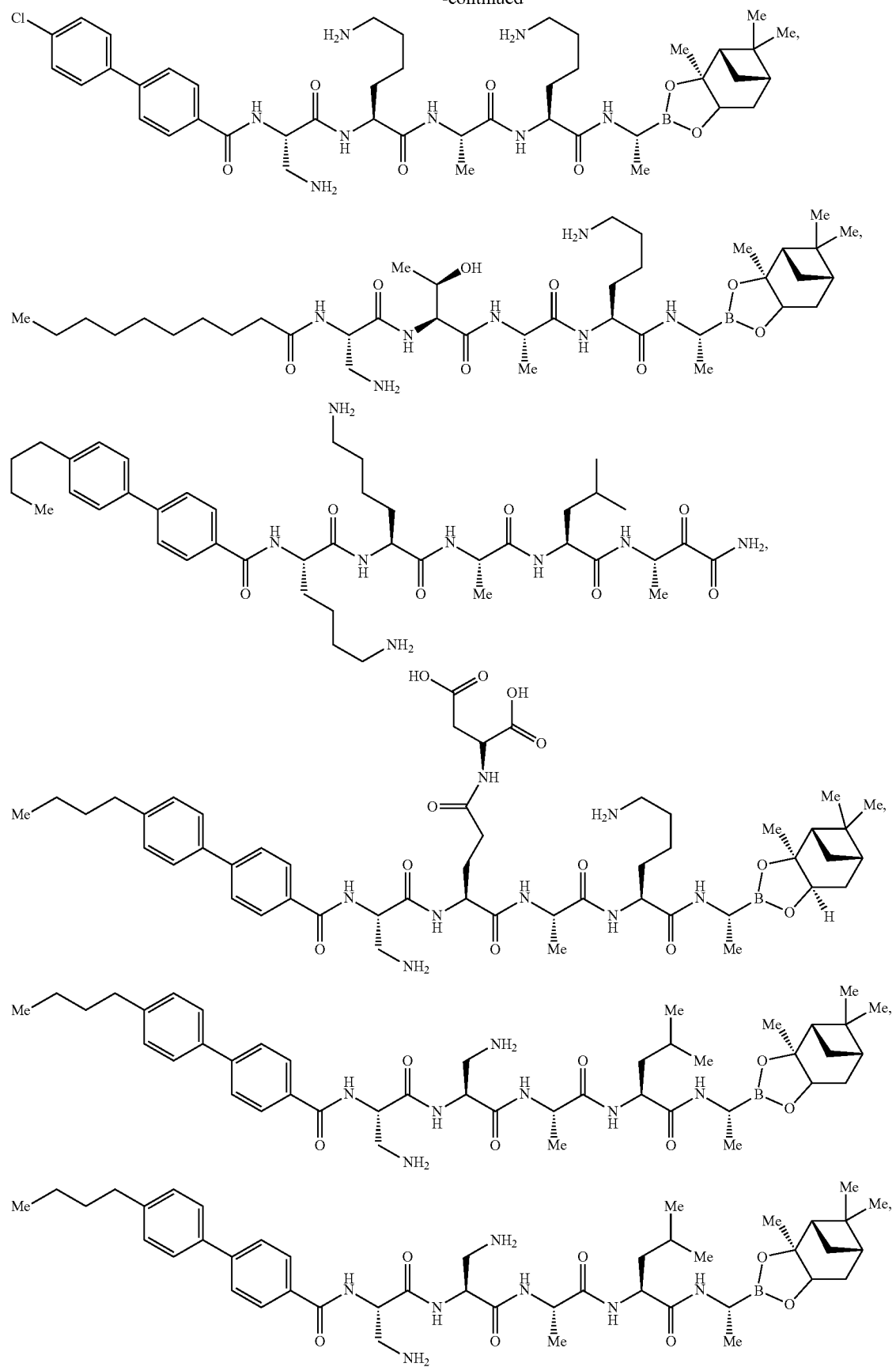

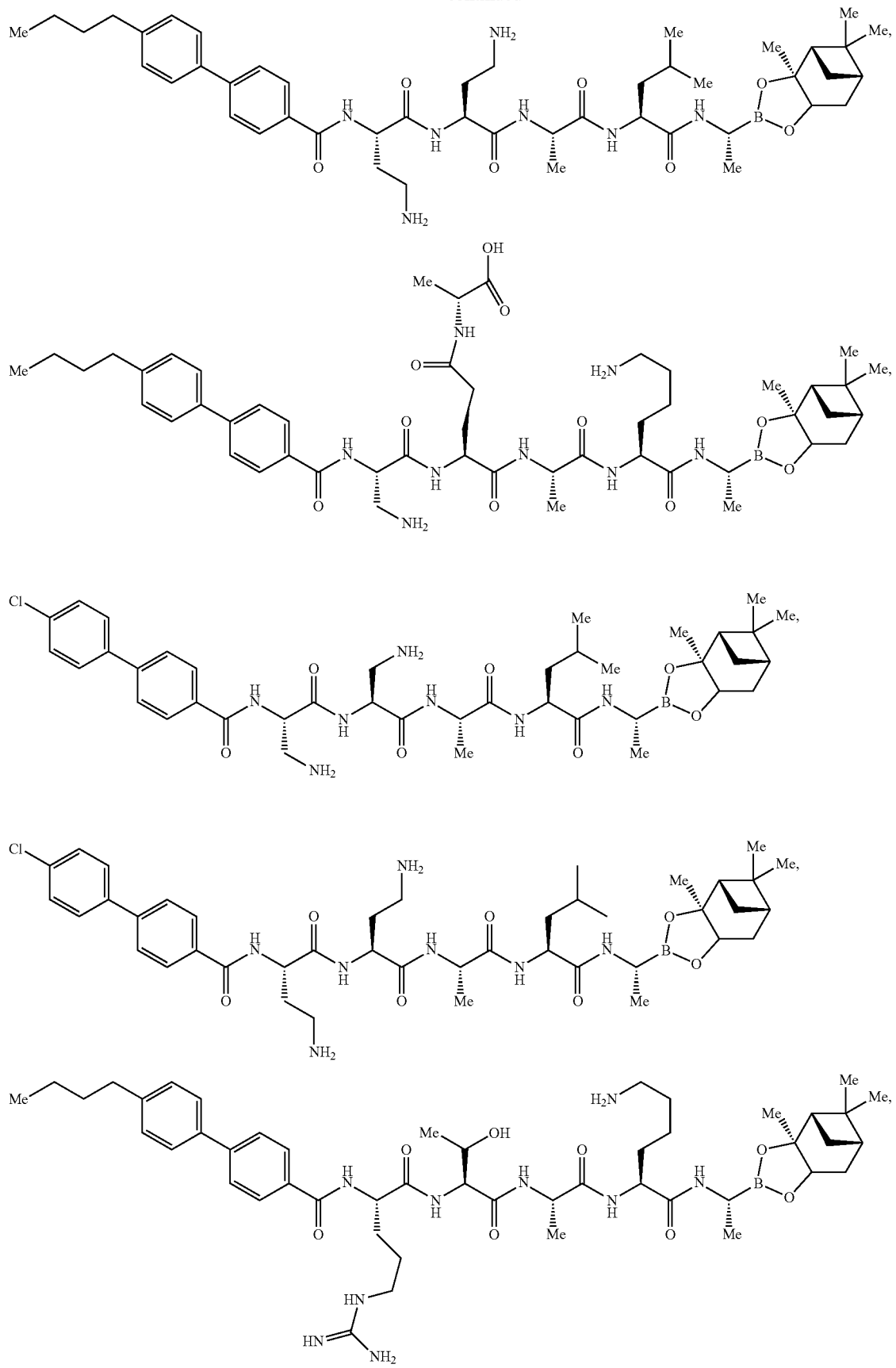

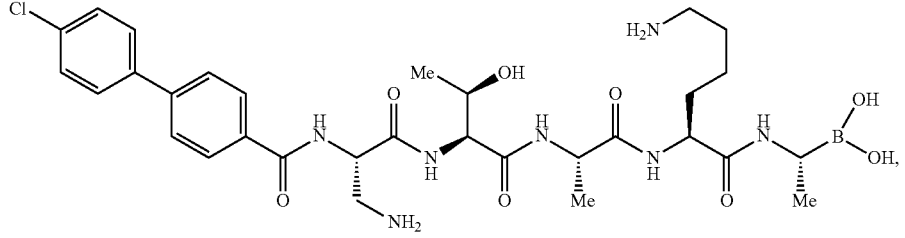
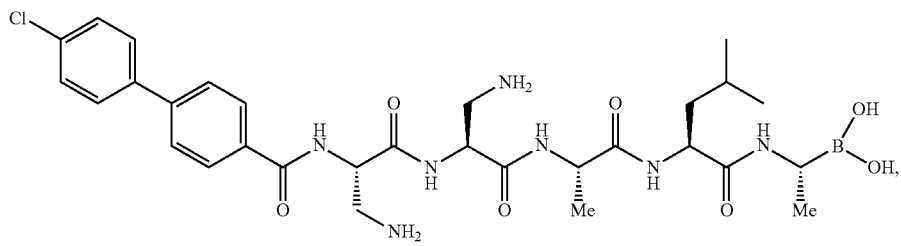
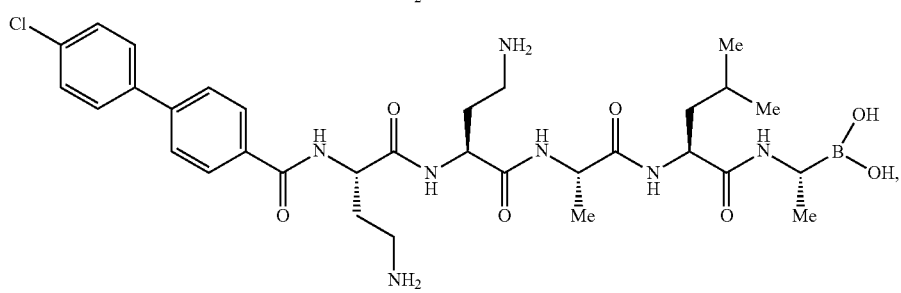
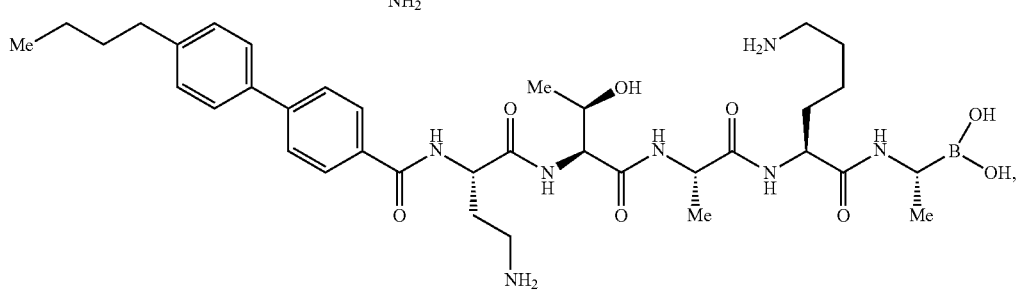
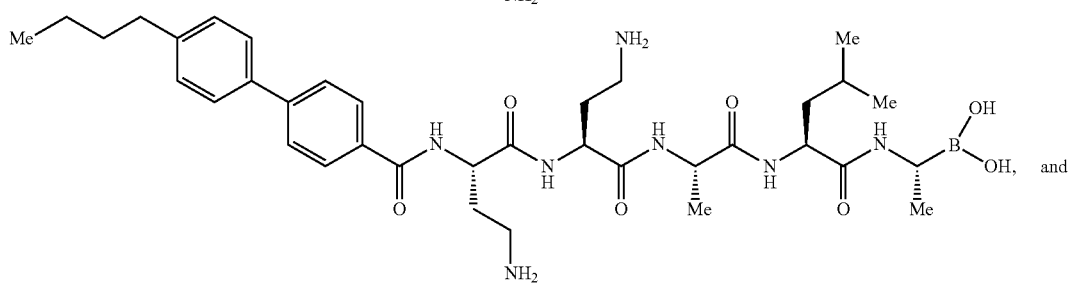
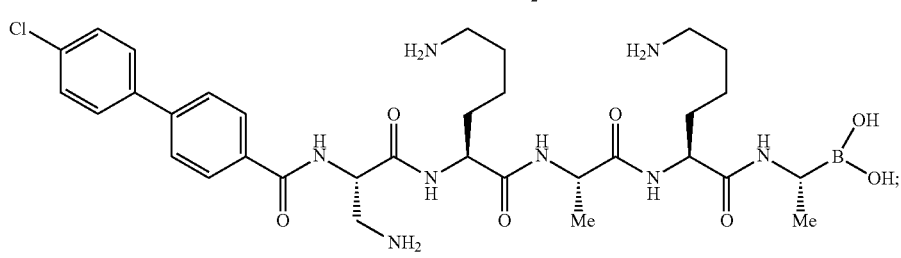
or a pharmaceutically acceptable salt, solvate, or prodrug thereof.

In another aspect are hydrates, or metabolites comprising any of the aforementioned compounds.

In another aspect are pharmaceutical compositions comprising any of the aforementioned compounds together with a pharmaceutically acceptable excipient.

In another aspect described herein is the use of a compound described herein in the manufacture of a medicament for treatment of a bacterial infection in a patient.

In another aspect are methods of treating a mammal in need of such treatment comprising administering to the mammal an antibacterial effective amount of any of the aforementioned compounds at a frequency and for a duration sufficient to provide a beneficial effect to the mammal. In a further embodiment, the causative bacteria species of the bacteria infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*. In another embodiment the bacterial infection is an infection involving a gram negative bacteria. In a further embodiment, the bacterial infection is an infection involving a gram positive bacteria. In another embodiment, the mammal has a bacteria-related infection that is resistant to treatment with arylomycin A2.

In another aspect are methods of treating a mammal in need of such treatment comprising administering to the mammal arylomycin A and/or arylomycin B and/or any of the aforementioned compounds, wherein the infection involves a bacterial species that expresses a signal peptidase without a proline residue within 10 amino acids N-terminal to the signal peptidase catalytic serine. In a further embodiment, the bacterial species encodes or expresses an SPase enzyme without a proline residue 5 to 7 amino acids N-terminal to the SPase catalytic serine. In another embodiment, the bacteria infection is an infection involving *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Staphylococcus carnosus, Staphylococcus cohnii, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oralis, Streptococcus pyogenes*, and/or *Streptococcus pneumoniae*. In another embodiment the bacterial infection is an infection involving a gram negative bacteria. In another embodiment, administering comprises a topical administration.

In another aspect are methods of treating a mammal in need of such treatment comprising administering to the mammal any one or any combination of the aforementioned compounds, wherein the infection involves a bacterial species that expresses a signal peptidase without a proline residue within 10 amino acids N-terminal to the signal peptidase catalytic serine. In a further embodiment, the bacterial species encodes or expresses an SPase enzyme without a proline residue 5 to 7 amino acids N-terminal to the SPase catalytic serine. In another embodiment, the bacteria infection is an infection involving *Staphylococcus capitis, Staphylococcus caprae* and/or *Yersinia pestis*.

In a further embodiment are methods of treating a mammal in need of such treatment comprising administering to the mammal a second therapeutic agent to any of the aforementioned methods of treatment. In another embodiment, the second therapeutic agent is a non-arylomycin antibiotic. In another embodiment, the non-arylomycin antibiotic is an aminoglycoside antibiotic, fluoroquinolone antibiotic, penicillin antibiotic, cephalosporin antibiotic, macrolide antibiotic, glycopeptide antibiotic, rifampicin, chloramphenicol, fluoramphenicol, colistin, mupirocin, bacitracin, daptomycin, or linezolid.

In one embodiment, is a compound described herein which displays antibiotic activity useful in the treatment of bacterial infections, such as by way of example only, various strains of *S. aureus, S. pneumoniae, E. faecalis, E. faecium, B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

Methicillin-Resistant *Staphylococcus aureus*

*Staphylococcus aureus* (*S. aureus*), a spherical bacterium, is the most common cause of staph infections. *S. aureus* has been known to cause a range of illnesses from minor skin infections, such as pimples, impetigo, boils, cellulitis folliculitis, furuncles, carbuncles, scalded skin syndrome, abscesses, to life-threatening diseases such as pneumonia, meningitis, osteomyelitis endocarditis, toxic shock syndrome, and septicemia. Further, *S. aureus* is one of the most common causes of nosocomial infections, often causing post-surgical wound infections.

Methicillin was introduced in the late 1950s to treat infections caused by penicillin-resistant *S. aureus*. It has been reported previously that *S. aureus* isolates had acquired resistance to methicillin (methicillin-resistant *S. aureus*, MRSA).

The methicillin resistance gene (mecA) encodes a methicillin-resistant penicillin-binding protein that is not present in susceptible strains. mecA is carried on a mobile genetic element, the staphylococcal cassette chromosome mec (SCCmec), of which four forms have been described that differ in size and genetic composition. The methicillin-resistant penicillin-binding protein allows for resistance to β-lactam antibiotics and obviates their clinical use during MRSA infections.

In one aspect is a method for treating a subject having a resistant bacterium comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof. In one embodiment, the bacterium is a Gram-positive bacteria. In another embodiment, the Gram-positive bacterium is S. aureus. In further embodiment, the S. aureus is resistant or refractory to a beta-lactam antibiotic. In yet a further embodiment, the beta-lactam antibiotic belongs to the class of penicillins. In a further embodiment, the beta-lactam antibiotic is methicillin. In yet another embodiment, the subject has a methicillin-resistant S. aureus bacteria. In one embodiment the beta-lactam antibiotic is flucloxacillin. In another embodiment is a method for treating a subject having a dicloxacillin-resistant bacteria comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the subject is refractory to dicloxacillin. Also disclosed herein is a method for treating a subject having a methicillin-resistant bacteria comprising administering a compound of Formula (I), (I'), (II), (II'), (III), or (III') or a pharmaceutically acceptable salt, ester, solvate, alkylated quaternary ammonium salt, stereoisomer, tautomer or prodrug thereof wherein the subject has been determined to have a methicillin-resistant bacteria. In one embodiment the subject is screened for methicillin-resistant bacteria. In another embodiment, the subject screening is performed through a nasal culture. In a further embodiment the methicillin-resistant bacteria is detected by swabbing the nostril(s) of the subject and isolating the bacteria. In another embodiment, Real-time PCR and/or Quantitative PCR is employed to determine whether the subject has a methicillin-resistant bacteria.

In one embodiment is a method for treating a subject having a first-generation cephalosporin-resistant bacteria comprising administering a compound of Formula (I) or (I), (I'), (Ia), (Ib), (Ibb), (Ic), (Id), (Ie), (II), or (II') or a pharmaceutically acceptable salt, ester, solvate, alkylated quaternary ammonium salt, stereoisomer, tautomer or prodrug thereof wherein the subject is refractory to a first-generation cephalosporin. In one embodiment, the bacteria is resistant to a first-generation cephalosporin. In a further embodiment, the bacteria is resistant to cefacetrile. In another embodiment, the bacteria is resistant to cefadroxil. In yet another embodiment, the bacteria is resistant to cefalexin. In one embodiment, the bacteria is resistant to cefaloglycin. In another embodiment, the bacteria is resistant to cefalonium. In another embodiment, the bacteria is resistant to cefaloridine. In yet another embodiment, the bacteria is resistant to cefalotin. In a further embodiment, the bacteria is resistant to cefapirin. In yet a further embodiment, the bacteria is resistant to cefatrizine. In one embodiment, the bacteria is resistant to cefazaflur. In another embodiment, the bacteria is resistant to cefazedone. In yet another embodiment, the bacteria is resistant to cefazolin. In a further embodiment, the bacteria is resistant to cefradine. In yet a further embodiment, the bacteria is resistant to cefroxadine. In one embodiment, the bacteria is resistant to ceftezole.

In one embodiment is a method for treating a subject having a second-generation cephalosporin-resistant bacteria comprising administering a compound of Formula (I) or (I), (I'), (Ia), (Ib), (Ibb), (Ic), (Id), (Ie), (II), or (II') or a pharmaceutically acceptable salt, ester, solvate, alkylated quaternary ammonium salt, stereoisomer, tautomer or prodrug thereof wherein the subject is refractory to a second-generation cephalosporin. In another embodiment, the bacteria is resistant to a second-generation cephalosporin. In a further embodiment, the bacteria is resistant to cefaclor. In another embodiment, the bacteria is resistant to cefonicid. In yet another embodiment, the bacteria is resistant to cefprozil. In one embodiment, the bacteria is resistant to cefuroxime. In another embodiment, the bacteria is resistant to cefuzonam. In another embodiment, the bacteria is resistant to cefmetazole. In yet another embodiment, the bacteria is resistant to cefotetan. In a further embodiment, the bacteria is resistant to cefoxitin.

In one embodiment is a method for treating a subject having a third-generation cephalosporin-resistant bacteria comprising administering a compound of Formula (I), (I'), (II), (II'), (III), or (III') or a pharmaceutically acceptable salt, ester, solvate, alkylated quaternary ammonium salt, stereoisomer, tautomer or prodrug thereof wherein the subject is refractory to a third-generation cephalosporin. In another embodiment, the bacteria is resistant to a third-generation cephalosporin. In a further embodiment, the bacteria is resistant to cefcapene. In another embodiment, the bacteria is resistant to cefdaloxime. In yet another embodiment, the bacteria is resistant to cefdinir. In one embodiment, the bacteria is resistant to cefditoren. In another embodiment, the bacteria is resistant to cefixime. In another embodiment, the bacteria is resistant to cefmenoxime. In yet another embodiment, the bacteria is resistant to cefodizime. In a further embodiment, the bacteria is resistant to cefotaxime. In yet a further embodiment, the bacteria is resistant to cefpimizole. In one embodiment, the bacteria is resistant to cefpodoxime. In another embodiment, the bacteria is resistant to cefteram. In yet another embodiment, the bacteria is resistant to ceftibuten. In a further embodiment, the bacteria is resistant to ceftiofur. In yet a further embodiment, the bacteria is resistant to ceftiolene. In one embodiment, the bacteria is resistant to ceftizoxime. In another embodiment, the bacteria is resistant to ceftriaxone. In yet another embodiment, the bacteria is resistant to cefoperazone. In yet a further embodiment, the bacteria is resistant to ceftazidime.

In one embodiment is a method for treating a subject having a fourth-generation cephalosporin-resistant bacteria comprising administering a compound of Formula (I), (I'), (II), (II'), (III), or (III') or a pharmaceutically acceptable salt, ester, solvate, alkylated quaternary ammonium salt, stereoisomer, tautomer or prodrug thereof wherein the subject is refractory to a fourth-generation cephalosporin. In another embodiment, the bacteria is resistant to a fourth-generation cephalosporin. In a further embodiment, the bacteria is resistant to cefclidine. In another embodiment, the bacteria is resistant to cefepime. In yet another embodiment, the bacteria is resistant to cefluprenam. In one embodiment, the bacteria is resistant to cefoselis. In another embodiment, the bacteria is resistant to cefozopran. In another embodiment, the bacteria is resistant to cefpirome. In yet another embodiment, the bacteria is refractory to cefquinome.

In one embodiment is a method for treating a subject having a carbapenem-resistant bacteria comprising administering a compound of Formula (I), (I'), (II), (II'), (III), or (III') or a pharmaceutically acceptable salt, ester, solvate, alkylated quaternary ammonium salt, stereoisomer, tautomer or prodrug thereof wherein the subject is refractory to a carbapenem. In another embodiment, the bacteria is resistant to a carbapenem. In a further embodiment, the bacteria is resistant to imipenem. In another embodiment, the bacteria is resistant to meropenem. In yet another embodiment, the bacteria is resistant to ertapenem. In one embodiment, the bacteria is resistant to faropenem. In another embodiment, the bacteria is resistant to doripenem. In another embodiment, the bacteria is resistant to panipenem. In yet another embodiment, the bacteria is resistant to biapenem, Vancomycin-Intermediate and Vancomycin-Resistant *Staphylococcus aureus*

Vancomycin-intermediate *Staphylococcus aureus* and vancomycin-resistant *staphylococcus aureus* are specific types of antimicrobial-resistant *Staph* bacteria that are refractory to vancomycin treatment. *S. aureus* isolates for which vancomycin MICs are 4-8 µg/mL are classified as vancomycin-intermediate and isolates for which vancomycin MICs are ≥16 µg/mL are classified as vancomycin-resistant (Clinical and Laboratory Standards Institute/NCCLS. Performance Standards for Antimicrobial Susceptibility Testing. Sixteenth informational supplement. M100-S16. Wayne, Pa.: CLSI, 2006).

As used herein, the term "minimum inhibitory concentration" (MIC) refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic is determined from the tube with the lowest concentration that shows no turbidity (no growth).

In one aspect is a method of treating a subject having a bacterial infection comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the bacterial infection comprises a vancomycin-intermediate *Staphylococcus aureus* bacterium. In one embodiment, the vancomycin-intermediate *Staphylococcus aureus* bacterium has a MIC of between about 4 to about 8 µg/mL. In another embodiment, the vancomycin-intermediate *Staphylococcus aureus* bacterium has a MIC of about 4 µg/mL. In yet another embodiment, the vancomycin-intermediate *Staphylococcus aureus* bacterium has a MIC of about 5 µg/mL. In a further embodiment, the vancomycin-intermediate *Staphylococcus aureus* bacterium has a MIC of about 6 µg/mL. In yet a further embodiment, the vancomycin-intermediate *Staphylococcus aureus* bacterium has a MIC of about 7 µg/mL. In one embodiment, the vancomycin-intermediate *Staphylococcus aureus* bacterium has a MIC of about 8 µg/mL.

In another aspect is a method of treating a subject having a bacterial infection comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the bacterial infection comprises a vancomycin-resistant *Staphylococcus aureus* bacterium. In one embodiment, the vancomycin-resistant *Staphylococcus aureus* bacterium has a MIC of between about 16 µg/mL. In another embodiment, the vancomycin-resistant *Staphylococcus aureus* bacterium has a MIC of about ≥16 µg/mL. In yet another embodiment, the vancomycin-resistant *Staphylococcus aureus* bacterium has a MIC of about 20 µg/mL. In a further embodiment, the vancomycin-resistant *Staphylococcus aureus* bacterium has a MIC of about 25 µg/mL.

In one embodiment, conditions treated by the compounds described herein include, but are not limited to, endocarditis, osteomyelitis, neningitis, skin and skin structure infections, genitourinary tract infections, abscesses, and necrotizing infections. In another embodiment, the compounds disclosed herein are used to treat conditions, such as, but not limited to, diabetic foot infections, decubitus ulcers, burn infections, animal or human bite wound infections, synergistic-necrotizing gangrene, necrotizing fasciitis, intra-abdominal infection associated with breeching of the intestinal barrier, pelvic infection associated with breeching of the intestinal barrier, aspiration pneumonia, and post-operative wound infections. In another embodiment, the conditions listed herein are caused by, contain, or result in the presence of VISA and/or VRSA.

Vancomycin-Resistant Enterococci

Enterococci are bacteria that are normally present in the human intestines and in the female genital tract and are often found in the environment. These bacteria sometimes cause infections. In some cases, enterococci have become resistant to vancomycin (also known as vancomycin-resistant enterococci or VRE.) Common forms of resistance to vancomycin occur in enterococcal strains that involve the acquisition of a set of genes endoding proteins that direct peptidoglycan precursors to incorporate D-Ala-D-Lac instead of D-Ala-D-Ala. The six different types of vancomycin resistance shown by *enterococcus* are: Van-A, Van-B, Van-C, Van-D, Van-E and Van-F. In some cases, Van-A VRE is resistant to both vancomycin and teicoplanin, while in other cases, Van-B VRE is resistant to vancomycin but sensitive to teicoplanin; in further cases Van-C is partly resistant to vancomycin, and sensitive to teicoplanin.

In one aspect, is a method of treating a subject having a vancomycin-resistant enterococci comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the enterococci has developed resistance to vancomycin. In one embodiment, the subject has been previously treated with vancomycin for a sustained period of time. In another embodiment, the subject has been hospitalized. In yet another embodiment, the subject has a weakened immune system such as patients in Intensive Care Units or in cancer or transplant wards. In a further embodiment, the subject has undergone surgical procedures such as, for example, abdominal or chest surgery. In yet a further embodiment, the subject has been colonized with VRE. In one embodiment, the subject has a medical device such that an infection has developed. In another embodiment, the medical device is a urinary catheter or central intravenous (IV) catheter.

In another embodiment, is a method of treating a subject having a vancomycin-resistant enterococci comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the *enterococcus* has Van-A resistance.

In another embodiment, is a method of treating a subject having a vancomycin-resistant enterococci comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the *enterococcus* has Van-B resistance.

In another embodiment, is a method of treating a subject having a vancomycin-resistant enterococci comprising administering to the subject a compound of Formula (I), (I'), (II), (II'), (III), or (III') or a pharmaceutically acceptable salt, ester, solvate, alkylated quaternary ammonium salt, stereoisomer, tautomer or prodrug thereof wherein the *enterococcus* has Van-C resistance.

Administration and Pharmaceutical Composition

Pharmaceutical compositions described herein comprise a therapeutically effective amount of a compound described herein (i.e., a compound of any of Formula (I), (I'), (II), (II'), (III), or (III')) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound of any of Formula (I), (I'), (II), (II'), (III), or (III')) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprises buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of a aerosol particles having with a mass medium average diameter predominantly between 1 to 5μ. Further, the formulation preferably has balanced osmolarity ionic strength and chloride concentration, and the smallest aerosolizable volume able to deliver effective dose of the compounds described herein compound described herein (i.e., a compound of any of Formula (I), (I'), (II), (II'), (III), or (III')) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5 microns. Predominantly in this application means that at least 70% but preferably more than 90% of all generated aerosol particles are within 1-5 micron range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, compounds described herein compound described herein (i.e., a compound of any of Formula (I), (I'), (II), (II'), (III), or (III')) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment;

drugs used in combination or coincidental with the specific compound employed; and like factors known in the medical arts.

The total daily dose of the compounds described herein compound described herein (i.e., a compound of any of Formula (I), (I'), (II), (II'), (III), or (III')) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Example 1

General Method 1:

The preparation of fully protected peptide fragments. Fully protected peptide fragments four to six amino acids in length terminated by a lipophilic carboxylic acid tail are synthesized on solid phase using chlorotrityl functionalized polystyrene resin (Trt-Cl) and an Fmoc/tBu/Trt/t-Boc protecting group strategy and is depicted in Scheme I. Cleavage of the fully protected peptide 1 is accomplished by repeated treatment of the resin with 1% TFA in $CH_2Cl_2$ and aqueous workup of the combined filtrates. A representative example of General Method 1 is depicted in Scheme 1A to afford peptide 1A.

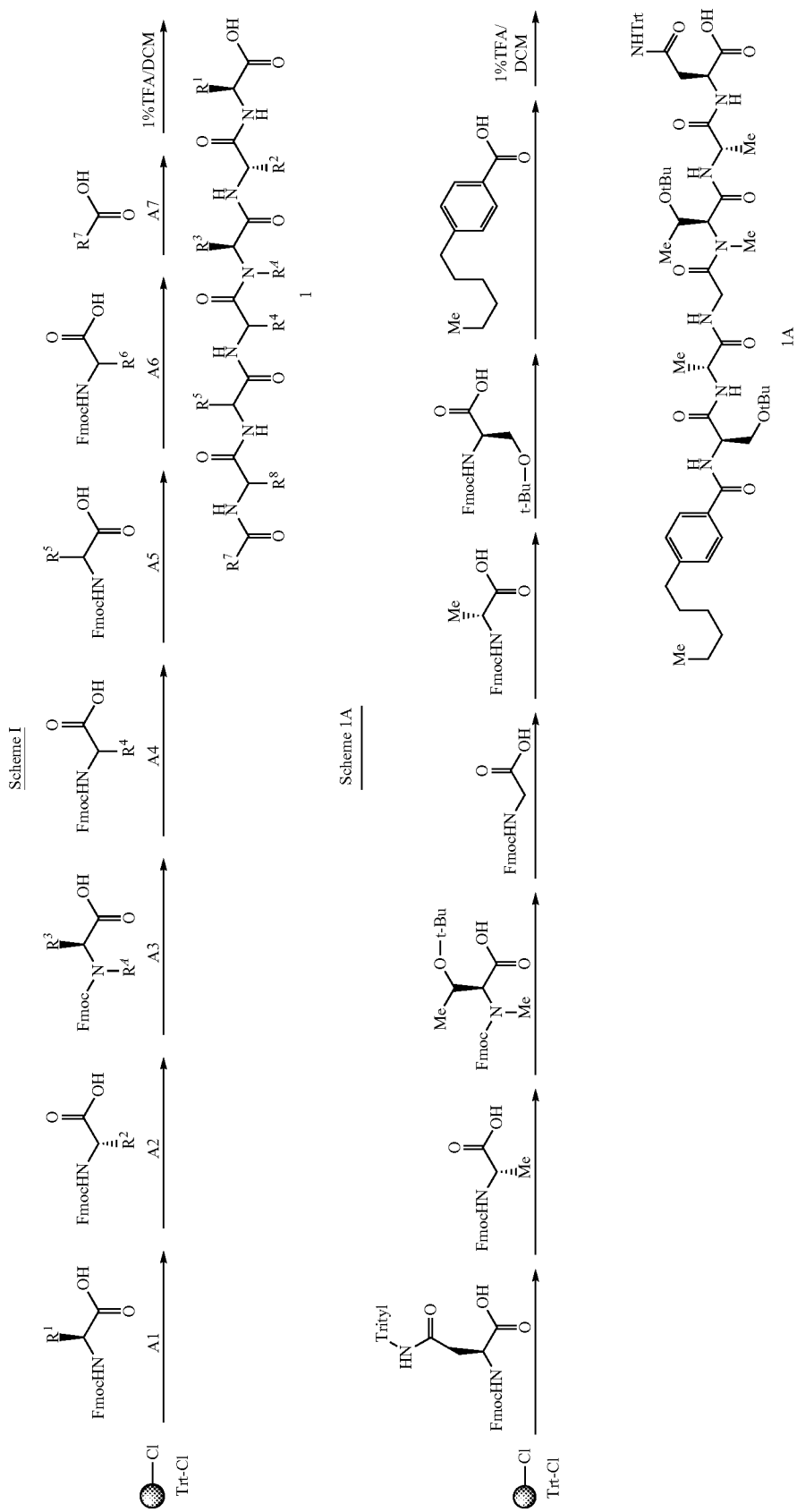

General Method 2:

The synthesis of aldehydes. The peptides from General Method 1 are used in the next steps without further purification as depicted in Scheme II. The peptide 1 is dissolved in a N,N-dimethylformamide, and to the reaction is sequentially added hydroxybenzotriazole (HOBt), aminoacetaldehyde dimethyl acetal (R=H) or 2-aminopropionaldehyde dimethyl acetal (R=Me) and 1-ethyl-3-(3-dimethylaminopropyl) carbodiimide (EDC). The reaction is then sealed and heated to 50° C. for 3 hrs. The reaction is then cooled to room temperature and diluted with water, 10% citric acid and ethyl acetate. The aqueous phase is extracted with ethyl acetate and the combined organic layers are washed with sodium bicarbonate solution, water and brine then dried over sodium sulfate and concentrated. The crude material is then treated with a mixture of 95:2.5:2.5 trifluoroacetic acid:dichloromethane:water for approximately 5 minutes. The volatile solvents are then evaporated, the crude material is taken up in dichloromethane and evaporated again. The crude material is purified by HPLC on a Hypersil Gold column (10 mm×250 mm, particle size—5 micron) to afford the desired compound.

Scheme II

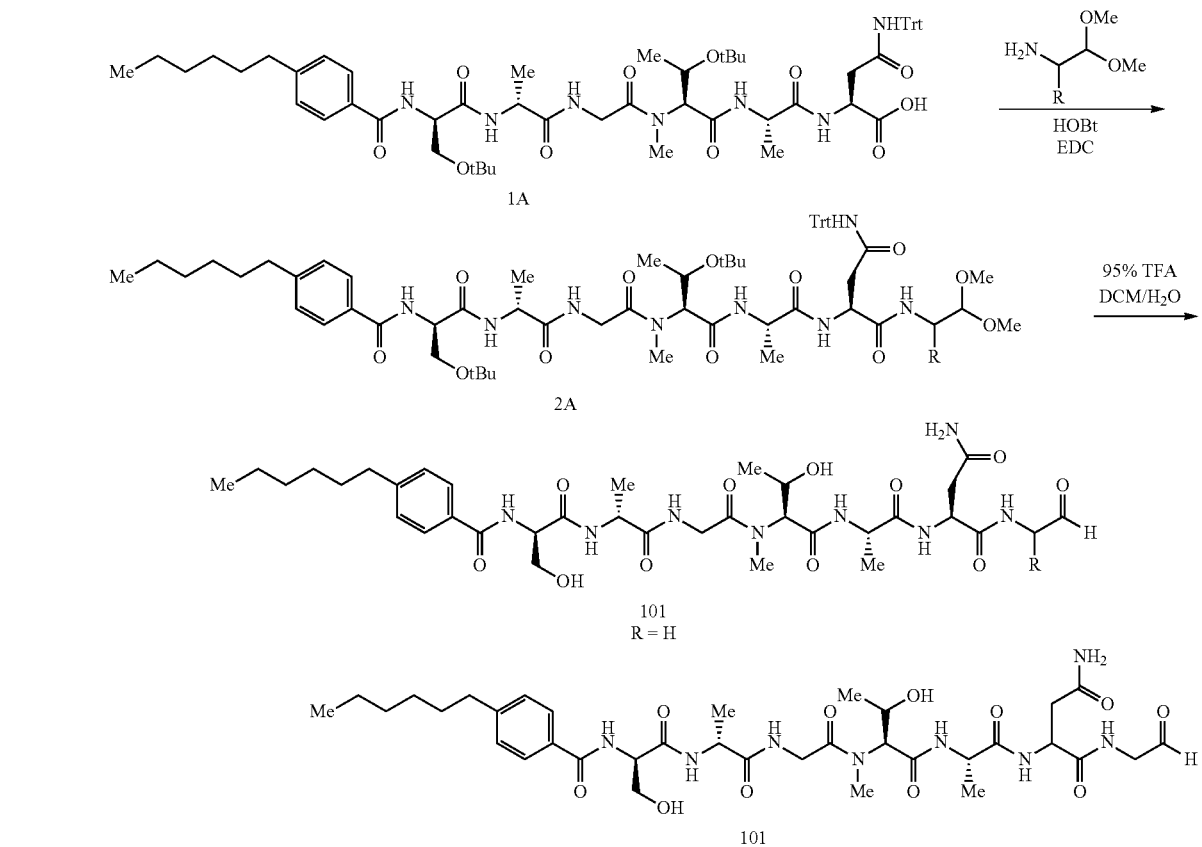

Compound 101: This compound was prepared according to General Method 1 and 2 to afford the title compound. MS (ESI) for ($C_{35}H_{54}N_8O_{11}$): m/z 763.1 (M+H).

Example 2

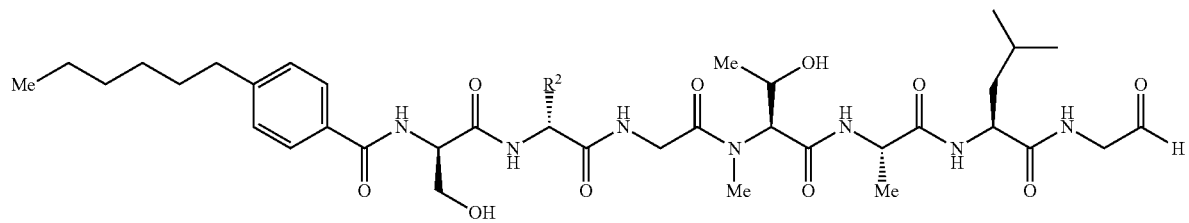

Compound 102: This compound was prepared according to General Method 1 and 2 to afford the title compound. MS (ESI) for ($C_{37}H_{59}N_7O_{10}$): m/z 762.1 (M+H).

Example 3

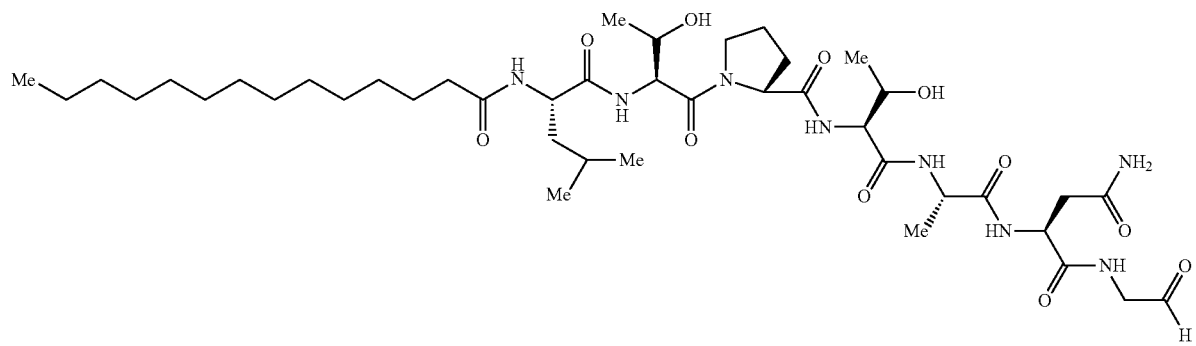

103

Compound 103: This compound was prepared according to General Method 1 and 2 to afford the title compound. MS (ESI) for ($C_{42}H_{74}N_8O_{11}$): m/z 867.3 (M+Na).

Example 4

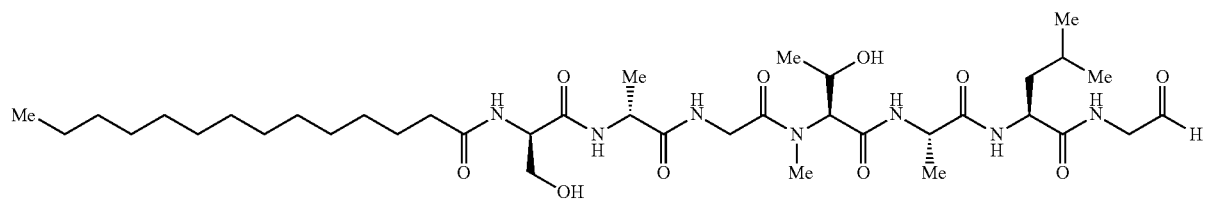

104

Compound 104: This compound was prepared according to General Method 1 and 2 to afford the title compound. MS (ESI) for ($C_{38}H_{69}N_7O_{10}$): m/z 784.3 (M+H).

Example 5

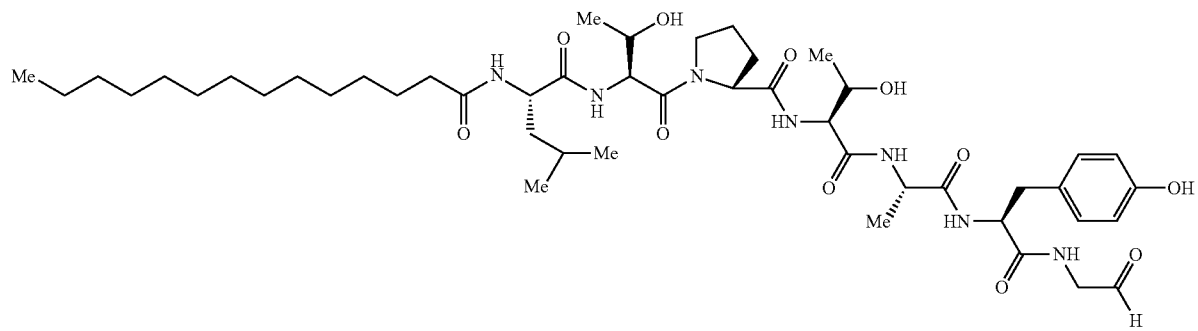

105

Compound 105: This compound was prepared according to General Method 1 and 2 to afford the title compound. MS (ESI) for ($C_{47}H_{77}N_7O_{11}$): m/z 938.5 (M+Na).

Example 6

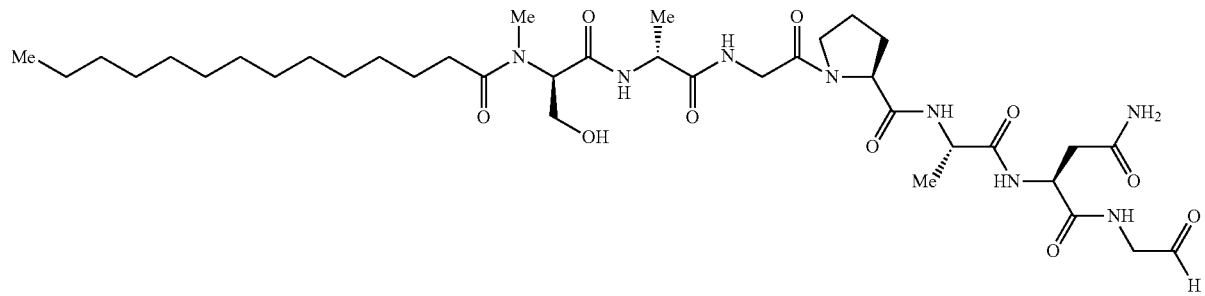

Compound 106: This compound was prepared according to General Method 1 and 2 to afford the title compound. MS (ESI) for ($C_{37}H_{64}N_8O_{10}$): m/z 767.3 (M+H).

Example 7

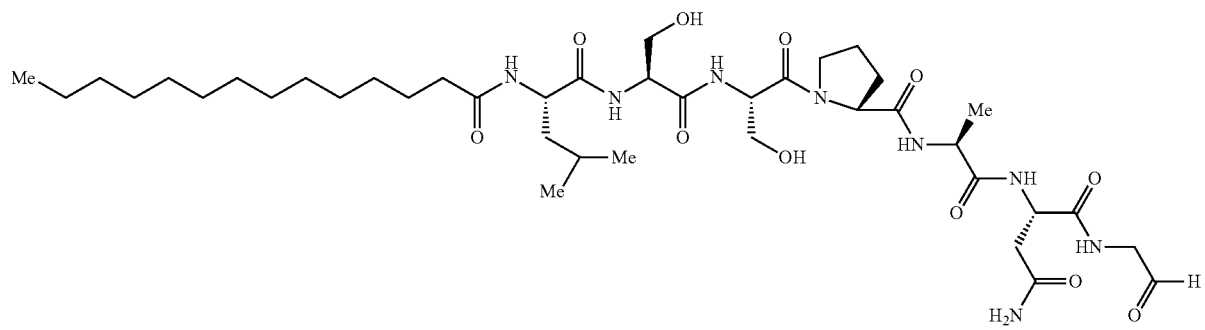

Compound 107: This compound was prepared according to General Method 1 and 2 to afford the title compound. MS (ESI) for ($C_{40}H_{70}N_8O_{11}$): m/z 839.4 (M+H).

Example 8

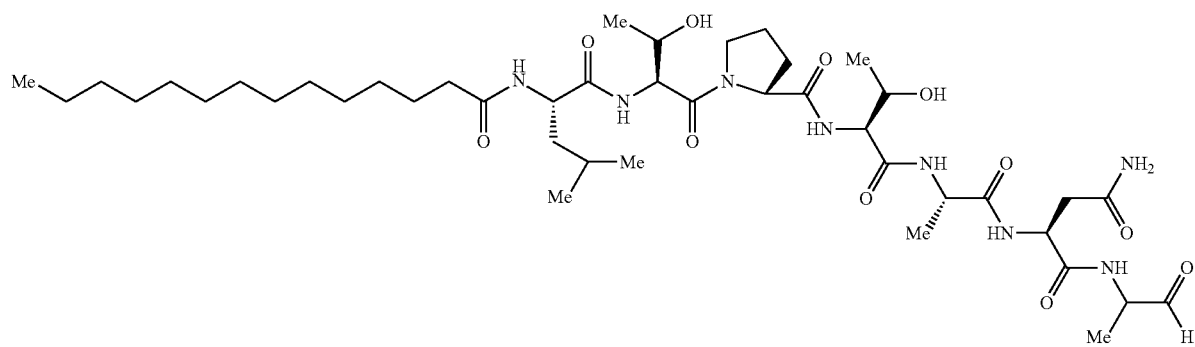

Compound 108: This compound was prepared according to General Method 1 and 2 to afford the title compound. MS (ESI) for ($C_{43}H_{76}N_8O_{11}$): m/z 881.6 (M+H).

Example 9

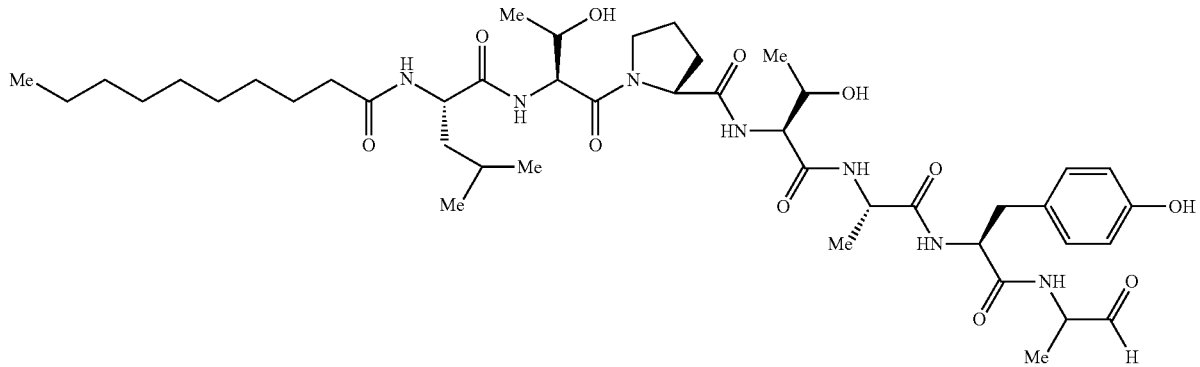

109

Compound 109: This compound was prepared according to General Method 1 and 2 to afford the title compound. MS (ESI) for ($C_{44}H_{71}N_7O_{11}$): m/z 874.5 (M+H).

Example 10

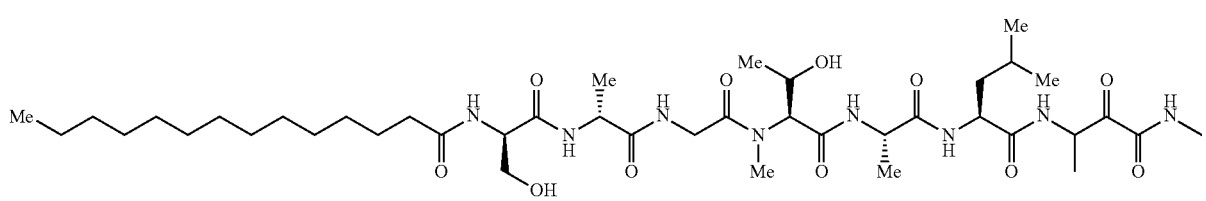

110

Compound 110: The synthesis of Compound 110 is depicted in Scheme III. Peptide 1-110 is prepared according to General Method 1. A solution of 1-110 (40 mg, 0.047 mmol) in anhydrous DMF (1 mL) was treated with EDCI (54 mg, 0.28 mmol) and HOBt (31.7 mg, 0.235 mmol) followed by DIEA (18.2 mg, 0.141 mmol) and K4 (6.2 mg, 0.047 mmol). The mixture was stirred at room temperature overnight. After ELSD showed the reaction was complete, the mixture was purified by prep-HPLC to afford 3-110 (17 mg, yield 37.4%). To a solution of 3-110 (17 mg, 0.018 mmol) in anhydrous dichloromethane (1 mL) was added Dess-Martin periodinane (22.9 mg, 0.054 mmol) in one portion at 0° C. The reaction mixture was allowed to stir at room temperature overnight. After HPLC showed the reaction was complete, the mixture was filtered and the filtrate was concentrated in vacuo at room temperature to afford 4-110 (16 mg) as a white solid. A solution of 4-110 (16 mg, 0.016 mmol) in 1 mL of trifluoroacetic acid containing 5% water and 5% dichloromethane was stirred at room temperature for 15 mins. After ELSD showed the reaction was complete, the solvent was removed. The residue was purified by prep-HPLC (Luna C8 5 μm 150×21.2 mm) to afford Compound 110 (1.6 mg, yield 13.7%) as a mixture of diastereomers. MS (ESI) for ($C_{41}H_{74}N_8O_{11}$): m/z 855.5 (M+H).

Scheme III

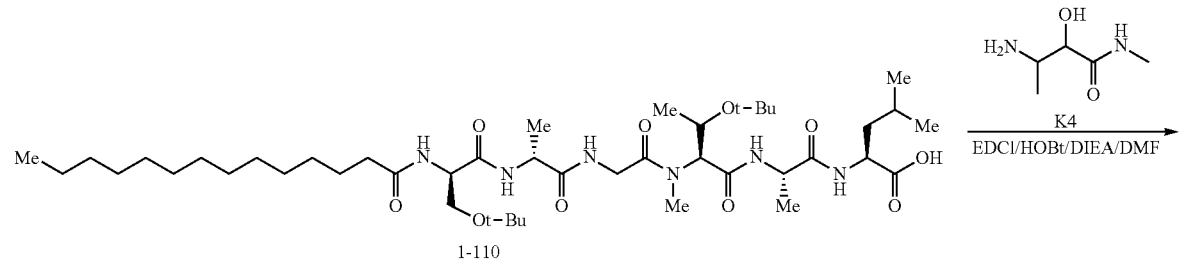

1-110

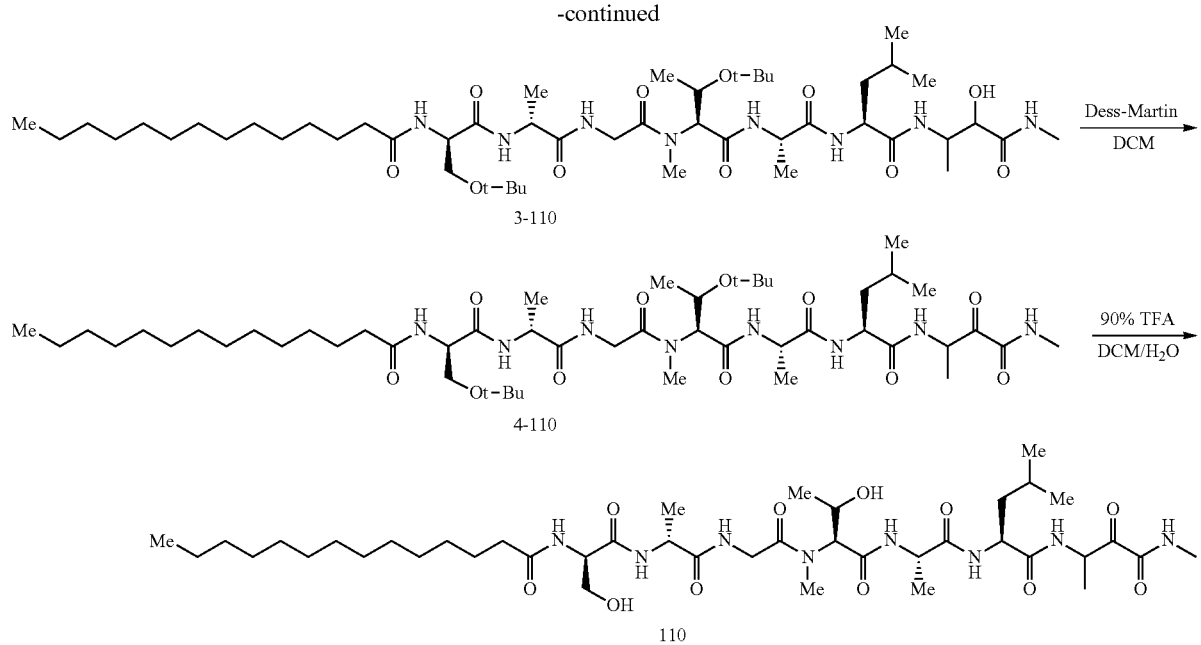

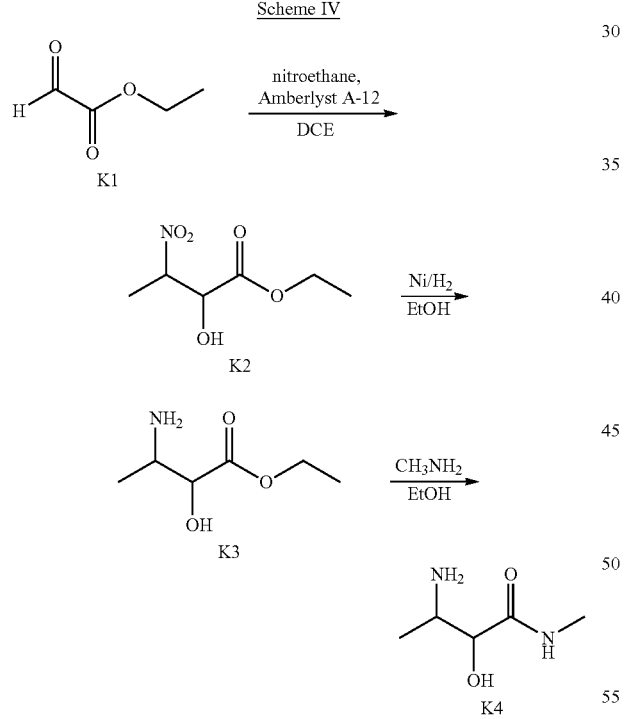

The preparation of K4 is depicted in Scheme IV.

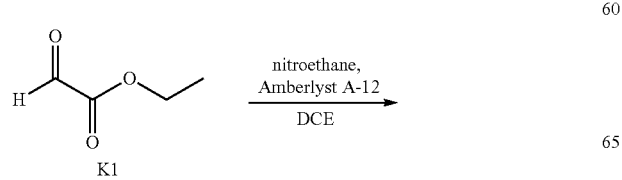

A mixture of nitroethane (3.6 g, 0.5 mol) and Amberlyst A-12 (20 g) in 1,2-dichloroethane (30 mL) was cooled to 0° C. K1 (5 g, 50% solution in toluene) was added. The resulting mixture was stirred at room temperature overnight. The mixture was filtered and the filtrate was concentrated in vacuo to give K2 (4.2 g, 97% yield), as an oil.

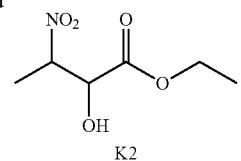

A mixture of K2 (0.2 g, 1.1 mmol) and Raney nickel (0.2 g) in ethanol (5 mL) was subjected to hydrogen gas at 30 psi hydrogen at room temperature for 10 hrs. The mixture was filtered and the filtrate was concentrated in vacuo to afford K3. The residue was used in the next step without further purification.

To a 30% solution of methylamine in absolute ethanol (20 mL) was added K3 (160 mg, 1 mmol). The solution was refluxed for 2 hrs. After evaporation of the solvent, the residue was recrystallized from dichloromethane/ethyl acetate to give K4 (100 mg, 70% yield), as a yellow solid.

Example 11

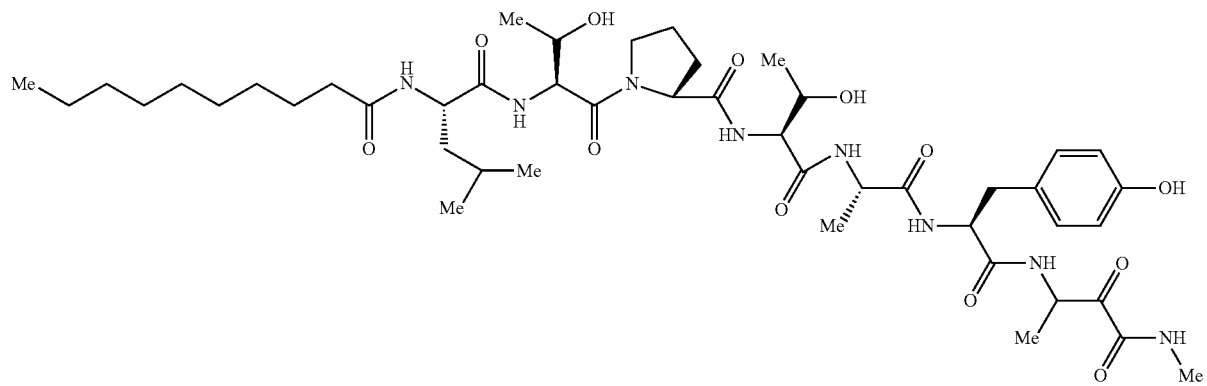

111

Compound 111: The synthesis of Compound 111 is depicted in Scheme V. Peptide 1-111 is prepared according to General Method 1. A solution of 1-111 (100 mg, 0.1 mmol) in anhydrous DMF (1 mL) was treated with EDCI (115.2 mg, 0.6 mmol) and HOBt (67.5 mg, 0.5 mmol) followed by DIEA (38.7 mg, 0.3 mmol) and K4 (13.2 mg, 0.1 mmol). The mixture was stirred at room temperature overnight. After ELSD showed the reaction was completed, the mixture was purified by prep-HPLC (Luna C8, 5 μm, 150×21.2 mm) to give 45 mg (40.5%) of 3-111 as a mixture of diastereomers.

To a solution of 3-111 in 1 mL of anhydrous dichloromethane was added Dess-Martin periodinane (3 eq) in one portion at 0° C. The reaction mixture was allowed to stir at room temperature overnight. After ELSD showed the reaction was complete, the mixture was filtered and the filtrate was concentrated in vacuo at room temperature to afford 45 mg (100%) of 4-111 as a mixture of diastereomers. A solution of 4-111 in 1 mL of trifluoroacetic acid containing 5% water and 5% dichloromethane was stirred at room temperature for 15 minutes. After ELSD showed the reaction was complete, the solvent was removed under reduced pressure. The residue was purified by prep-HPLC (Luna C8, 5 μm, 150×21.2 mm) to afford 2.6 mg (6.8%) of Compound 111 as a mixture of diastereomers. MS (ESI) for ($C_{46}H_{74}N_8O_{12}$): m/z 931.5 (M+H).

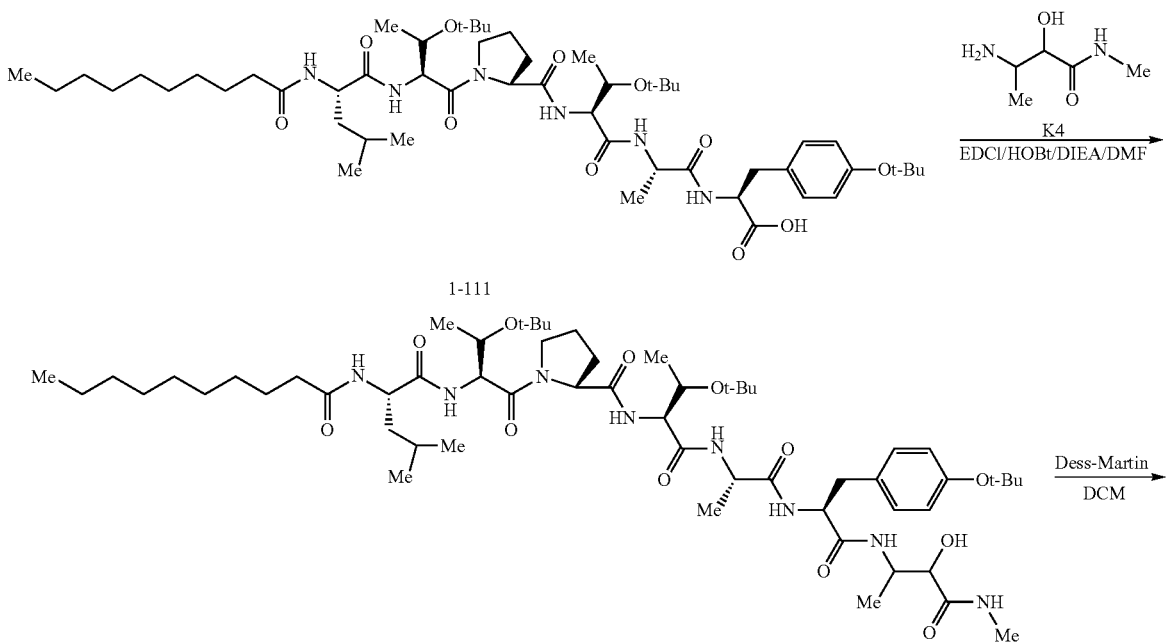

Scheme V

-continued

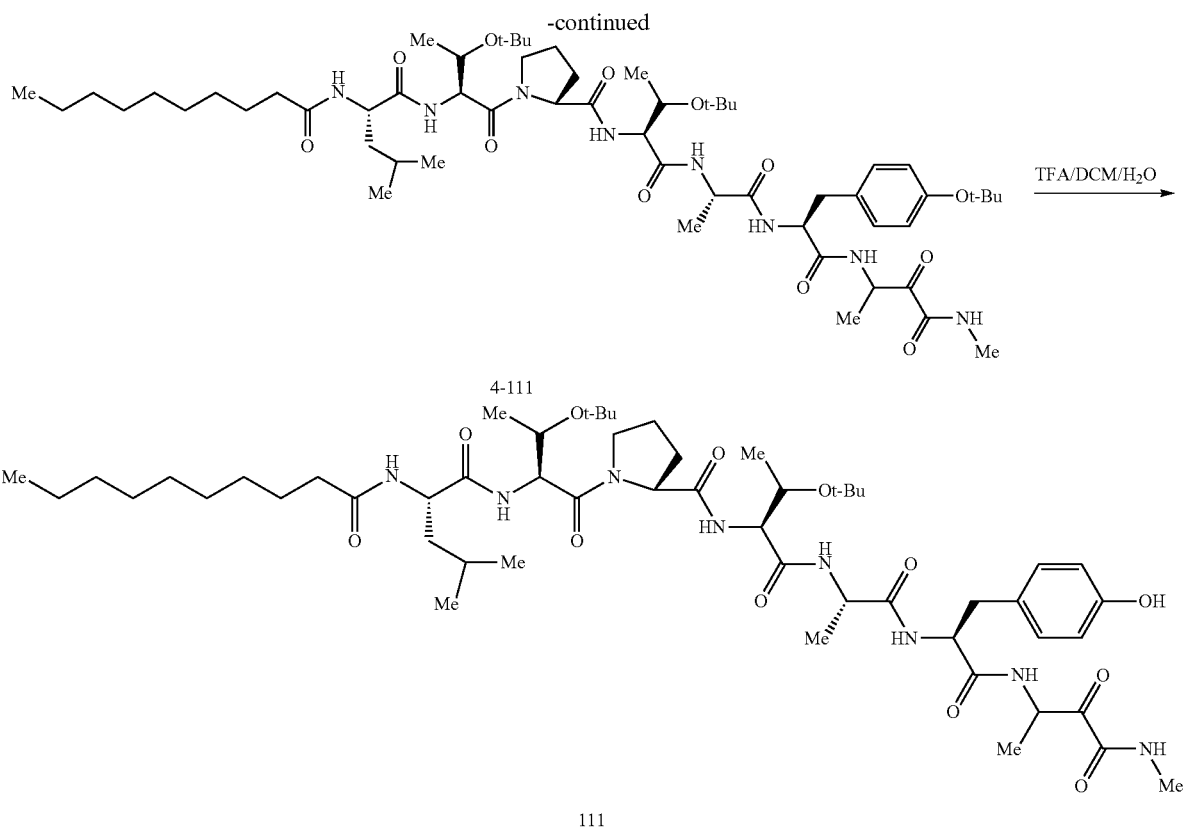

111

Example 12

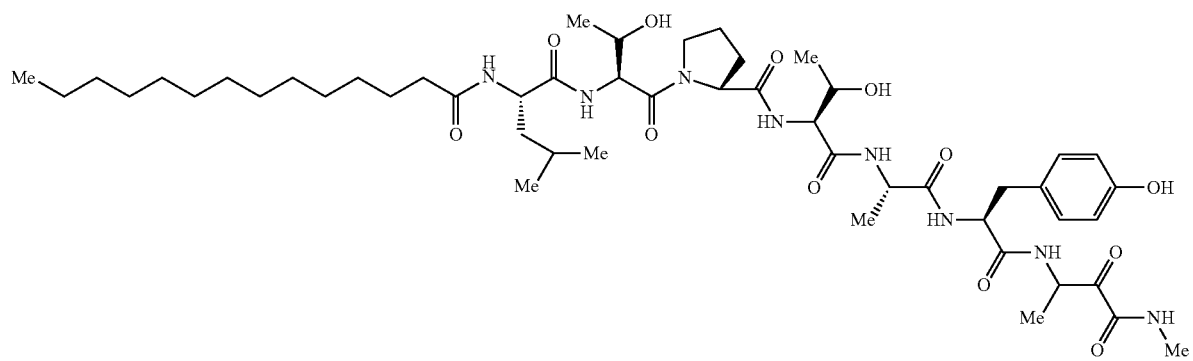

112

The synthesis of Compound 112 is depicted in Scheme VI. Peptide 1-112 is prepared according to General Method 1. A solution of 1-112 (100 mg, 0.096 mmol) in anhydrous DMF (1 mL) was treated with EDCI (96 mg, 0.5 mmol) and HOBt (67.5 mg, 0.5 mmol) followed by DIEA (64.5 mg, 0.5 mmol) and K4 (13.2 mg, 0.1 mmol). The mixture was stirred at room temperature overnight. After ELSD showed the reaction was complete, the mixture was purified by prep-HPLC (Luna C8, 5 µm, 150×21.2 mm) to give 32 mg (29%) of 3-112 as a mixture of diastereomers. To a solution of 3-112 in 1 mL of anhydrous dichloromethane was added Dess-Martin periodinane (3 equv.) in one portion at 0° C. The reaction mixture was allowed to stir at room temperature overnight. After ELSD showed the reaction was complete, the mixture was filtered and the filtrate was concentrated in vacuo at room temperature to give 31 mg (100%) of 4-112 as a mixture of diastereomers. A solution of 4-112 in 1 mL of trifluoroacetic acid containing 5% water and 5% dichloromethane was stirred at room temperature for 15 minutes. After ELSD showed the reaction was complete, the solvent was removed under reduced pressure. The residue was purified by prep-HPLC (Luna C8, 5 µm, 150×21.2 mm) to give 5.1 mg (19%) of Compound 112 as a mixture of diastereomers. MS (ESI) for ($C_{50}H_{82}N_8O_{12}$): m/z 987.5 (M+H).

Scheme VI
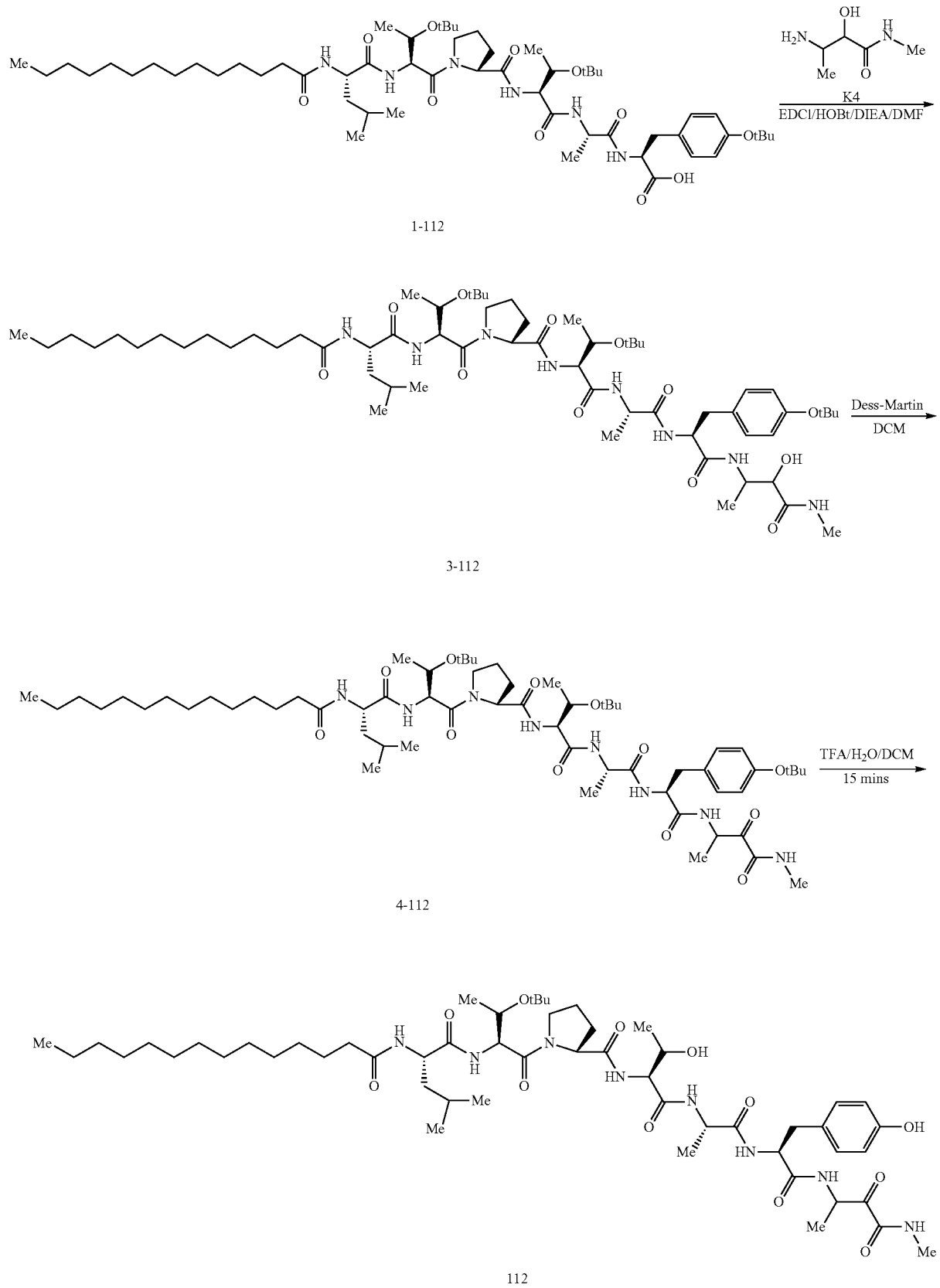

Example 13

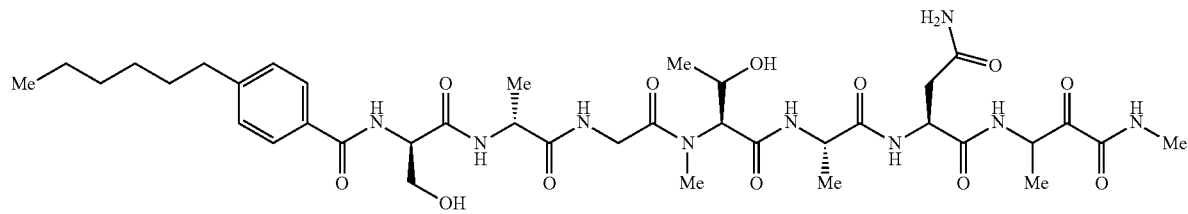

113

Compound 113: The synthesis of Compound 113 is depicted in Scheme VII. Peptide 1A (EXAMPLE 1) was prepared according to General Method 1. A solution of 1A (100 mg, 0.096 mmol) in anhydrous DMF (1 mL) was treated with EDCI (96 mg, 0.5 mmol) and HOBt (67.5 mg, 0.5 mmol) followed by DIEA (64.5 mg, 0.5 mmol) and K4 (13.2 mg, 0.1 mmol). The mixture was stirred at room temperature overnight. After ELSD showed the reaction was com the mixture was purified by prep-HPLC (Luna C8, 5 μm, 150×21.2 mm) to give 3-113 (40 mg, 38.1% yield). To a solution of 3-113 in 1 mL of anhydrous dichloromethane was added Dess Martin periodinane (3 eq) in one portion at 0° C. The reaction mixture was allowed to stir at room temperature overnight. After ELSD showed the reaction was complete, the mixture was filtered and the filtrate was concentrated in vacuo at room temperature to give 4-113 (40 mg, yield 100%). A solution of 4-113 (40 mg, 0.034 mmol) in 1 mL of trifluoroacetic acid containing 5% water and 5% dichloromethane was stirred at room temperature for 15 minutes. After ELSD showed the reaction was complete, the solvent was removed under reduced pressure. The residue was purified by prep-HPLC (Luna C8, 5 μm, 150×21.2 mm) to give 6 mg (20%) of Compound 113, as a mixture of diastereomers. MS (ESI) for ($C_{38}H_{59}N_9O_{12}$): 834.4 m/z (M+H).

Scheme VII

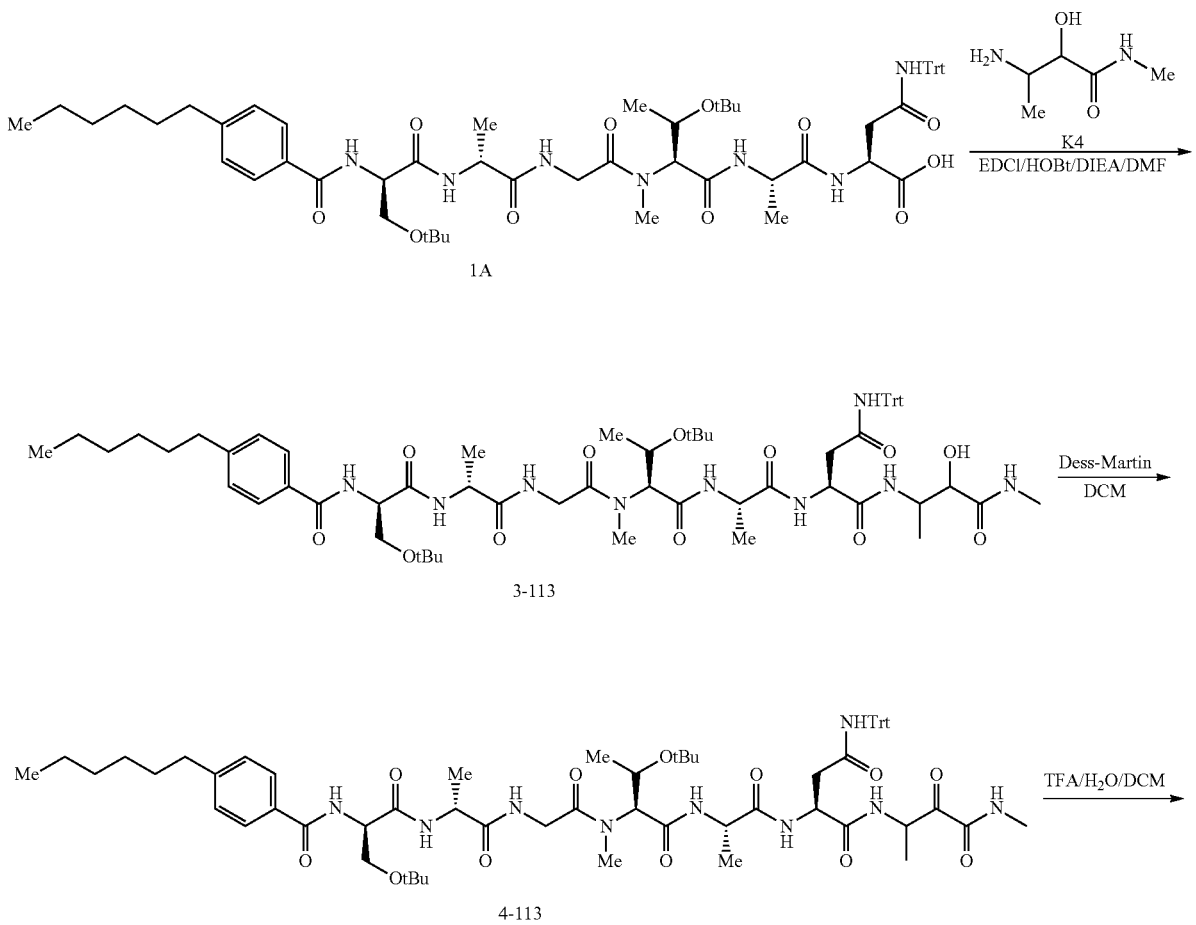

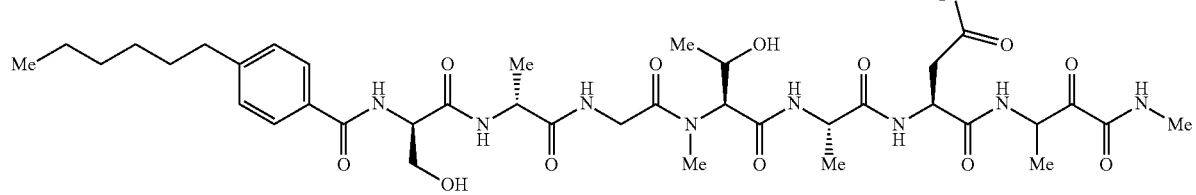

113

Example 14

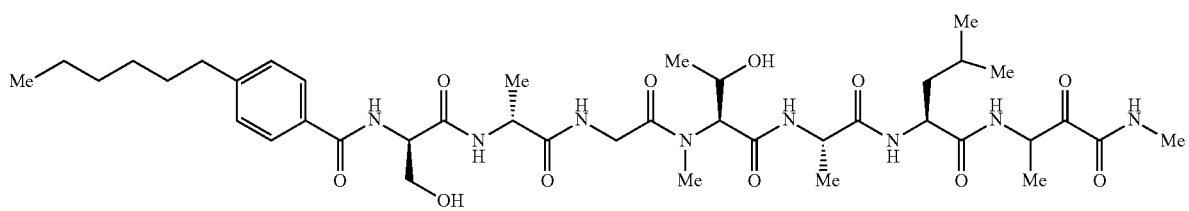

114

Compound 114: The synthesis of Compound 114 is depicted in Scheme VIII. Peptide 1-114 was prepared according to General Method 1. A solution of 1-114 (100 mg, 0.12 mmol) in anhydrous DMF (1 mL) was treated with EDCI (115.2 mg, 0.6 mmol) and HOBt (81 mg, 0.6 mmol) followed by DIEA (77.4 mg, 0.6 mmol) and K4 (15.8 mg, 0.12 mmol). The mixture was stirred at room temperature overnight. After ELSD showed the reaction was complete, the mixture was purified by prep-HPLC (Luna C8, 5 μm, 150×21.2 mm) to give 43 mg (47%) of 3-114 as a mixture of diastereomers. To a solution of 3-114 in 1 mL of anhydrous dichloromethane was added Dess Martin periodinane (3 eq.) in one portion at 0° C. The reaction mixture was allowed to stir at room temperature overnight. After ELSD showed the reaction was complete, the mixture was filtered and the filtrate was concentrated in vacuo at room temperature to yield 62 mg (100%) of 4-114 as a mixture of diastereomers. A solution of 4-114 in 1 mL of trifluoroacetic acid containing 5% anisole and 5% thioanisole was stirred at room temperature for 15 minutes. After ELSD showed the reaction was complete, the solvent was removed. The residue was purified by prep-HPLC (Luna C8, 5 μm, 150×21.2 mm) to afford Compound 114 as a mixture of diastereomers. MS (ESI) for ($C_{40}H_{64}N_8O_{11}$): 833.4 m/z (M+H).

Scheme VIII

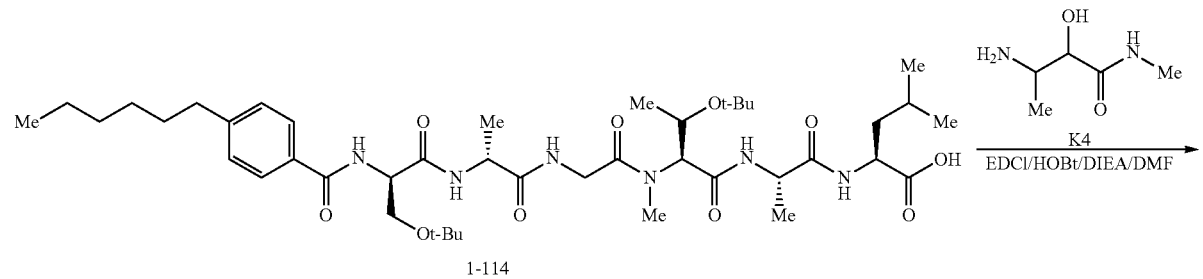

1-114

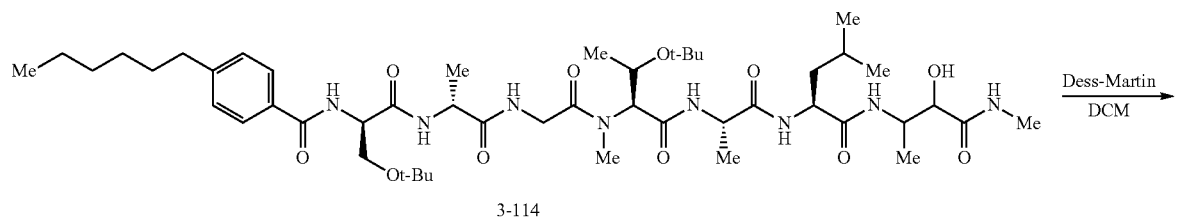

3-114

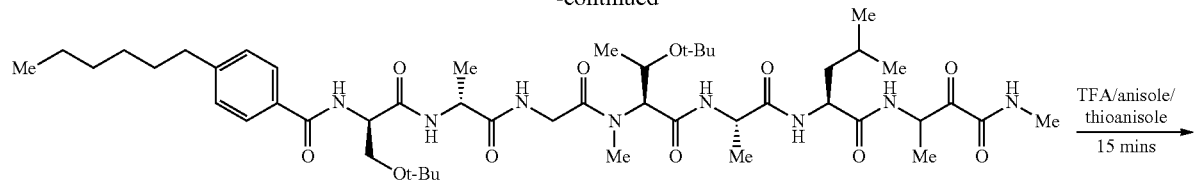

4-114

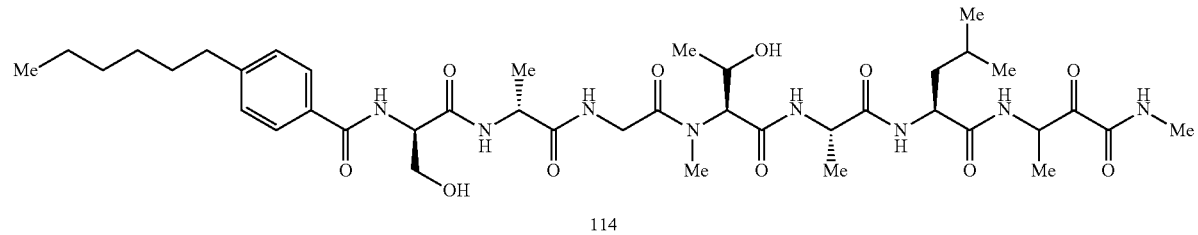

114

Example 15

General Method 3:

Addition of a (bis(trimethylsilyl)amino)methylboronic acid ester to a peptidyl carboxylic acid (Scheme IX). A mixture of a peptidyl carboxylic acid (consisting of 4-7 residues) (1 eq), HATU (1.5-2.0 eq), [bis(trimethylsilyl)amino]methylboronic acid pinacol ester (B1) (2.5 eq) is cooled to 0° C., whereupon dichloromethane (0.1 M) and DMF (0.1 M) are added. Sufficient DMF is added where most of the starting material is dissolved. Then diisopropylethylamine (DIEA, 3 eq) is added, followed by the addition of water (6 eq). The mixture is allowed to warm to room temperature. After 2 to 8 hr, the mixture is partitioned between dichloromethane and water. The aqueous layer is extracted twice with dichloromethane. The combined organic layers are washed with dilute (0.05 M) HCl, then dilute (0.2 M) NaHCO$_3$. The organic layers are dried over Na$_2$SO$_4$, with a small amount of methanol added if necessary, then filtered, and concentrated. The resultant oil was precipitated with either a cold ether wash or 1:1 ether:hexanes wash to afford the corresponding amidoboronic acid (5-115), which was carried on without further purification.

General Method 4:

Acid-catalyzed deprotection of O-t-butyl and/or trityl residues using thioanisole and anisole as a trap (Scheme IX). To a mixture of the amidoboronic acid (1 eq), anisole (2 eq), and thioanisole (2 eq) is added dichloromethane (0.02 M), then TFA (0.02 M) at 0° C. in a 1:1 ratio. The reaction is allowed to warm to room temperature. The reaction is monitored by LC-MS until starting material has been consumed. The solvents were evaporated, and the product precipitated with either cold ether or cold ether:hexanes (1:1). The crude product was purified by prep HPLC (Hypersil column, 10×250 mm, 5 micron) to afford the desired boronic acid product.

Scheme IX

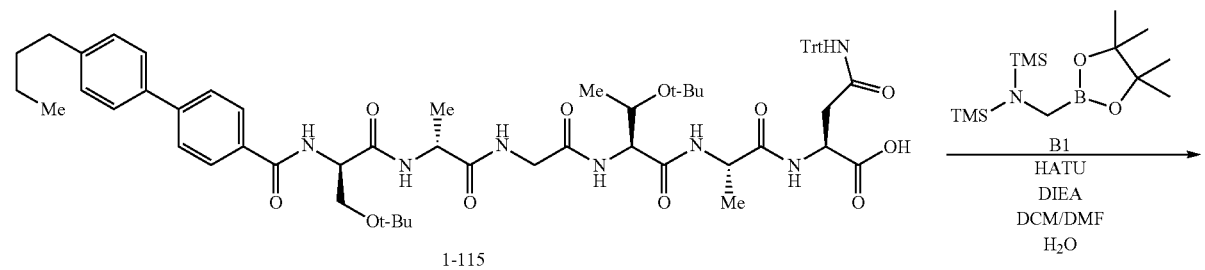

1-115

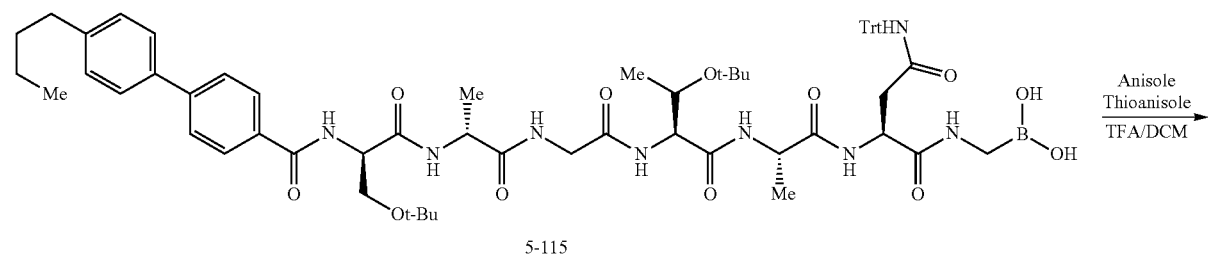

5-115

-continued

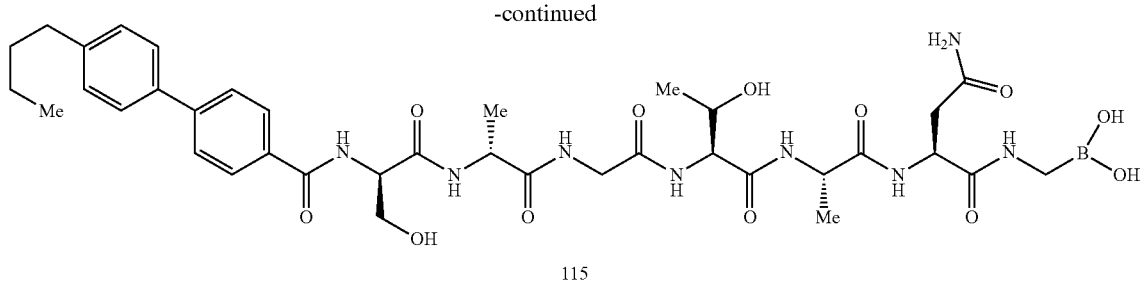

115

Compound 115: Compound 1-115 was prepared according to General Method 1. Compound 1-115 was subjected to General Method 3 and General Method 4 to afford Compound 115. MS (ESI) for ($C_{37}H_{53}BN_6O_{12}$): m/z 835.2 (M+Na).

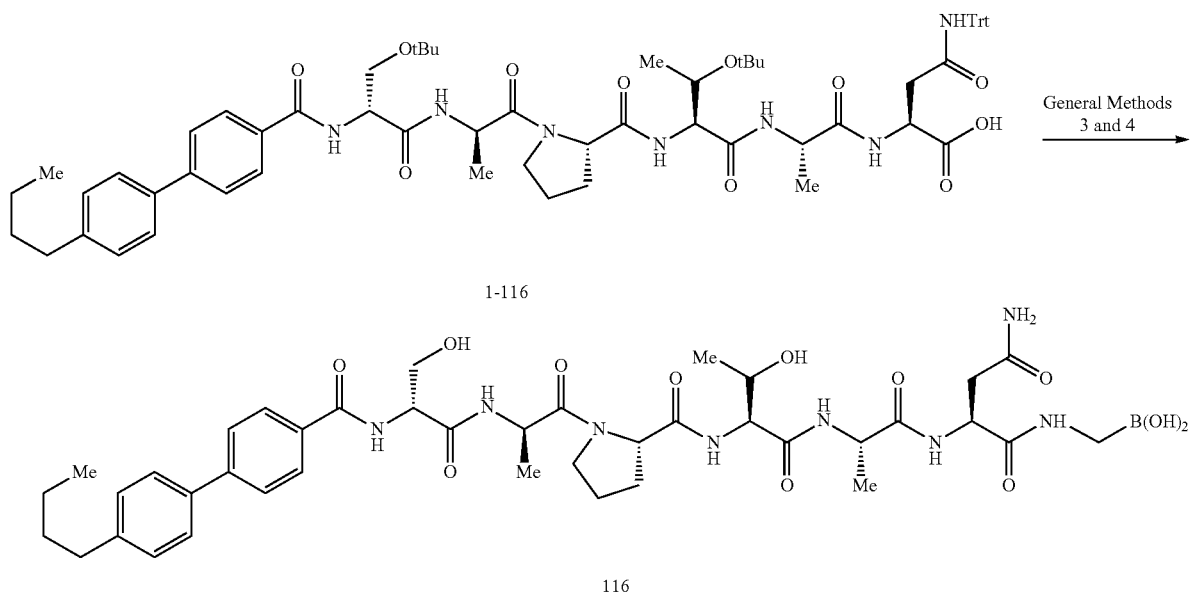

Example 16

Compound 116: Compound 1-116 was prepared according to General Method 1. Compound 1-116 was subjected to General Method 3 and General Method 4 to afford Compound 116. MS (ESI) for ($C_{40}H_{57}BN_8O_{12}$): m/z 875.3 (M+Na).

Example 17

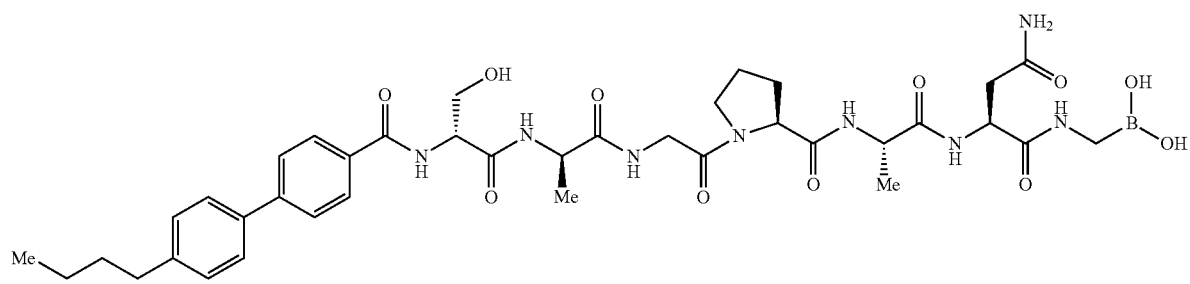

117

Compound 117: Compound 117 was prepared according to General Methods 1, 3, and 4.
Example 18
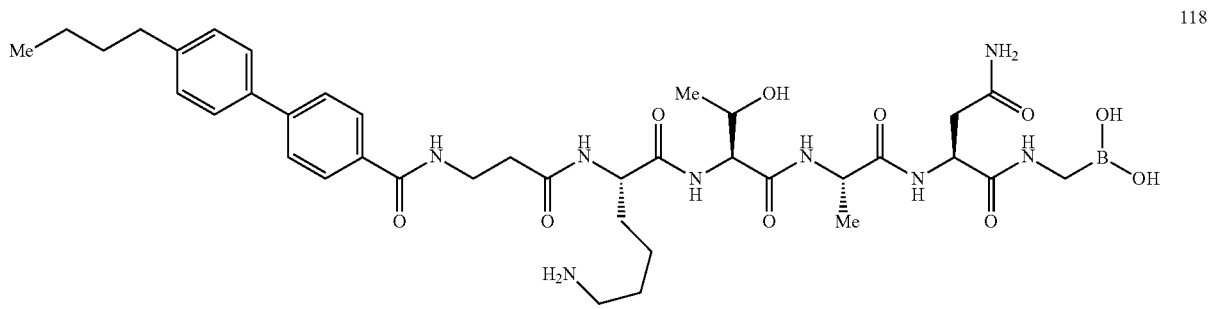 [SMILES: CCCCc1ccc(-c2ccc(C(=O)NCCC(=O)N[C@@H](CCCCN)C(=O)N[C@H](C(=O)N[C@@H](C)C(=O)N[C@@H](CC(N)=O)C(=O)NCB(O)O)C(C)O)cc2)cc1]
Compound 118: Compound 118 was prepared according to General Methods 1, 3, and 4.
Example 19
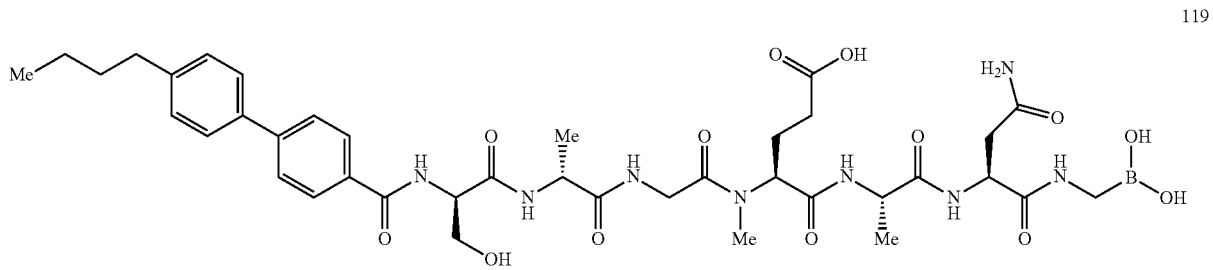 [SMILES: CCCCc1ccc(-c2ccc(C(=O)N[C@H](CO)C(=O)N[C@H](C)C(=O)NCC(=O)N(C)[C@@H](CCC(=O)O)C(=O)N[C@@H](C)C(=O)N[C@@H](CC(N)=O)C(=O)NCB(O)O)cc2)cc1]
Compound 119: Compound 119 was prepared according to General Methods 1, 3, and 4.
Example 20
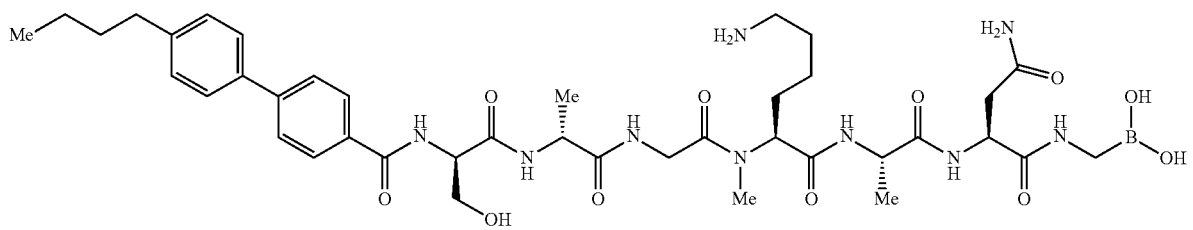
Compound 120: Compound 120 was prepared according to General Methods 1, 3, and 4.

Example 21

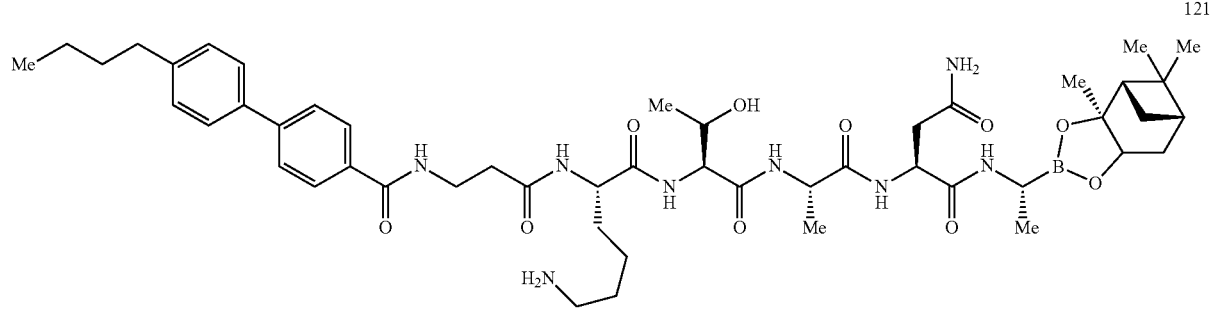 [SMILES: CCCCc1ccc(-c2ccc(C(=O)NCCC(=O)N[C@@H](CCCCN)C(=O)N[C@H](C(=O)N[C@@H](C)C(=O)N[C@@H](CC(N)=O)C(=O)N[C@@H](C)B3OC4C[C@@H]5C[C@@H](C5(C)C)[C@]4(C)O3)C(C)O)cc2)cc1]

Compound 121: Compound 121 was prepared according to General Methods 1, 3, and 4.

Example 22

Scheme X

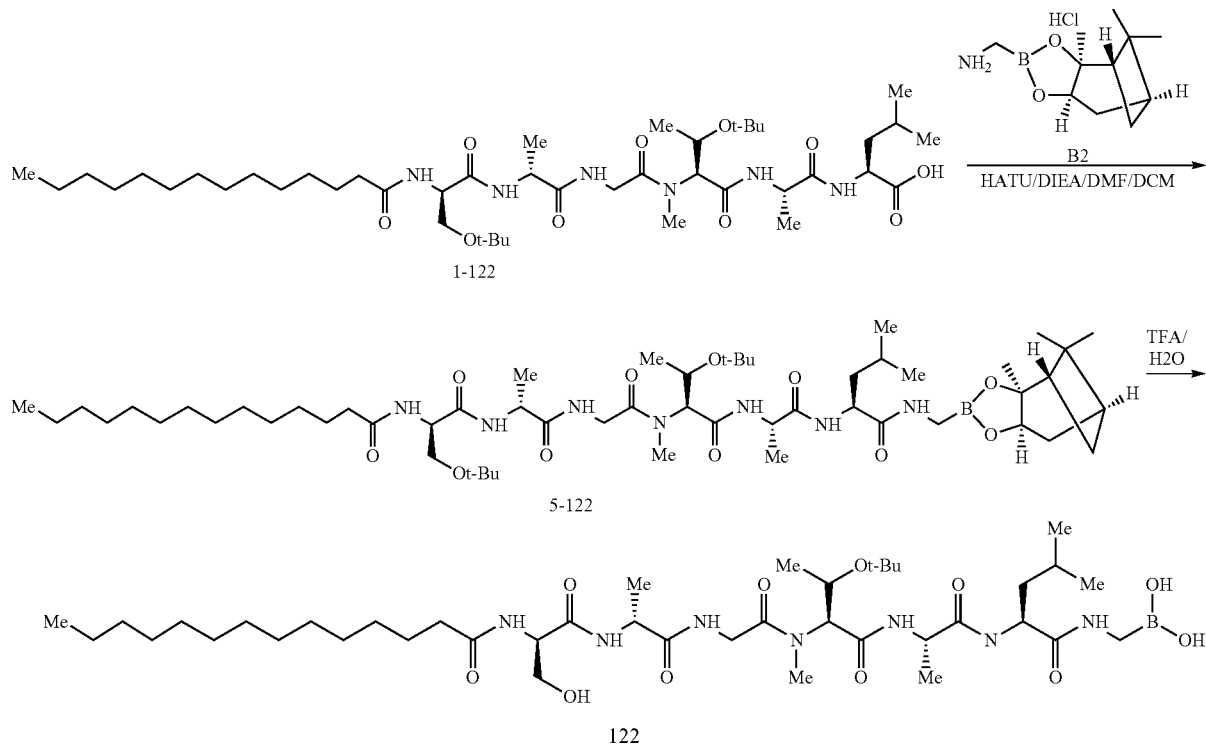

Compound 122: Compound 122 was prepared as depicted in Scheme X. Compound 1-122 was prepared according to General Method 1. Compound 1-122 (100 mg, 0.117 mmol), HATU (89 mg, 0.234 mmol), then B2 (57.3 mg, 0.234 mmol) was placed in an ice bath. To this mixture, 2.4 Ml of DCM and 0.8 Ml of DMF was added. To the mixture was added DIEA (45.4 mg, 0.351 mmol). After 15-30 minutes, the reaction was allowed to warm room temperature and stirred at room temperature for 30 minutes. After ELSD showed the reaction was complete, the mixture was extracted with DCM (10 Ml) and water (5 Ml). The resulting mixture was extracted with DCM (5 Ml×2). The combined organic layers were washed sequentially with dilute HCl (<0.1 M), $NaHCO_3$ solution and brine. The solvents were evaporated, and the residue was extracted with EA (30-50 Ml):water (10-15 Ml). The organic layers were washed sequentially with water (10 Ml), and brine, dried over $Na_2SO_4$, and filtered. The filtrate was concentrated. The residue was crystallized from acetonitrile to give 5-122 (100 mg, 86%). To a solution of 5-122 (70 mg, 0.067 mmol) in 95% TFA/$H_2O$ (1 Ml) was stirred at room temperature for 2 hrs. Then TFA was evaporated with a stream of $N_2$. The crude residue was dissolved in MeOH and purified by prep-HPLC (Luna C8 5 μm 150×21.2 mm) to give 12 mg (22%) of Compound 122. MS (ESI) for ($C_{37}H_{70}BN_7O_{11}$): m/z 822.5 (M+Na).

Example 23

Scheme XI

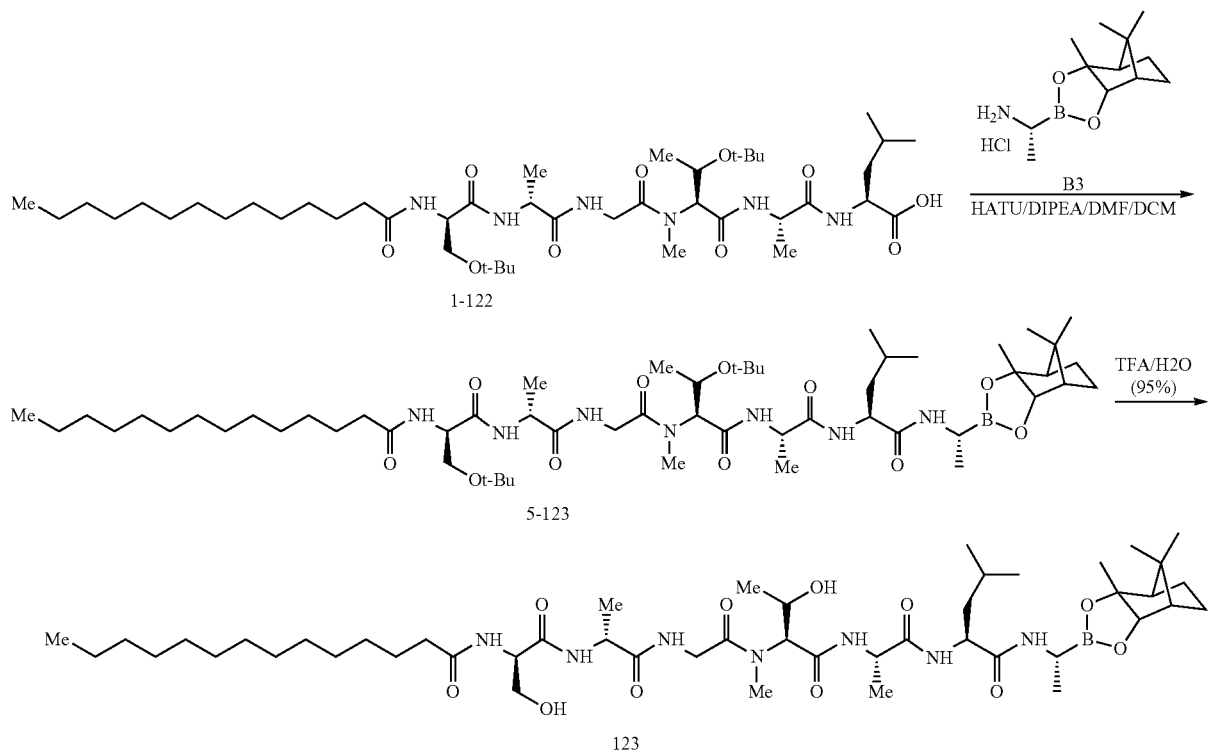

Compound 123: Compound 123 was prepared according to Scheme XI. Compound 1-122 (EXAMPLE 22) was prepared according to General Method 1. Compound 1-123 (100 mg, 0.117 mmol), HATU (89 mg, 0.234 mmol), then B3 (60.7 mg, 0.234 mmol) were combined in a flask and cooled in an ice bath. To this mixture was added 2.4 Ml DCM and 0.8 Ml DMF. DIEA (45.4 mg, 0.351 mmol) was added to the mixture, and after 15-30 minutes the reaction was allowed to warm room temperature and stirred at room temperature for 30 minutes. After ELSD showed the reaction was complete, the mixture was treated with DCM (10 Ml) and water (5 Ml). The aqueous layer was extracted with DCM (10 Ml). The combined organic layers were rinsed with dilute HCl (<0.1 M), then NaHCO$_3$ solution, then brine, and the solvent was evaporated under reduced pressure. The residue was extracted with EA (30-50 Ml):water (10-15 Ml), and the EA layer was washed with water (10 Ml), then brine, dried over Na$_2$SO$_4$, filtered and concentrated. The reside was crystallized from acetonitrile to afford 5-123 (80 mg, 64%). To a solution of 5-123 (25 mg, 0.024 mmol in 95% TFA/H$_2$O (1 Ml) was stirred at room temperature for 20 minutes. Then TFA was evaporated with a stream of N$_2$ and ELSD showed the reaction was completed. The residue was crystallized from acetonitrile to give the crude product. Then the crude reside was purified by prep-HPLC (Luna C8 5 μm 150×21.2 mm) to give Compound 123 (5 mg, yield: 54%). MS (ESI) for (C$_{48}$H$_{86}$BN$_7$O$_{11}$): m/z 948.5 (M+H).

Example 24

Scheme XII

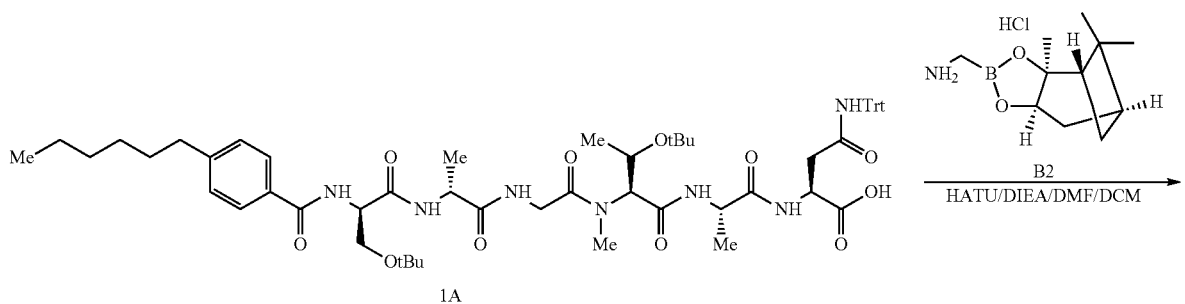

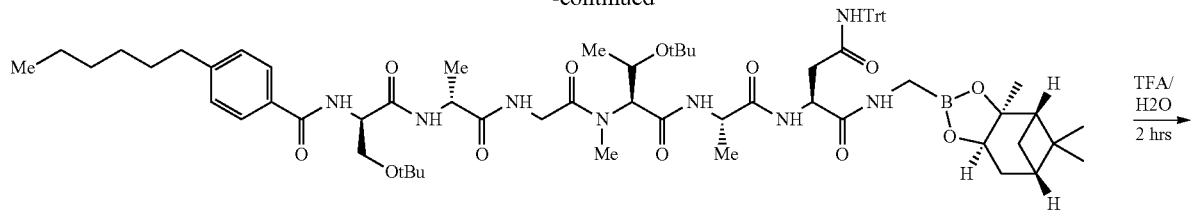

5-124

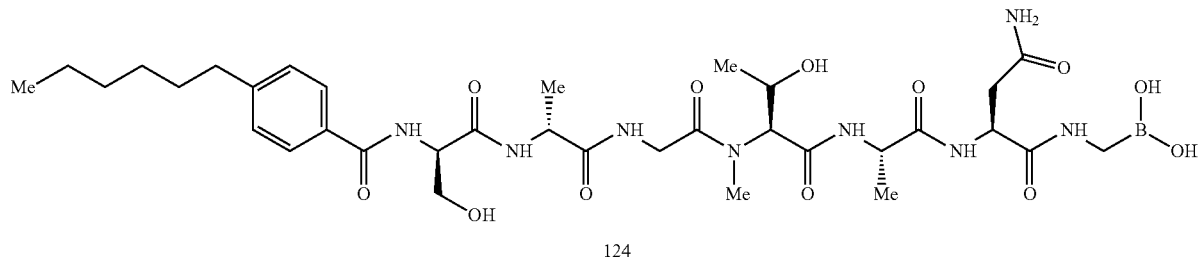

124

Compound 124: Compound 124 was prepared according to Scheme XII. Compound 1A (EXAMPLE 1) was prepared according to General Method 1. In a rb flask, Compound 1-124 (100 mg, 0.093 mmol), HATU (70 mg, 0.186 mmol), then B2 (39 mg, 0.186 mmol was placed in an ice bath. To this mixture was added 2.4 mL of DCM and 0.8 mL of DMF. DIEA (24 mg, 0.186 mmol) was added, and after 15-30 minutes the reaction was allowed to warm room temperature and stirred at room temperature for 30 minutes. After ELSD showed the reaction was complete, the mixture was treated with DCM (10 mL) and water (5 mL). The mixture was extracted with DCM (5 mL×2). The combined organic layers were washed sequentially with dilute HCl (<0.1 M), NaHCO$_3$ solution, and brine. The solvent was evaporated, and the residue was extracted with EA (30-50 mL) and water (10-15 mL). The organic layers were washed with water (10 mL), brine, and dried with Na$_2$SO$_4$, filtered, and concentrated. The reside was crystallized from acetonitrile to give 5-124 (100 mg, yield: 85.5%). A solution of 5-124 (100 mg, 0.079 mmol) in 95% TFA/H$_2$O (1 mL) was stirred at room temperature for 2 hrs. Then TFA was evaporated and ELSD showed the reaction was completed. The crude reside was purified by prep-HPLC (Luna C8 5 μm 150×21.2 mm) to give Compound 124 (16 mg, 26%). MS (ESI) for ($C_{34}H_{55}BN_8O_{12}$): m/z 801.3 (M+Na).

Example 25

Scheme XIII

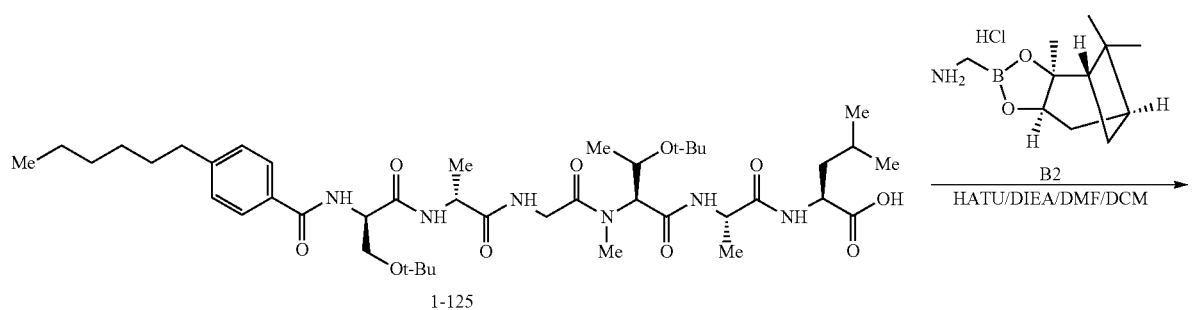

1-125

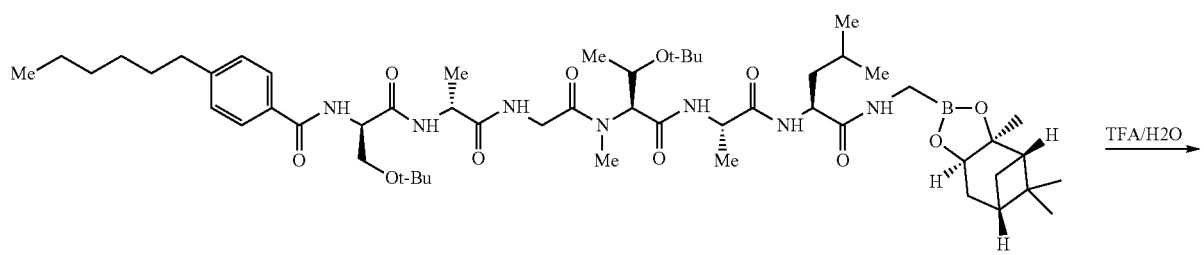

5-125

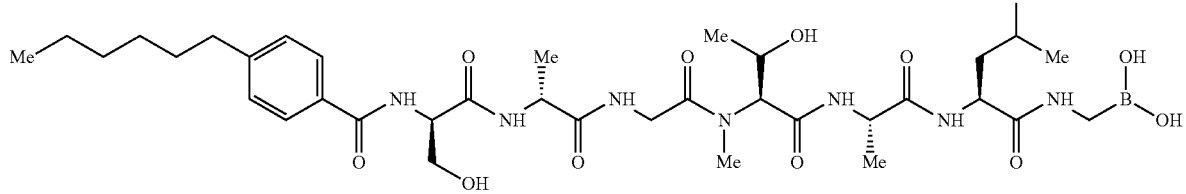

125

Compound 125: Compound 125 was prepared according to Scheme XIII. Compound 1-125 was prepared according to General Method 1. Compound 1-125 (100 mg, 0.12 mmol), HATU (91.2 mg, 0.24 mmol), and B2 (50 mg, 0.24 mmol) were added to a small rb flask and cooled in an ice bath. To this mixture was added 2.4 mL DCM and 0.8 mL DMF. DIEA (31 mg, 0.24 mmol) was added, and after 15-30 minutes the reaction was allowed to warm room temperature and stirred at room temperature for 30 minutes. After ELSD showed the reaction was complete, the mixture was extracted with DCM (10 mL) and water (5 mL). The mixture was extracted with DCM (5 mL×2). The combined layers were washed sequentially with dilute HCl (<0.1 M), NaHCO$_3$ solution, and brine. The solvent was evaporated, and the residue was extracted with EA (30-50 mL):water (10-15 mL). The organic layer was washed with sequentially with water (10 mL) and brine, dried Na$_2$SO$_4$, filtered and concentrated. The residue was crystallized from acetonitrile to give 5-125 (100 mg, 80.3%). MS (ESI) for (C$_{36}$H$_{60}$BN$_7$O$_{11}$): m/z 800.3 (M+Na). A solution of 5-125 (40 mg, 0.039 mmol) in 95% TFA/H$_2$O (1 mL) was stirred at room temperature for 2 hrs. Then TFA was evaporated and ELSD showed the reaction was completed. Then the crude reside was purified by prep HPLC to give Compound 125 (2.4 mg, 7.9%). MS (ESI) for (C$_{36}$H$_{60}$BN$_7$O$_{11}$): m/z 800.3 (M+Na).

Example 26

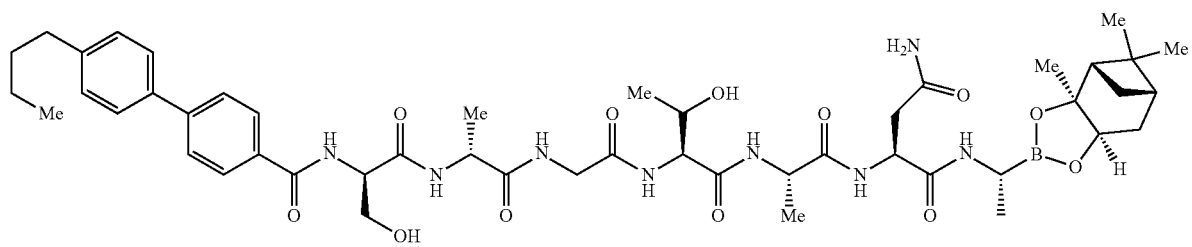

126

Compound 126: This compound was prepared in a manner similar to Compound 122 (EXAMPLE 22) from General Methods 1, 3, and 4 to afford the title compound.

Example 27

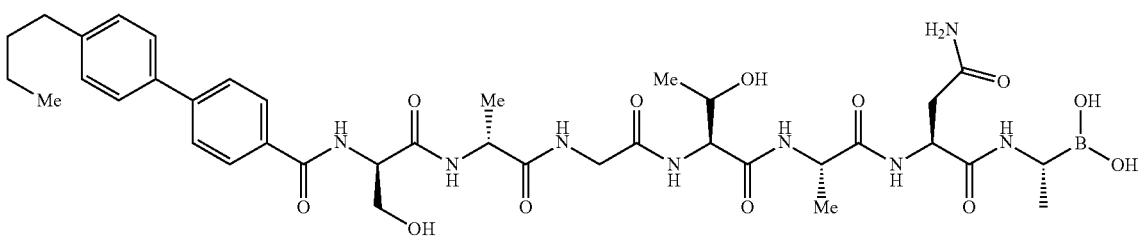

127

Compound 127: Compound 126 (EXAMPLE 26) (9 mg) was dissolved in MeOH and diluted with water and acetic acid to a final mixture of 80% MeOH:19% water:1% acetic acid to a final concentration of 5 mg/mL. The solution was heated and sonicated as needed to facilitate dissolution. The reaction was monitored by LC-MS, which indicated a 1:1 mixture of starting material:product. Prep HPLC afforded 1 mg of Compound 127.

Example 28
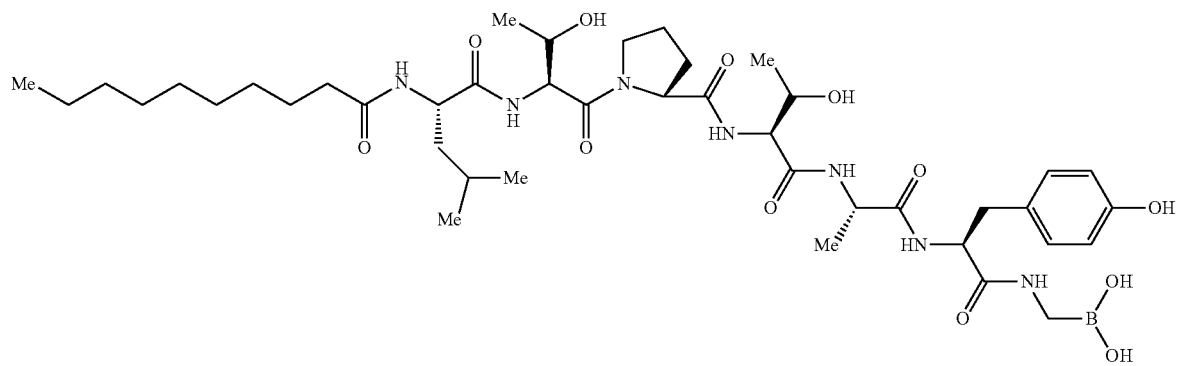
128
Compound 128: Compound 1-128 was treated in a manner similar to Compound 124 (EXAMPLE 24) to afford the title compound.
Examples 29-130
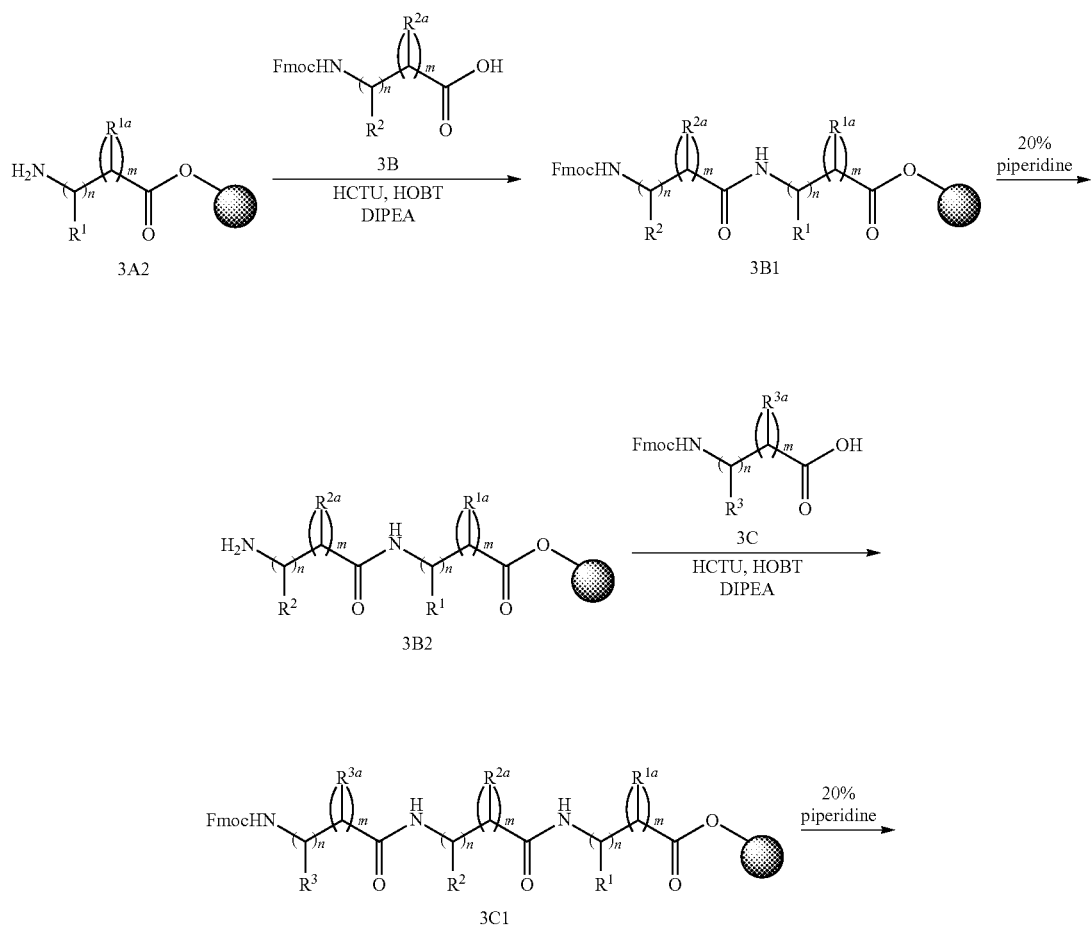

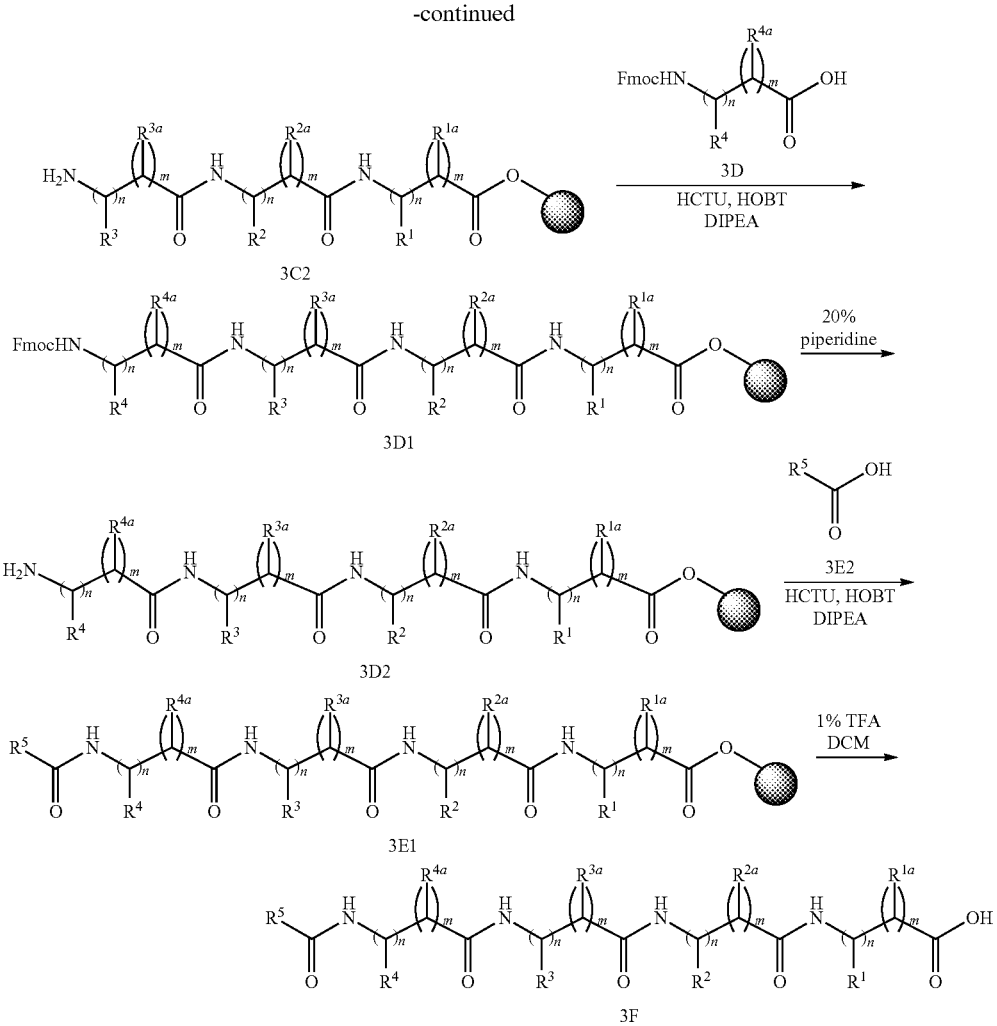

Fully protected peptide fragments up to six amino acids in length terminated by a lipophilic carboxylic acid tail are synthesized on solid phase using chlorotrityl functionalized polystyrene resin (Trt-Cl) and an Fmoc/tBu/Trt/t-Boc protecting group strategy. A representative scheme of a four-amino acid fragment terminated with a lipophilic carboxylic acid is depicted in Scheme XIV. Cleavage of the fully protected peptide 3F is accomplished by repeated treatment of the resin with 1% TFA in $CH_2Cl_2$ and aqueous workup of the combined filtrates.

General Method 5:

Attachment of an Fmoc-protected amino acid onto a 2-chlorotrityl resin is depicted in Scheme XV.

Scheme XV

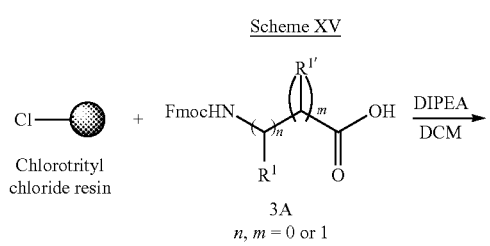

Step 1: A mixture of 2-chlorotrityl resin (500 mg, 0.5 mmol), diisopropylethylamine (DIPEA) (0.26 g, 2 mmol) in dry DCM (10 mL) was added a solution of an Fmoc-protected amino acid 3A (1.5 mmol) in dry DCM (10 ml) at 0° C. Then the mixture was shaken for 5 hr at room temperature. The mixture was filtered and the cake was washed with DCM (30 ml×3), DMF (30 mL×3) and MeOH (30 mL×3) to afford Compound 3A1.

Step 2: To the above resin was added approximately 20% piperidine/DMF (70 mL) to remove the Fmoc group. The mixture was shaken for 10 mins and the cycle was repeated three times. The mixture was washed with DCM (2×30 mL) and DMF (3×30 mL) to give Compound 3A2.

General Method 6:

Solid phase peptide coupling of varying lengths and Fmoc cleavage from the peptide. The coupling of peptide and/or amide fragments of amino acids in length followed by Fmoc removal is depicted in Scheme XVI.

Scheme XVI

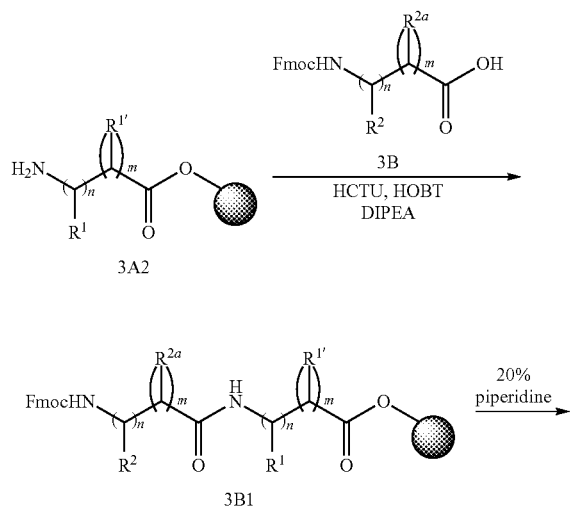

Step 1: A mixture of amino acid 3B (1.5 eq), HCTU (1.5 eq), HOBT (1.5 eq) and DIPEA (1.5 eq) in dry DMF (6-8 mL/eq) was stirred at 20° C. for 30 min. Then the above mixture was added to Compound 3A2 (1 eq) and shaken at 20° C. for 1.5 hrs. After LCMS showed the reaction was completed, the mixture was filtered and the residue was washed with DMF (3×10 mL/mmol) and DCM (3×10 mL/mmol) to give Compound 3B1. An analytical portion of resin 3B1 was treated and mixed in 1% TFA/DCM to cleave the peptide from the resin, and the desired product was detected by MS with confirmation that no starting material remains. In cases where the peptide coupling is slow or does not go to completion, HCTU can be replaced with EDCI.

Step 2: To 3B1 was added 20% piperidine/DMF (70 mL) to remove the Fmoc group. The mixture was shaken for 10 min and the cycle was repeated three times. The mixture was washed with DCM (2×30 mL) and DMF (3×30 mL) to give Compound 3B2. In cases where there is more than one protected amine present, a protecting group other than Fmoc, for example, t-Boc or CBz, is utilized so only one reactive amine is present after Fmoc deprotection.

Step 3 and Step 4: The process of Step 1 and Step 2 can be repeated on 3B2 as depicted in Scheme I.

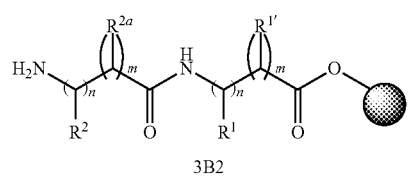

General Method 7:

The coupling of an amide to a resin on solid phase is depicted in Scheme IV. In cases where a coupling partner is an amide instead of an Fmoc-protected amino acid, the following procedure is used and is illustrated in Scheme XVII.

Scheme XVII

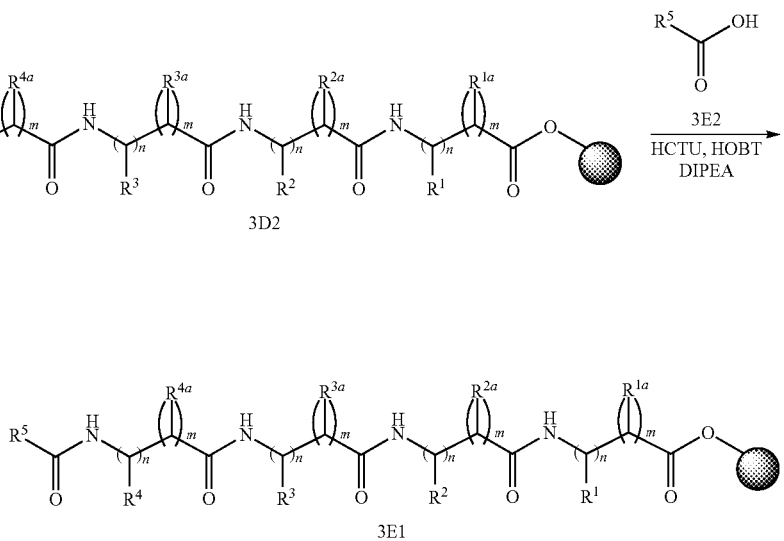

A mixture of amino acid 3D2 (1.5 eq), HCTU (1.5 eq), HOBT (1.5 eq) and DIPEA (1.5 eq) in dry DMF (6-8 mL/eq) was stirred at 20° C. for 30 min. Then the above mixture was added to Compound 3E2 (1 eq) and shaken at 20° C. for 1.5 hrs. After LCMS showed the reaction was completed, the mixture was filtered and the residue was washed with DMF (3×10 mL/mmol) and DCM (3×10 mL/mmol) to give Compound 3E1.

General Method 8:

Cleavage from the resin with 1% TFA is depicted in Scheme XVIII.

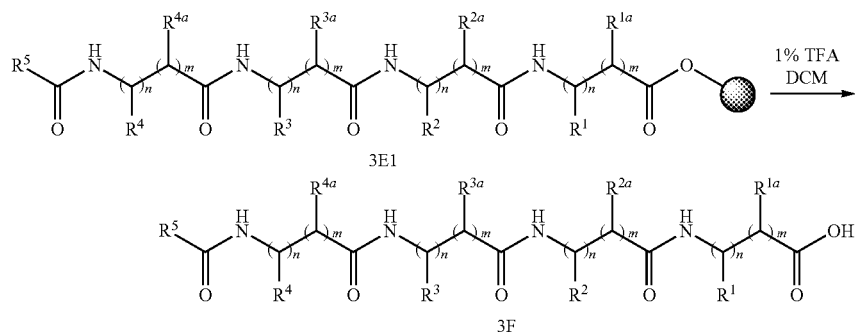

Scheme XVIII

Cleavage of the Compound 3E1 is accomplished by repeated treatment of the resin with 1% TFA in $CH_2Cl_2$ as shown in the following example. A mixture of Compound 3E1 (3 mmol) was treated with 1% TFA/DCM (3-4 mL/mmol) for 5 min and filtered. This operation was repeated three times. The filtrate was treated with saturated $NaHCO_3$ solution until pH ~7-8. The aqueous layer was adjusted to pH ~3-4 with citric acid. The mixture was extracted with DCM (6-8 mL/mmol) three times, then the combined organic layers were washed with brine, dried over $Na_2SO_4$ and concentrated to give Compound 3F. The reported yields are based on the theoretical loading of the chlorotrityl chloride resin.

then washed with DCM (2×30 mL) and DMF (3×30 mL) to give Compound 129A2.

A mixture of Fmoc-L-Ala-OH (0.62 g, 2 mmol), HCTU (0.83 g, 2 mmol), HOBT (0.27 g, 2 mmol) and DIPEA (0.26 g, 2 mmol) in dry DMF (20 mL) was stirred at 25° C. for 20 mins. Then the above mixture was added to Compound 129A2 (1 mmol) and shaken at 25° C. for 1.5 hrs. After LCMS showed the reaction was completed, the mixture was filtered and the residue was washed with DCM (2×30 mL) and DMF (3×30 mL). To the above resin was added approximately 150 mL 20% piperidine/DMF to remove the Fmoc group. The mixture was shaken for 10 mins and repeated three times. The mixture was then washed with DCM (2×30 mL), DMF (3×30 mL) to give Compound 129B2.

A mixture of Fmoc-L-Thr(tBu)-OH (2 mmol), HCTU (0.83 g, 2 mmol), HOBT (0.27 g, 2 mmol) and DIPEA (0.26 g, 2 mmol) in dry DMF (20 mL) was stirred at 25° C. for 20 mins. Then the above mixture was added to Compound 129B2 (1 mmol) and shaken at 25° C. for 1.5 hrs. After LCMS showed the reaction was completed, the mixture was filtered and the residue was washed with DCM (2×30 mL) and DMF (3×30 mL). To the above resin was added approximately 150

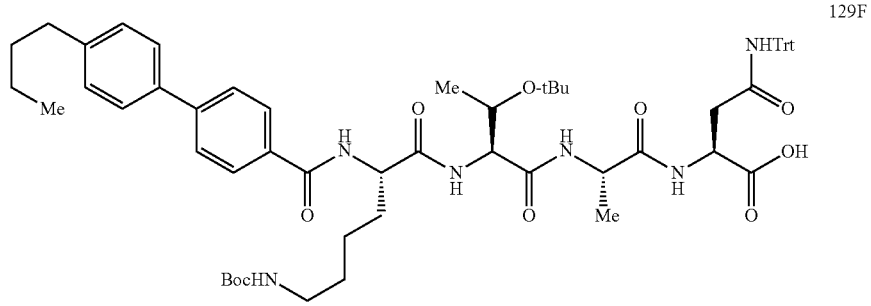

129F

Compound 129F: The compound was prepared using General Methods 6-8 as shown in Scheme XIX. A mixture of Trt resin (1 g, 1 mmol), Fmoc-Asn(Trt)-OH (1.2 g, 2 mmol) and DIPEA (258 mg, 2 mmol) in dry DCM (20 mL) was shaken at 25° C. for 4 hrs. The mixture was filtered and the cake was washed with DCM (2×30 mL), DMF (2×30 mL) and MeOH (2×30 mL, to quench the possible unreacted trityl resin). To the above resin was added approximately 20% piperidine/DMF (70 mL) to remove the Fmoc group. The mixture was shaken for 10 mins and repeated three times. The mixture was mL 20% piperidine/DMF to remove the Fmoc group. The mixture was shaken for 10 mins and repeated three times. The mixture was then washed with DCM (2×30 mL), DMF (3×30 mL) to give Compound 129C2.

A mixture of Fmoc-L-Lys(Boc)-OH (0.62 g, 2 mmol), HCTU (0.83 g, 2 mmol), HOBT (0.27 g, 2 mmol) and DIPEA (0.26 g, 2 mmol) in dry DMF (20 mL) was stirred at 25° C. for 20 mins. Then the above mixture was added to Compound 129C2 (1 mmol) and shaken at 25° C. for 1.5 hrs. After LCMS showed the reaction was completed, the mixture was filtered and the residue was washed with DCM (2×30 mL) and DMF (3×30 mL). To the above resin was added approximately 150 mL 20% piperidine/DMF to remove the Fmoc group. The mixture was shaken for 10 mins and repeated three times. The mixture was then was washed with DCM (2×30 mL), DMF (3×30 mL) to give Compound 129D2.

A mixture of 4-(4-butylphenyl)benzoic acid (1.5 eq), HCTU (1.5 eq), HOBT (1.5 eq) and DIPEA (1.5 eq) in dry DMF (6-8 mL/eq) was stirred at 20° C. for 30 min. Then the above mixture was added to Compound 129D2 (1 eq) and shaken at 20° C. for 1.5 hrs. After LCMS showed the reaction was completed, the mixture was filtered and the residue was washed with DMF (3×10 mL/mmol), DCM (3×10 mL/mmol), THF (3×10 mL/mmol) and petroleum ether (3×10 mL/mmol) to give Compound 129E1.

A mixture of Compound 129E1 (1 mmol) was treated with 1% TFA/DCM (4 mL) for 5 min and filtered. This operation was repeated three times. The filtrate was treated with saturated $NaHCO_3$ solution until pH ~7-8. The aqueous layer was adjusted to pH ~3-4 with citric acid. The mixture was extracted with DCM (8 mL) three times, and then the combined organic layers were washed with brine, dried over $Na_2SO_4$ and concentrated to give Compound 129F. MS (ESI) m/z 1067.4 $(M+H)^+$.

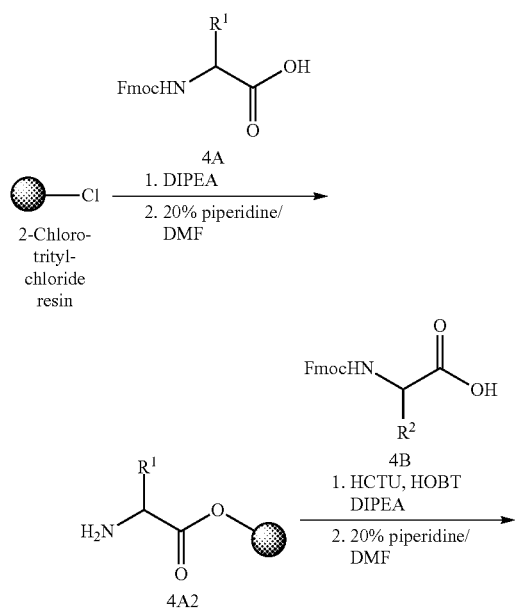

Scheme XIX

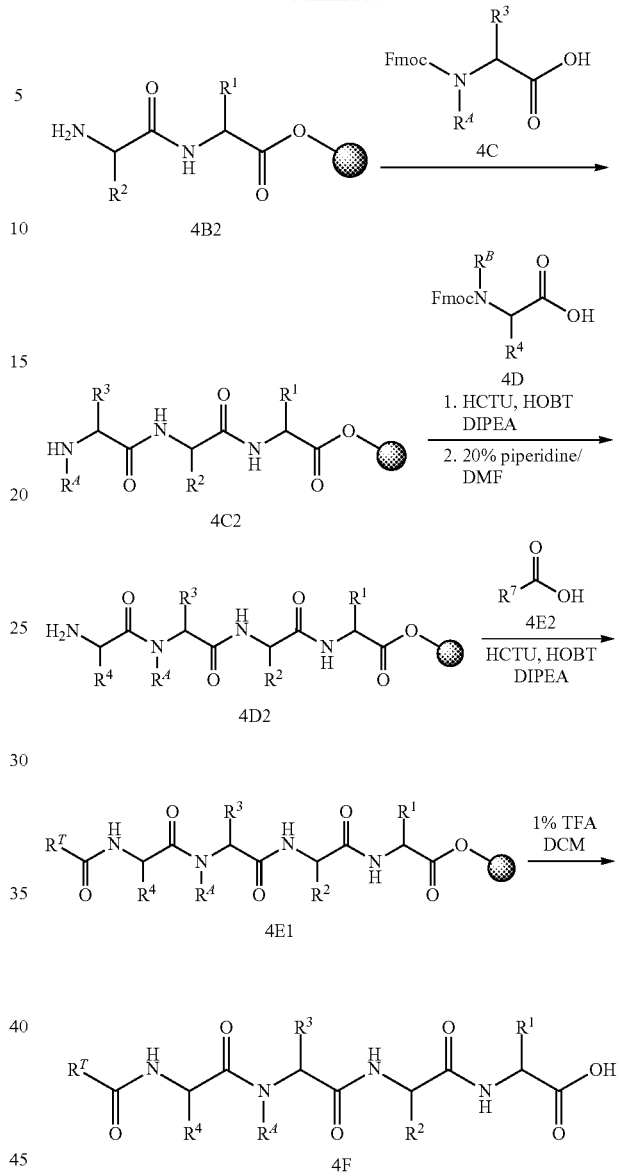

Using the procedures described in General Methods 6-8 and Scheme XIX, the following carboxylic acids were prepared:

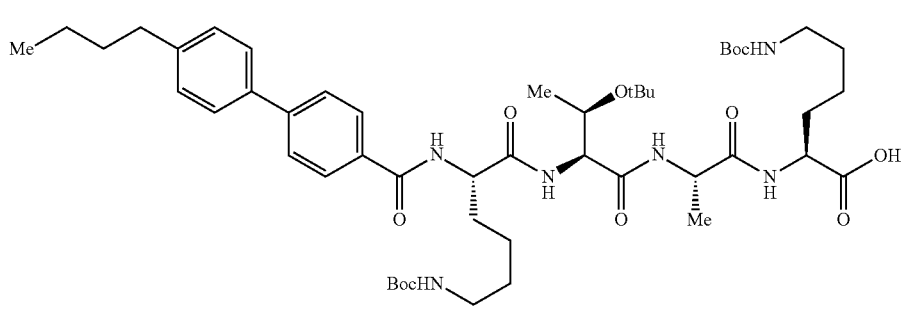

132F

MS (ESI) m/z 939.5 $(M + H)^+$

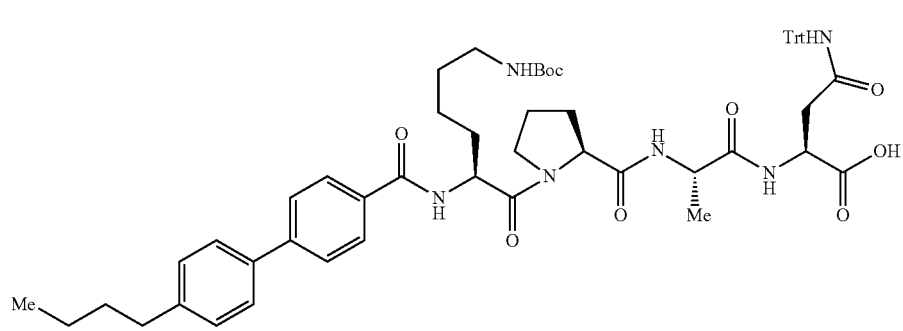
133F
MS (ESI) m/z 1078.5 (M + H)+
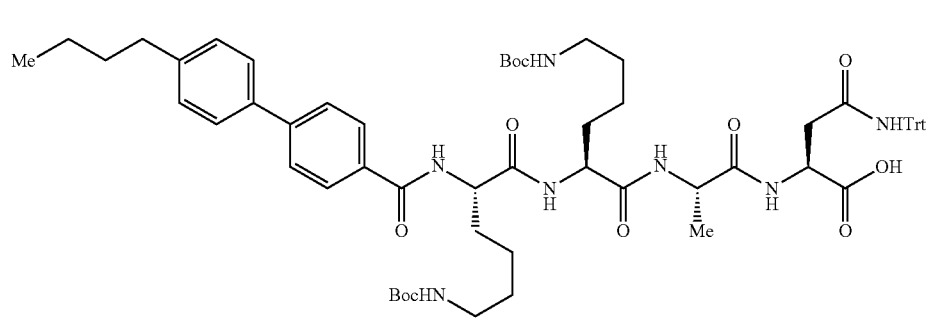
134F
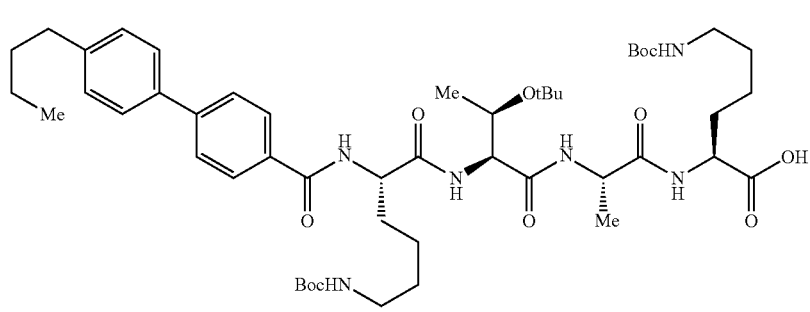
135F
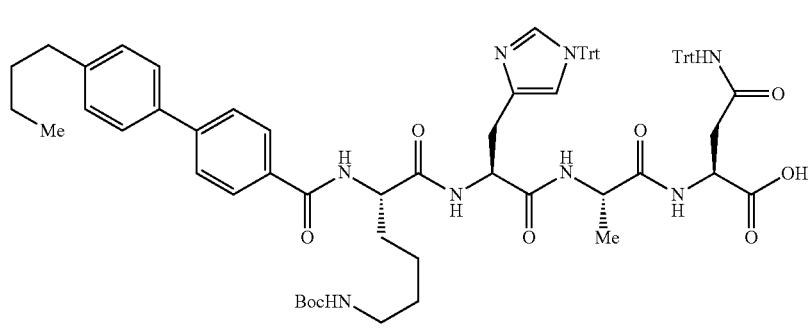
136F
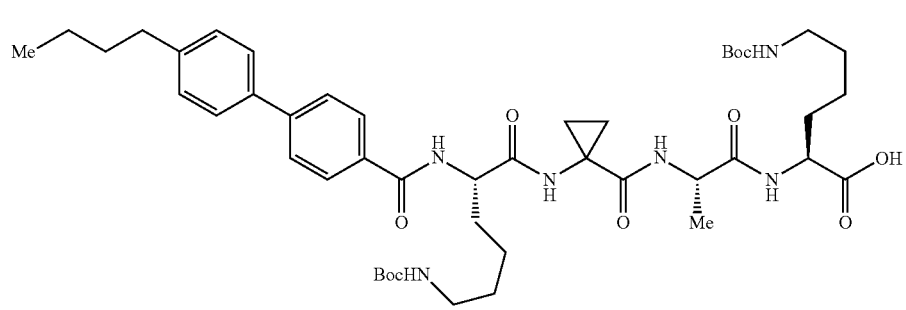
137F
MS (ESI) m/z 865.3 (M + H)+

-continued
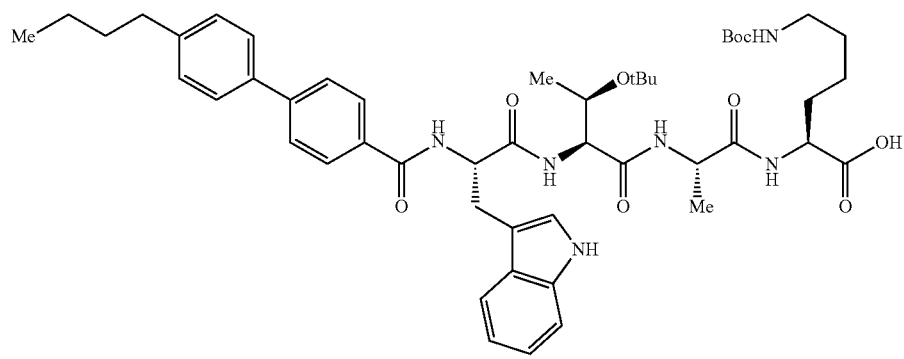
138F
MS (ESI) m/z 897.3 (M + H)+
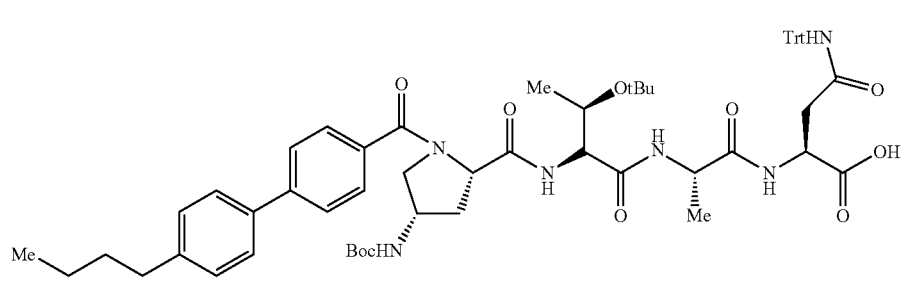
139F
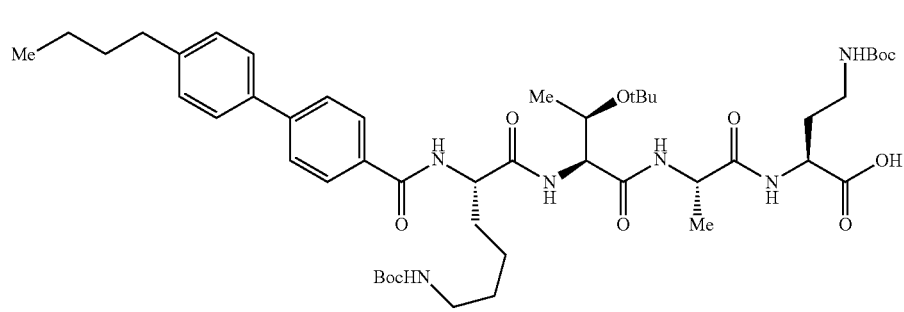
140F
MS (ESI) m/z 911.4 (M + H)+
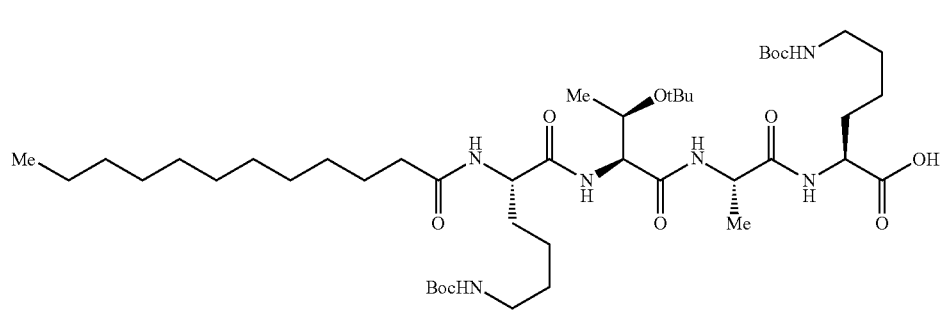
141F
MS (ESI) m/z 885.5 (M + H)+

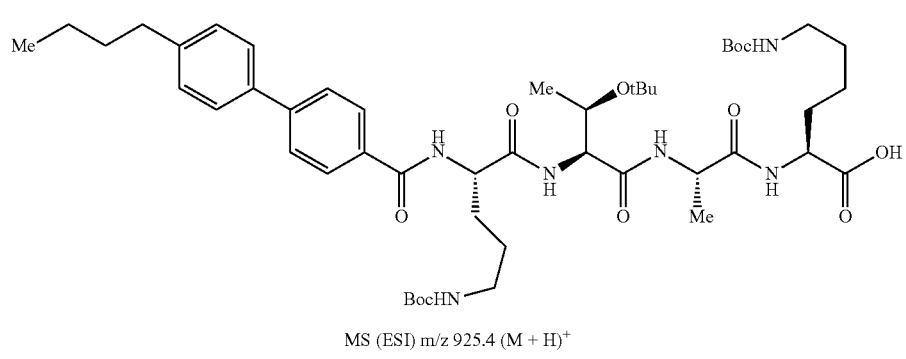
142F
MS (ESI) m/z 925.4 (M + H)+
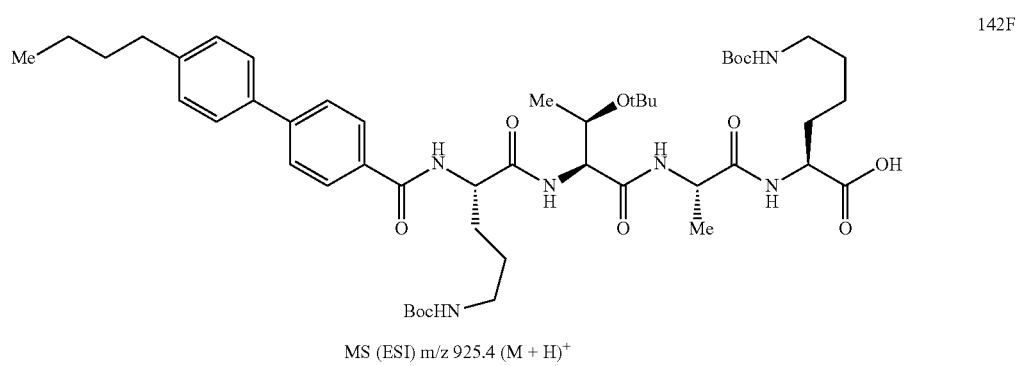
142F
MS (ESI) m/z 925.4 (M + H)+
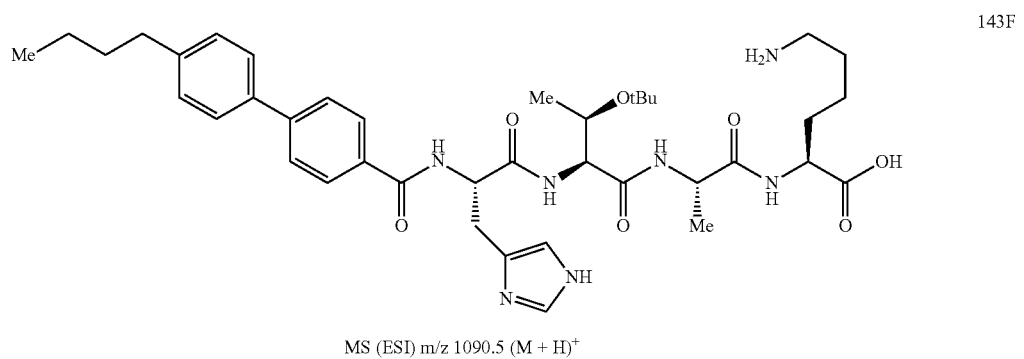
143F
MS (ESI) m/z 1090.5 (M + H)+
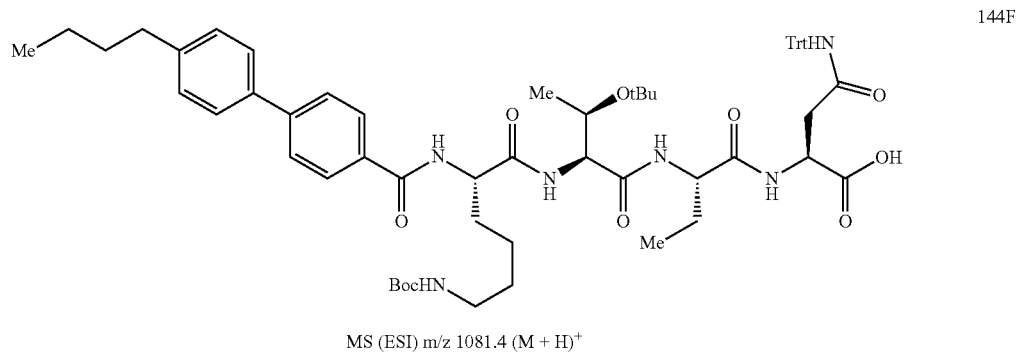
144F
MS (ESI) m/z 1081.4 (M + H)+

145F
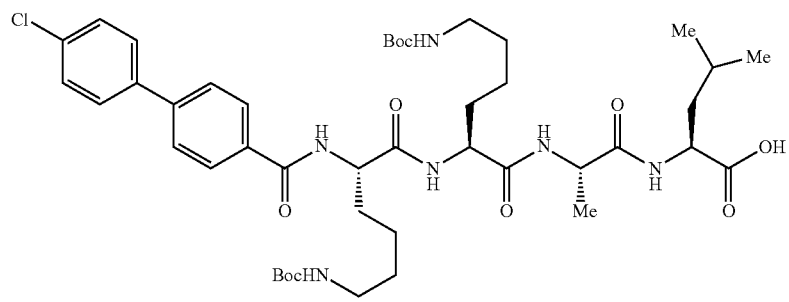
146F
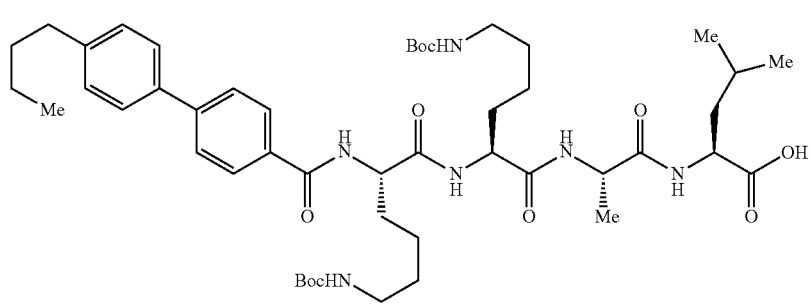
MS (ESI) m/z 966.6 (M + H)+
147F
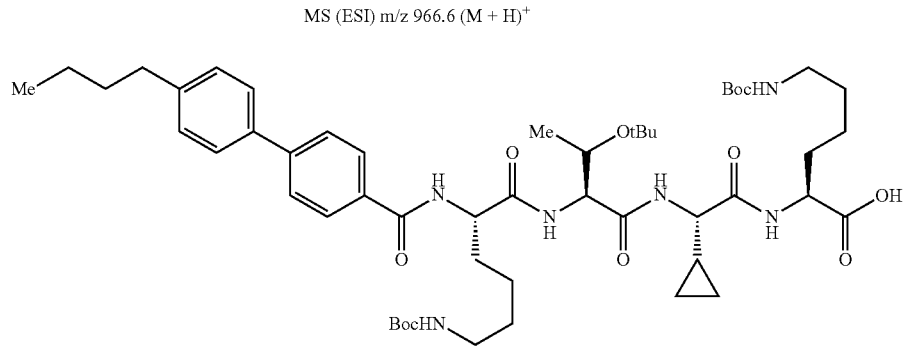
MS (ESI) m/z 965.4 (M + H)+
148F
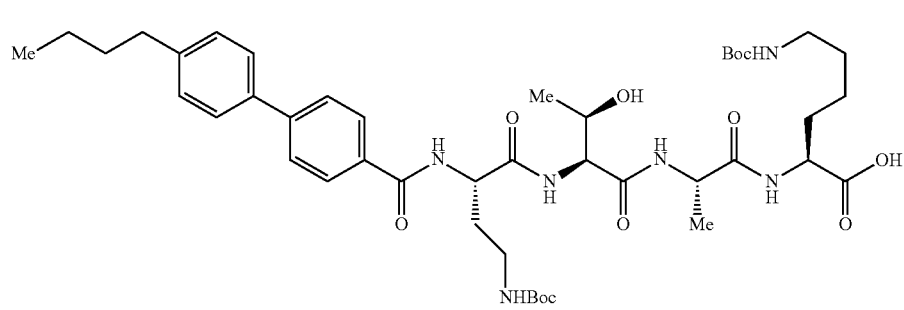
MS (ESI) m/z 911.4 (M + H)+
149F
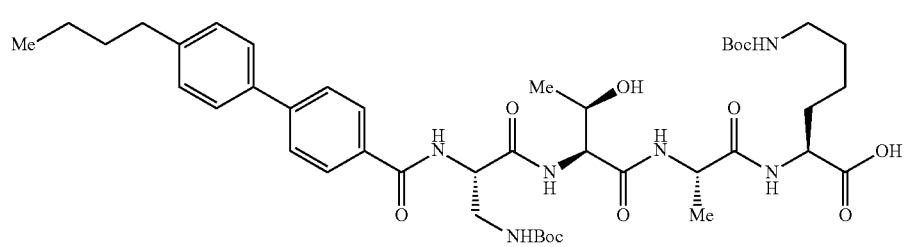
MS (ESI) m/z 897.4 (M + H)+

150F
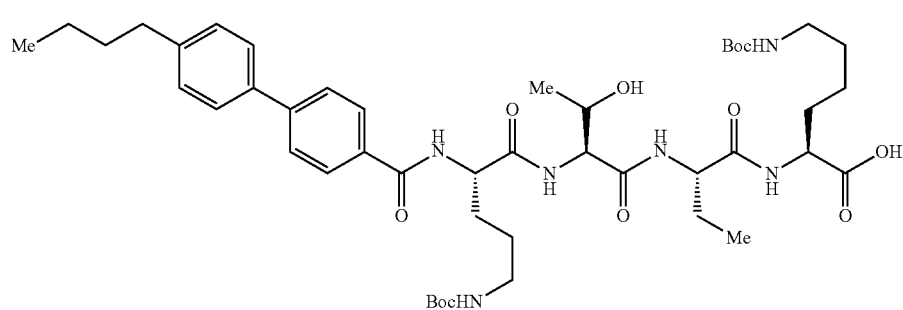
151F
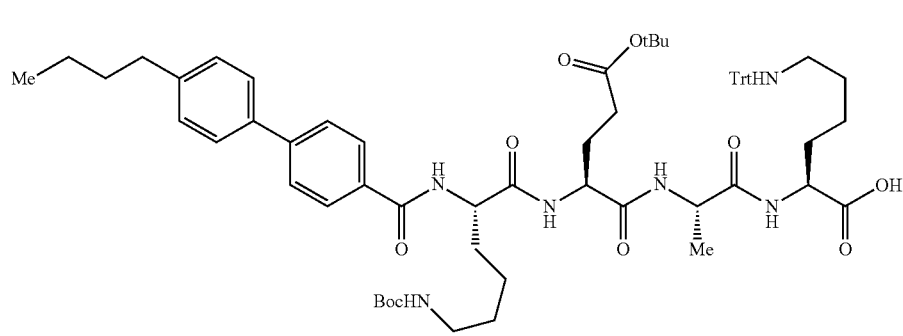
MS (ESI) m/z 967.5 (M + H)+
152F
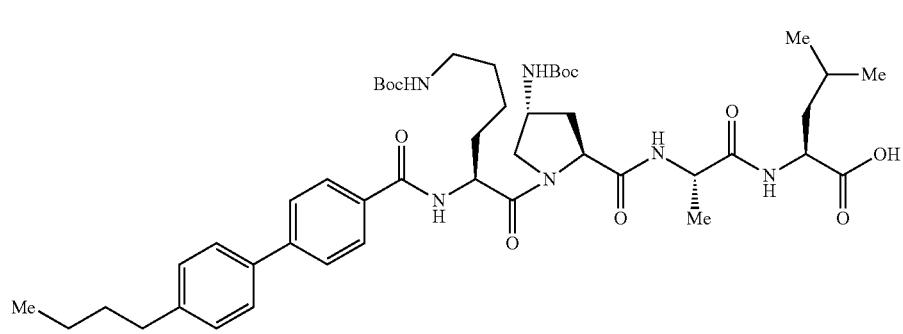
MS (ESI) m/z 879.4 (M + H)+
153F
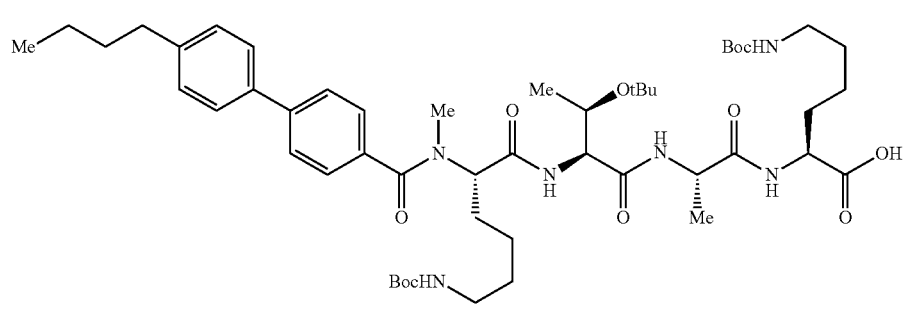
MS (ESI) m/z 953.5 (M + H)+

154F
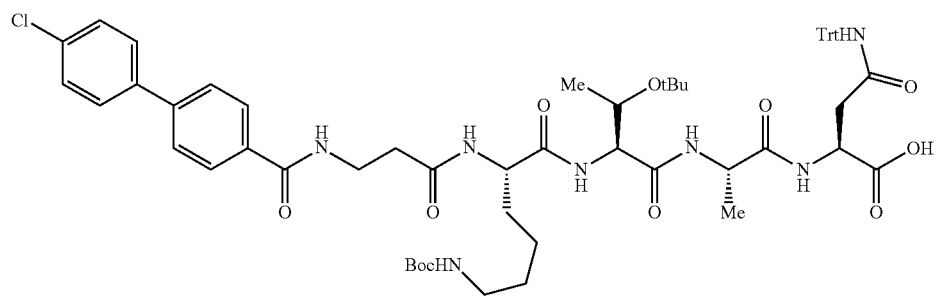
155F
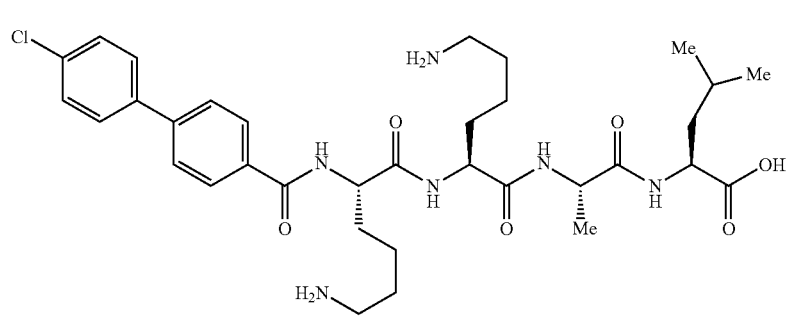
156F
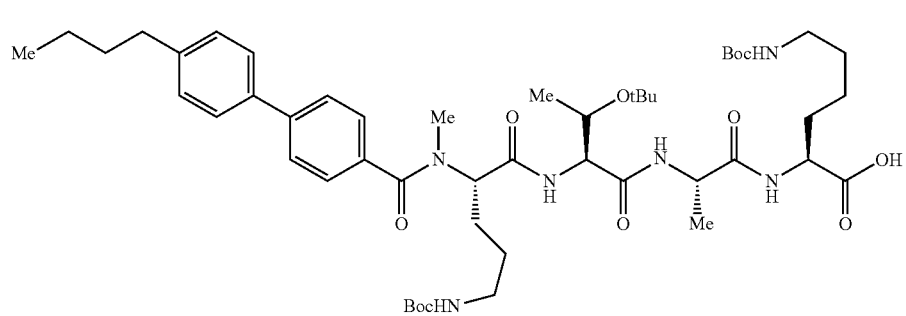
157F
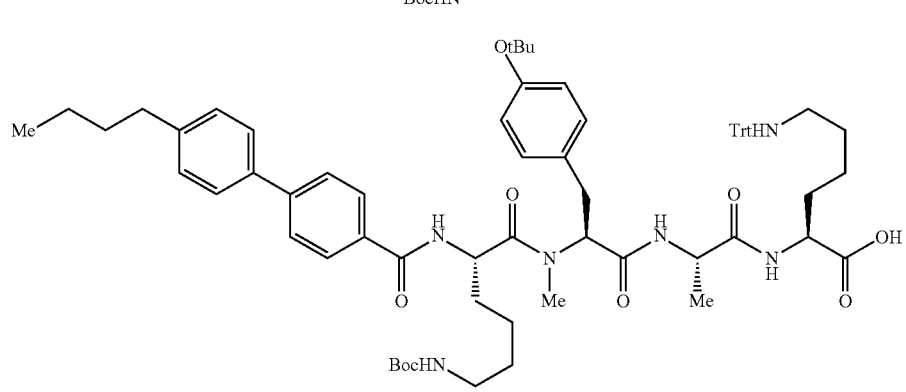
MS (ESI) m/z 915.5 (M - t-Boc + H)+
158F
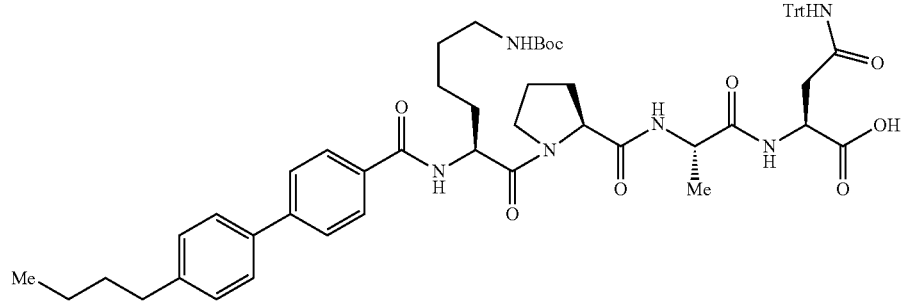

-continued
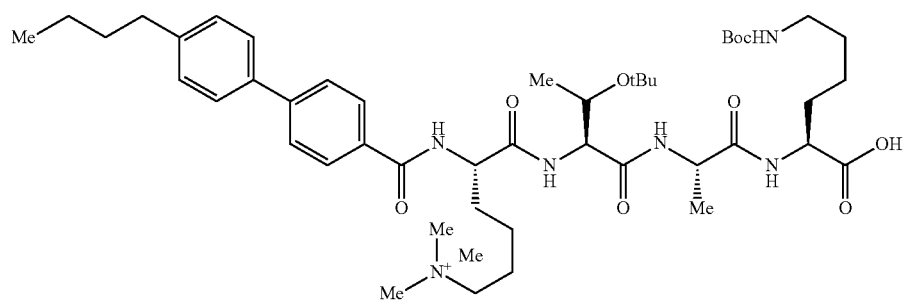
159F
MS (ESI) m/z 881.6 (M + H)+
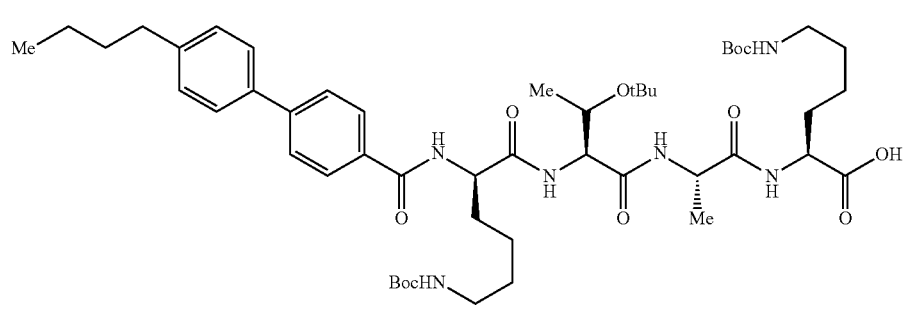
160F
MS (ESI) m/z 839.5 (M - t-Boc + H)+
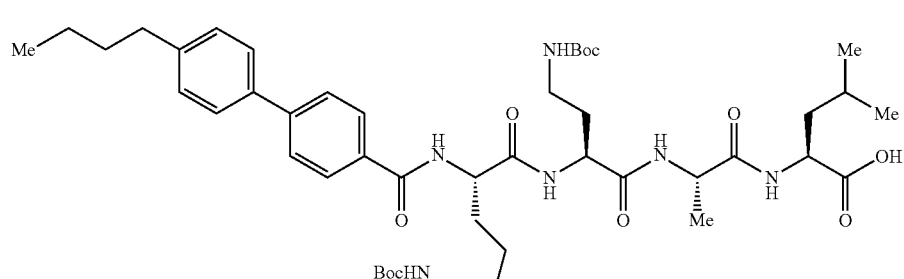
161F
MS (ESI) m/z 867.4 (M + H)+
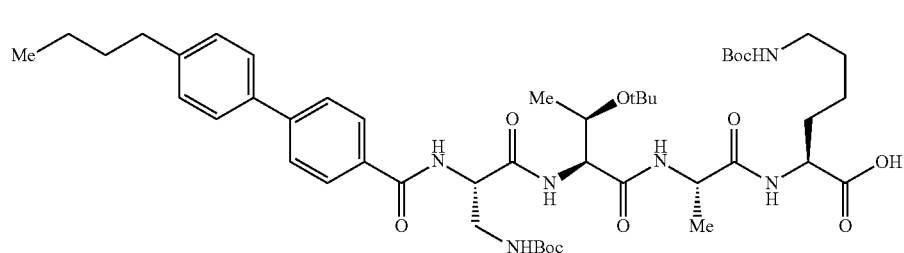
162F
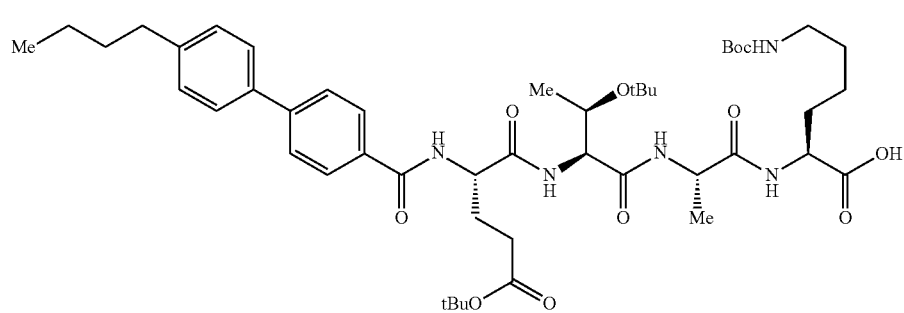
163F
MS (ESI) m/z 896.5 (M + H)+

-continued
164F
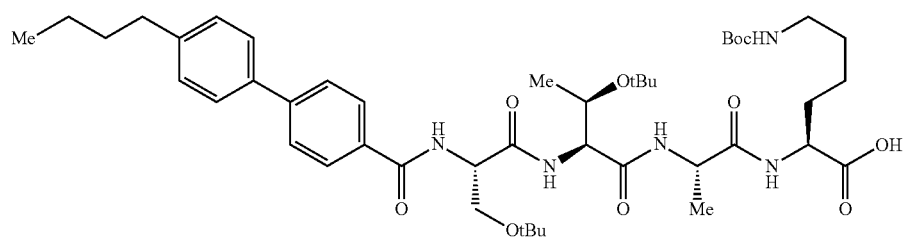
165F
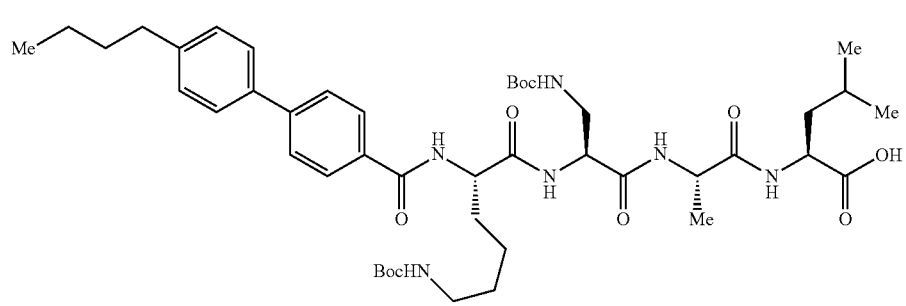
MS (ESI) m/z 853.5 (M + H)⁺
166F
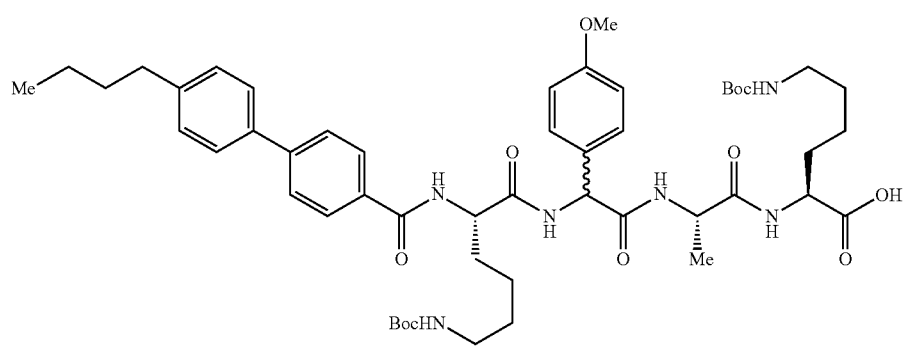
MS (ESI) m/z 945.3 (M + H)⁺
167F
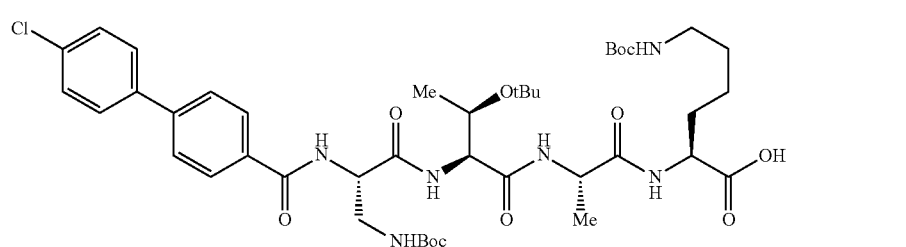
MS (ESI) m/z 875.1 (M + H)⁺
168F
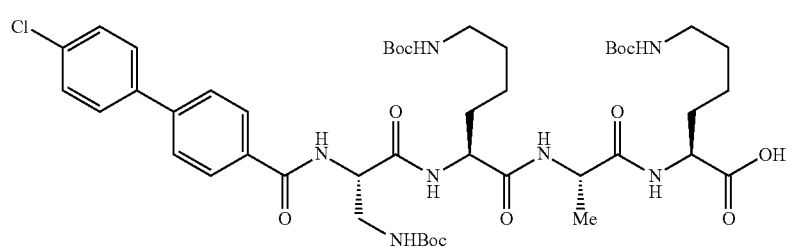
MS (ESI) m/z 946.1 (M + H)⁺

-continued
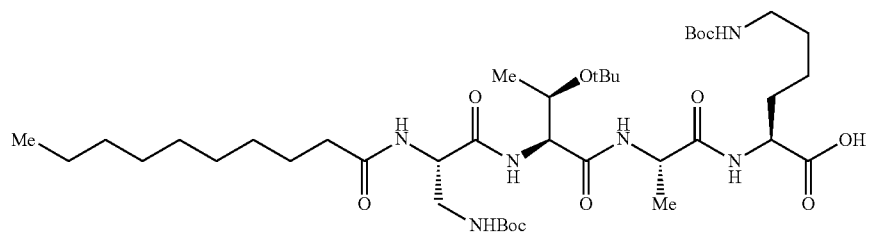
169F
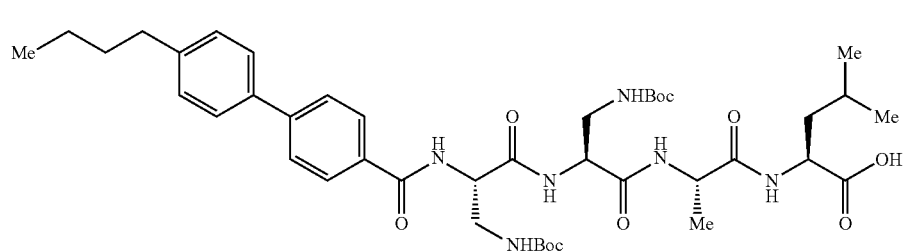
170F
MS (ESI) m/z 811.5 (M + H)+
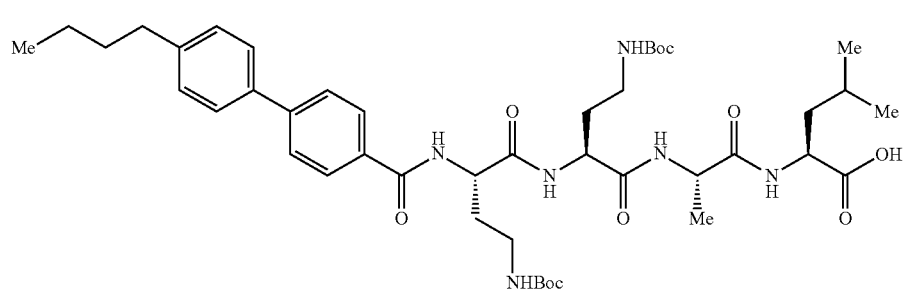
171F
MS (ESI) m/z 840.9 (M + H)+
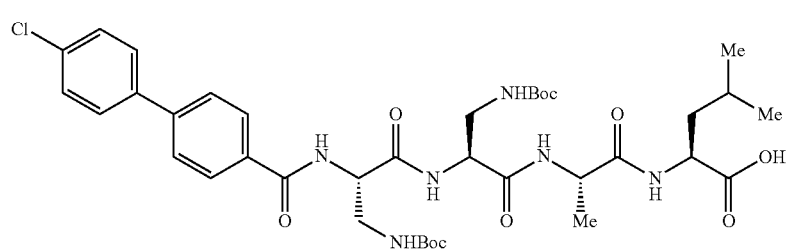
172F
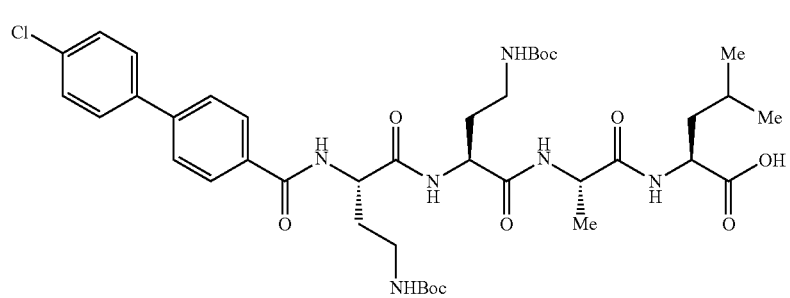
173F
MS (ESI) m/z 817.4 (M + H)+

-continued
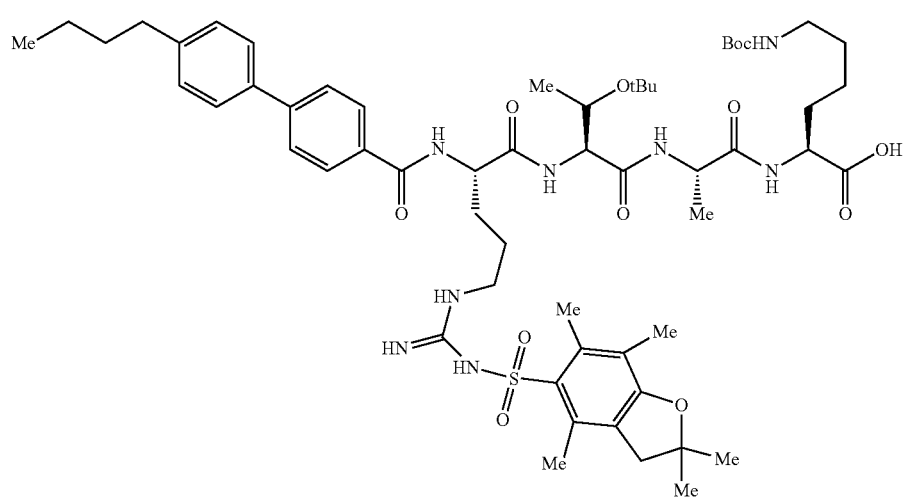
174F
MS (ESI) m/z 1119.2 (M + H)+
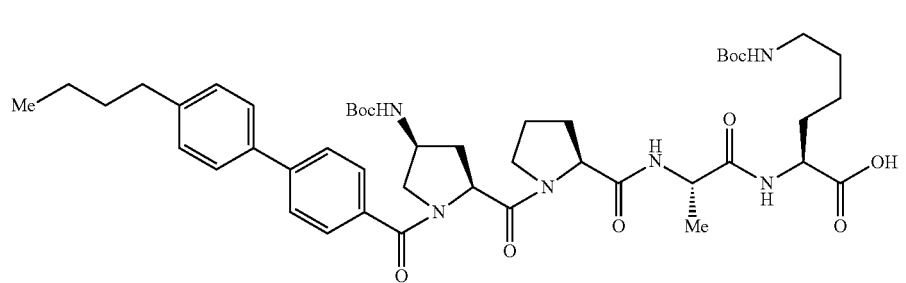
181F
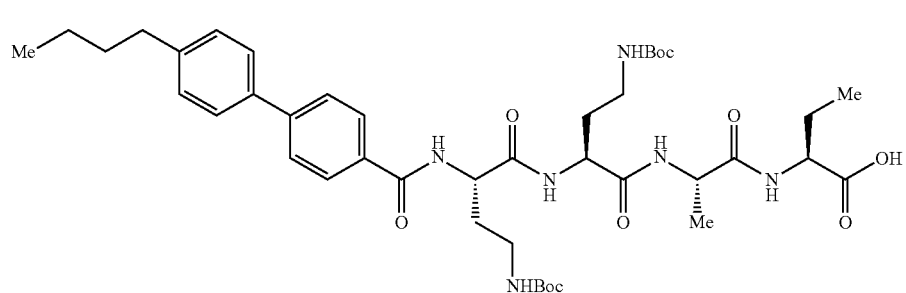
182F
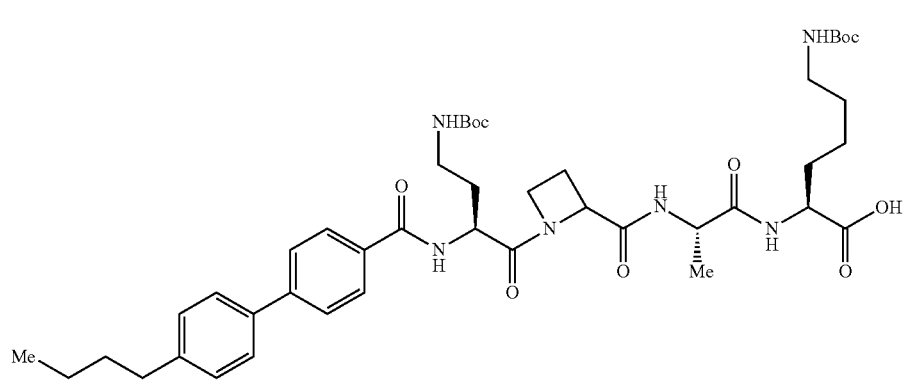
183F
MS (ESI) m/z 837.7 (M + H)+

-continued
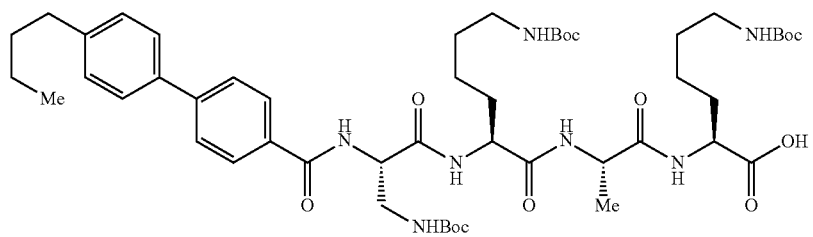
184F
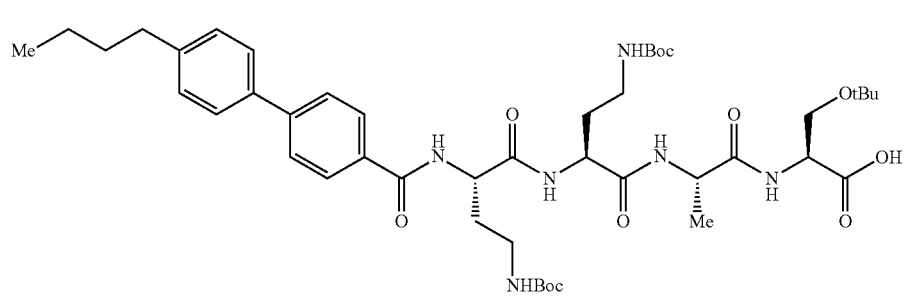
185F
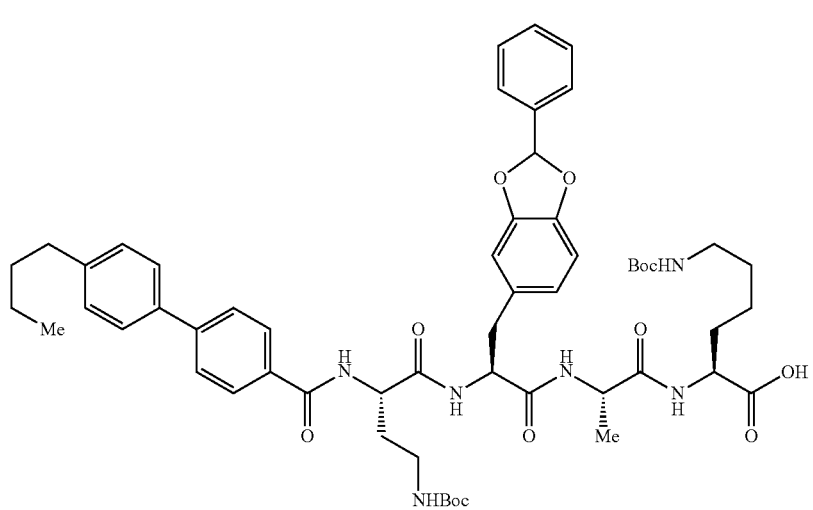
188F
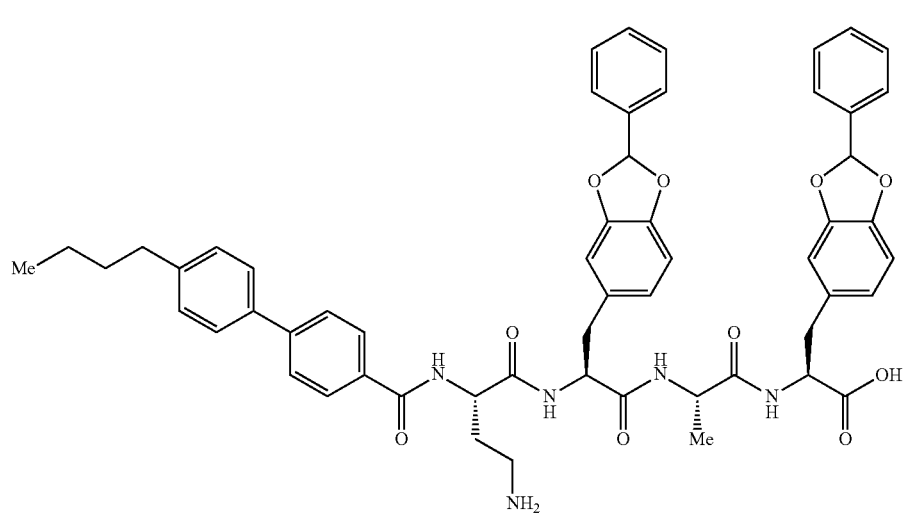
189F

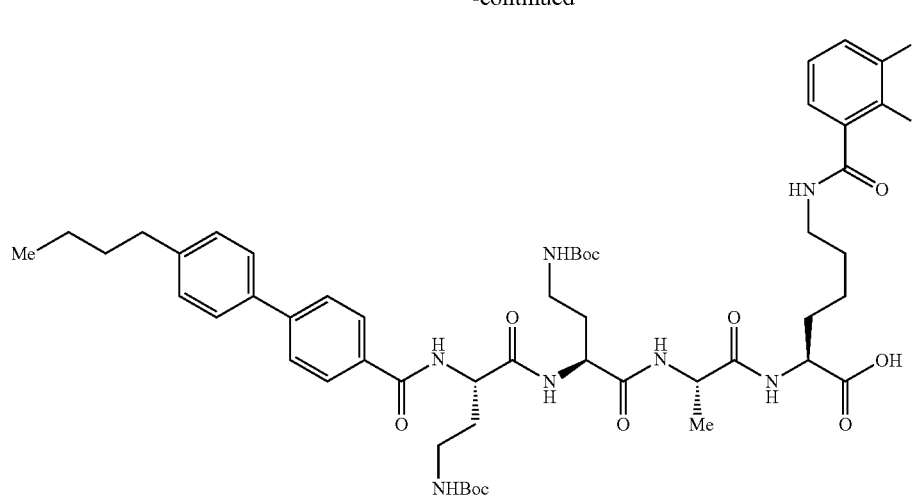
190F
Using the procedures described in General Methods 6-8, the following carboxylic acids were prepared:
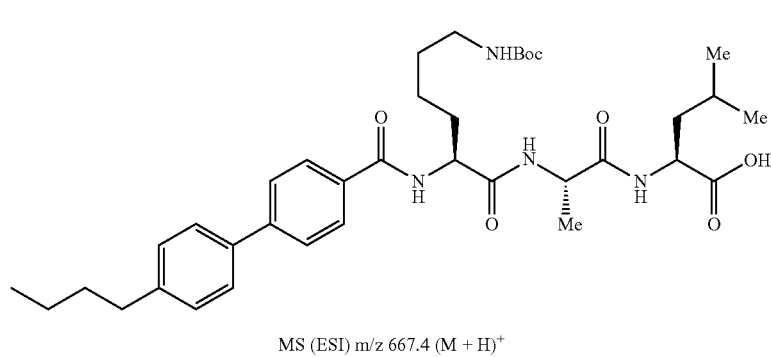
191E
MS (ESI) m/z 667.4 (M + H)+
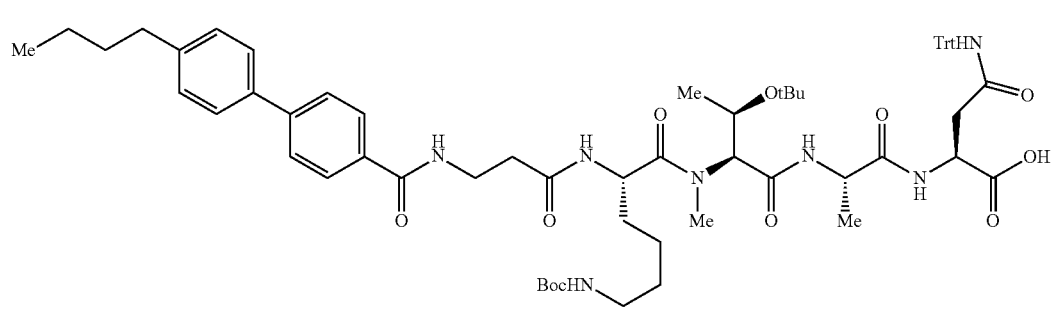
192G
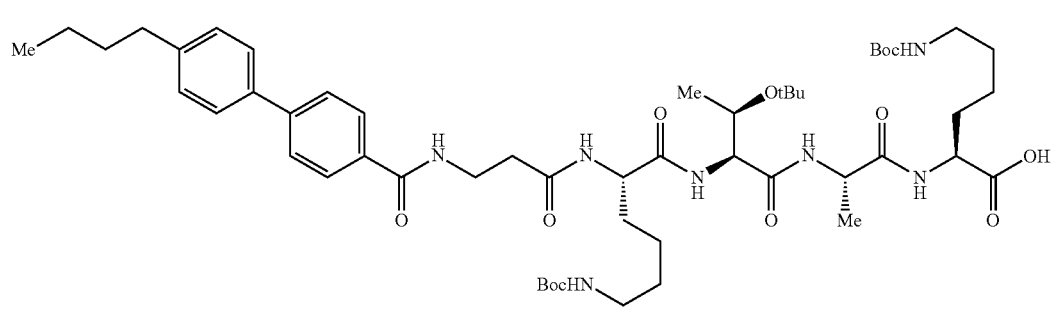
193G

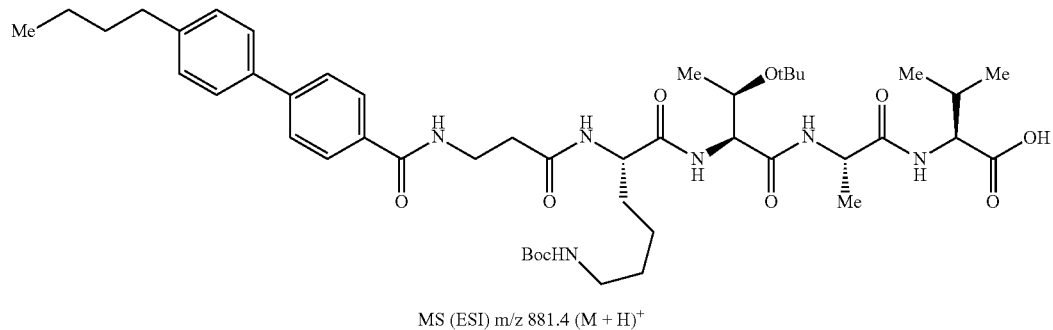
194G
MS (ESI) m/z 881.4 (M + H)+
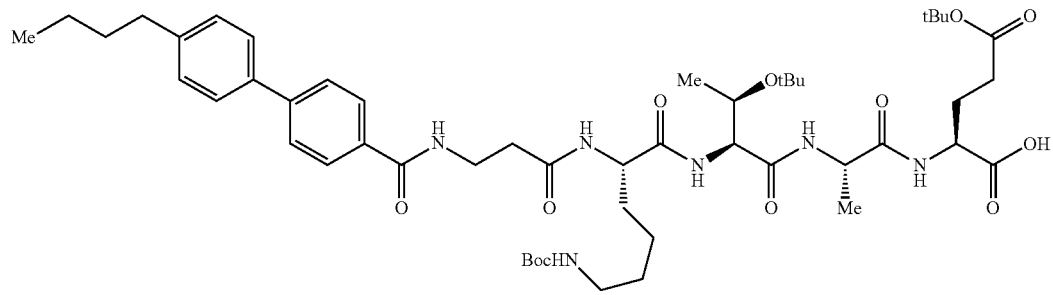
195G
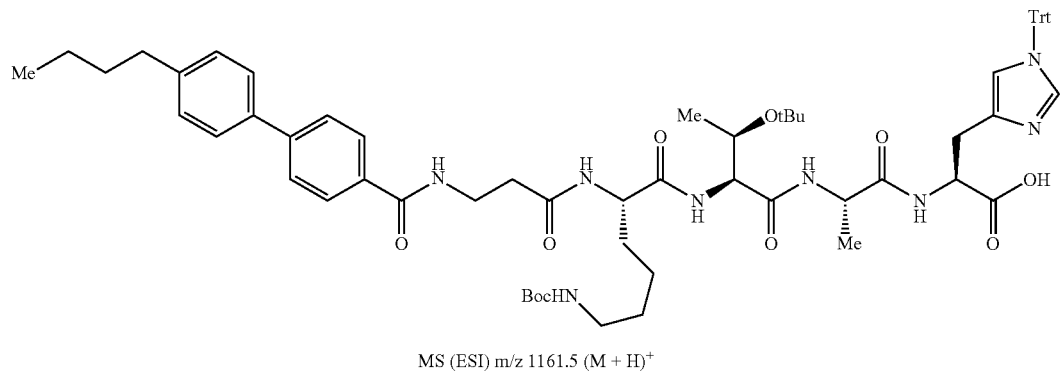
196G
MS (ESI) m/z 1161.5 (M + H)+
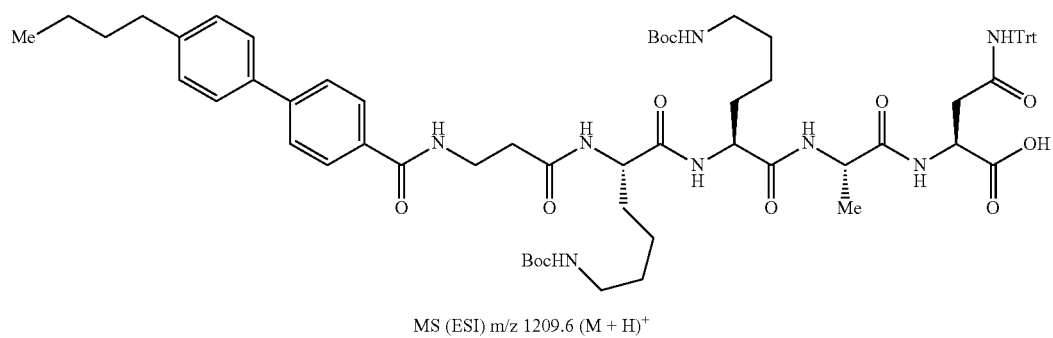
197G
MS (ESI) m/z 1209.6 (M + H)+

-continued
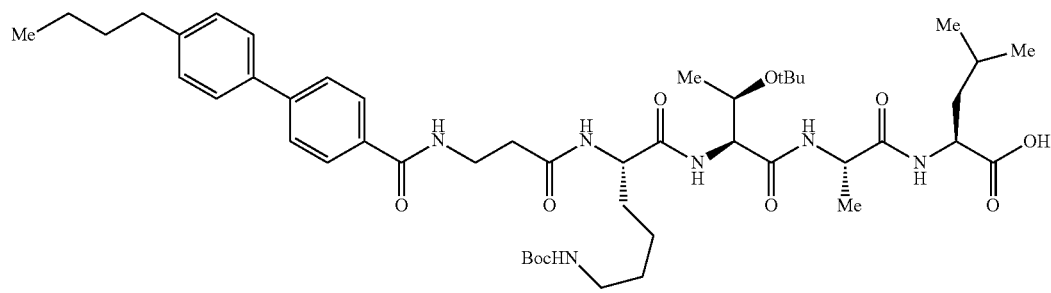
198G
MS (ESI) m/z 895.8 (M + H)+
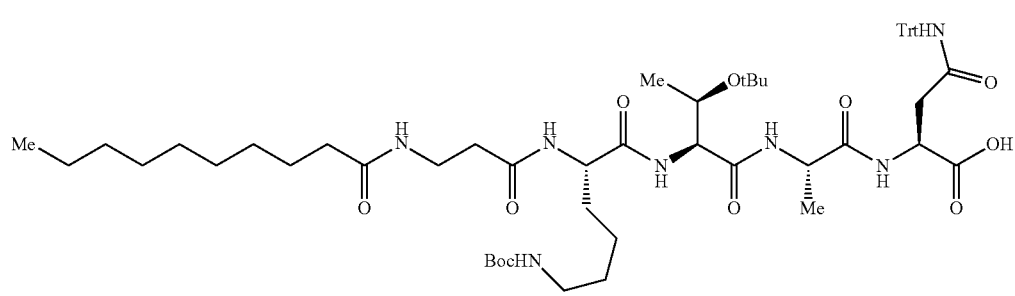
199G
MS (ESI) m/z 1056.6 (M + H)+
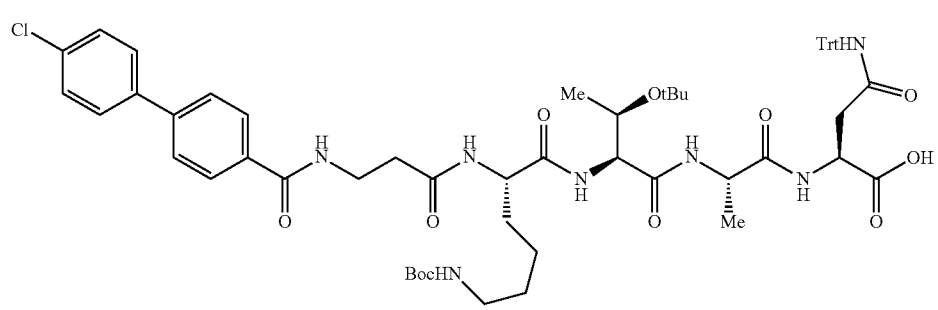
201G
MS (ESI) m/z 1116.7 (M + H)+
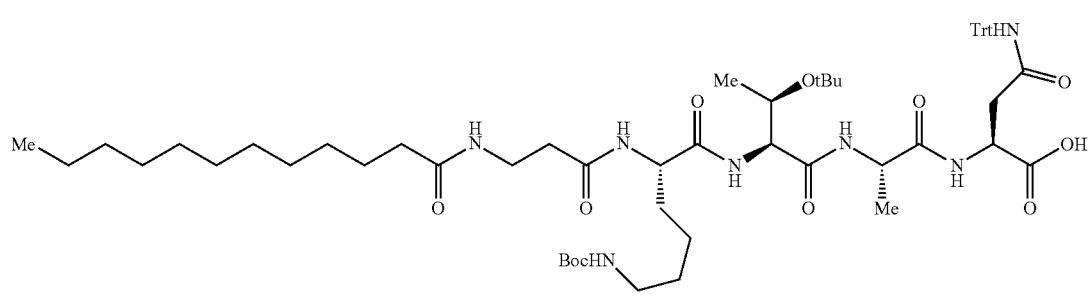
202G
MS (ESI) m/z 1084.5 (M + H)+
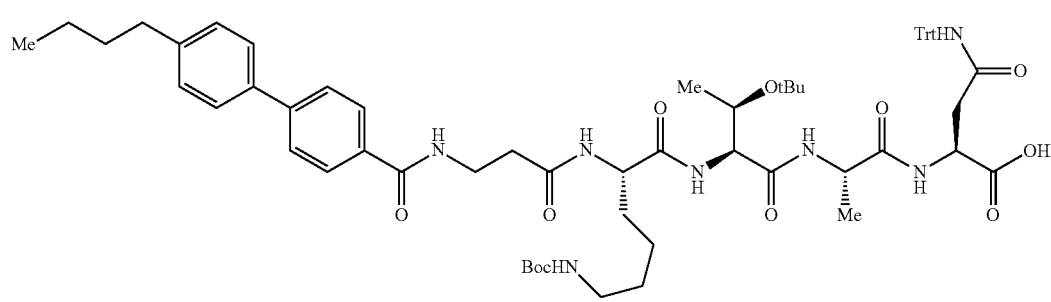
203G

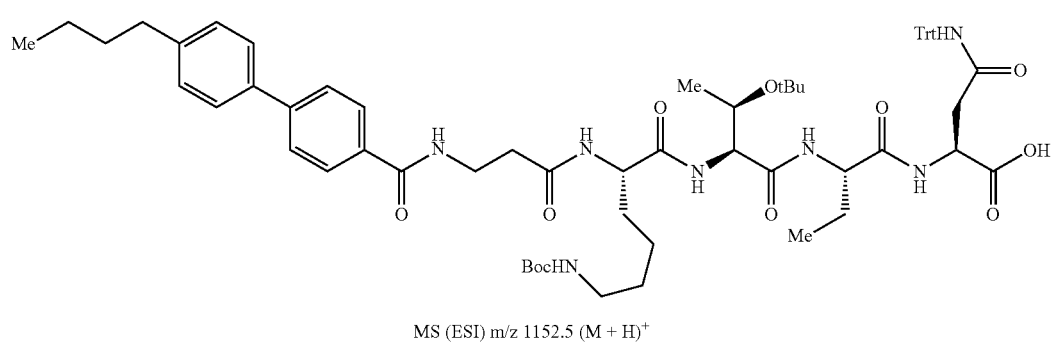
205G
MS (ESI) m/z 1152.5 (M + H)+
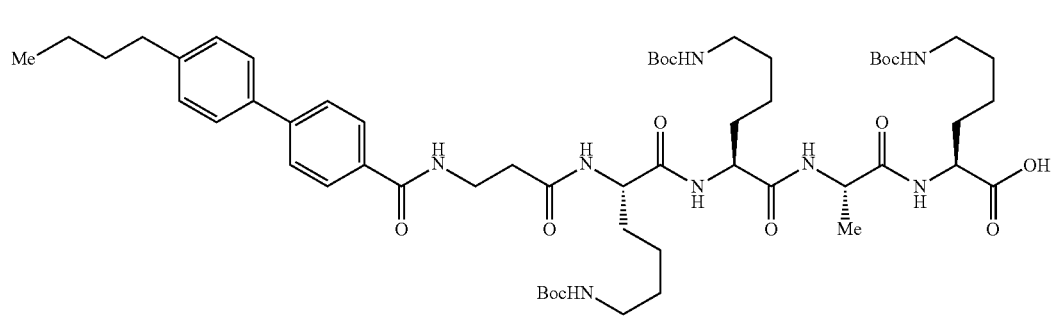
207G
MS (ESI) m/z 1081.5 (M + H)+
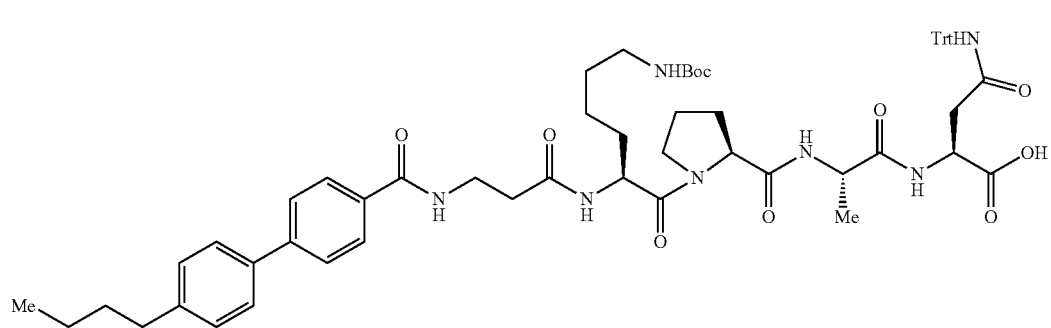
208G
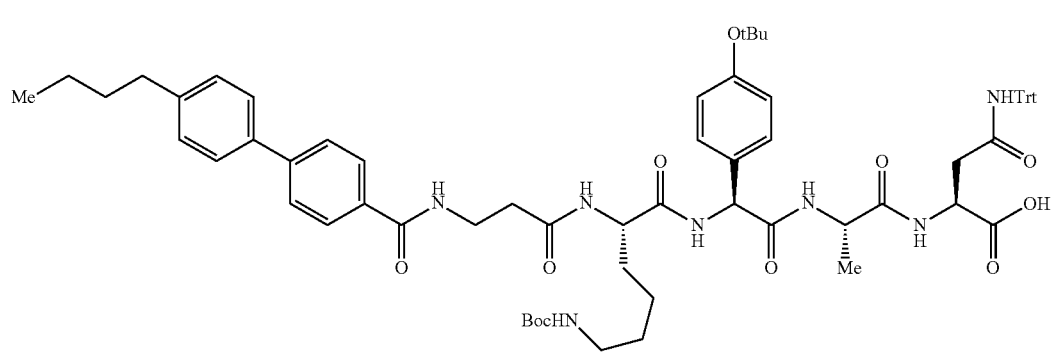
209G
MS (ESI) m/z 967.5 (M + H)+

210G
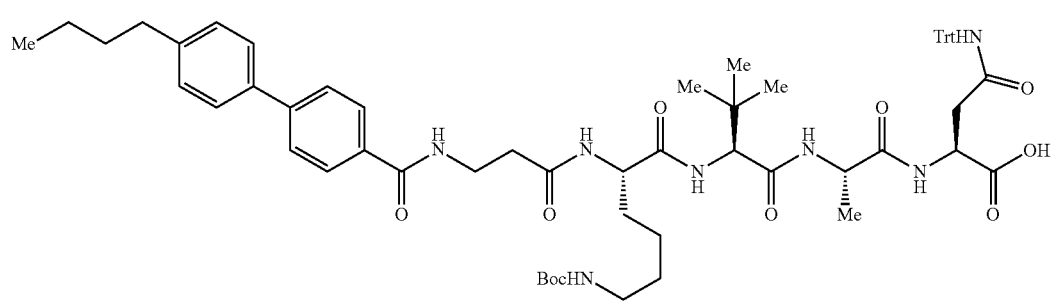
MS (ESI) m/z 1094.3 (M + H)+
211G
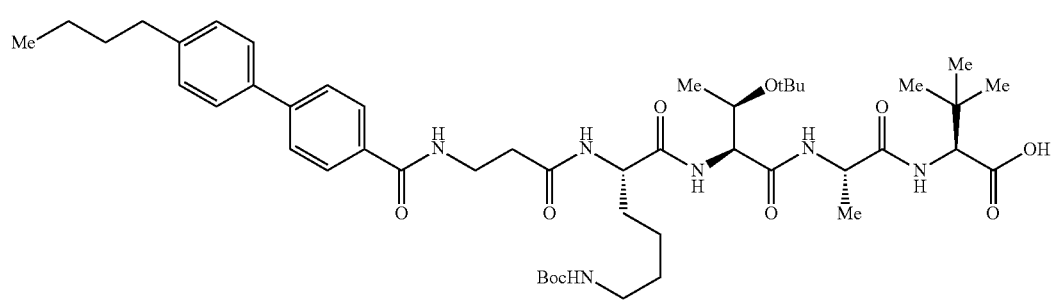
MS (ESI) m/z 895.5 (M + H)+
212G
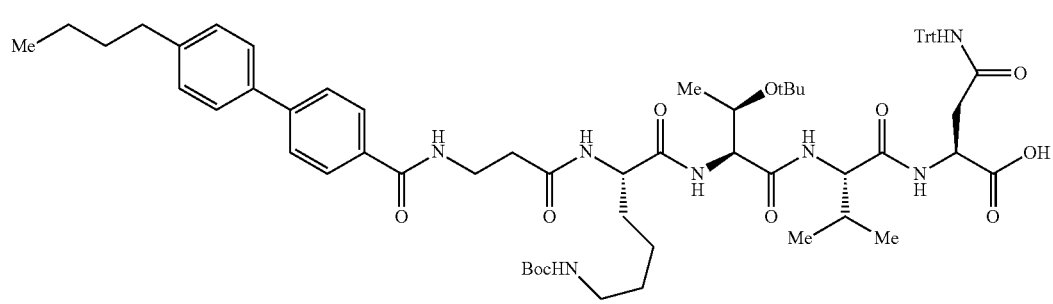
213G
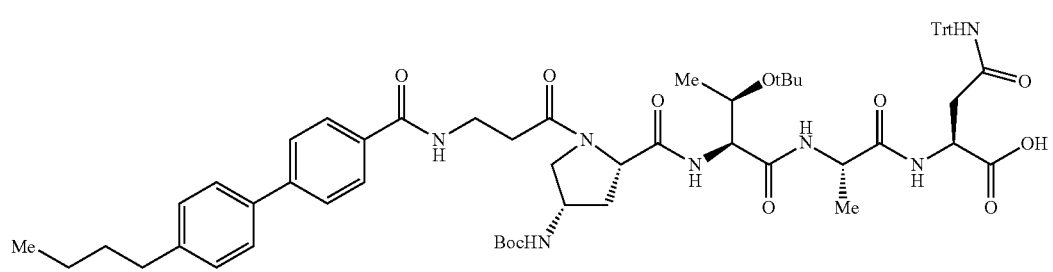
MS (ESI) m/z 1122.5 (M + H)+
214F
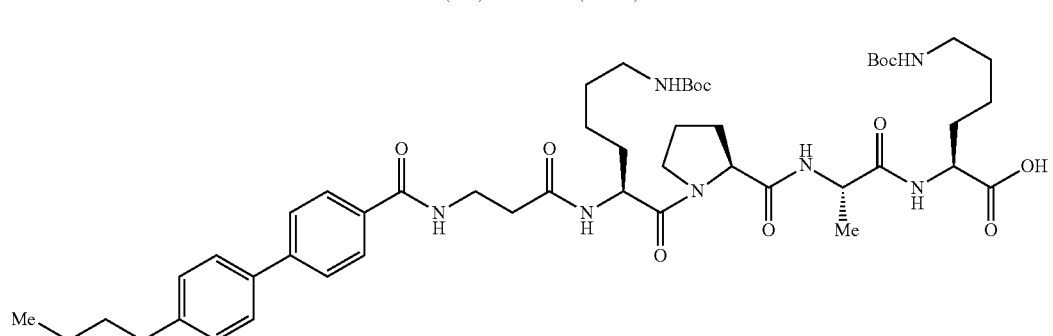
MS (ESI) m/z 950.4 (M + H)+

215F
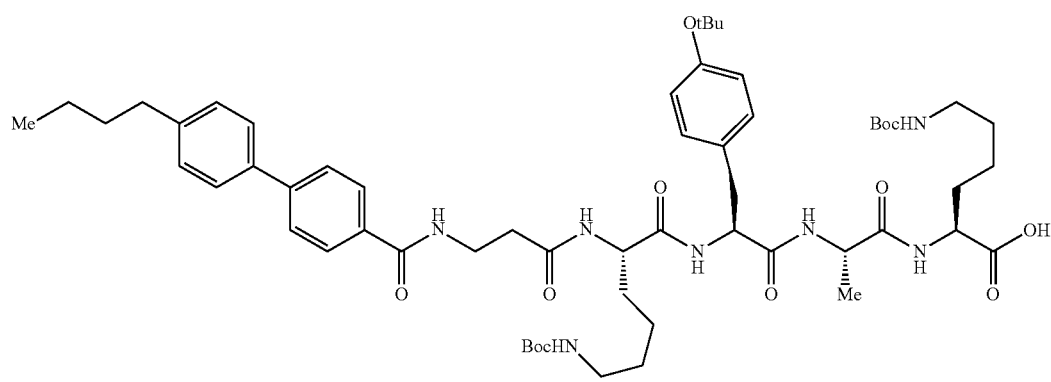
MS (ESI) m/z 1072.4 (M + H)+
216F
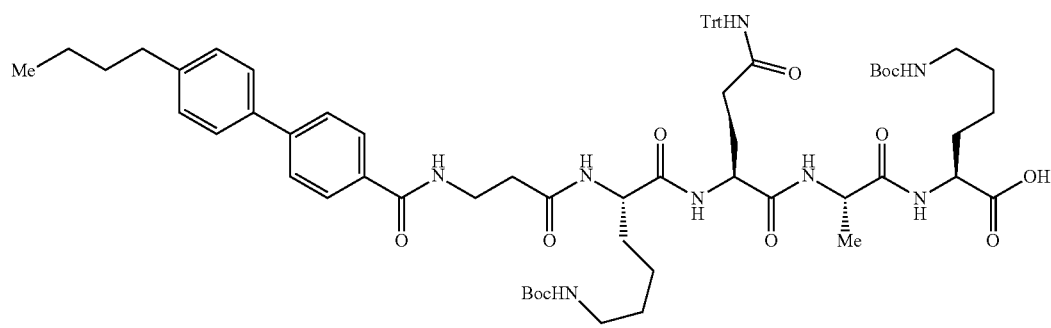
MS (ESI) m/z 1223.5 (M + H)+
217G
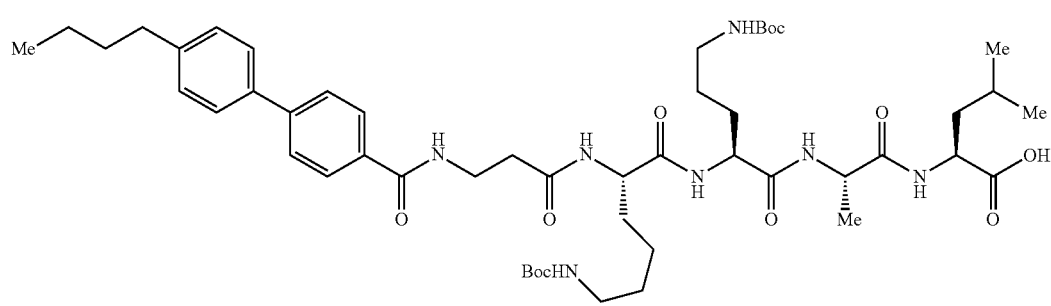
MS (ESI) m/z 952.6 (M + H)+
218G
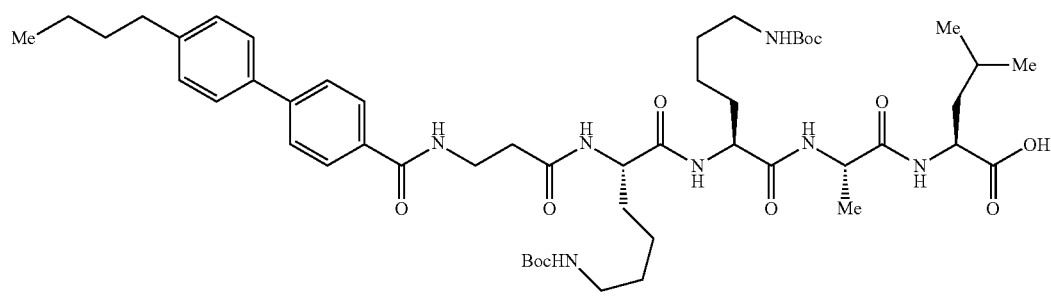
MS (ESI) m/z 966.6 (M + H)+

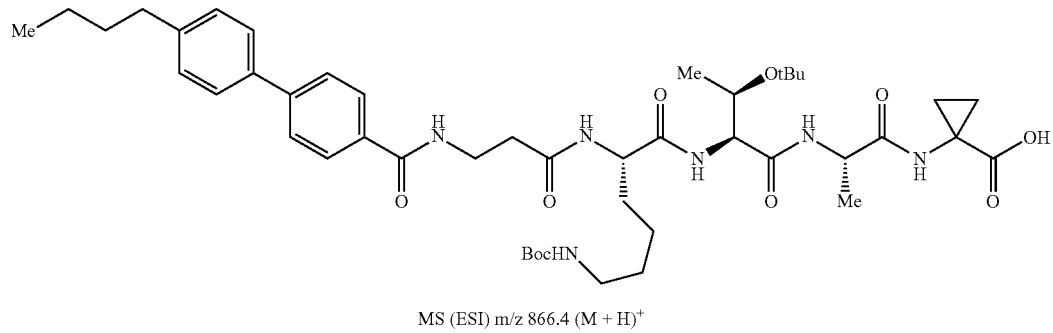
219G
MS (ESI) m/z 866.4 (M + H)⁺
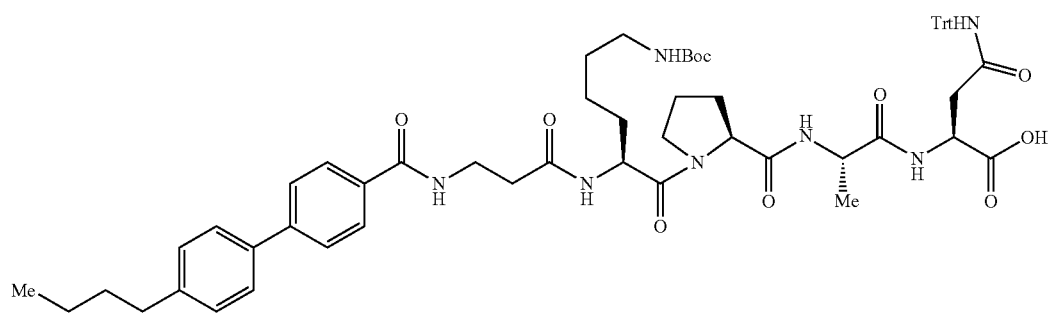
220G
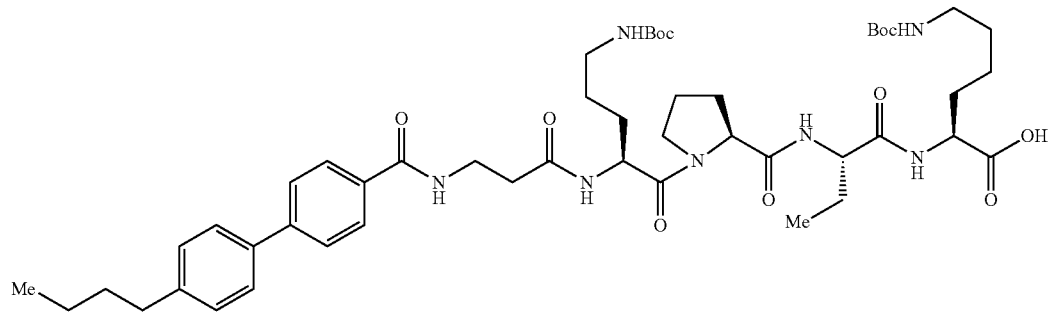
221G
MS (ESI) m/z 950.4 (M + H)⁺
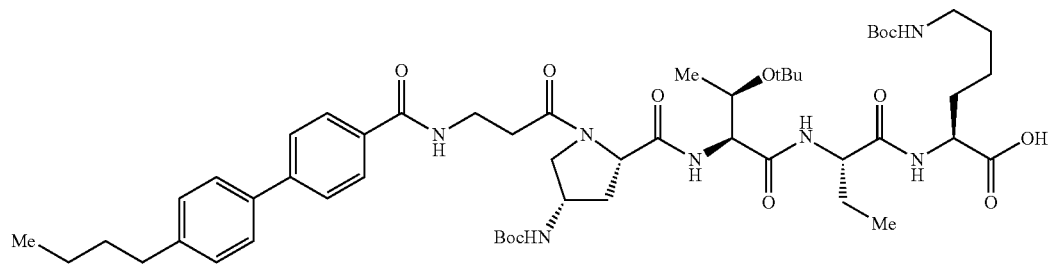
222G
MS (ESI) m/z 1008.5 (M + H)⁺

-continued
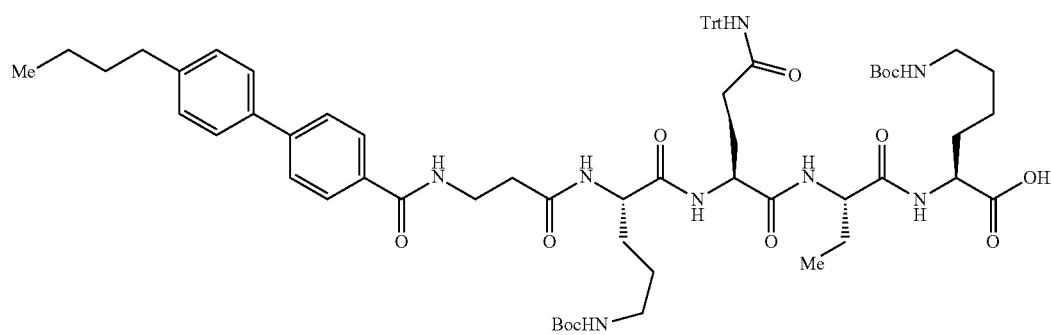
223G
MS (ESI) m/z 1223.6 (M + H)+
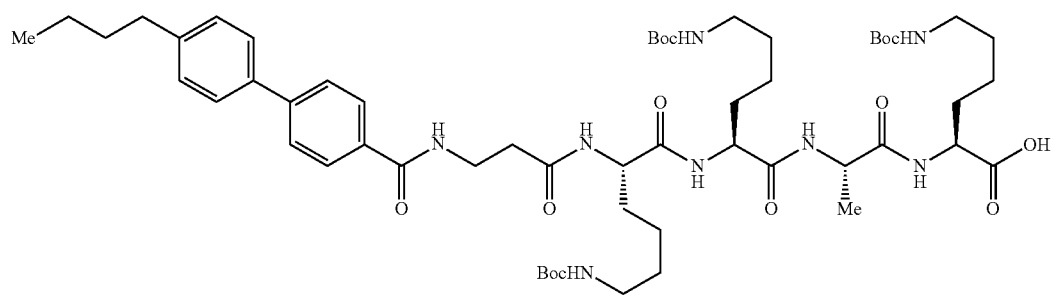
224G
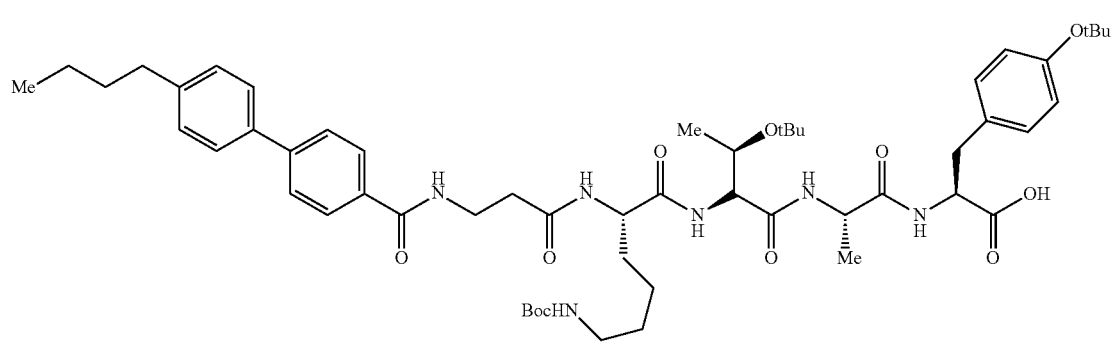
225G
MS (ESI) m/z 1001.8 (M + H)+
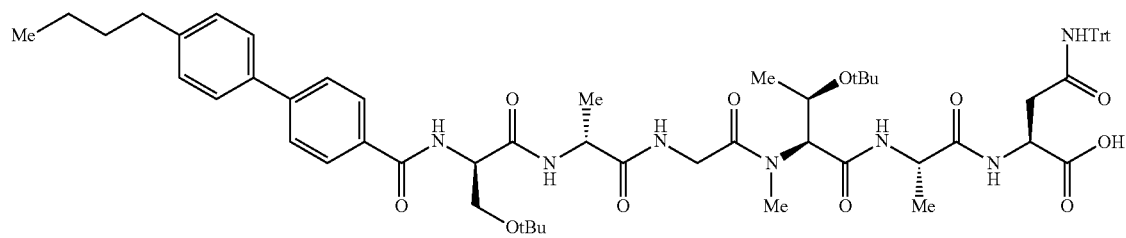
226H
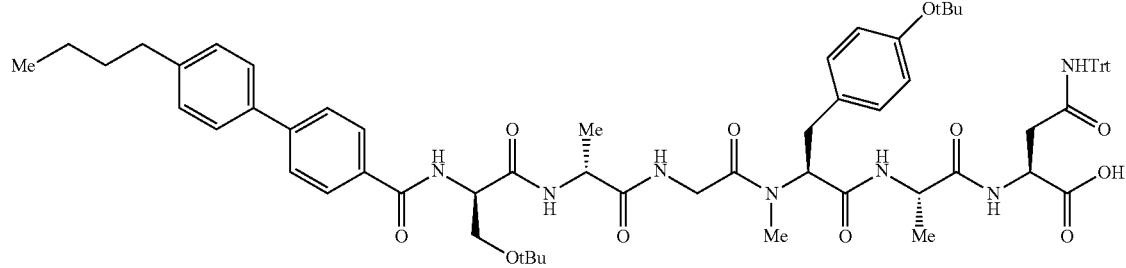
227H -continued

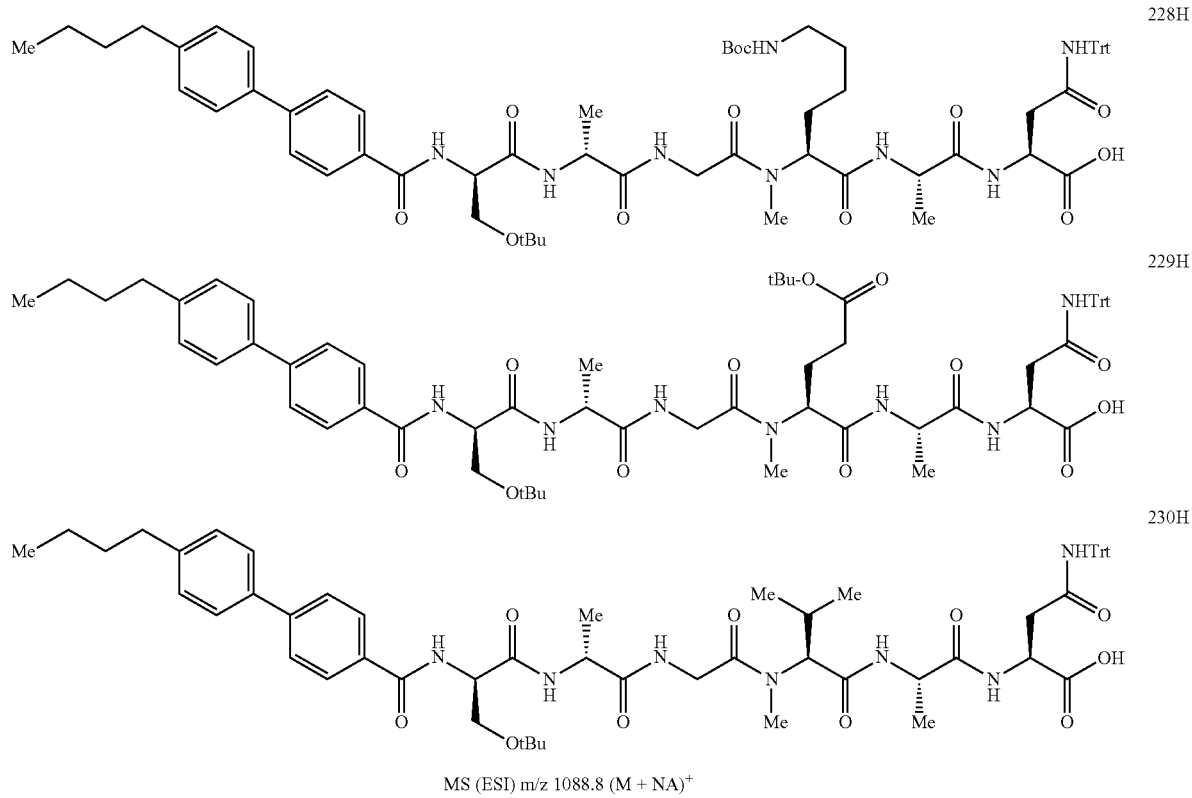

MS (ESI) m/z 1088.8 (M + NA)+

General Method 9:

The coupling of an aminoboronate ester to a carboxylic acid is depicted in Scheme XIX.

Scheme XIX

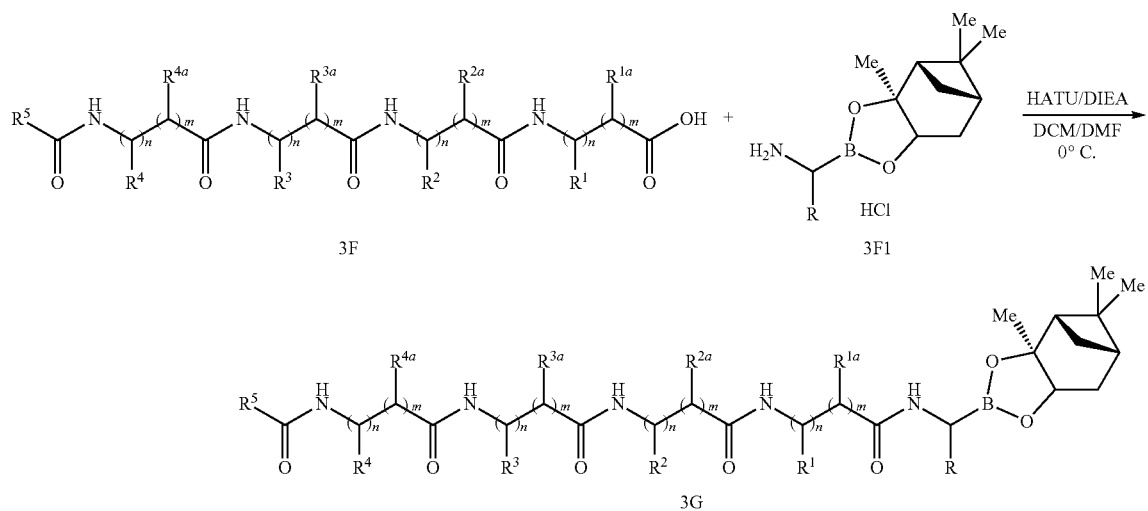

Compound 3F (1 eq), HATU (2.0 eq) and aminoboronate ester 3F1 (1.5 eq) was added to a round-bottom flask and cooled in an ice bath. DCM and DMF were added in a 3:1 ratio (0.03-0.05 M). In cases where solubility is limiting, additional DMF can be added. After 15-30 minutes, the reaction was allowed to warm to room temperature and stirred for 30 minutes. After LCMS analysis showed the reaction to be complete, the mixture was distributed between DCM and water, and the aqueous layer was extracted twice with DCM. The combined organic layers were washed sequentially with diluted HCl (<0.1 M), NaHCO₃ solution, and brine. The solvent was removed under reduced pressure. The solid residue was washed with acetonitrile to afford the desired compound. In cases where there is excessive DMF remaining, the residue was distributed between EA (300 mL/mmol) mL):water (100 mL/mmol). The organic layers were washed sequentially with water and brine, and dried over $Na_2SO_4$. The mixture was filtered and concentrated, and the resulting solid washed with acetonitrile.

General Method 10:

The deprotection of acid sensitive protecting groups (N-Boc, O-t-butyl, and/or C(O)NH-trityl) with TFA and triethylsilane. A solution of the fully protected Compound 3G (100 mg, 0.070-0.12 mmol) in TFA:DCM:TES (50:45:5) (1 mL) was stirred at room temperature for 30 min. When analysis by LC-MS showed the reaction was complete, the TFA was evaporated and ELSD showed the reaction was complete. The crude residue was then taken up in DMSO and purified by prep-HPLC. In cases where the mobile phase was acetonitrile/water with 0.1% TFA, the resultant salt is the TFA salt. In instances where the mobile phase was acetonitrile/water with 0.1% HCl, the resultant salt is the HCl salt.

A representative example of General Methods 9 and 10 is shown in Scheme XX.

Compound 173: A flask containing Compound 173F (100 mg, 0.12 mmol), HATU (91 mg, 0.24 mmol), then 3F2 (47 mg, 0.18 mmol) was placed in an ice bath. DCM (2.4 mL) and DMF (0.80 mL) were added. To this mixture was added DIEA (46.2 mg, 0.358 mmol). After 15-30 mins the reaction was warmed to room temperature and stirred for 30 mins. After ELSD showed the reaction was complete, water (1 ml) was added and the mixture was filtrated. The filter cake was washed sequentially with water and petroleum ether to afford Compound 173-I (70 mg, 56%).

A solution of Compound 173-I (70 mg, 0.069 mmol) in TFA:DCM:TES (50:45:5) (1 mL) was stirred at 23° C. for 2 hrs until ELSD showed the reaction was completed, then TFA was evaporated. Then the crude residue was taken up in DMSO and purified by prep-HPLC to give Compound 173 (13 mg, 23%).

General Method 11:

Scheme XX

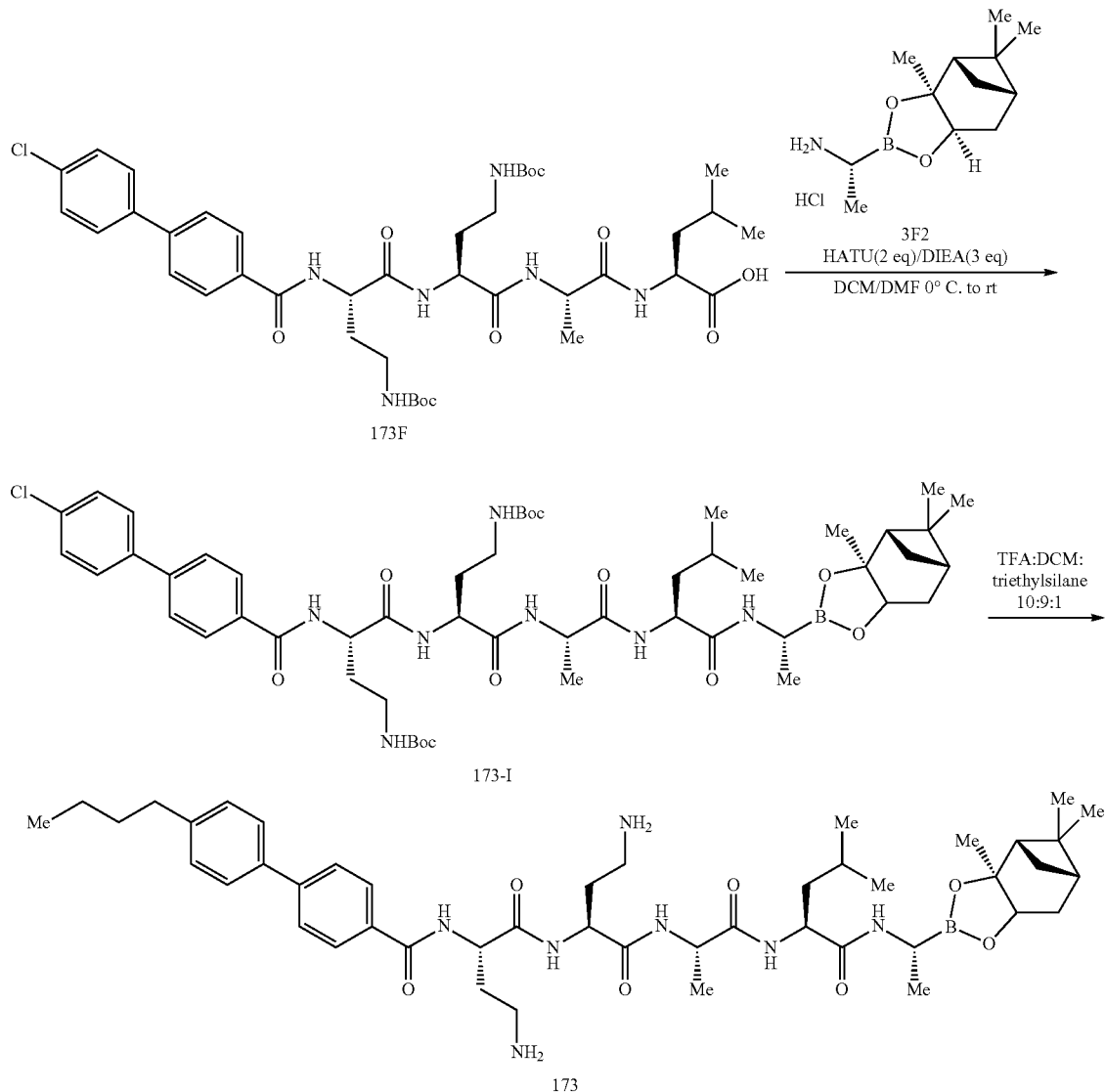

The deprotection of the pinanediol protecting group to the free boronic acid by transesterification with $Ph(BOH)_2$ is depicted in Scheme XXI.

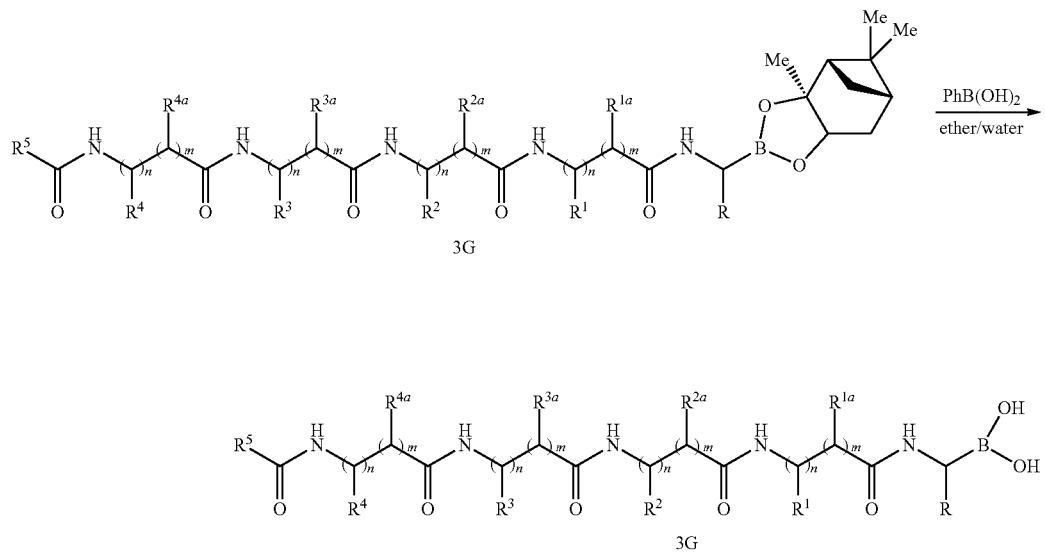

A solution of the pinanediol (0.05 mmol) in water (2 mL) was stirred for five minutes until the compound dissolves and forms clear solution. Added ether (3 mL) and phenyl boronic acid (3 eq) dissolved in water (1 mL). The mixture was stirred at 25° C. overnight. After LCMS analysis showed the reaction was complete, the water layer was evaporated under reduced pressure. The crude residue was washed with $Et_2O$ to afford the free boronic acid (25.0 mg, yield: 74.6%). If further purification is necessary, the crude product was dissolved in DMSO and purified by preparative HPLC. In cases where the mobile phase was acetonitrile/water with 0.1% TFA, the resultant salt is the TFA salt. In instances where the mobile phase was acetonitrile/water with 0.1% HCl, the resultant salt is the HCl salt. A representative example is shown in Scheme XXII.

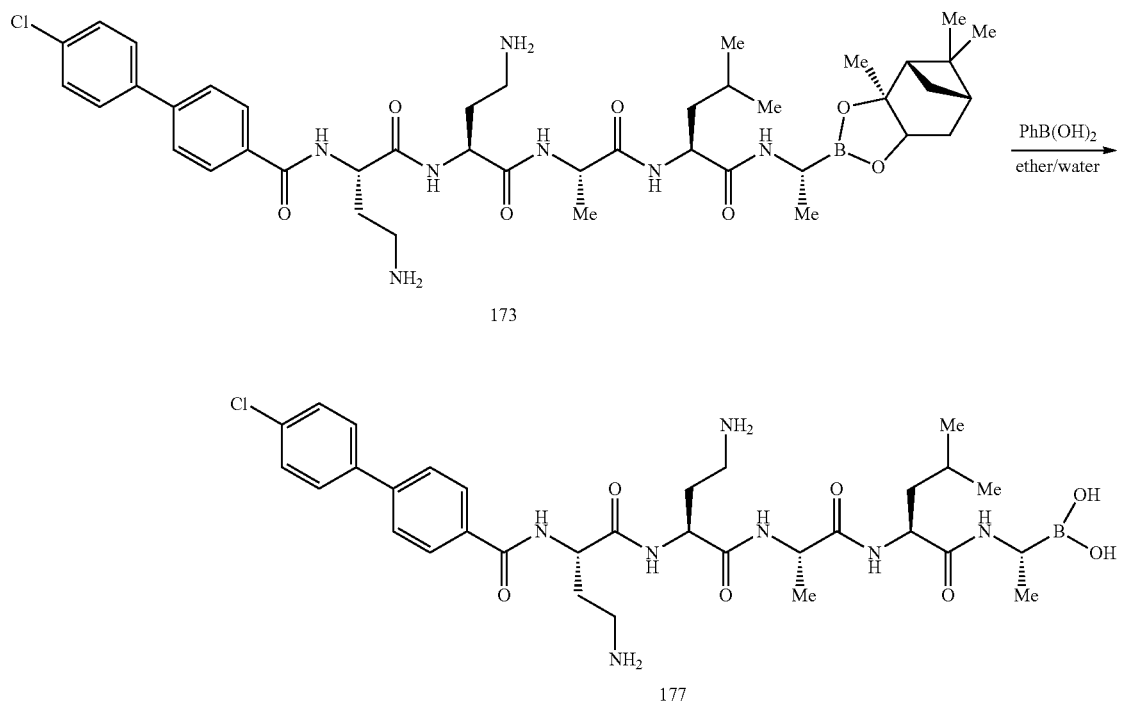

A solution of Compound 173 (9.0 mg, 0.011 mmol) in water (2 mL) was stirred for five minutes until the compound dissolved and formed clear solution. Ether (3 mL) and a solution of phenyl boronic acid (4.00 mg, 0.033 mmol) dissolved in water (1 mL) were added. The mixture was stirred at 23° C. for 12 h. After LCMS showed the reaction was completed, water was evaporated. The crude residue was then washed with Et$_2$O to give Compound 177 (7.0 mg, yield: 93%) as an off-white solid.

Using the procedures described in General Methods 9 and 10 for the preparation of the boronate esters or General Methods 9, 10 and 11 for the preparation of the boronic acids, the following boronate ester or boronic acid were prepared from the corresponding carboxylic acid described above:

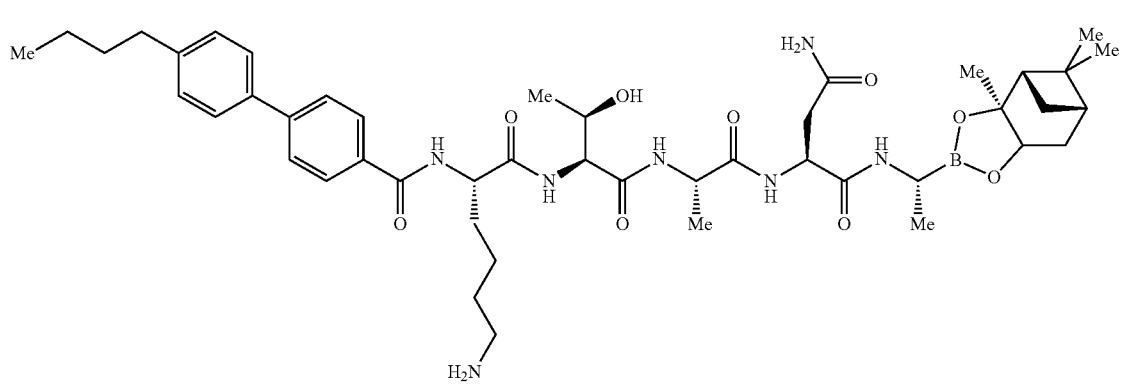

MS (ESI) m/z 874.7 (M + H)$^+$

129

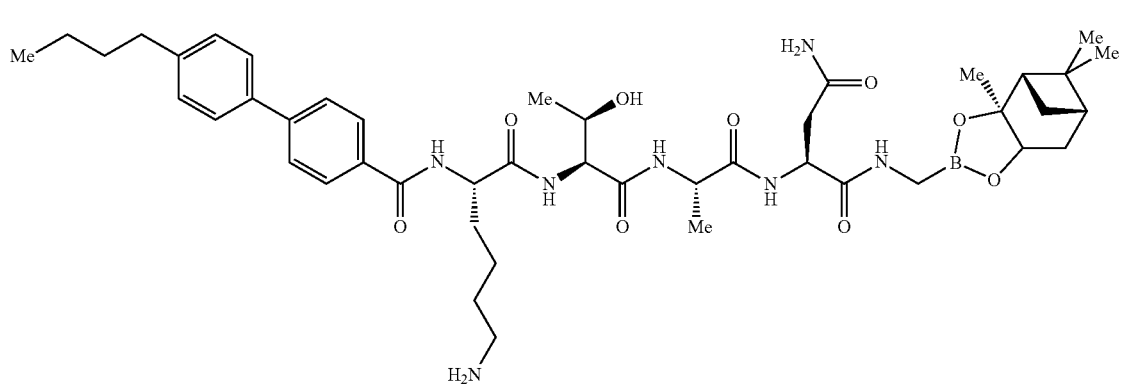

MS (ESI) m/z 860.3 (M + H)$^+$

130

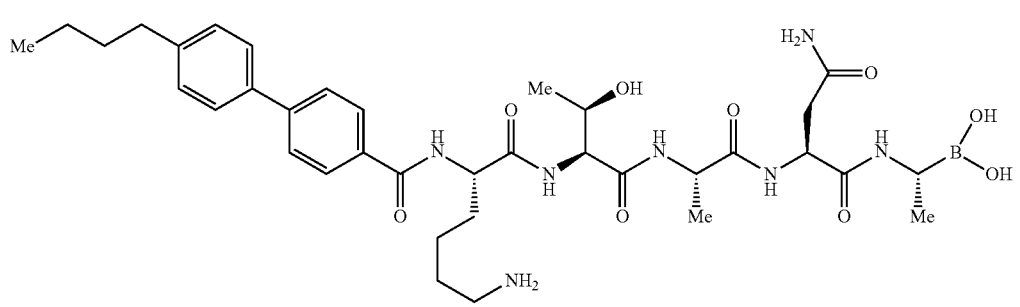

MS (ESI) m/z 722.2 (M - H$_2$O + H)$^+$

131

-continued
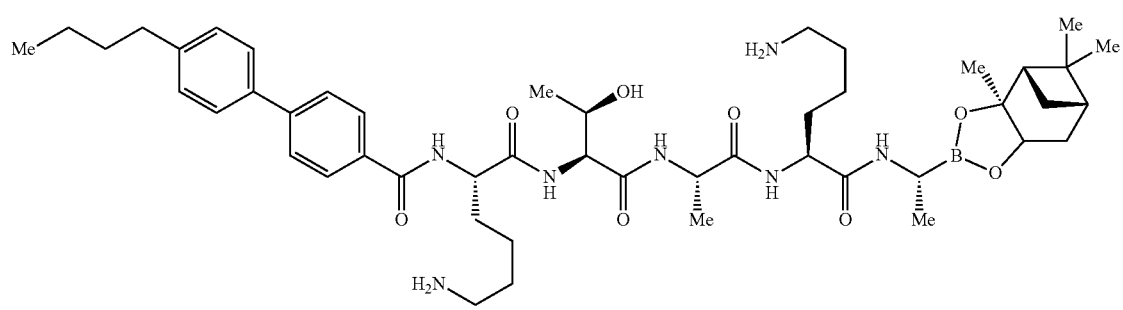
132
MS (ESI) m/z 888.5 (M + H)+
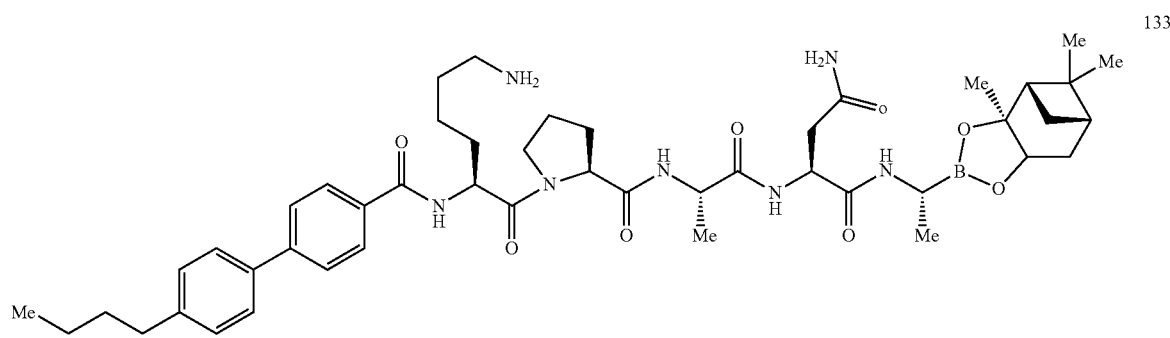
133
MS (ESI) m/z 870.4 (M + H)+
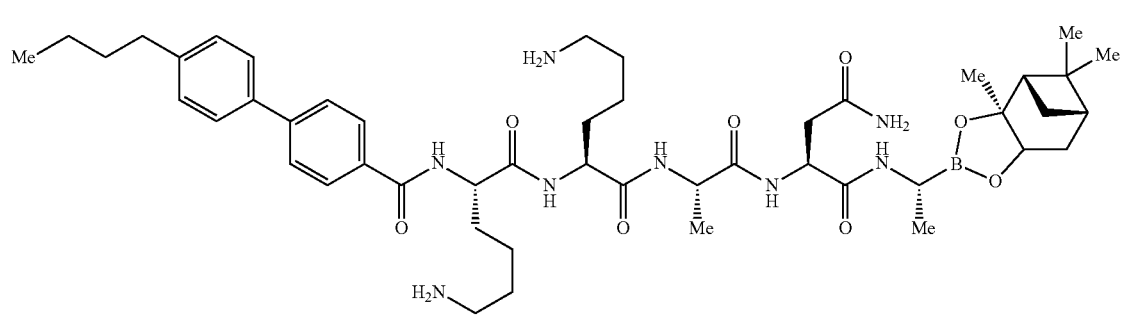
134
MS (ESI) m/z 901.4 (M + H)+
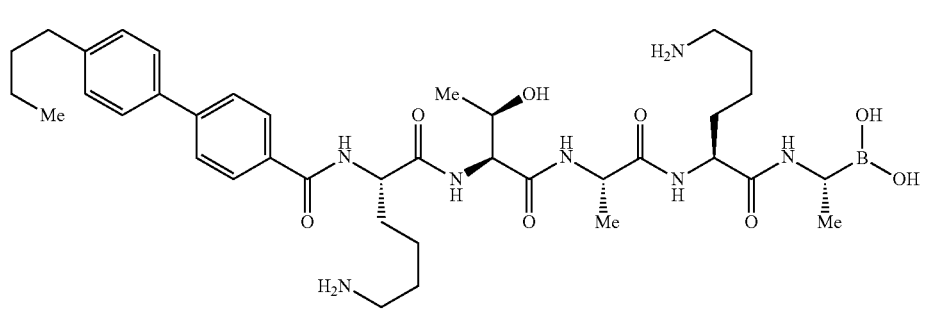
135
MS (ESI) m/z 722.2 (M − H₂O + H)+

-continued
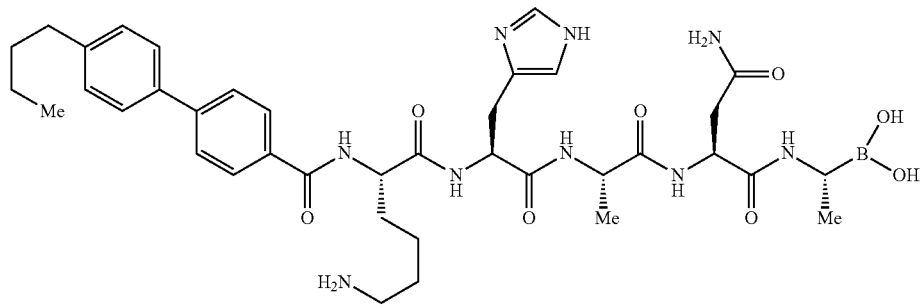
MS (ESI) m/z 758.3 (M - H₂O + H)⁺
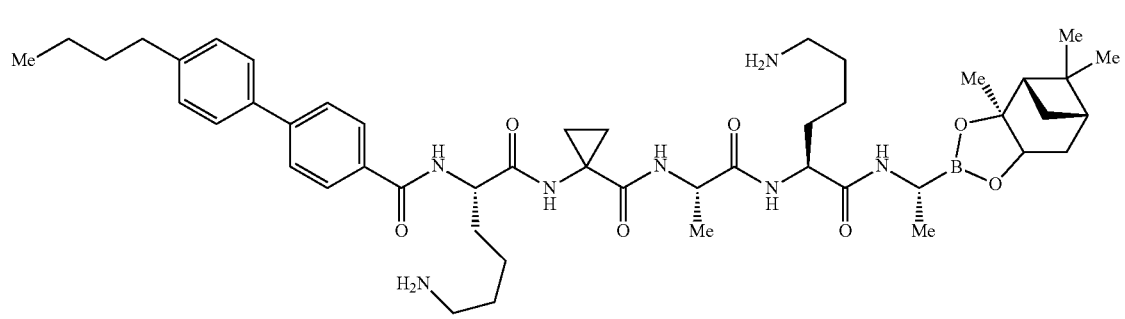
MS (ESI) m/z 870.4 (M + H)⁺
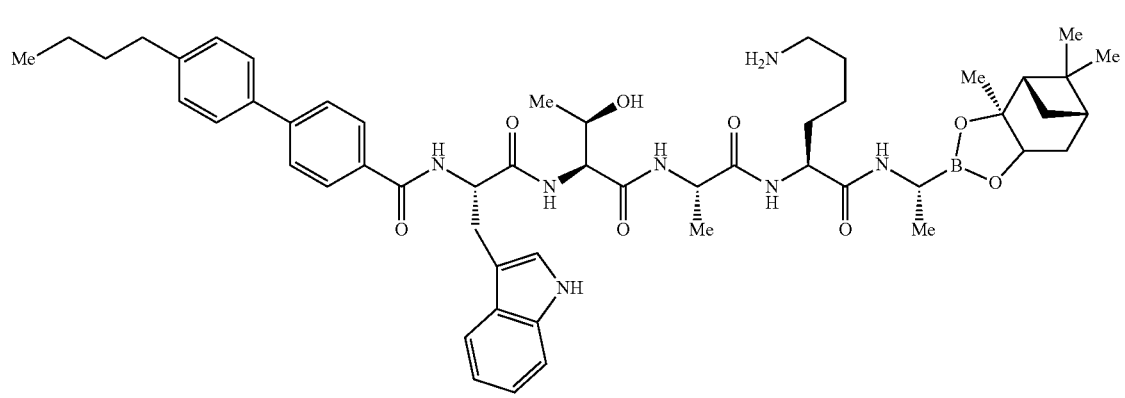
MS (ESI) m/z 946.3 (M + H)⁺
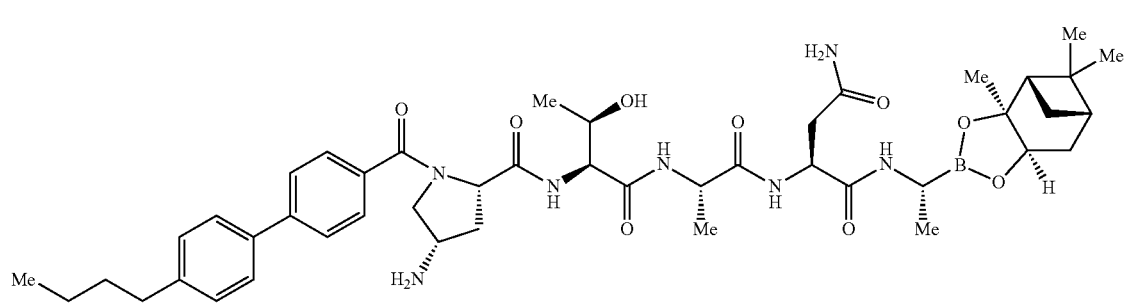
MS (ESI) m/z 858.3 (M + H)⁺

-continued
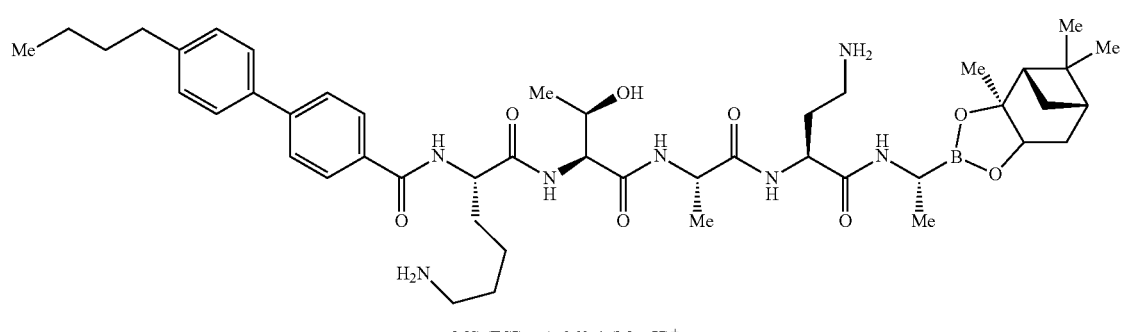
MS (ESI) m/z 860.4 (M + H)+
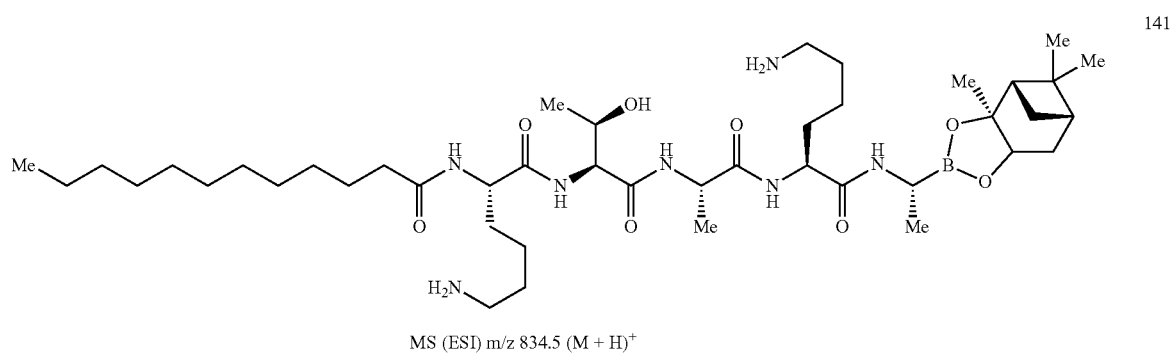
MS (ESI) m/z 834.5 (M + H)+
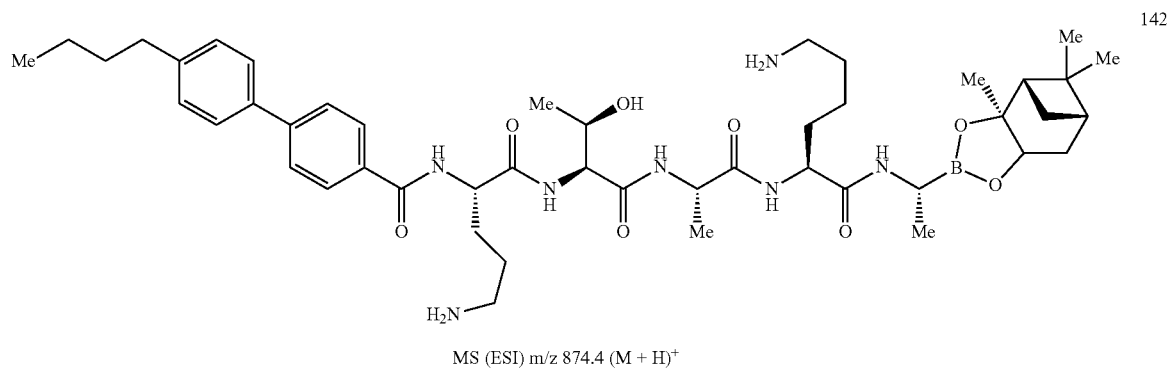
MS (ESI) m/z 874.4 (M + H)+
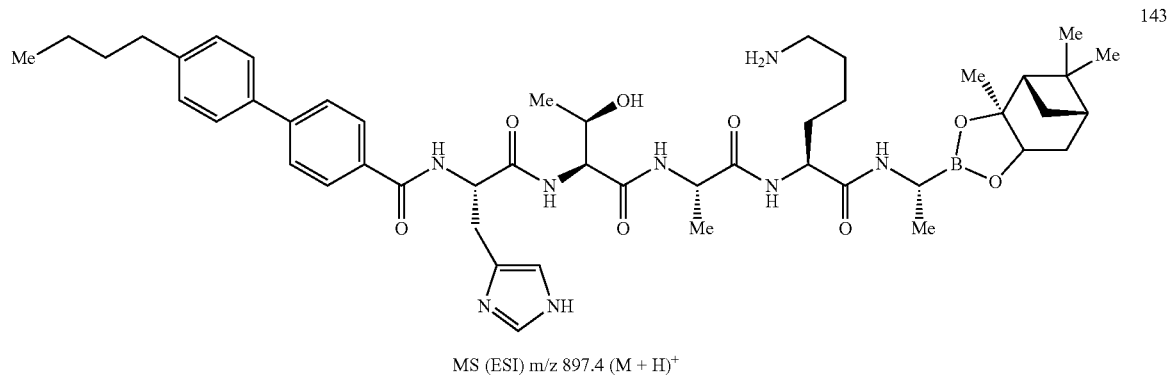
MS (ESI) m/z 897.4 (M + H)+

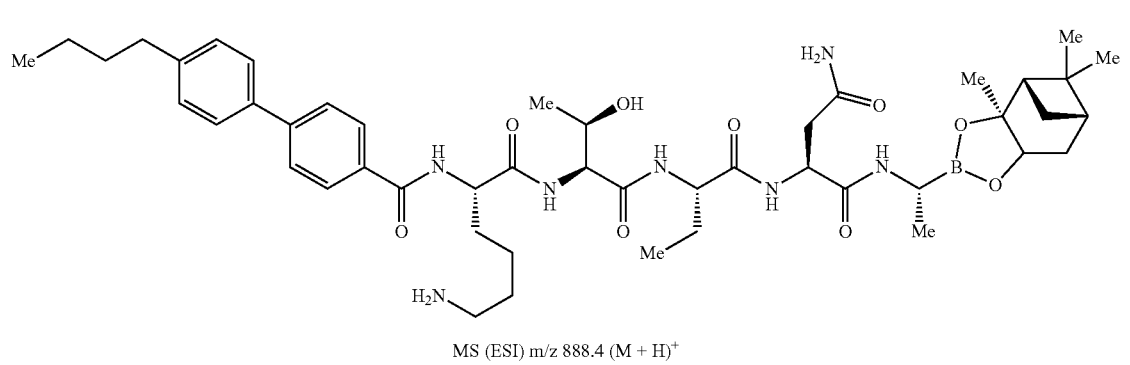
144
MS (ESI) m/z 888.4 (M + H)+
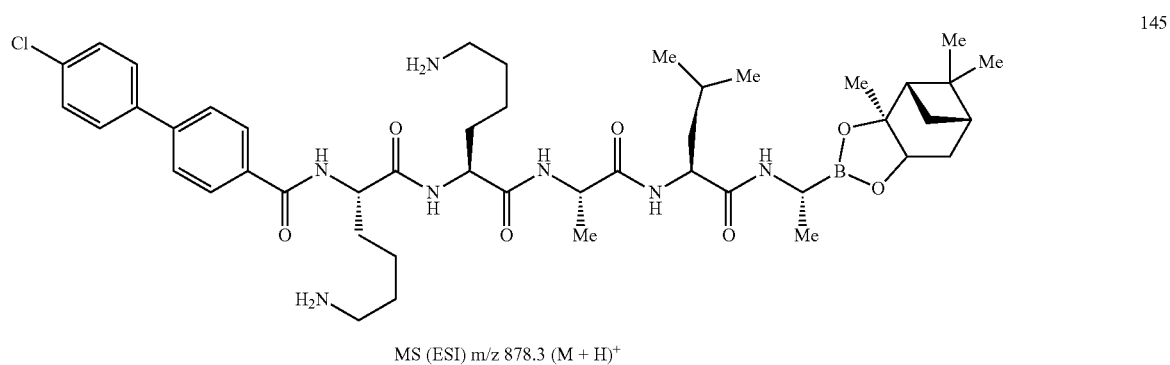
145
MS (ESI) m/z 878.3 (M + H)+
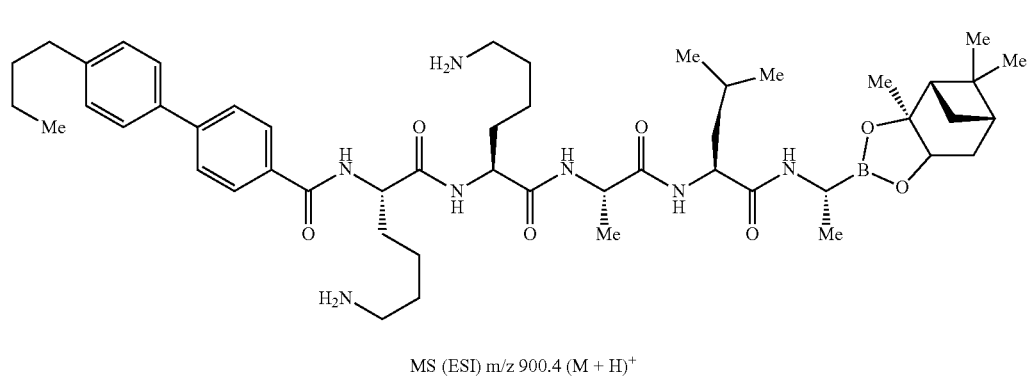
146
MS (ESI) m/z 900.4 (M + H)+
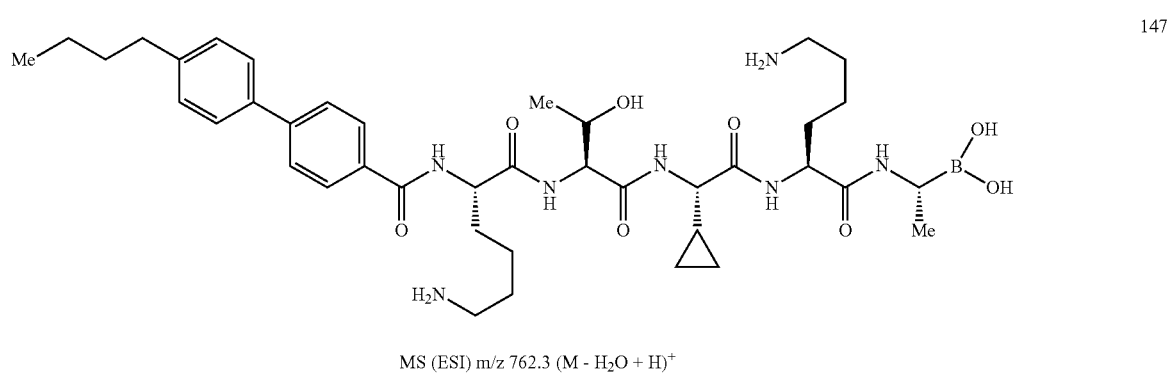
147
MS (ESI) m/z 762.3 (M − H₂O + H)+

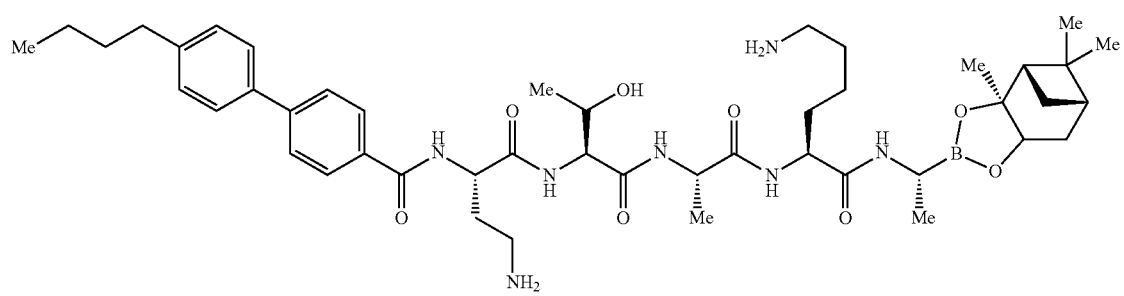
148
MS (ESI) m/z 860.4 (M + H)+
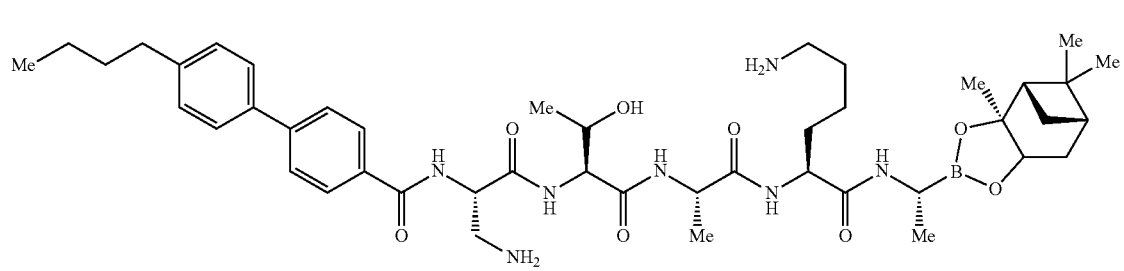
149
MS (ESI) m/z 846.4 (M + H)+
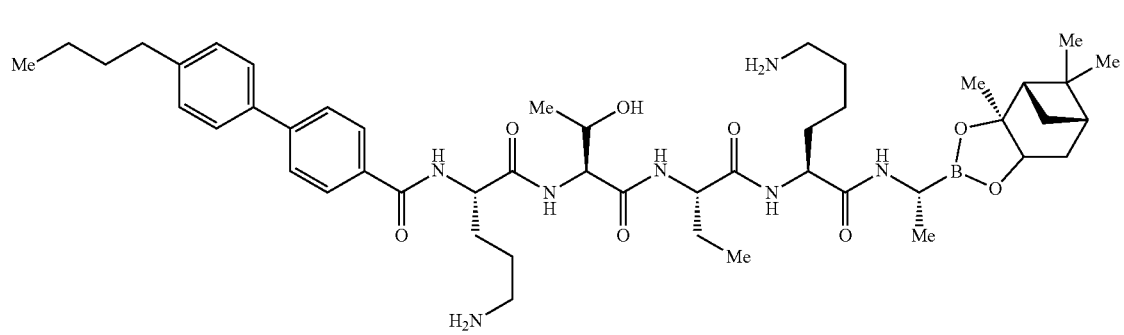
150
MS (ESI) m/z 888.4 (M + H)+
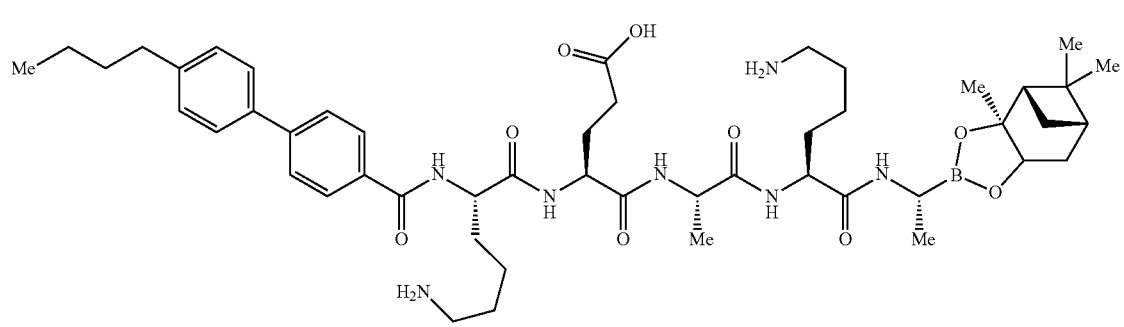
151
MS (ESI) m/z 916.4 (M + H)+

152
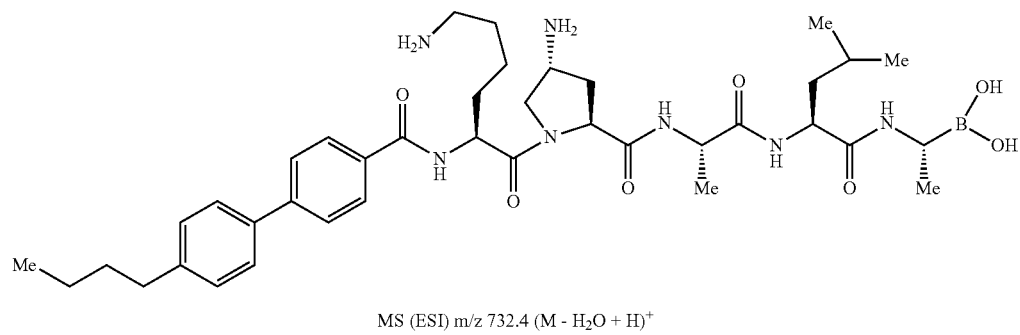
MS (ESI) m/z 732.4 (M - H₂O + H)⁺
153
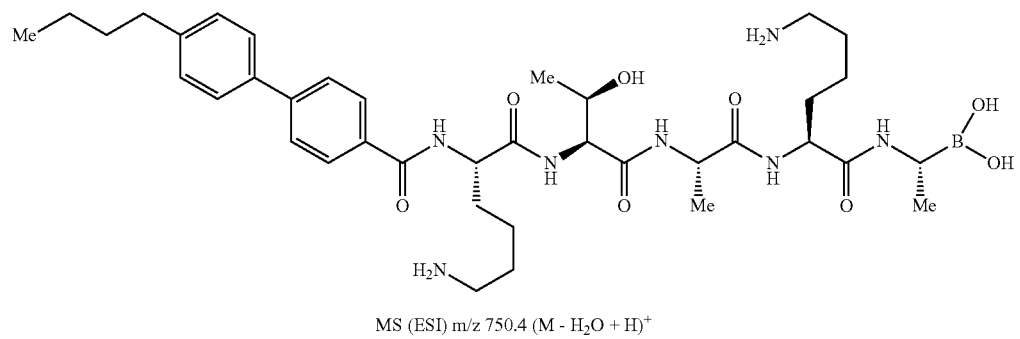
MS (ESI) m/z 750.4 (M - H₂O + H)⁺
154
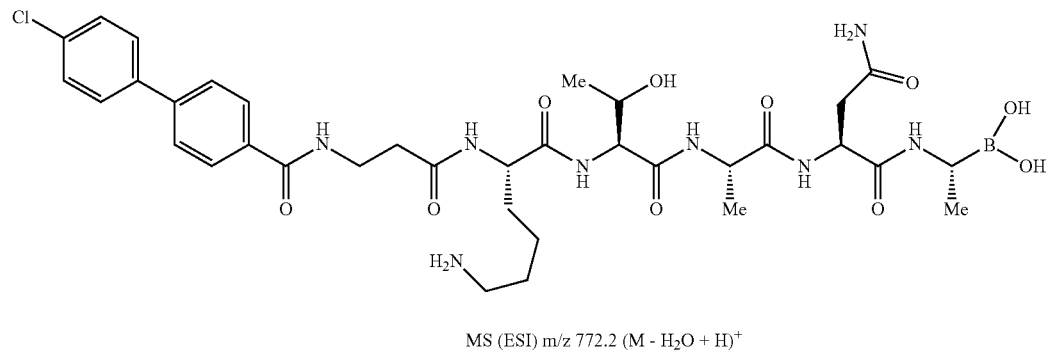
MS (ESI) m/z 772.2 (M - H₂O + H)⁺
155
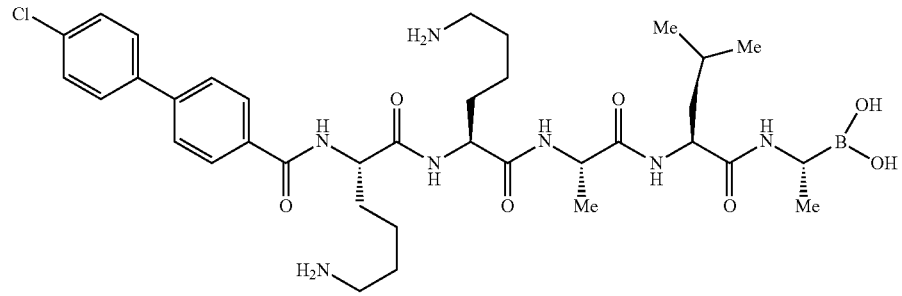
MS (ESI) m/z 728.3 (M - H₂O + H)⁺

-continued
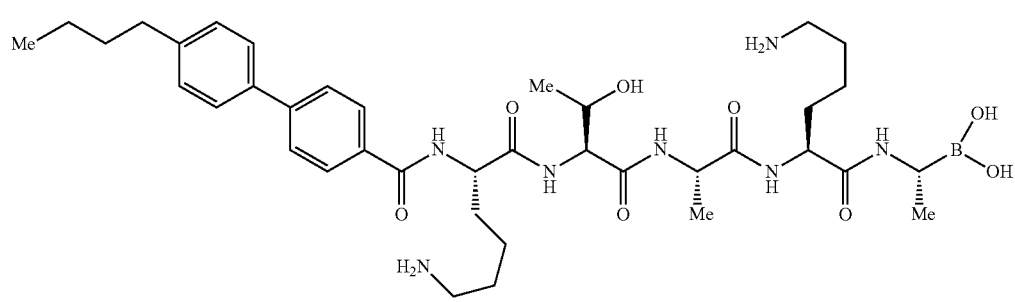
156
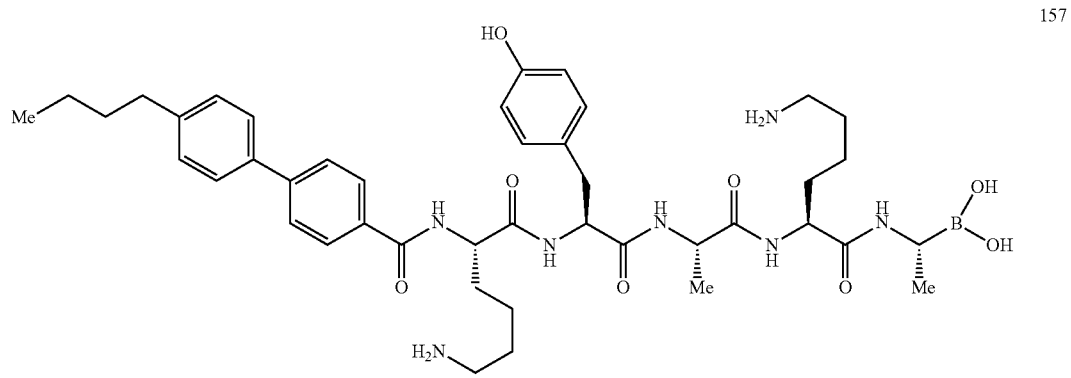
157
MS (ESI) m/z 812.4 (M − H₂O + H)⁺
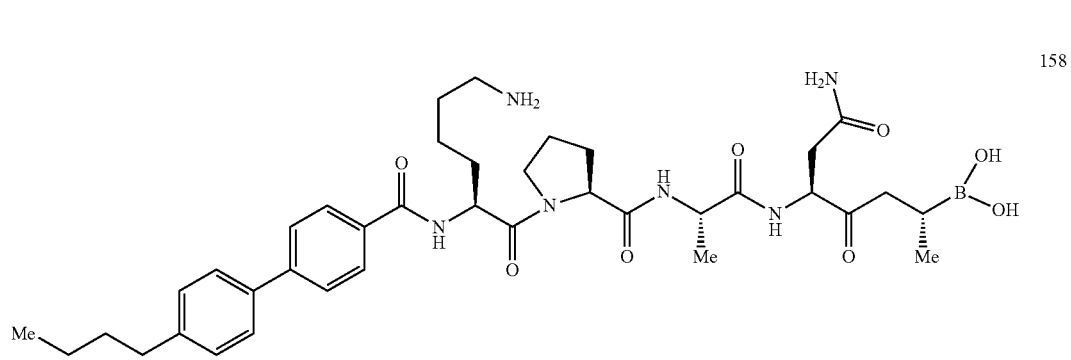
158
MS (ESI) m/z 718.4 (M − H₂O + H)⁺
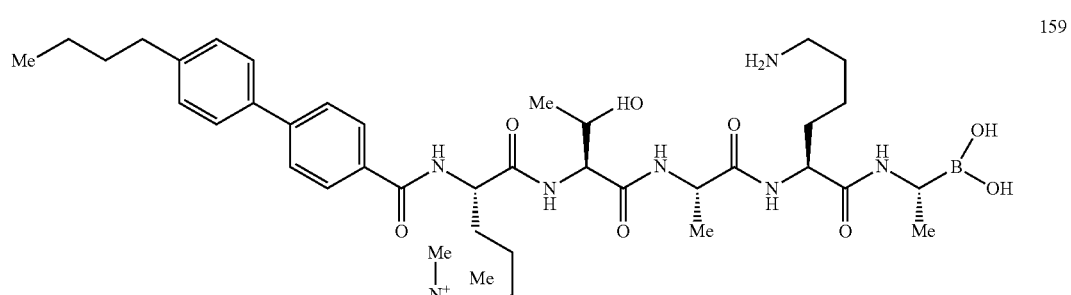
159
MS (ESI) m/z 796.5 (M + H)⁺

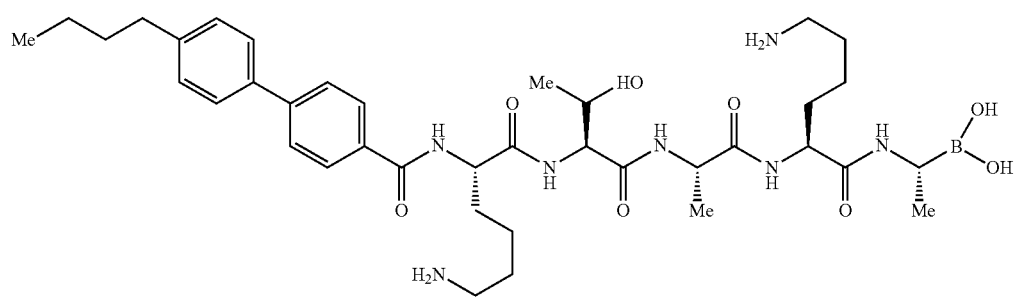
160
MS (ESI) m/z 736.4 (M − H₂O + H)⁺
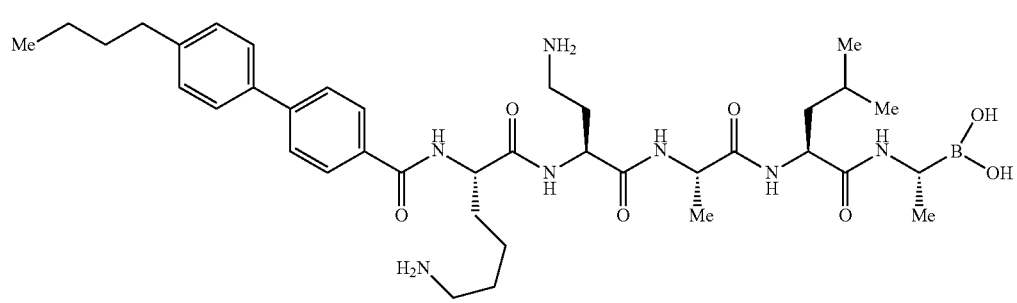
161
MS (ESI) m/z 760.3 (M + H)⁺
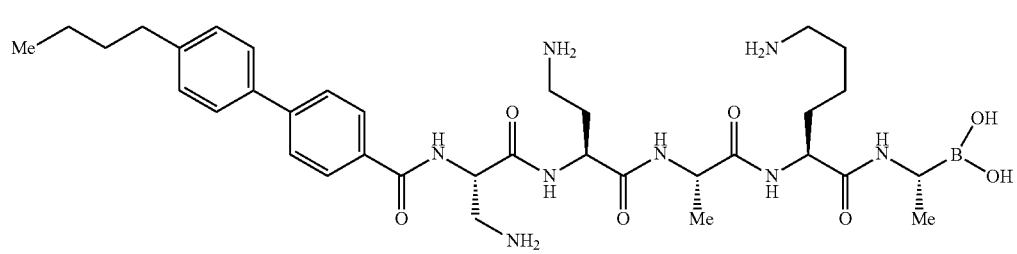
162
MS (ESI) m/z 694.4 (M − H₂O + H)⁺
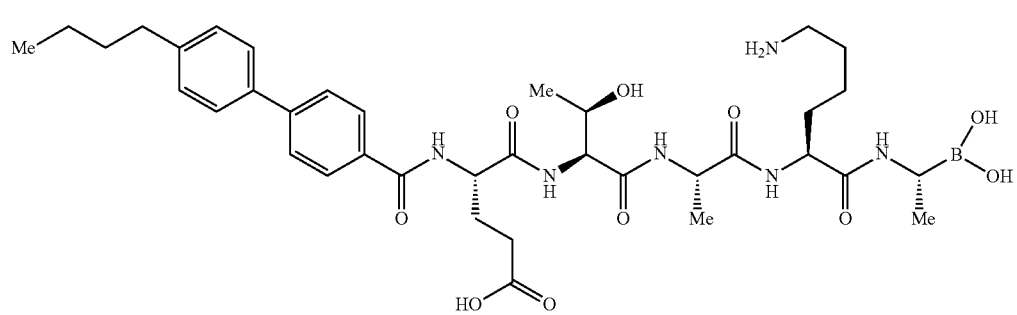
163
MS (ESI) m/z 737.3 (M − H₂O + H)⁺
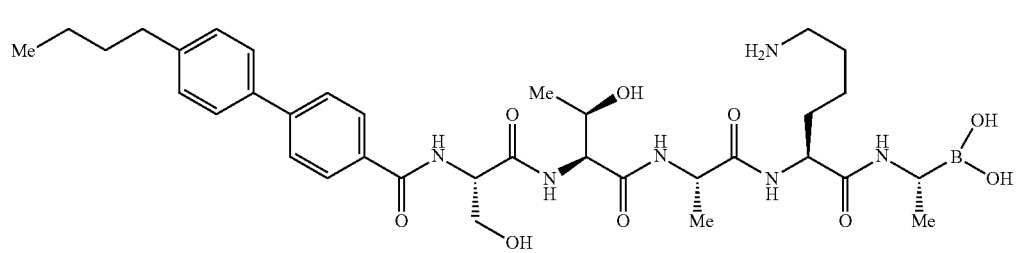
164
MS (ESI) m/z 695.4 (M − H₂O + H)⁺

165
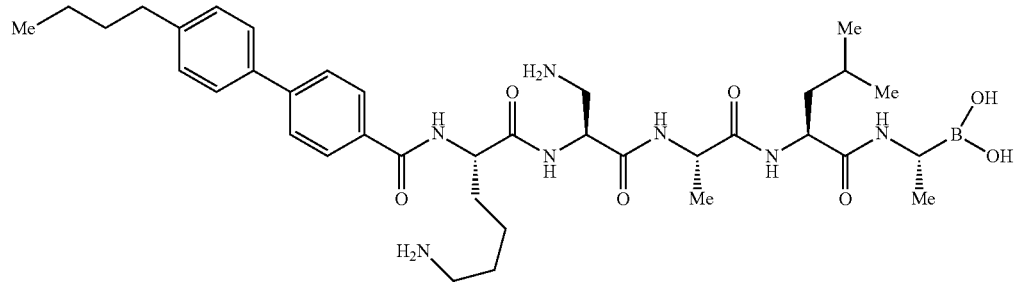
MS (ESI) m/z 706.3 (M − H₂O + H)⁺
166
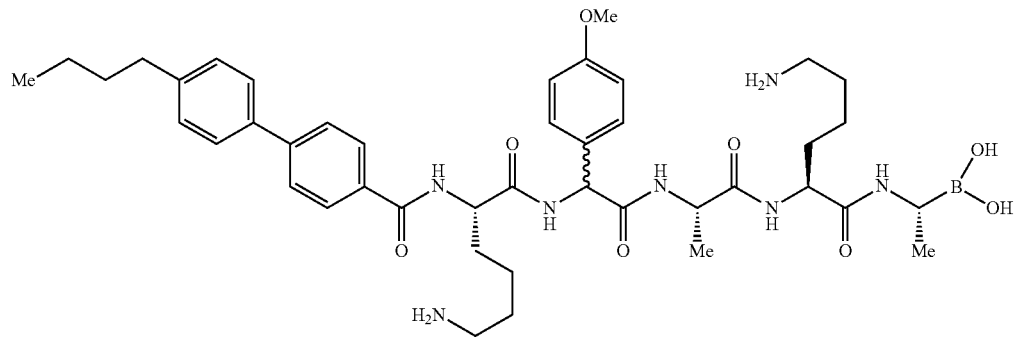
MS (ESI) m/z 798.5 (M − H₂O + H)⁺
167
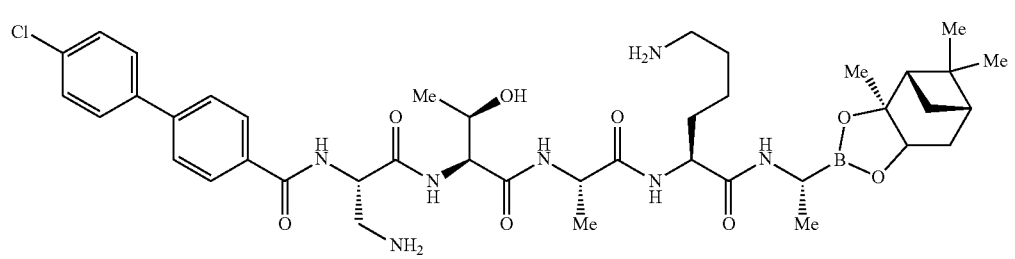
MS (ESI) m/z 824.2 (M + H)⁺
168
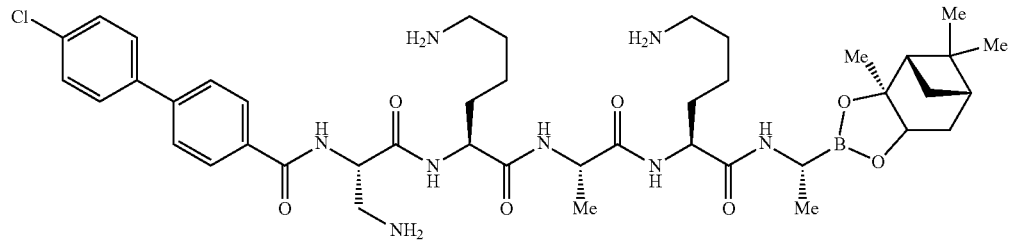
MS (ESI) m/z 851.2 (M + H)⁺
169
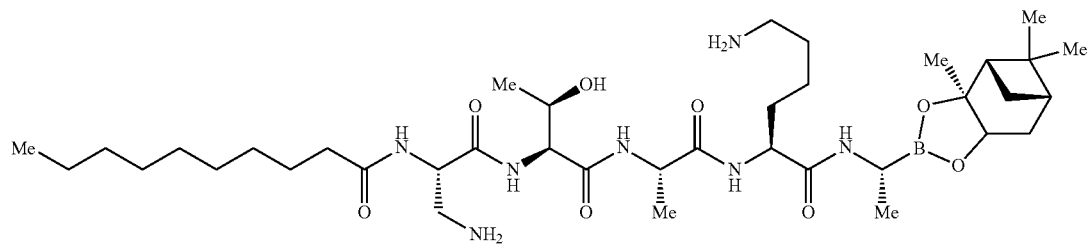
MS (ESI) m/z 764.9 (M + H)⁺

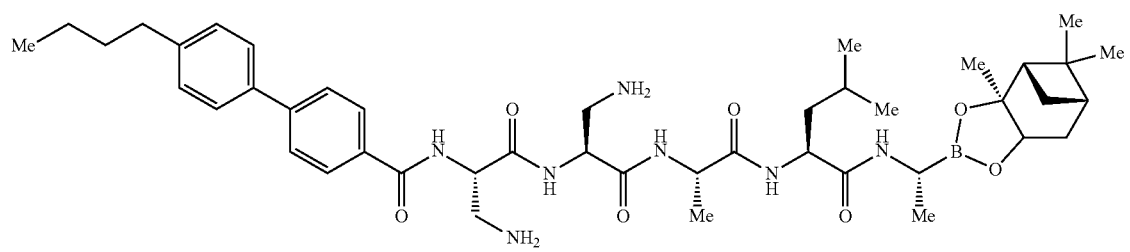
MS (ESI) m/z 816.6 (M + H)+
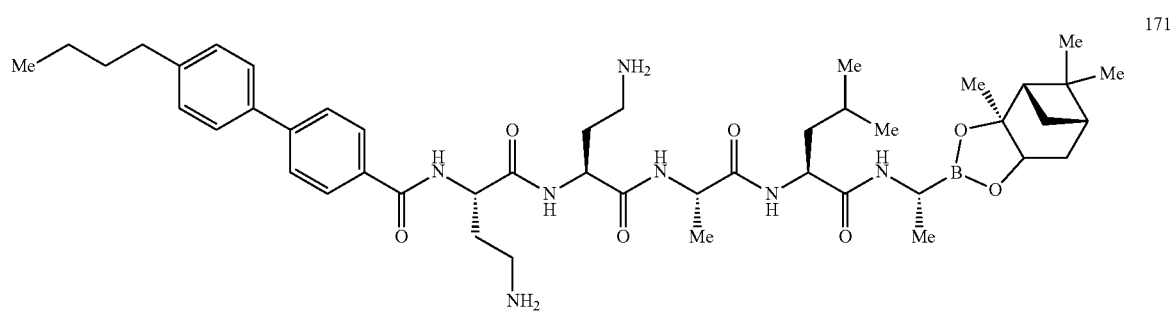
MS (ESI) m/z 844.3 (M + H)+
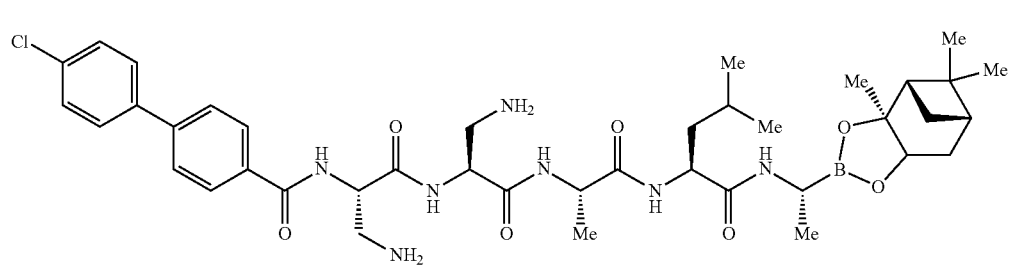
MS (ESI) m/z 794.0 (M + H)+
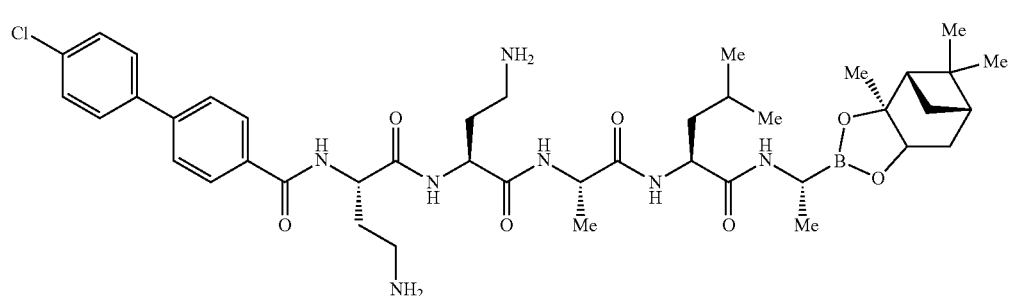
MS (ESI) m/z 822.1 (M + H)+

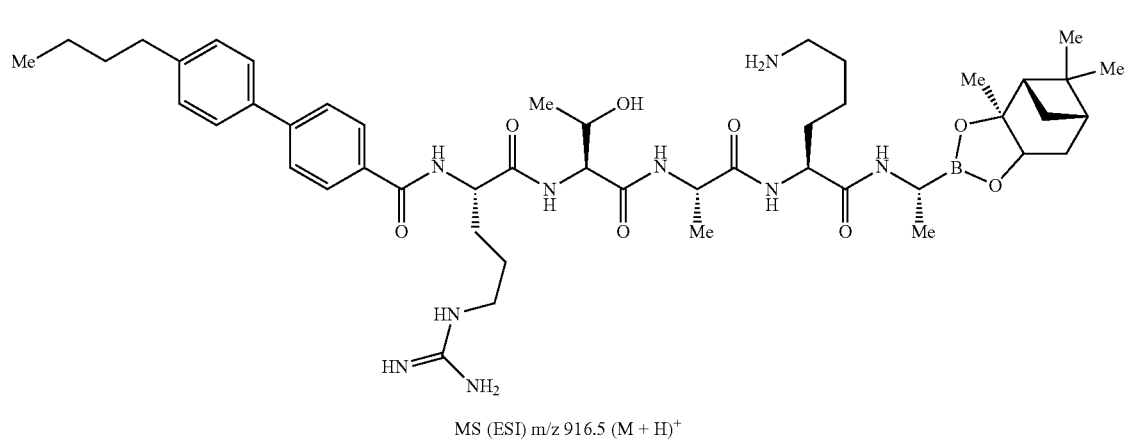
MS (ESI) m/z 916.5 (M + H)⁺
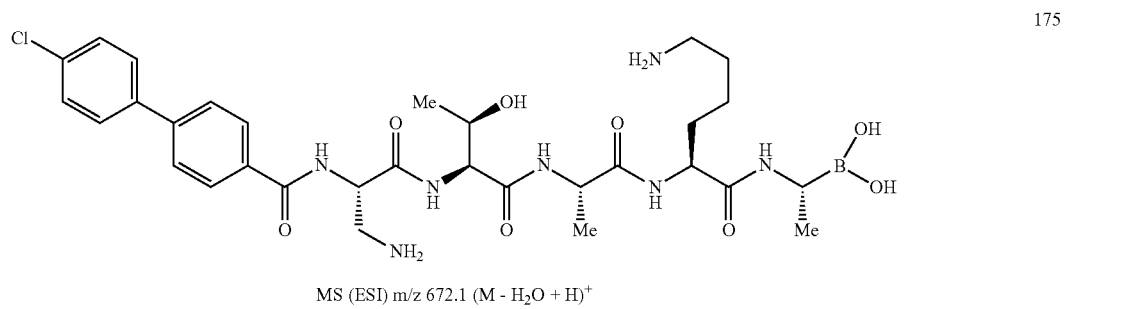
MS (ESI) m/z 672.1 (M - H₂O + H)⁺
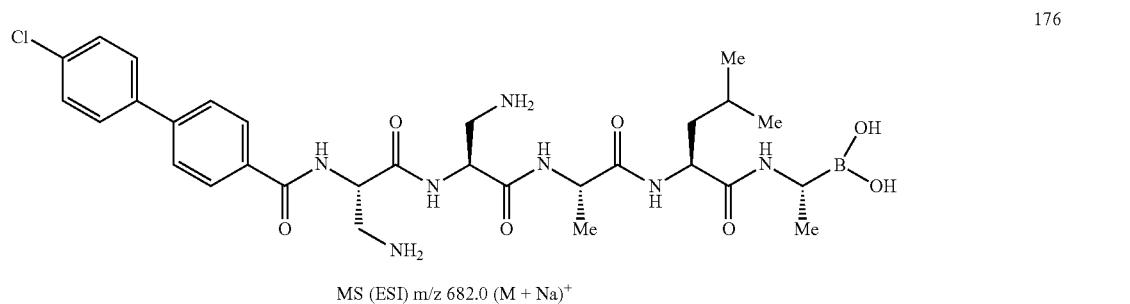
MS (ESI) m/z 682.0 (M + Na)⁺
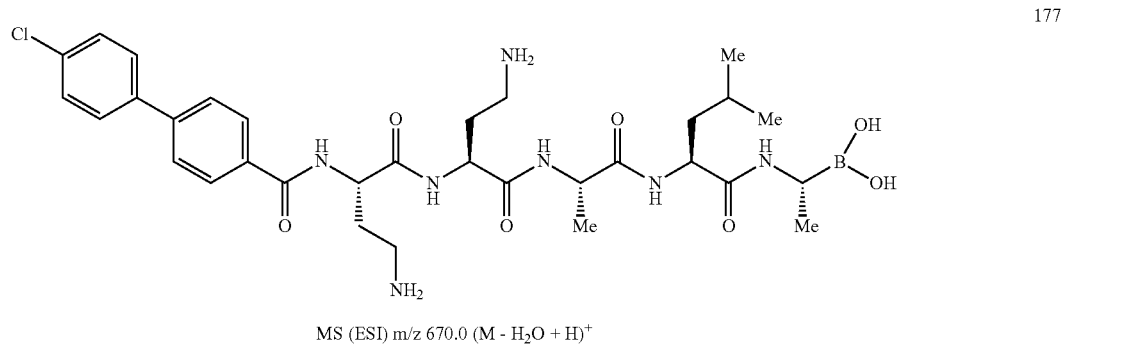
MS (ESI) m/z 670.0 (M - H₂O + H)⁺

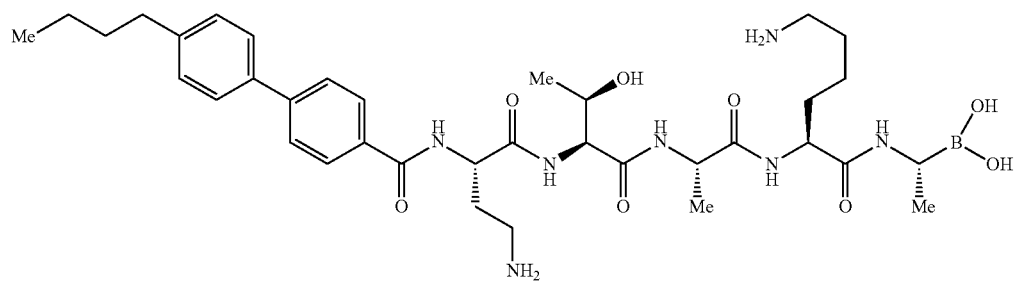
MS (ESI) m/z 726.0 (M + H)⁺
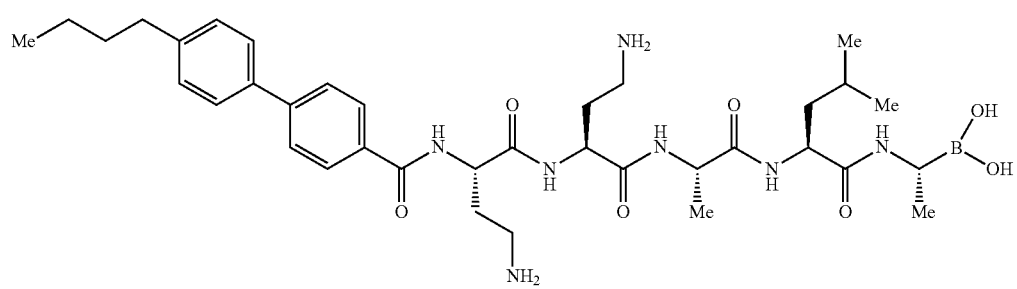
MS (ESI) m/z 692.1 (M - H$_2$O + H)⁺
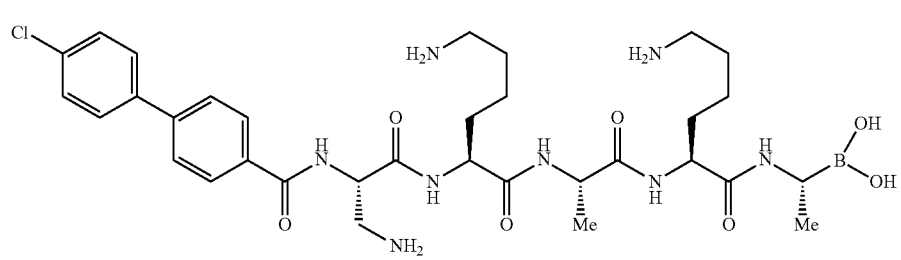
MS (ESI) m/z 699.2 (M - H$_2$O + Na)⁺
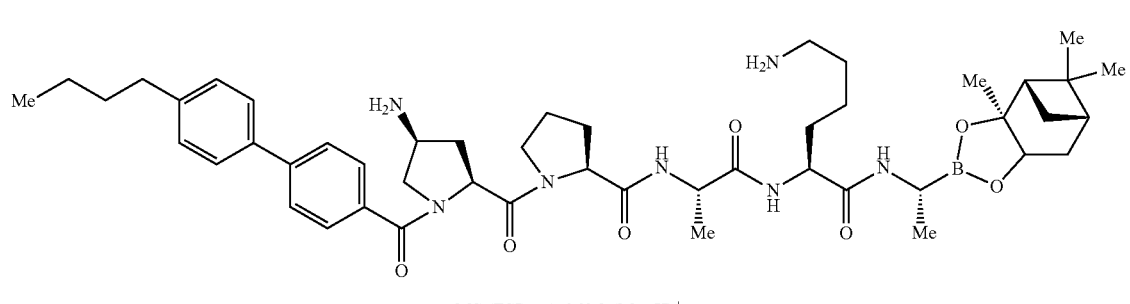
MS (ESI) m/z 868.3 (M + H)⁺
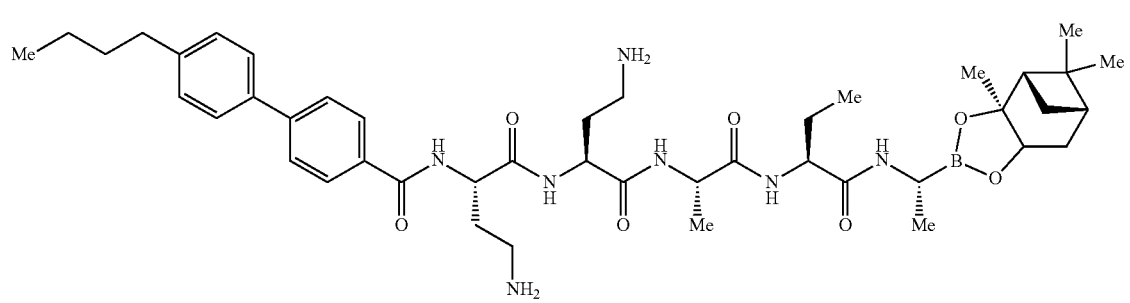
MS (ESI) m/z 816.4 (M + H)⁺

-continued
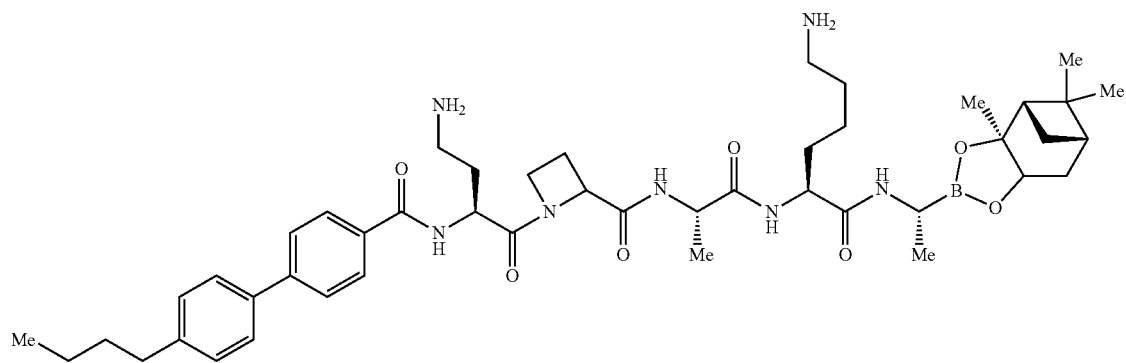
MS (ESI) m/z 816.4 (M + H)+
183
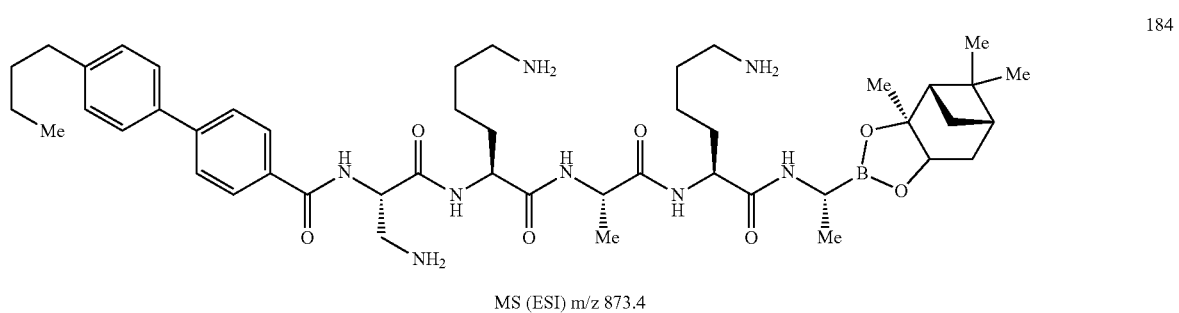
MS (ESI) m/z 873.4
184
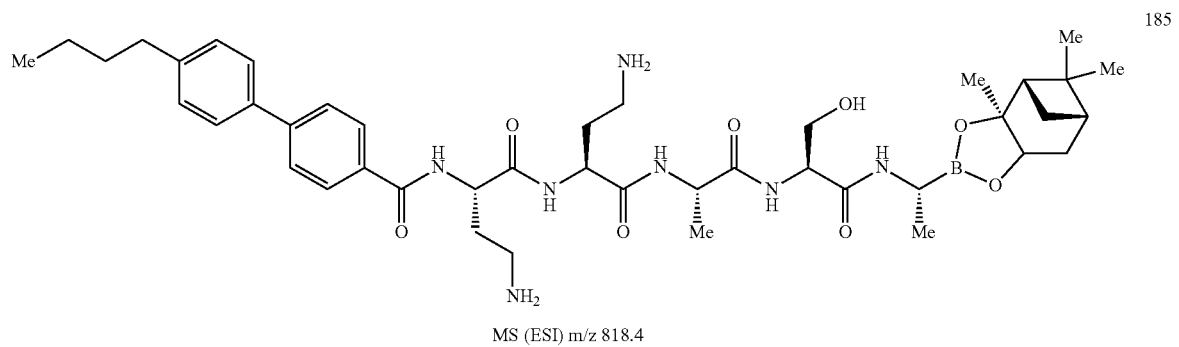
MS (ESI) m/z 818.4
185
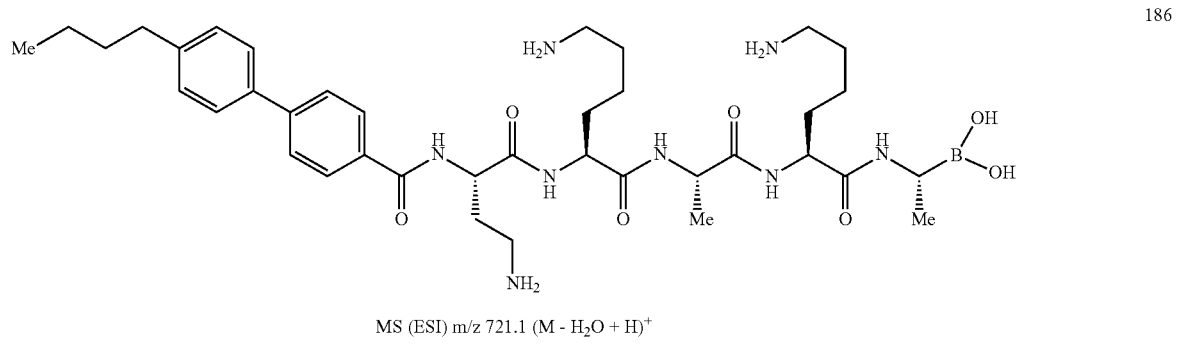
MS (ESI) m/z 721.1 (M - H$_2$O + H)+
186

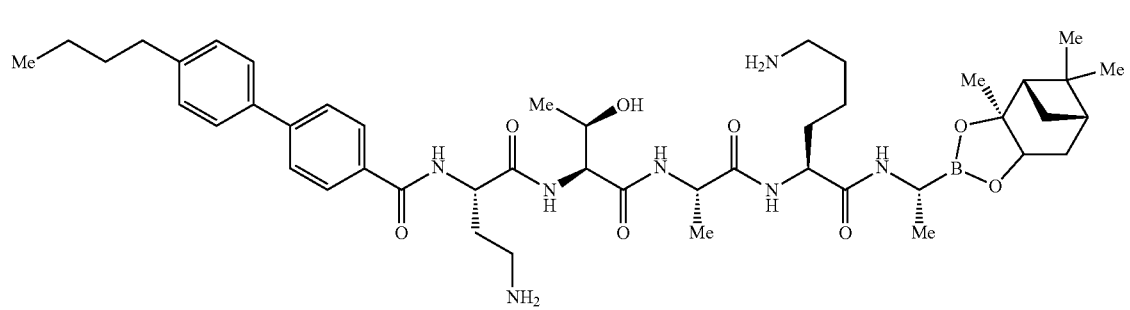
187
MS (ESI) m/z 860.3 (M + H)+
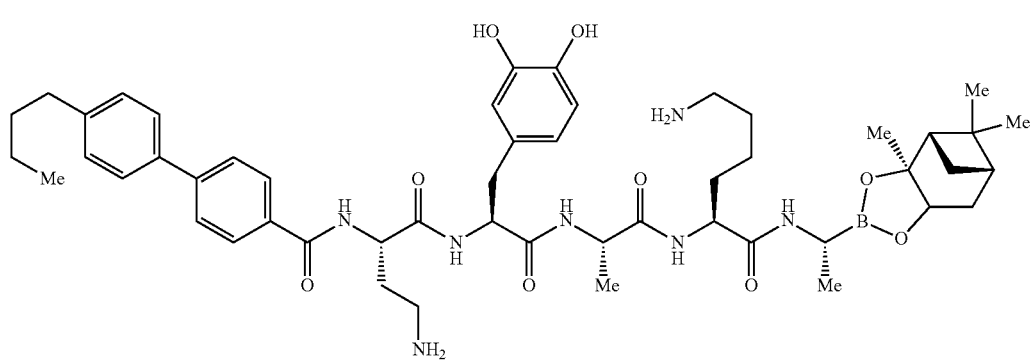
188
MS (ESI) m/z 938.4 (M + H)+
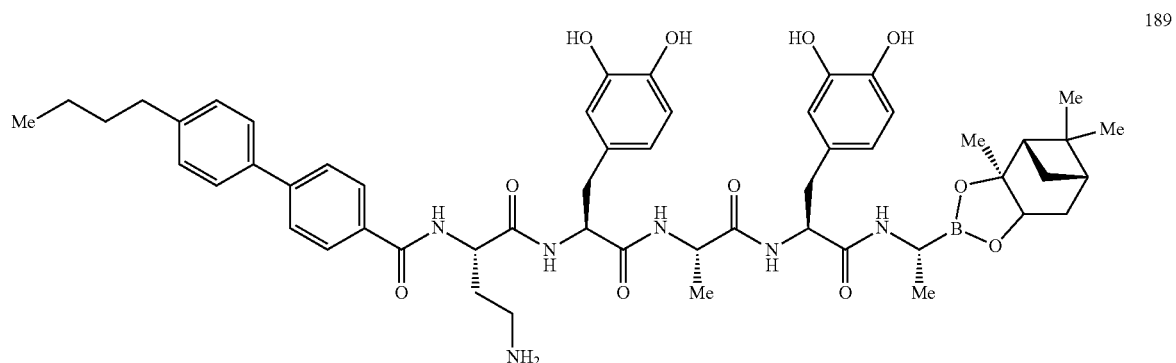
189
MS (ESI) m/z 990.3

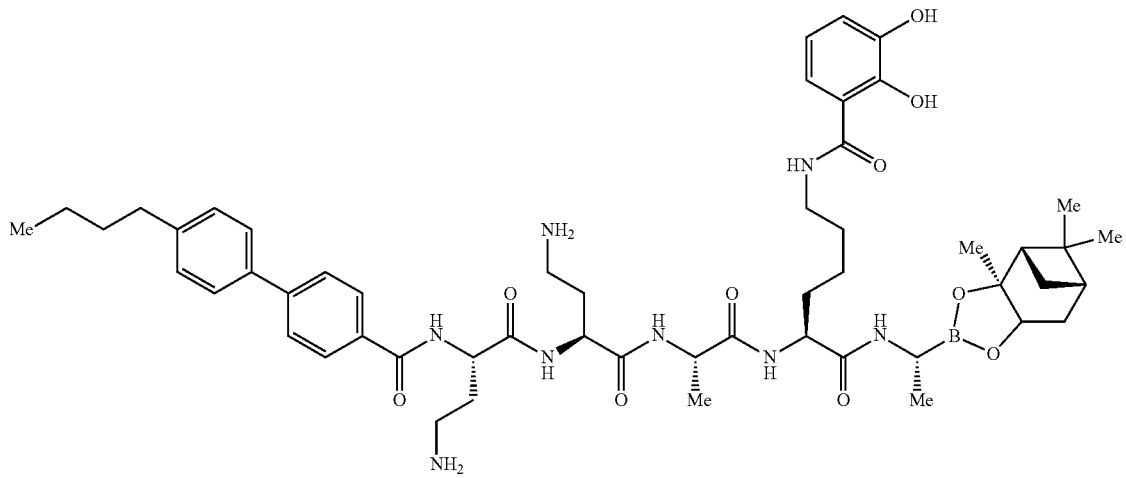
190
MS (ESI) m/z 995.2 (M + H)+
Using the procedures described in General Methods 9 and 10 for the preparation of the boronate esters or General Methods 9, 10, and 11 for the preparation of the boronic acids, the following boronate ester or boronic acid of varying length were prepared from the corresponding carboxylic acid described above:
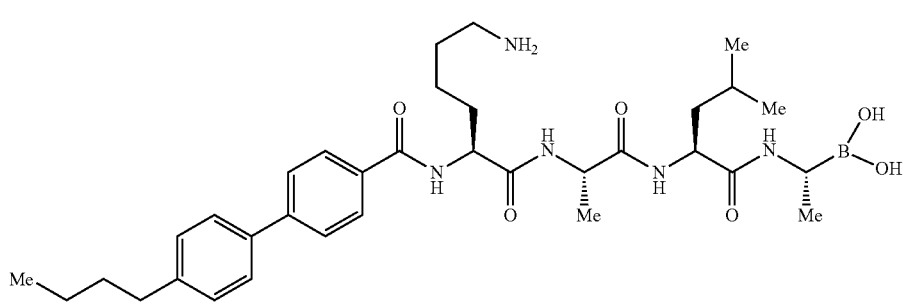
191
MS (ESI) m/z 620.3 (M - H2O + H)+
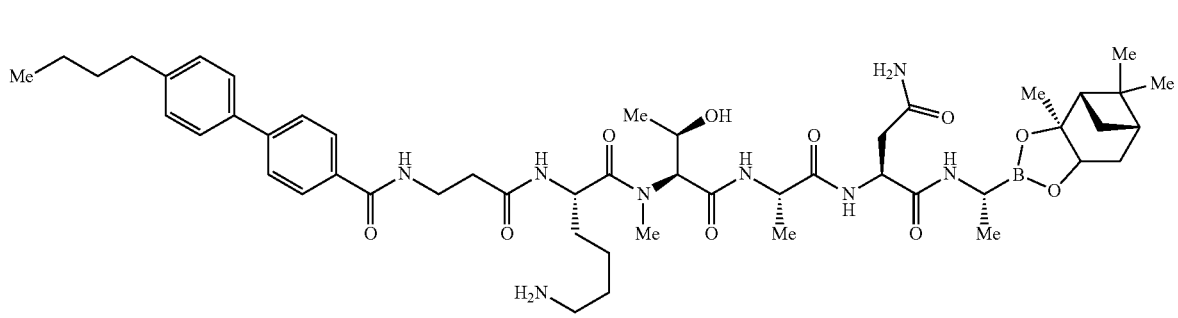
192
MS (ESI) m/z 959.8 (M + H)+

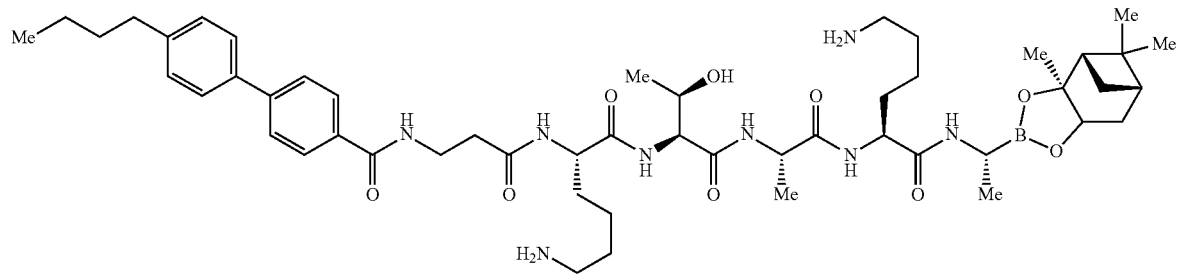
MS (ESI) m/z 959.8 (M + H)⁺
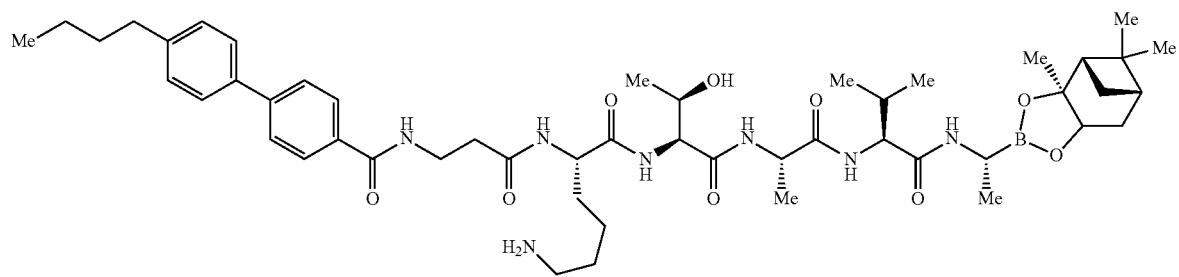
MS (ESI) m/z 930.8 (M + H)⁺
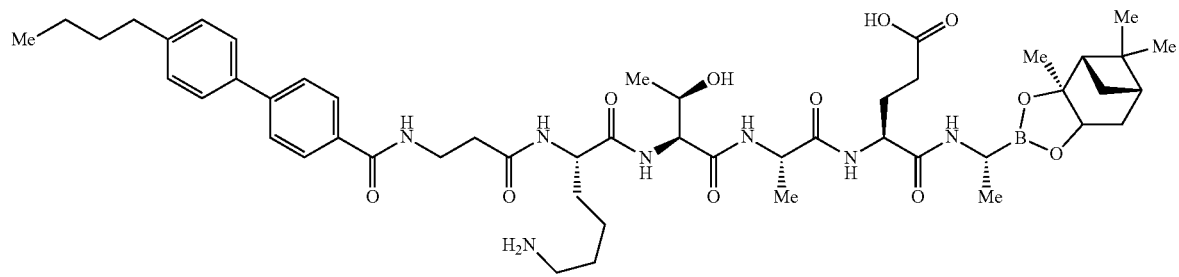
MS (ESI) m/z 960.8 (M + H)⁺
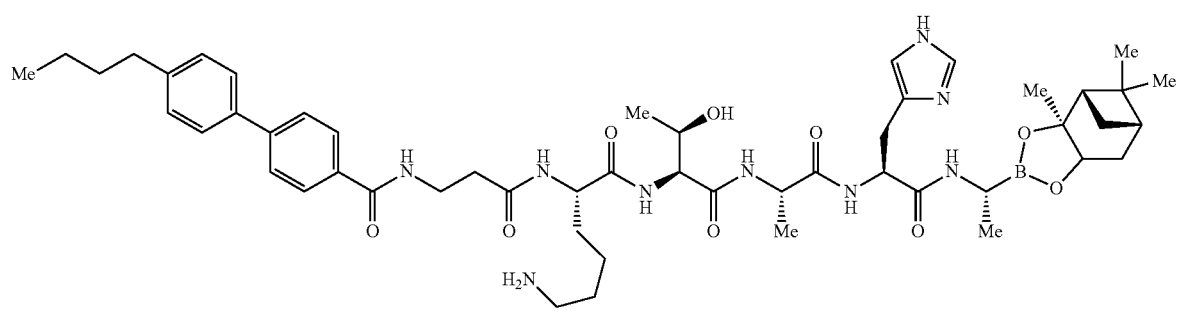
MS (ESI) m/z 968.9 (M + H)⁺

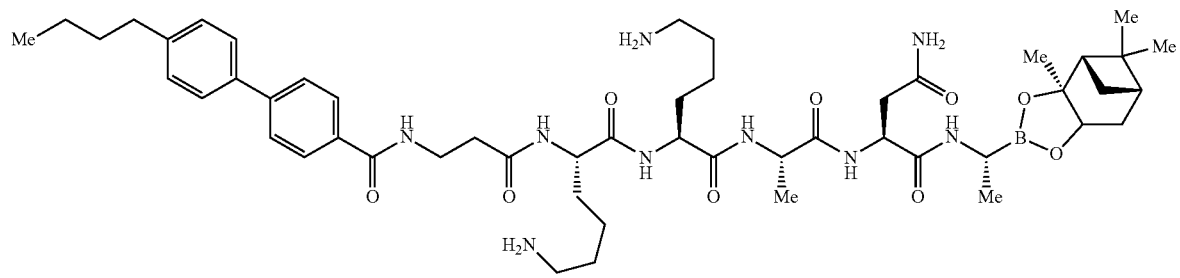
MS (ESI) m/z 972.8 (M + H)+
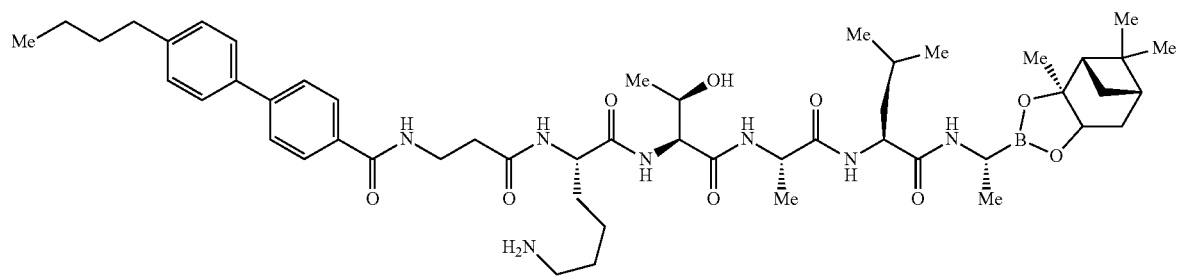
MS (ESI) m/z 944.6 (M + H)+
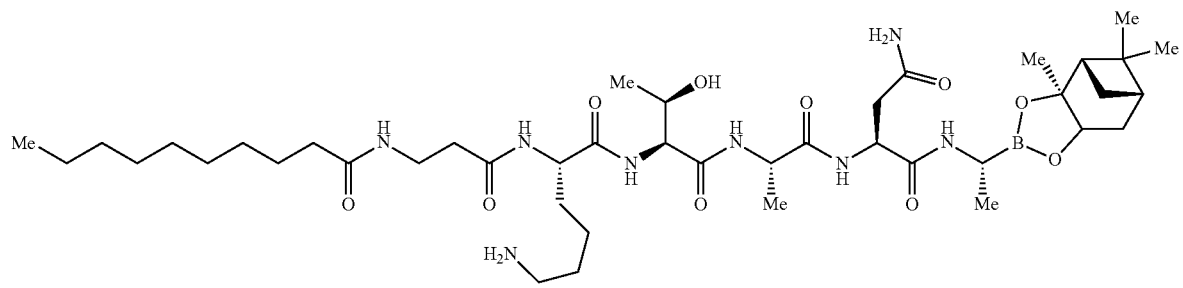
MS (ESI) m/z 863.4 (M + H)+
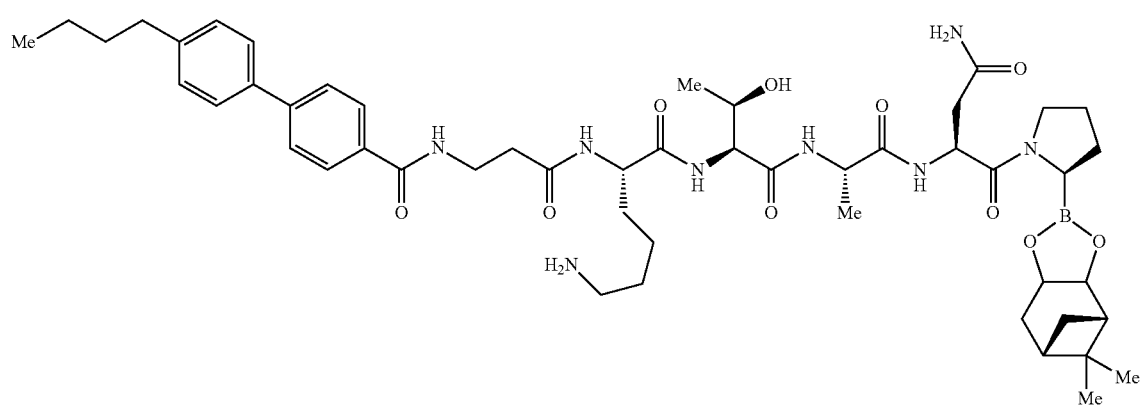
MS (ESI) m/z 971.4 (M + H)+

-continued
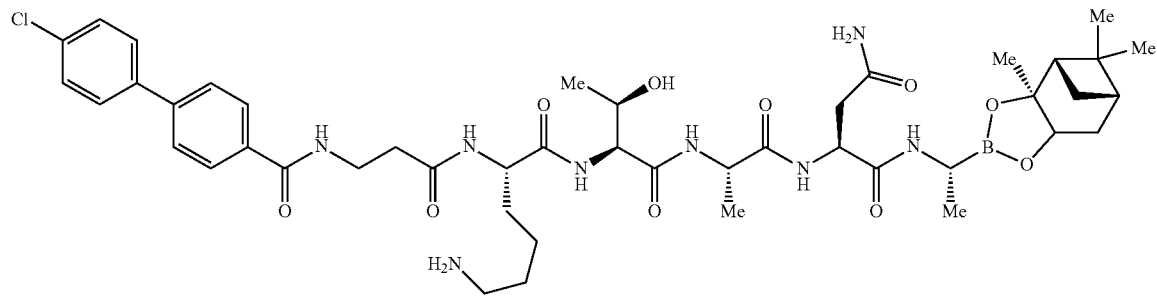
MS (ESI) m/z 923.4 (M + H)+
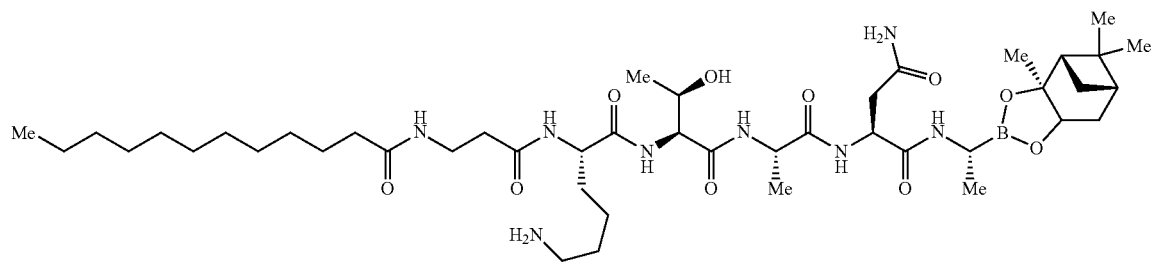
MS (ESI) m/z 891.5 (M + H)+
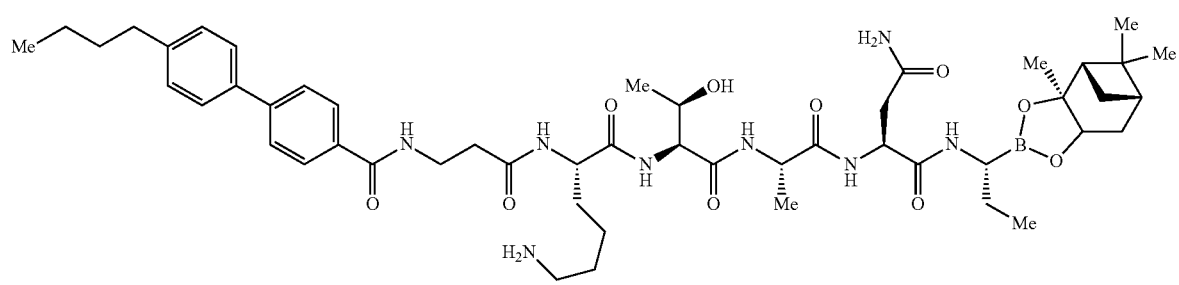
MS (ESI) m/z 959.8 (M + H)+
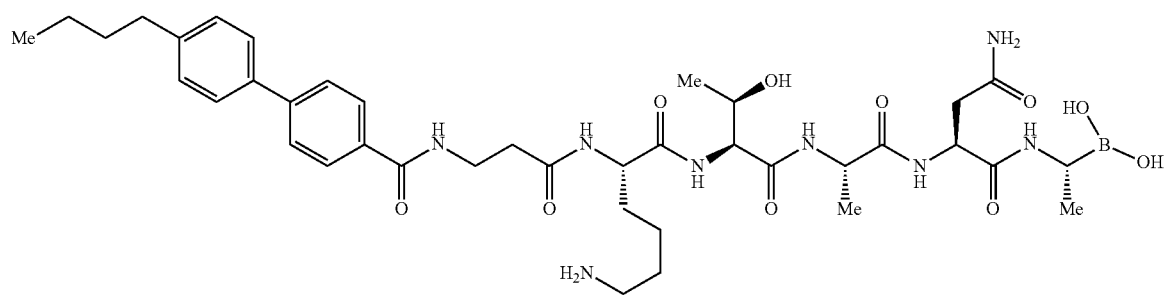
MS (ESI) m/z 923.4 (M + H)+
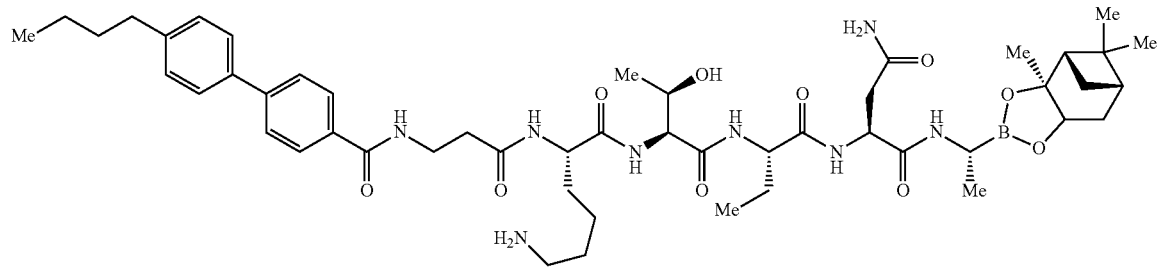
MS (ESI) m/z 973.5 (M + H)+

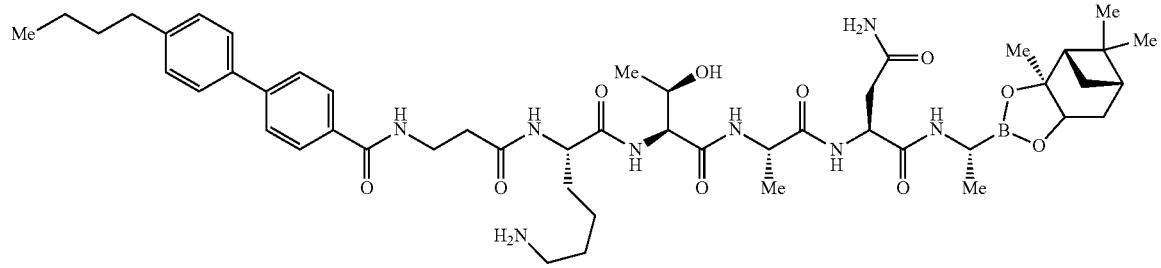
206
MS (ESI) m/z 959.4 (M + H)+
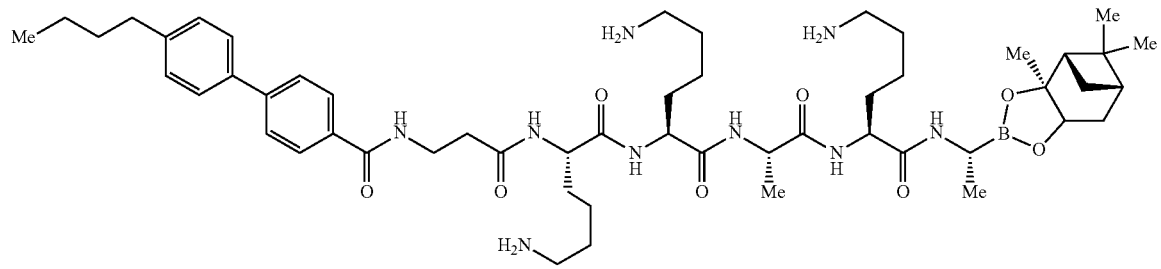
207
MS (ESI) m/z 986.5 (M + H)+
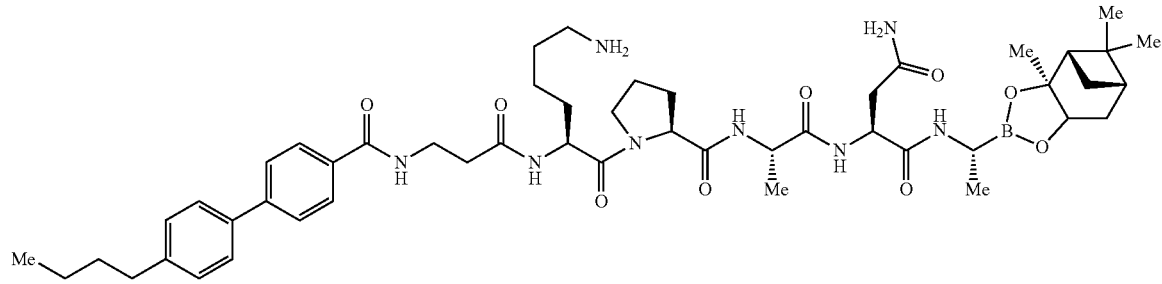
208
MS (ESI) m/z 941.4 (M + H)+
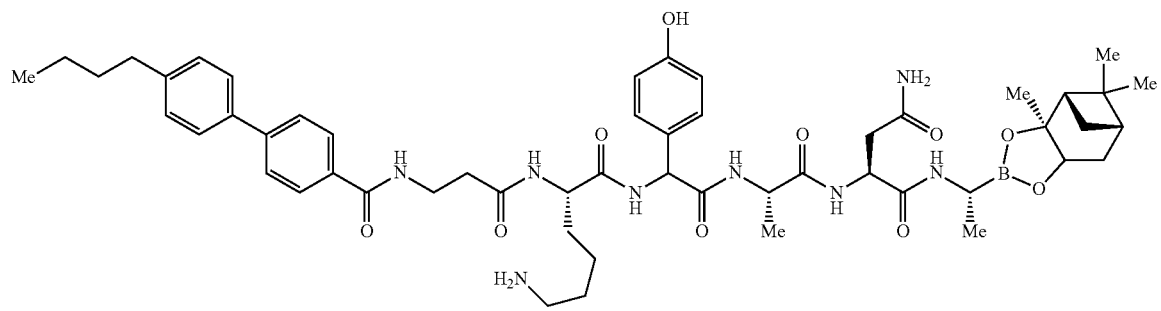
209
MS (ESI) m/z 994.6 (M + H)+
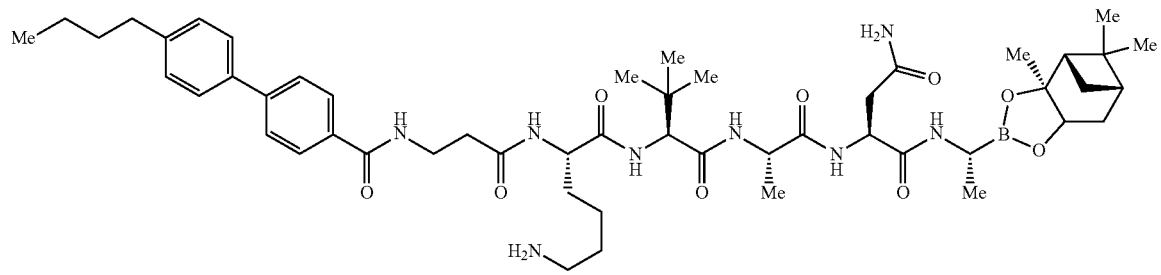
210
MS (ESI) m/z 957.5 (M + H)+

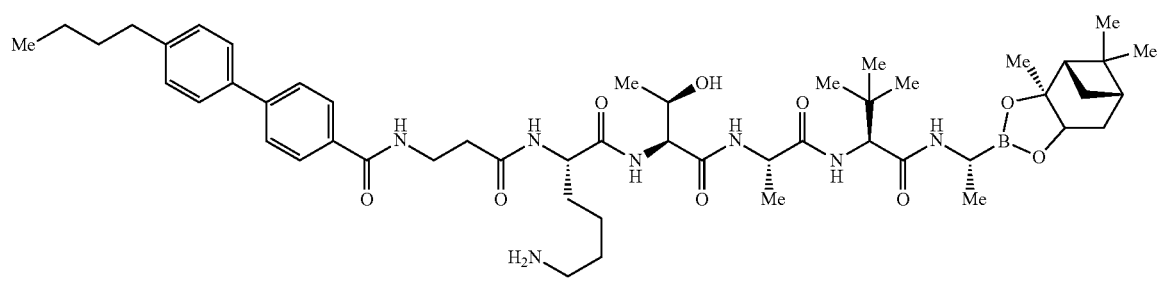
MS (ESI) m/z 944.5 (M + H)+
211
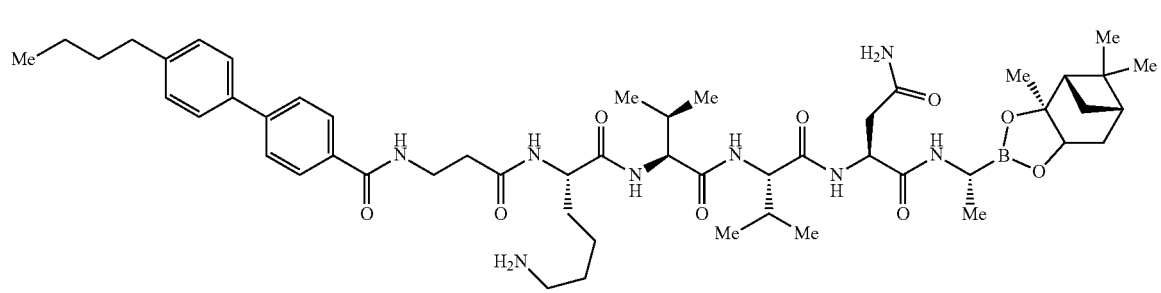
MS (ESI) m/z 973.4 (M + H)+
212
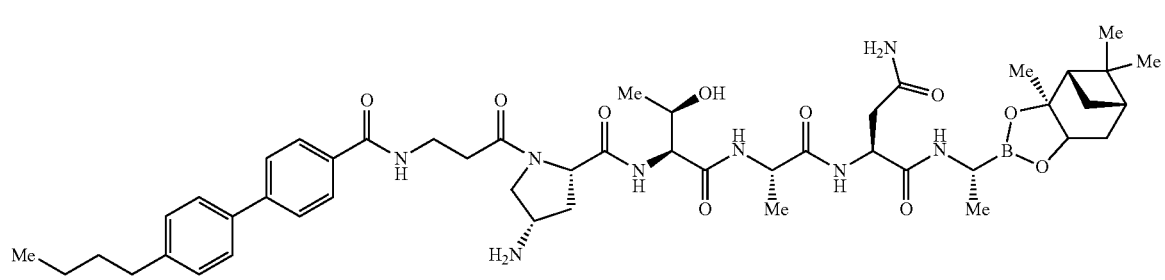
MS (ESI) m/z 929.4 (M + H)+
213
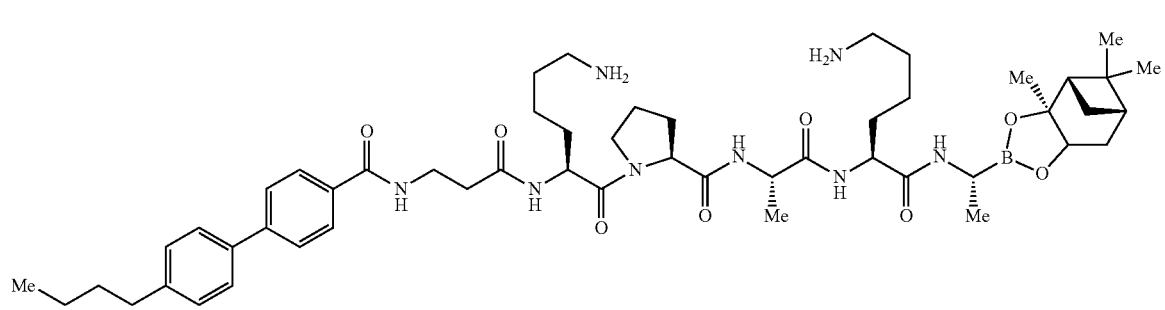
MS (ESI) m/z 955.4 (M + H)+
214

215
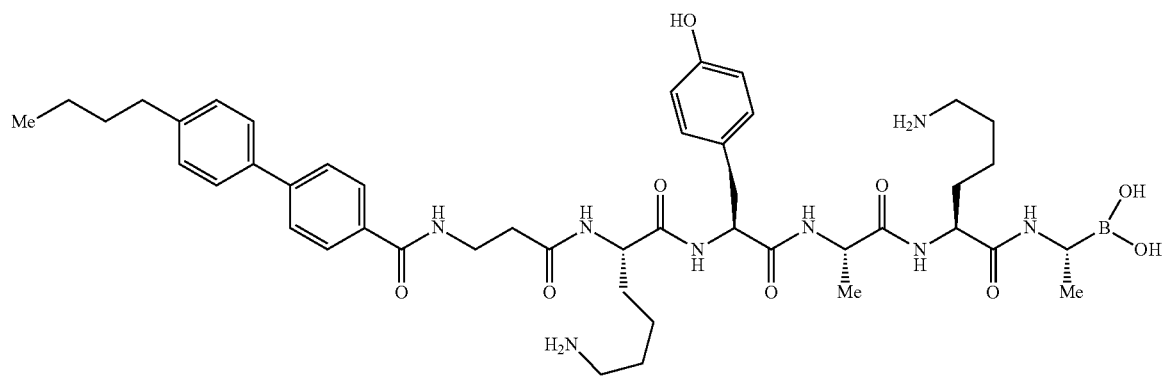
216
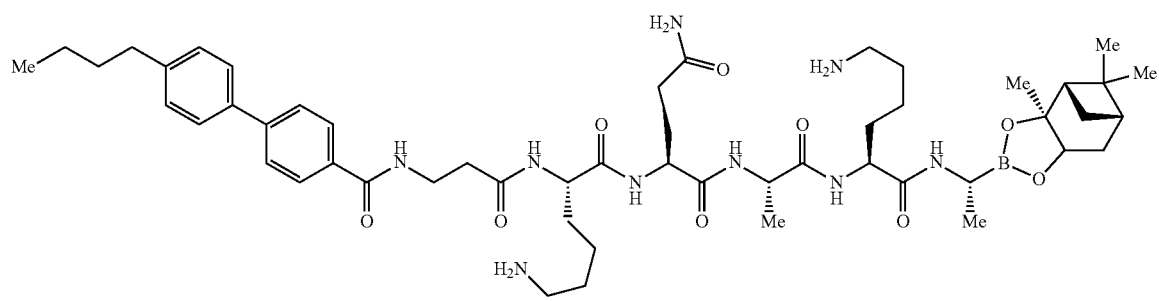
MS (ESI) m/z 986.5 (M + H)+
217
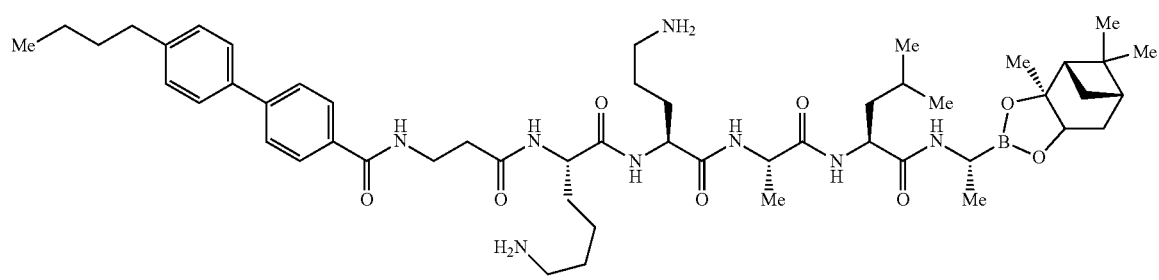
MS (ESI) m/z 957.7 (M + H)+
218
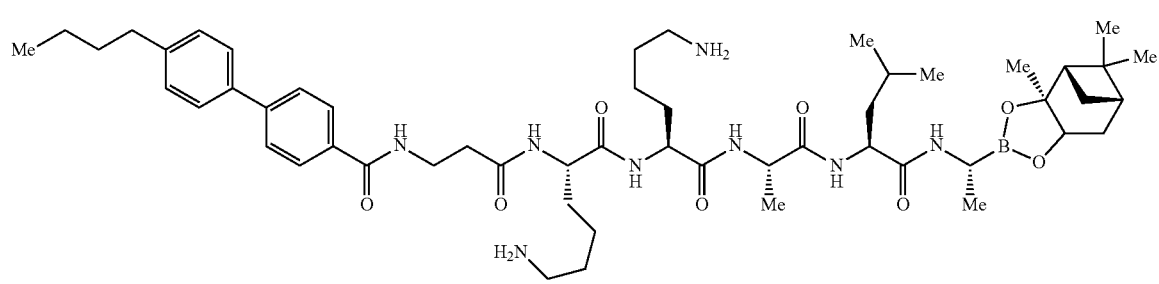
MS (ESI) m/z 971.8 (M + H)+

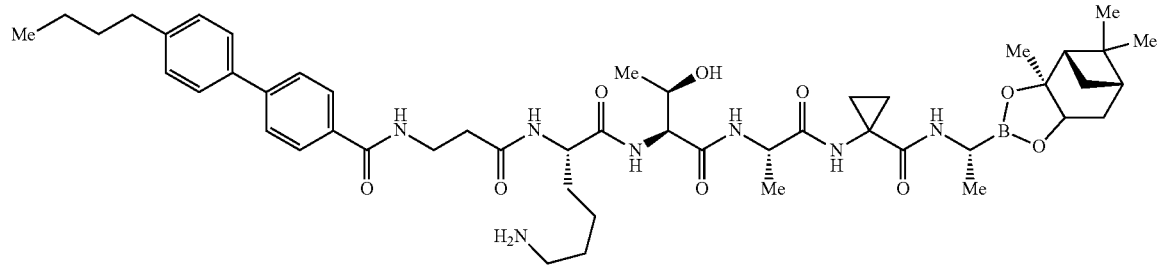
219
MS (ESI) m/z 914.4 (M + H)+
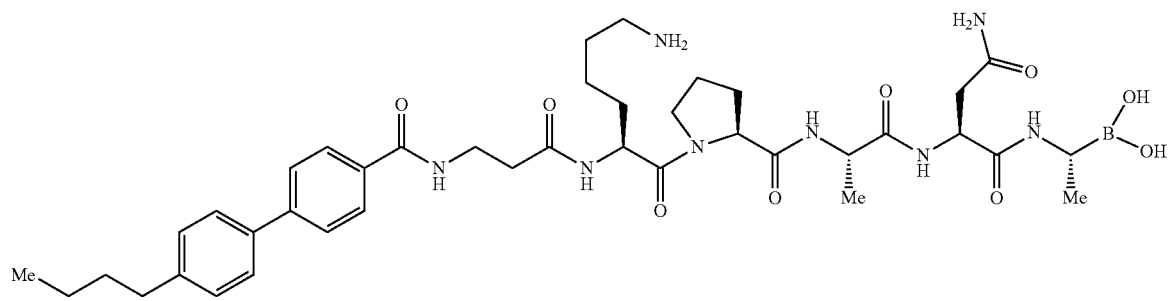
220
MS (ESI) m/z 789.3 (M - H₂O + H)+
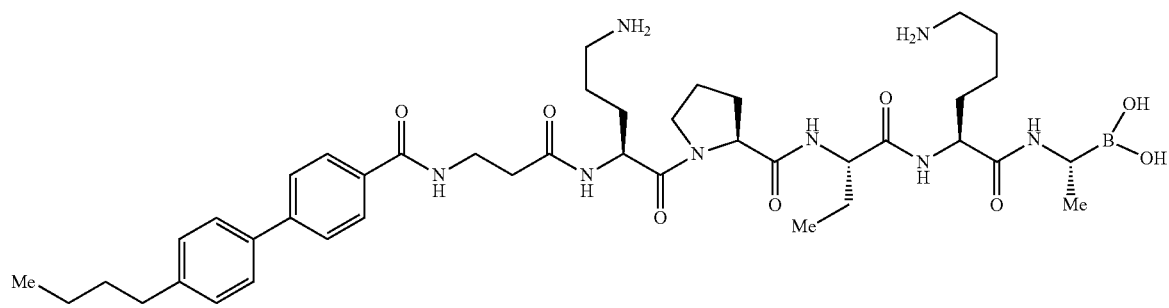
221
MS (ESI) m/z 803.3 (M - H₂O + H)+
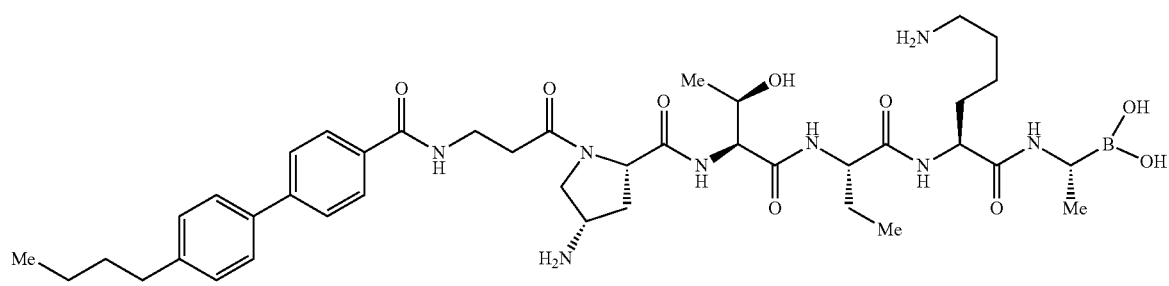
222
MS (ESI) m/z 752.4 (M - H₂O + H)+

-continued
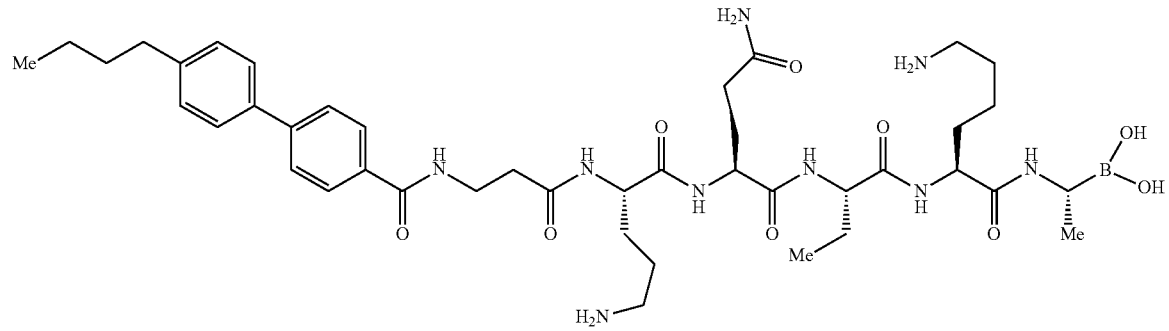
223
MS (ESI) m/z 834.3 (M - H₂O + H)⁺
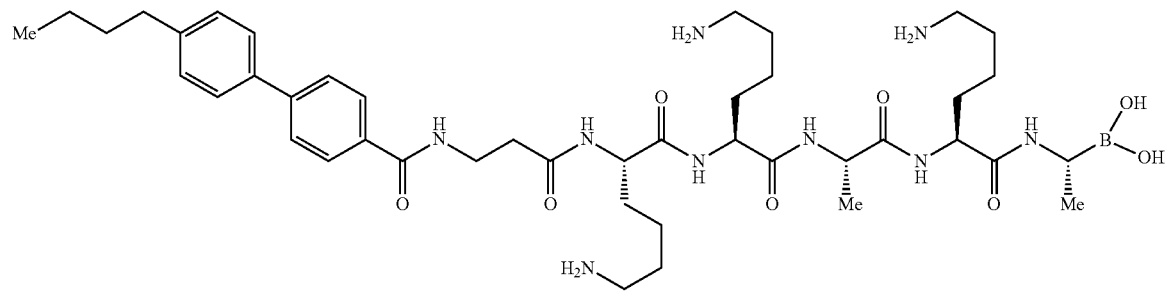
224
MS (ESI) m/z 834.5 (M - H₂O + H)⁺
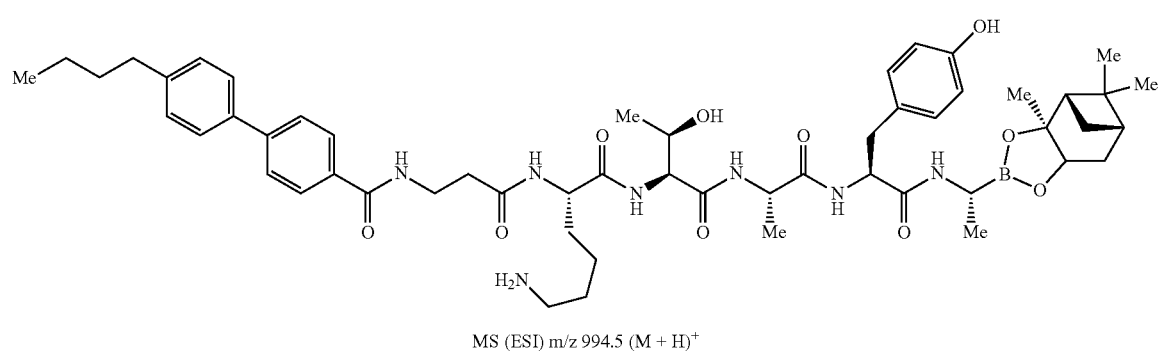
225
MS (ESI) m/z 994.5 (M + H)⁺
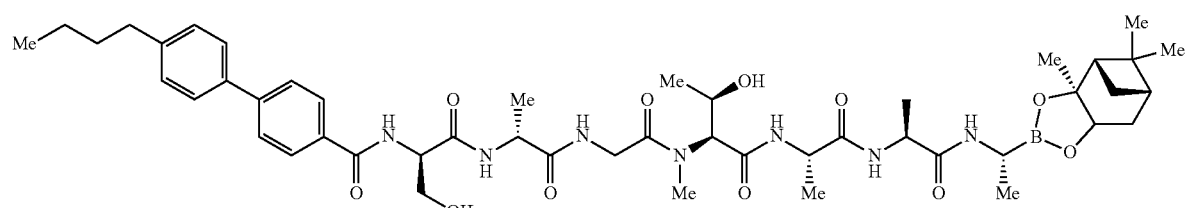
226
MS (ESI) m/z 975.5 (M + H)⁺

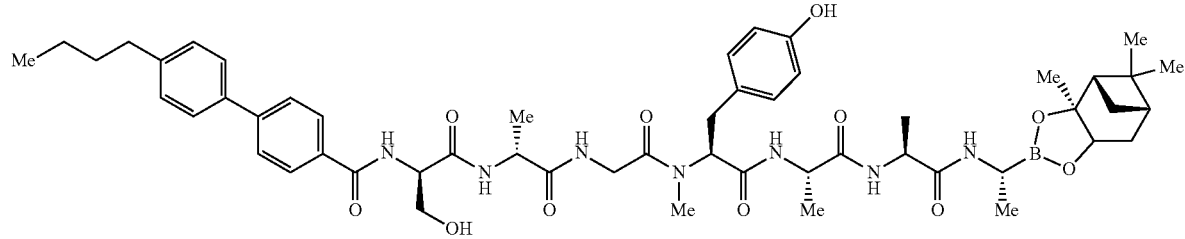
227
MS (ESI) m/z 1037.7 (M + H)+
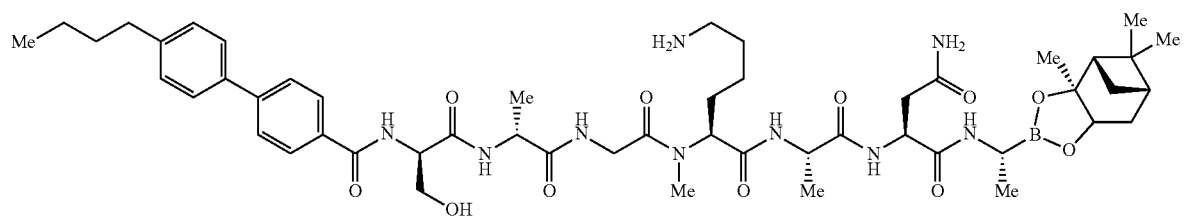
228
MS (ESI) m/z 1002.4 (M + H)+
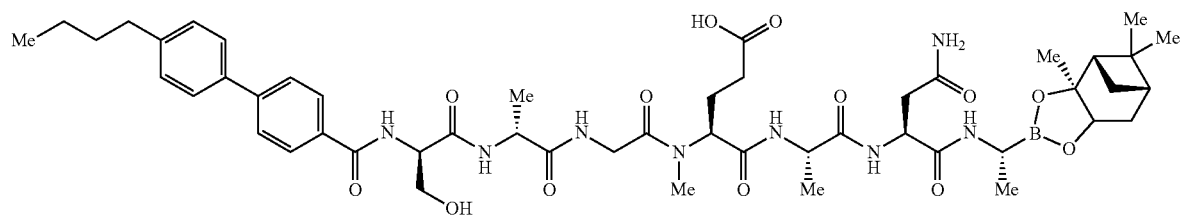
229
MS (ESI) m/z 1003.2 (M + H)+
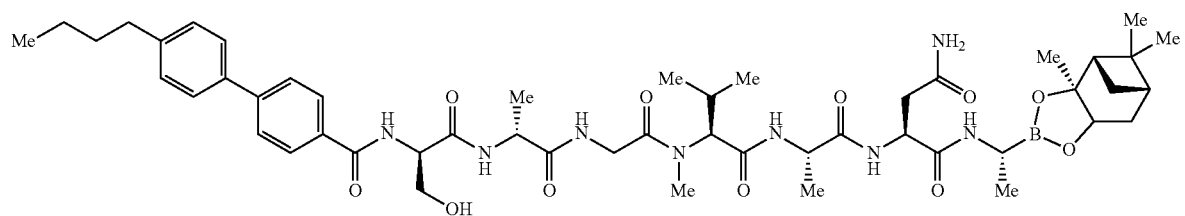
230
MS (ESI) m/z 973.5 (M + H)+

Examples 131-150
Scheme XXIII
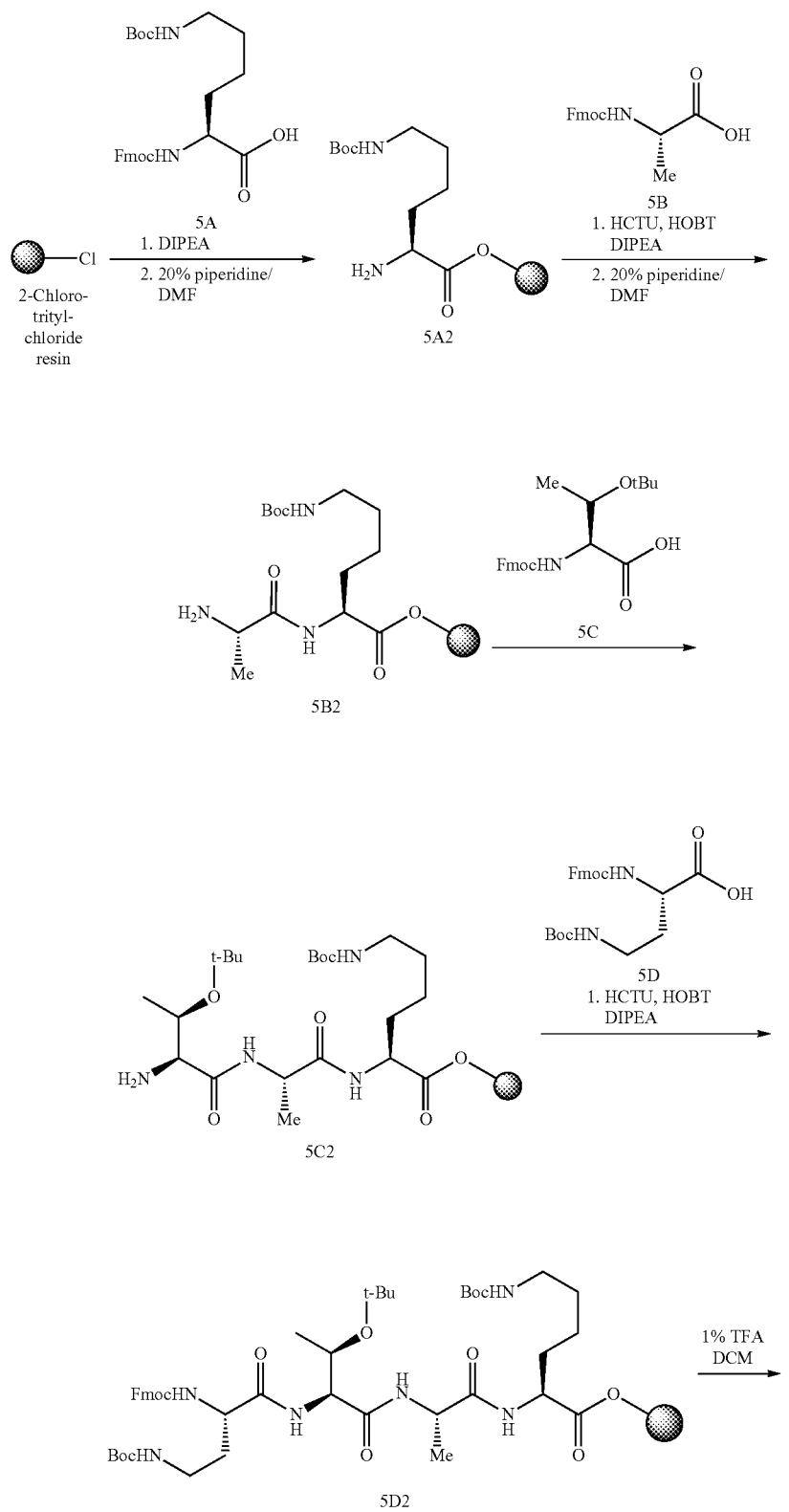

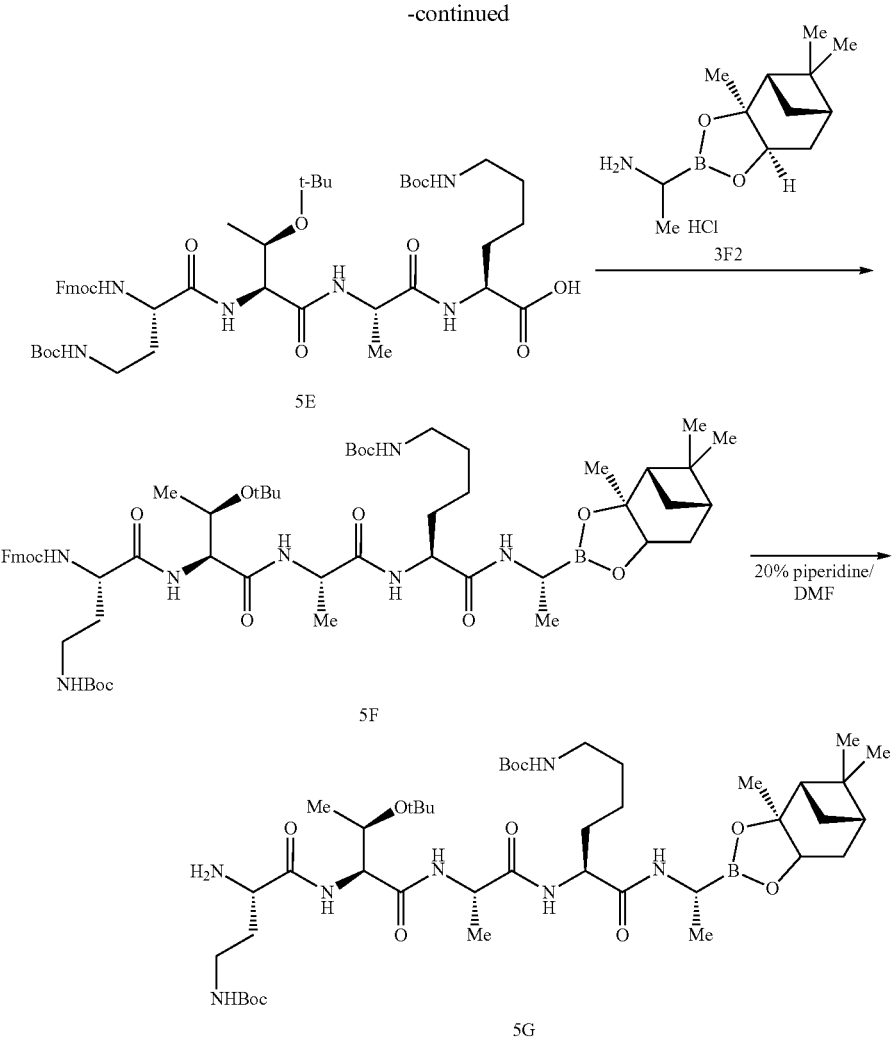

Compound 5G: The synthesis of Compound 5G is depicted in Scheme XXIII. A mixture of 2-chlorotrityl resin (0.320 g, 0.416 mmol), DIEA (0.215 g, 1.66 mmol) in dry DCM (15.0 mL) was added to a solution of Fmoc-L-Lys(Boc)-OH (0.389 g, 0.832 mmol) in dry DCM (10.0 mL) at 0° C. The mixture was then shaken for 5 hrs at room temperature. The mixture was filtered and the cake was washed with DCM (20.0 mL×3), DMF (20.0 mL×3) MeOH (20.0 mL×3). To the above resin was added 20% piperidine/DMF (approximately 20.0 mL) to remove the Fmoc group. The mixture was shaken for 10 mins and the cycle was repeated three times. The mixture was then washed with DCM (20.0 mL×3 mL) and DMF (20.0 mL×3) to give Compound 5A2.

To a mixture of Fmoc-L-Ala-OH (0.259 g, 0.832 mmol) in dry DMF (15.0 mL) was added HCTU (0.344 g, 0.832 mmol), HOBt (0.112 g, 0.832 mmol), DIEA (0.215 g, 1.66 mmol) at 0° C. The mixture was then was stirred at 16° C. for 30 mins. The mixture was added to a suspension of Compound 5A2 (0.416 mmol) in DMF (10.0 mL). The mixture was stirred at room temperature for 1.5 hrs. After ELSD showed the reaction was completed, the mixture was filtered. The cake was washed with DMF (20.0 mL×3), DCM (20.0 mL×3). To the above resin was added approximately 20.0 mL 20% piperidine/DMF to remove the Fmoc group. The mixture was shaken for 10 mins and the cycle was repeated three times. The mixture was then washed with DCM (20.0 mL×3 mL) and DMF (20.0 mL×3) to give Compound 5B2.

Compound 5C2 was made using the same method as for Compound 5B2 except Fmoc-L-Thr(tBu)-OH was utilized in the coupling reaction in place of Fmoc-L-Ala-OH.

Compound 5D2 was made from Compound 5C2 using the same method as for Compound 5C2 except Fmoc-L-Dab (Boc)-OH was utilized in the coupling reaction in place of Fmoc-L-Thr(tBu)-OH.

A mixture of Compound 5D2 (2.00 mmol) in TFA/DCM (1%, 20.0 mL) was shaken at 15° C. for 10 mins. The mixture was then filtered and the filtrate was treated saturated NaHCO$_3$ solution until pH=7~8. The mixture was treated with DCM (20.0 mL). The aqueous layer was added citric acid until pH ~3-4. The mixture was extracted with DCM (20.0 mL×3). The combined organic layers were washed with brine, dried over Na$_2$SO$_4$ and concentrated to give Compound 5E (1.1 g, 61.5%). MS (ESI) m/z 919.3 (M+Na)$^+$.

Compound 5E (250 mg, 0.279 mmol), HATU (212 mg, 0.558 mmol) and Compound 3F2 (108 mg, 0.419 mmol) were placed in the flask in an ice bath, then DCM (2.40 mL) and DMF (0.800 mL) were added. DIEA (108 mg, 0.837 mmol) was then added to the mixture. The reaction mixture was stirred at −5° C. for 30 mins. The crude residue was taken up in DMSO. A second experiment starting from 250 mg of Compound 5E was repeated and combined with this experiment. The combined batches were purified by prep-HPLC to give Compound 5F (200 mg, 81.4%) as white solid. MS (ESI) m/z 1102.4 (M+H)+.

To a solution of Compound 5F (400 mg, 0.363 mmol) in MeCN (3 ml) was added Et$_2$NH (79.6 mg, 1.09 mmol). The mixture was then stirred at 16° C. for 12 hrs until TLC (DCM:MeOH 10:1, R$_f$=0.5) showed the reaction was complete. The mixture was concentrated and the residue was purified by column chromatography to give Compound 5G (280 mg, 87.8%). MS (ESI) m/z 880.6 (M+Na)+.

General Method 12:

Coupling of Compound 5G with a carboxylic acid in solution phase followed by deprotection of acid sensitive protecting groups with TFA in the presence of a reducing agent. A specific example is shown in Scheme XXIV to illustrate this method.

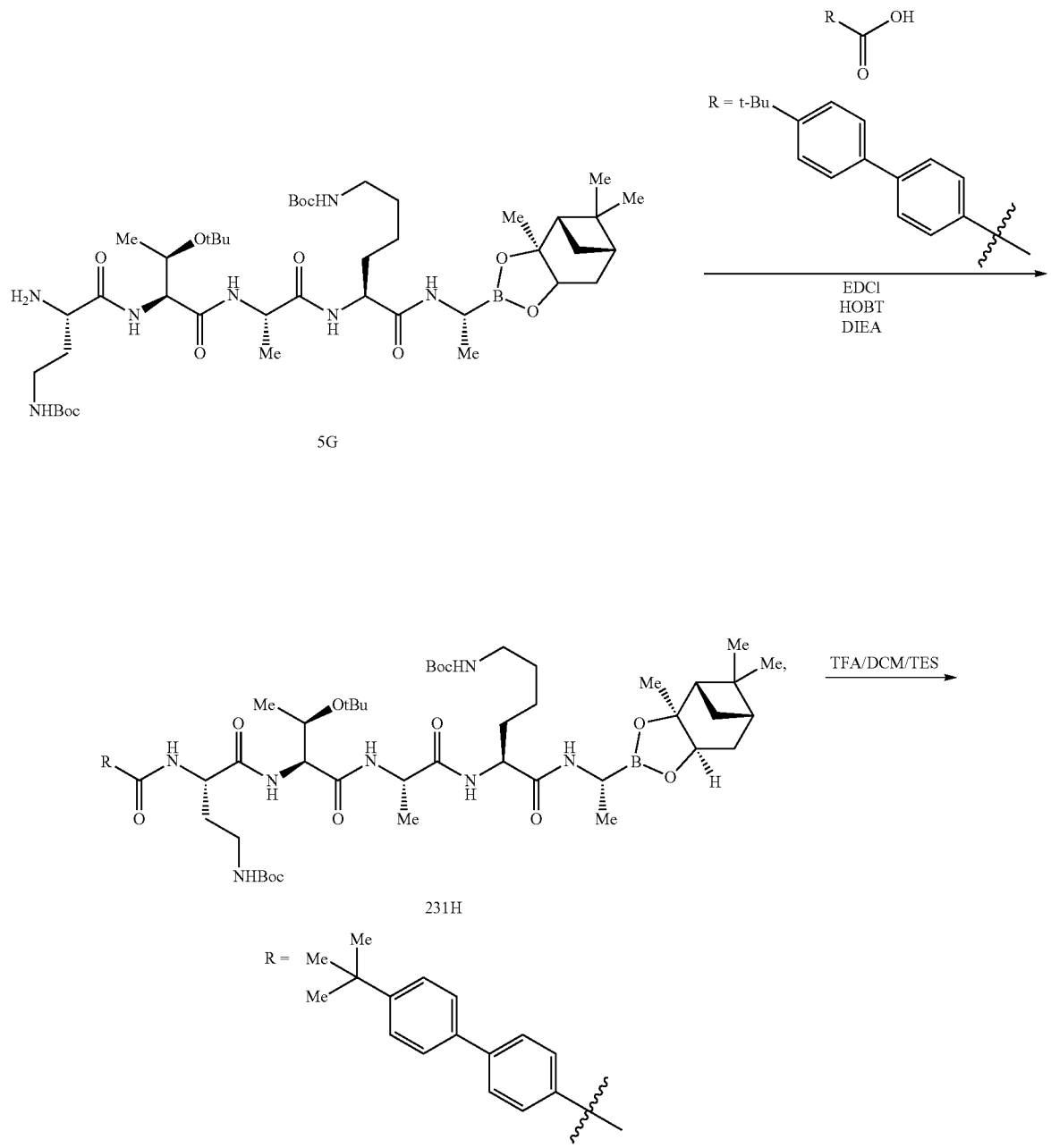

Scheme XXIV

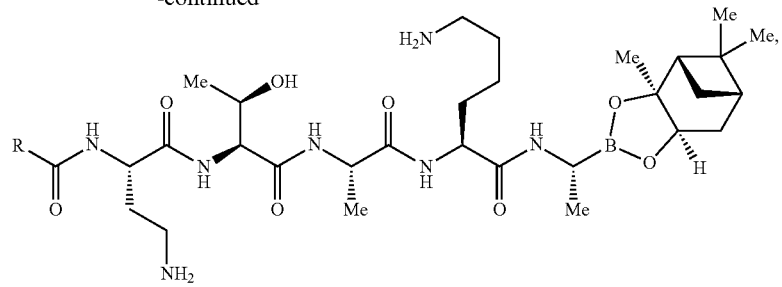

231

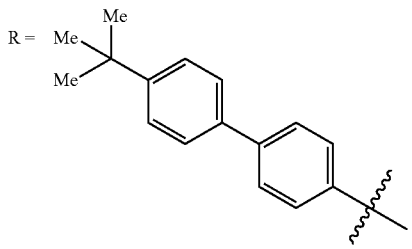

Compound 231: To a mixture of Compound 5G (60 mg, 0.068 mmol), 4-(4t-butylphenyl)benzoic acid (17.3 mg, 0.0683 mmol), EDCI (26.2 mg, 0.137 mmol), HOBt (18.4 mg, 0.137 mmol) in DMF (2.00 mL) was added DIEA (17.6 mg, 0.137 mmol). The mixture was then stirred at room temperature for 12 hrs. When TLC analysis (DCM:MeOH 10:1, $R_f$=0.5) showed the reaction was complete, the mixture was diluted with water, filtered and the filter cake was washed with water, dried to afford Compound 231H (50 mg, yield: 633%) as brown solid.

A solution of Compound 231H (50.0 mg, 0.0448 mmol) in TFA:DCM:TES (50:45:5) (2.00 mL) was stirred at 12° C. for 0.5 h, then TFA was removed and ELSD showed the reaction was complete. The crude residue was taken up in DMSO and purified by prep-HPLC to give Compound 231 (6.3 mg, 16.4%) as an off-white solid. MS (ESI) m/z 860.6 (M+H)$^+$.

Using the procedures described in General Method 12, the following compounds were prepared:

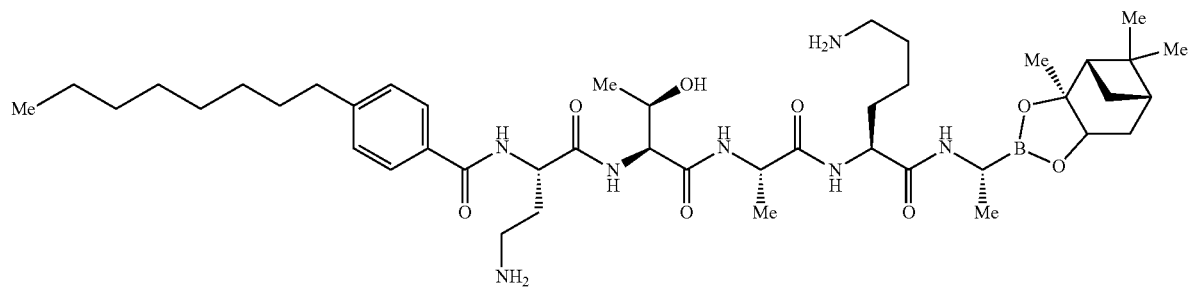

MS (ESI) m/z 840.3 (M + H)$^+$

232

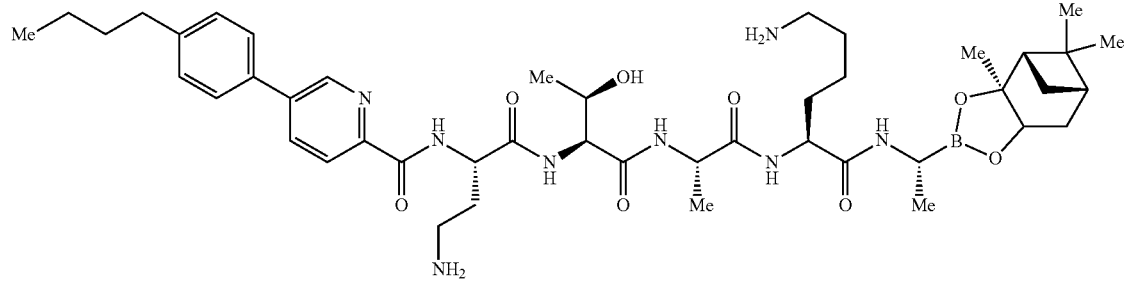

MS (ESI) m/z 861.4 (M + H)$^+$

233

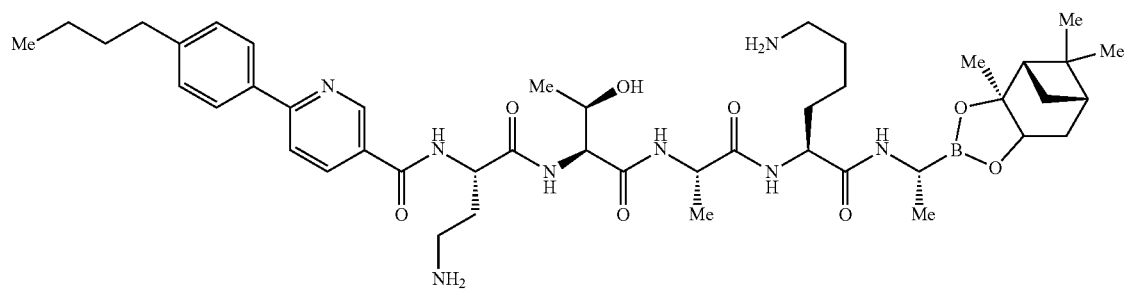
MS (ESI) m/z 861.7 (M + H)+
234
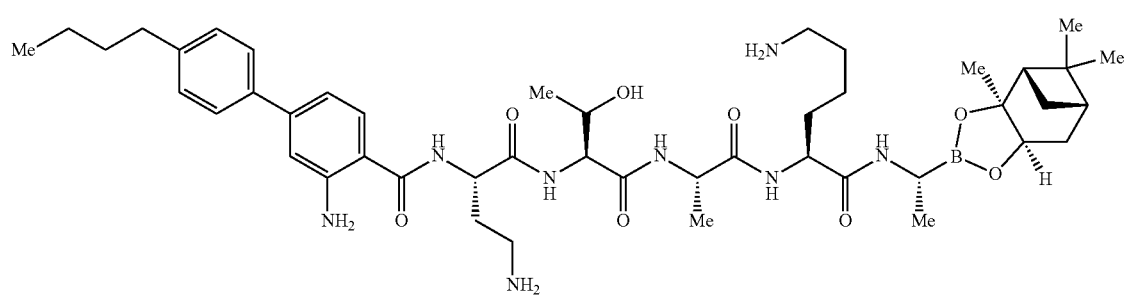
MS (ESI) m/z 861.7 (M + H)+
235
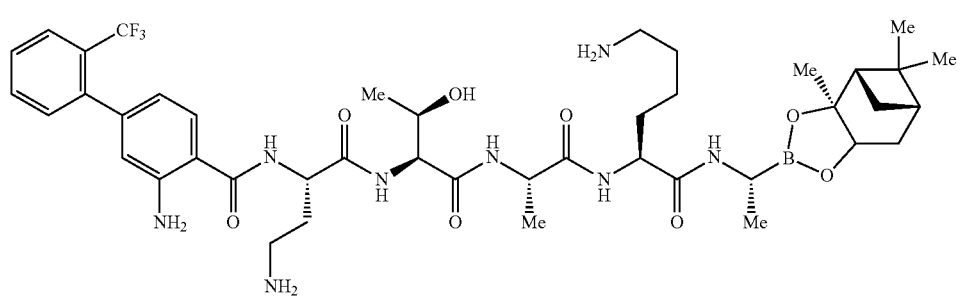
MS (ESI) m/z 872.4 (M + H)+
236
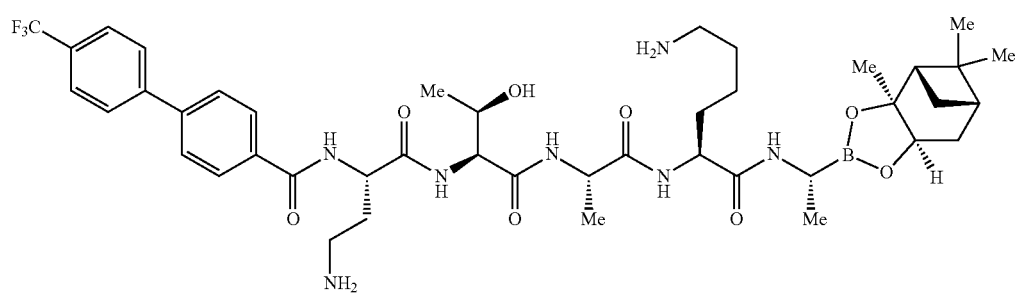
MS (ESI) m/z 872.1 (M + H)+
237

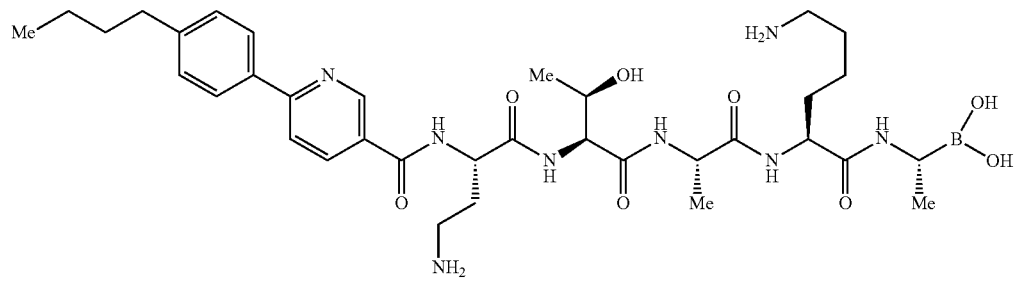
MS (ESI) m/z 709.1 (M − H₂O + H)⁺                                       238
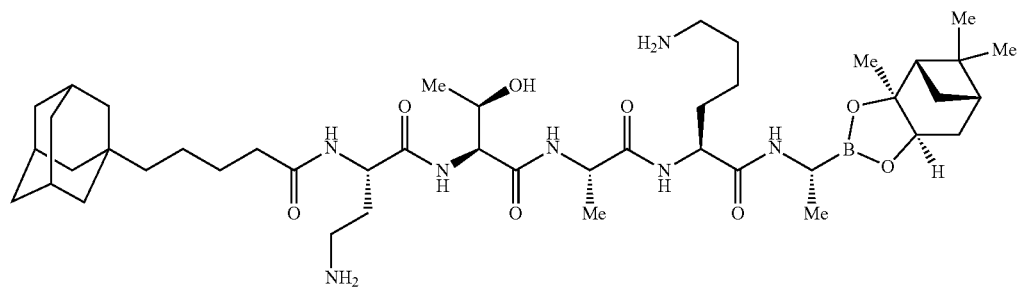
MS (ESI) m/z 842.2 (M + H)⁺                                             239
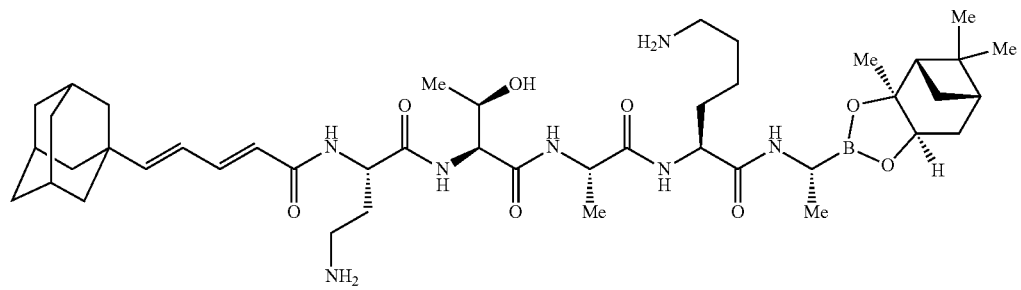
MS (ESI) m/z 838.4 (M + H)⁺                                             240
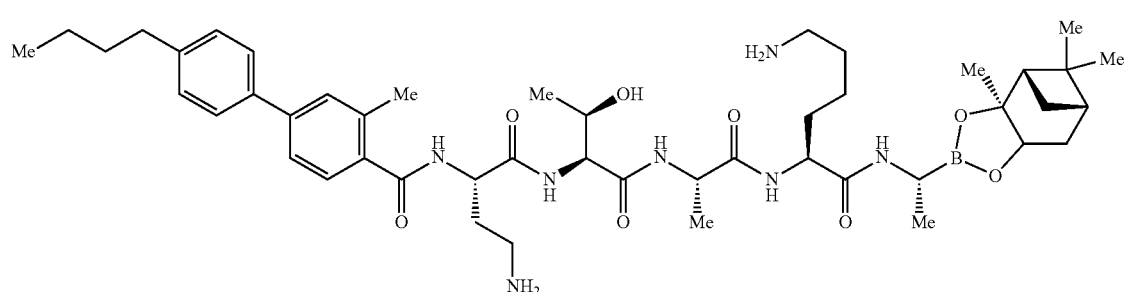
MS (ESI) m/z 874.3 (M + H)⁺                                             241

-continued
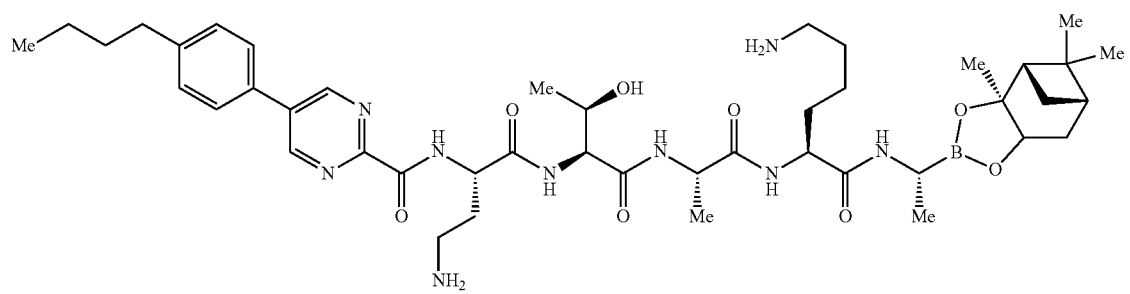
242
MS (ESI) m/z 862.5 (M + H)+
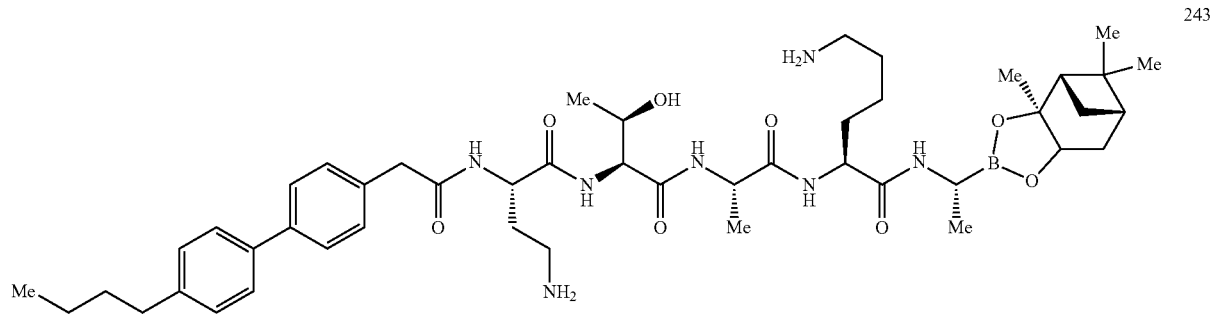
243
MS (ESI) m/z 874.6 (M + H)+
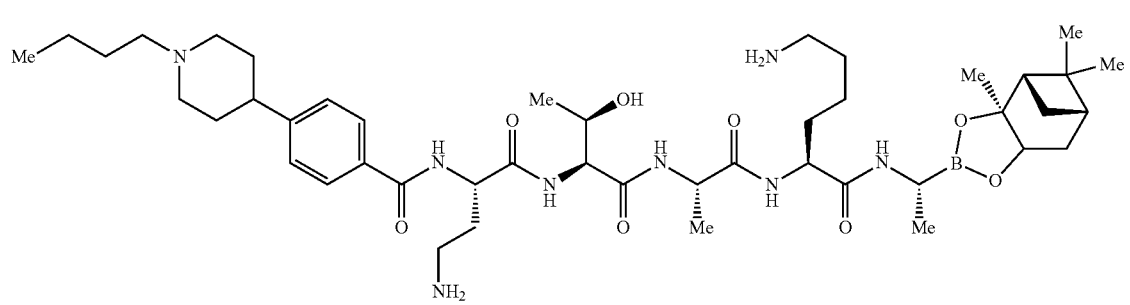
244
MS (ESI) m/z 867.3 (M + H)+
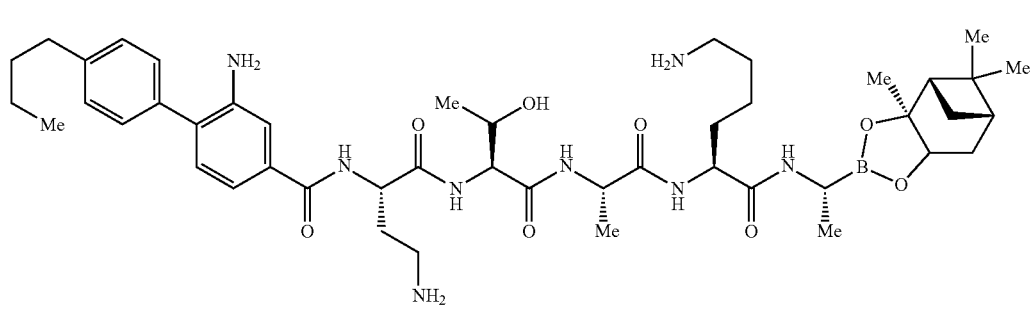
245
MS (ESI) m/z 874.3 (M + H)+

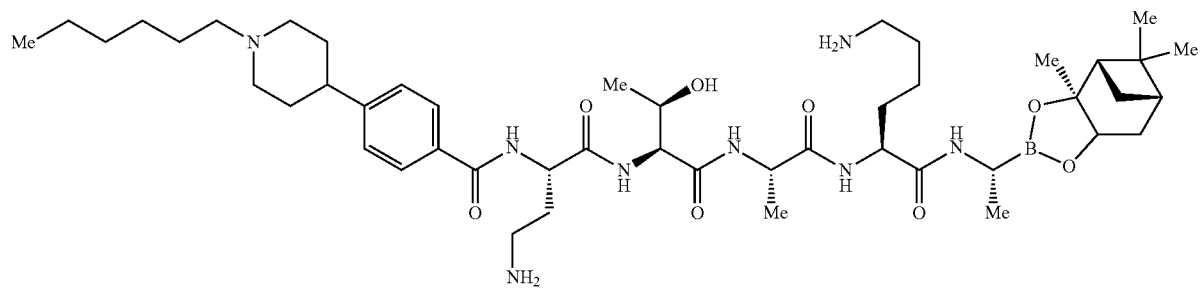
246
MS (ESI) m/z 895.6 (M + H)+
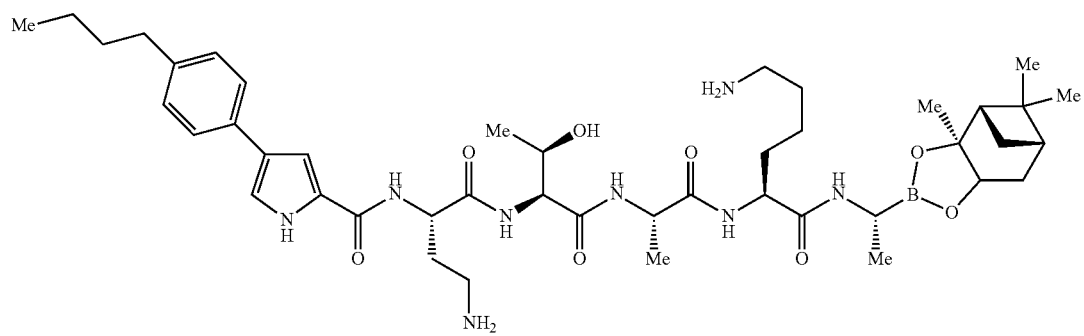
247
MS (ESI) m/z 849.5 (M + H)+
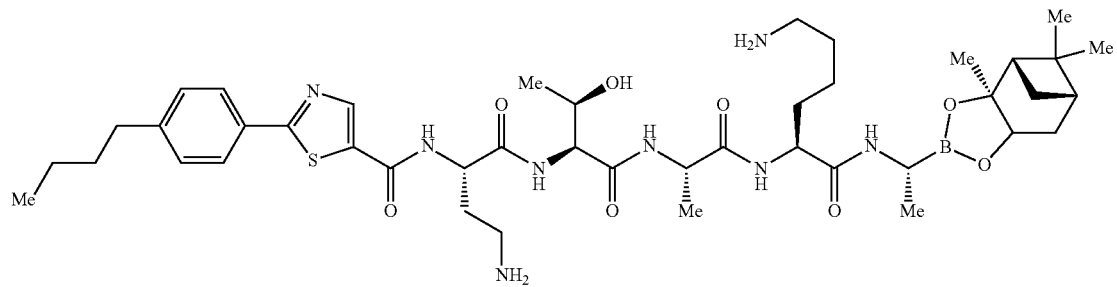
248
MS (ESI) m/z 867.0 (M + H)+
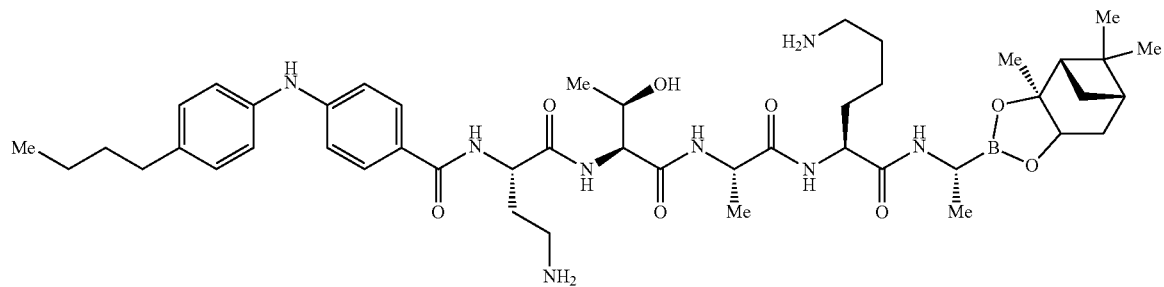
249
MS (ESI) m/z 875.4 (M + H)+

250

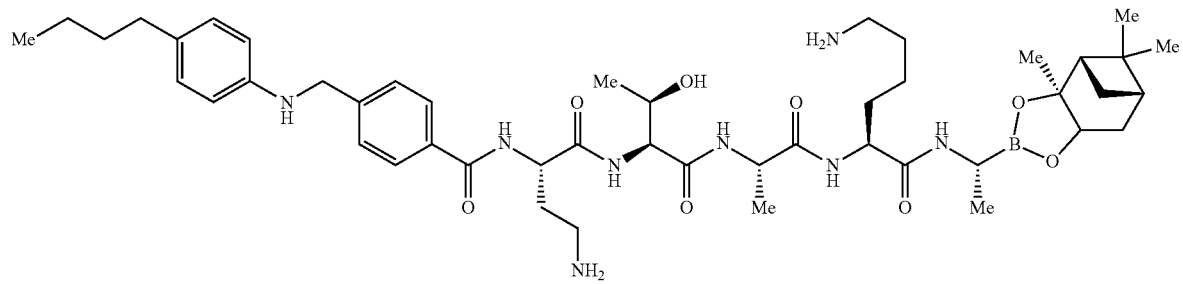

MS (ESI) m/z 889.4 (M + H)+

Example 151

General Method 13:

The synthesis of a biaryl or aryl-heteroaryl carboxylic acid from 1-bromo-4-butylbenzene and an aryl- or heteroaryl boronic acid. An illustration of this method is depicted for 4-(4-butylphenyl)benzoic acid.

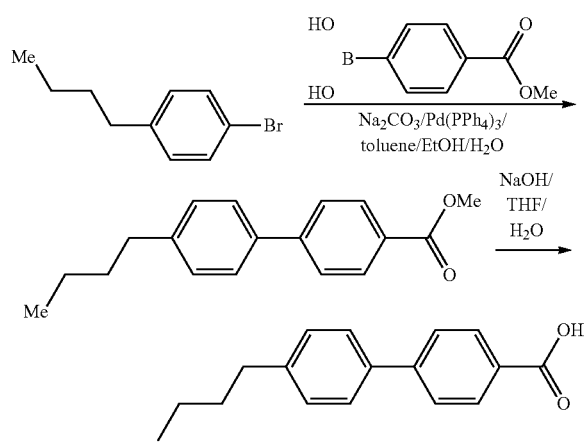

A solution of 1-bromo-4-butylbenzene (100 g, 0.472 mol), 4-(methoxycarbonyl)phenylboronic acid (82.0 g, 0.456 mol), 2 M $Na_2CO_3$ (150 g, 1.42 mol) in toluene/EtOH (900 mL/300 mL) was degassed with $N_2$ three times, then $Pd(PPh_3)_4$ (27.2 g, 23.6 mmol) was added. The resulting mixture was degassed with $N_2$ three times and then heated to reflux for 5 hrs. After TLC showed the reaction was complete, toluene and EtOH was removed under vacuum. The residue was extracted with EA (30 mL×3). The combined organic layers were washed with brine, dried with $Na_2SO_4$. The solvent was removed to give the crude product. The crude product was purified by column chromatography on silica gel eluted with PE, PE:EA (150:1). The solvent was removed to give methyl 4-(4-butylphenyl)benzoate (105 g, yield: 86.0%), as a white solid.

A mixture of methyl 4-(4-butylphenyl)benzoate (89.0 g, 0.332 mol), NaOH (26.6 g, 0.664 mol) in THF/$H_2O$ (500 mL/100 mL) was heated to reflux overnight. After TLC showed the reaction was complete, THF was removed. The residue was adjusted pH ~3-4 with 2 N HCl solution. The resulting mixture was filtered and the cake was washed with water, dried to give 4-(4-butylphenyl)benzoic acid (60.0 g, yield: 71.1%), as a white solid. (ESI) m/z 255.0 (M+H)+.

General Method 14:

The synthesis of a biaryl or aryl-heteroaryl carboxylic acid from 4-butylbenzeneboronic acid or 4-butylbenzeneboronic acid pinacol ester and an aryl- or heteroaryl halide. An illustration of this method is depicted for Compound 248A. A solution of 4-butylphenylboronic acid pinacol ester (937 mg, 3.60 mmol) in dioxane/$H_2O$ (40 mL, v/v, 1/1) was added Compound 14A (400 mg, 1.80 mmol) and $K_2CO_3$ (497 mg, 3.60 mmol). The mixture was then degassed with $N_2$ 3 times before adding Pd(dppf)$Cl_2$ (132 mg, 0.180 mmol) and degassing with $N_2$ 3 times. The mixture was heated to reflux for 7 hrs. The reaction mixture was cooled to room temperature and concentrated after TLC showed the reaction was complete. The residue was adjusted pH ~4-5 with 1 N HCl solution. After that, the resulting mixture was filtered and the filter cake was washed with water, dried to give Compound 248A (200 mg, yield: 42.6%), as a brown solid.

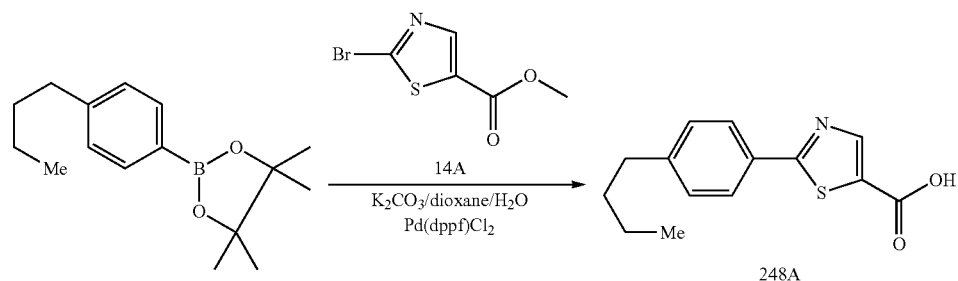

248A

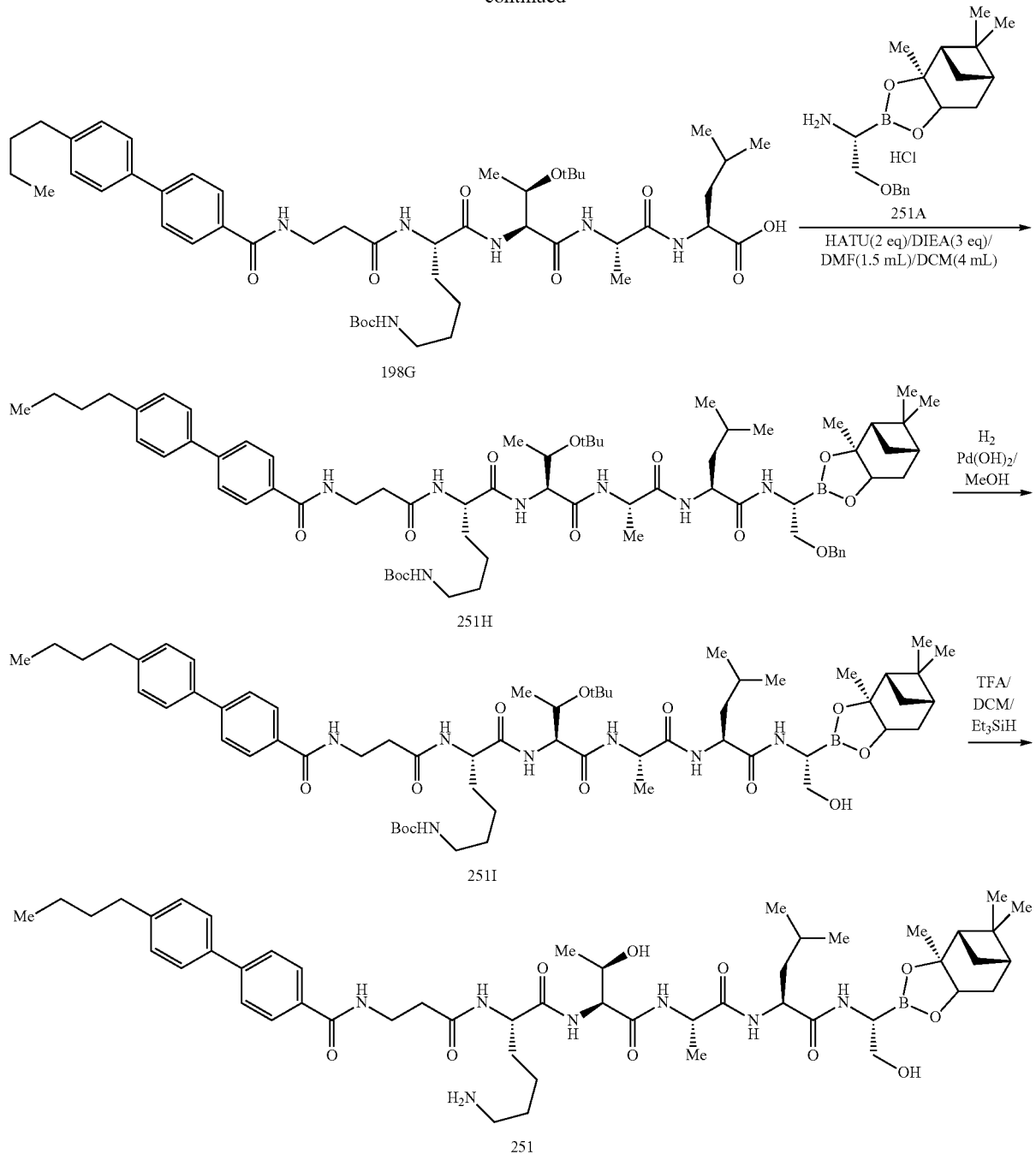

Compound 251: To a mixture of Compound 198G (100 mg, 0.112 mmol), HATU (85.1 mg, 0.224 mmol), and Compound 251A (61.4 mg, 0.168 mmol) in DCM (2.4 mL) and DMF (0.5 mL) at 0° C. was added DIEA (43.3 mg, 0.336 mmol). After 15-30 min the reaction was allowed to warm to room temperature and stirred for 30 min. After ELSD showed the reaction was complete, the mixture was extracted with DCM (30 mL) and water (15 mL). The resulting mixture was extracted with DCM (30 mL×2). The combined organic layers were washed with diluted HCl (<0.1 M), then NaHCO$_3$ solution, brine. The solvent was removed and the residue was extracted with EA (30-50 mL):water (10-15 mL). The organic layers were washed with water (2 mL), then brine, dried over Na$_2$SO$_4$. The mixture was filtered and the filtrate was concentrated. The crude residue was purified by prep-HPLC to give Compound 251H (50.0 mg, yield: 37.1%). MS (ESI) m/z 1206.7 (M+H)$^+$.

A suspension of Compound 251H (50.0 mg, 0.0415 mmol) and 50% Pd(OH)$_2$ (10.0 mg) in MeOH (2 mL) under H$_2$ was stirred at 25° C. overnight and ELSD showed the reaction was completed. The catalyst was filtered and the solvent was evaporated, the crude residue was purified by prep-HPLC to give Compound 251I (20.0 mg, yield: 43.2%). MS (ESI) m/z 1116.6 (M+H)$^+$.

A solution of Compound 251I (10.0 mg, 0.0090 mmol) in TFA:DCM:TES (50:45:5) (1 mL) was stirred at room temperature 2 hrs, then TFA was evaporated and ELSD showed the reaction was completed. The crude residue was taken up in DMSO and purified by prep-HPLC to give Compound 251 (2.8 mg, yield: 33%). MS (ESI) m/z 960.8 (M+H)+.

Example 152

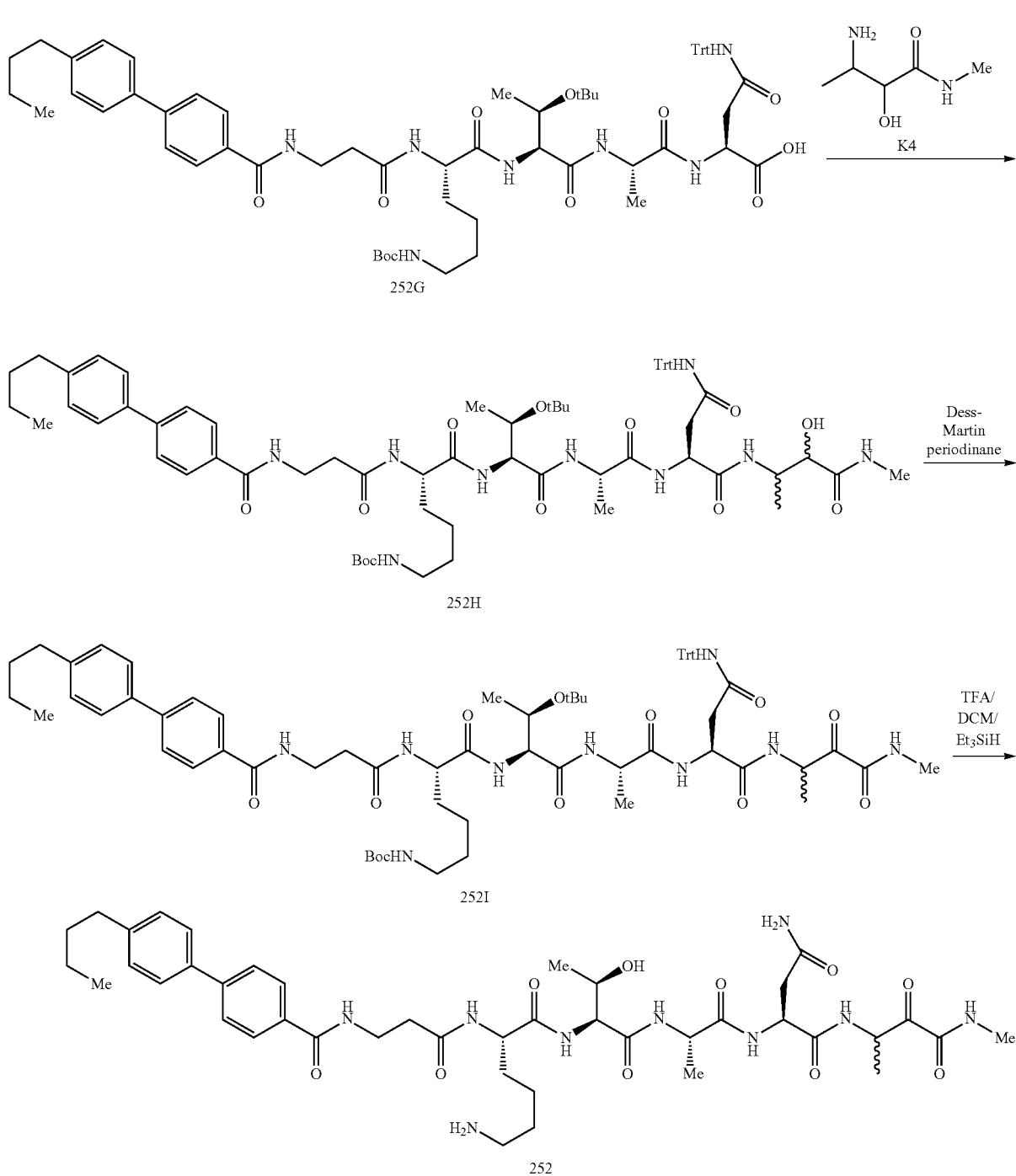

Compound 252: Compound 252G was prepared according General Methods 6-8. MS (ESI) m/z 1153.4. Compound 252 was prepared using the methods described for Compound 111 from Compound 252G and Compound K4. MS (ESI) m/z 852.2 (M+H)+.

291 292
Example 153
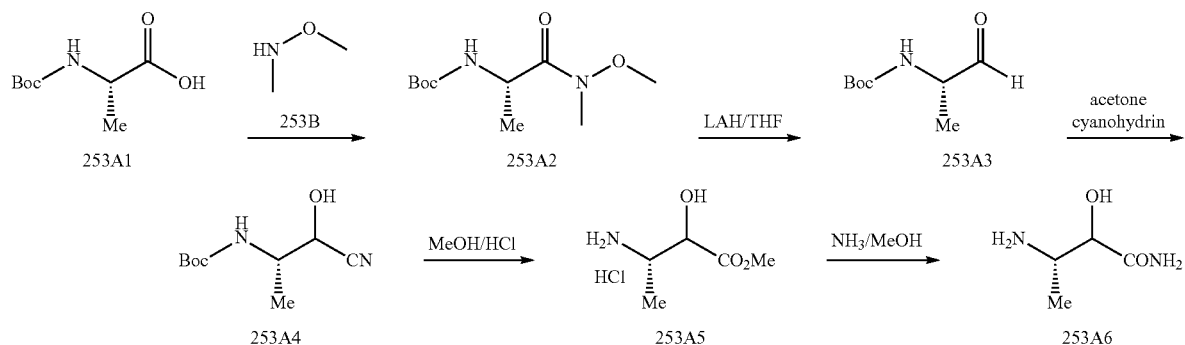
253A1 → 253A2 → 253A3 →
253A4 → 253A5 → 253A6
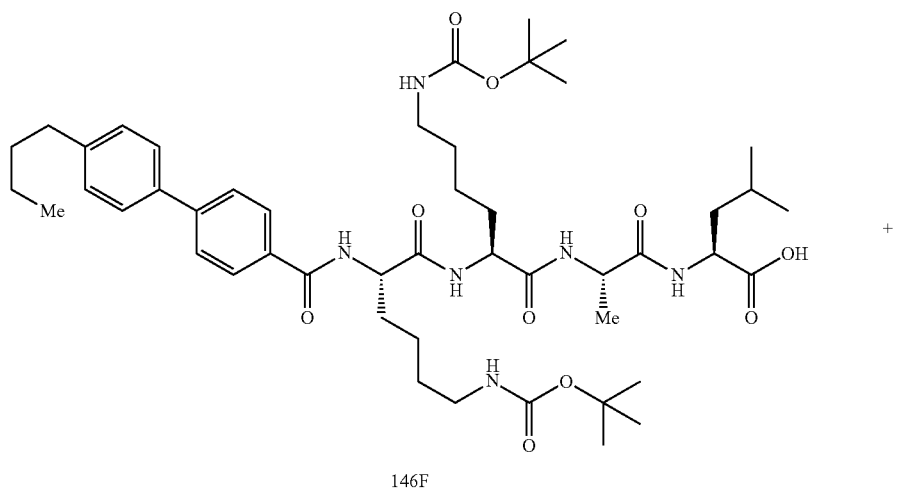
146F
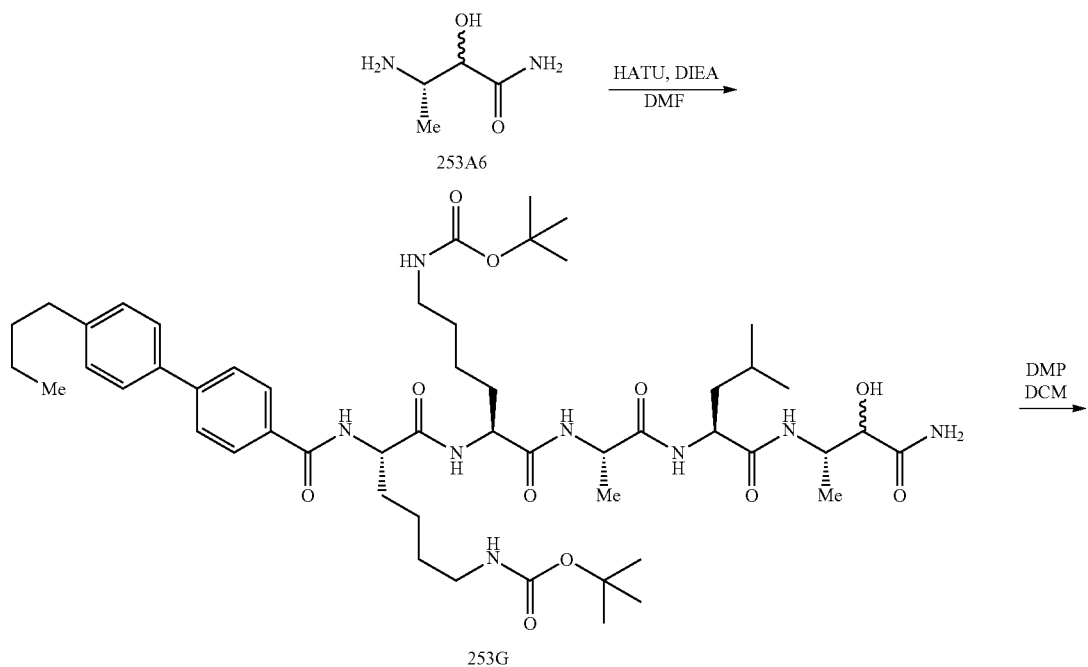
253G -continued

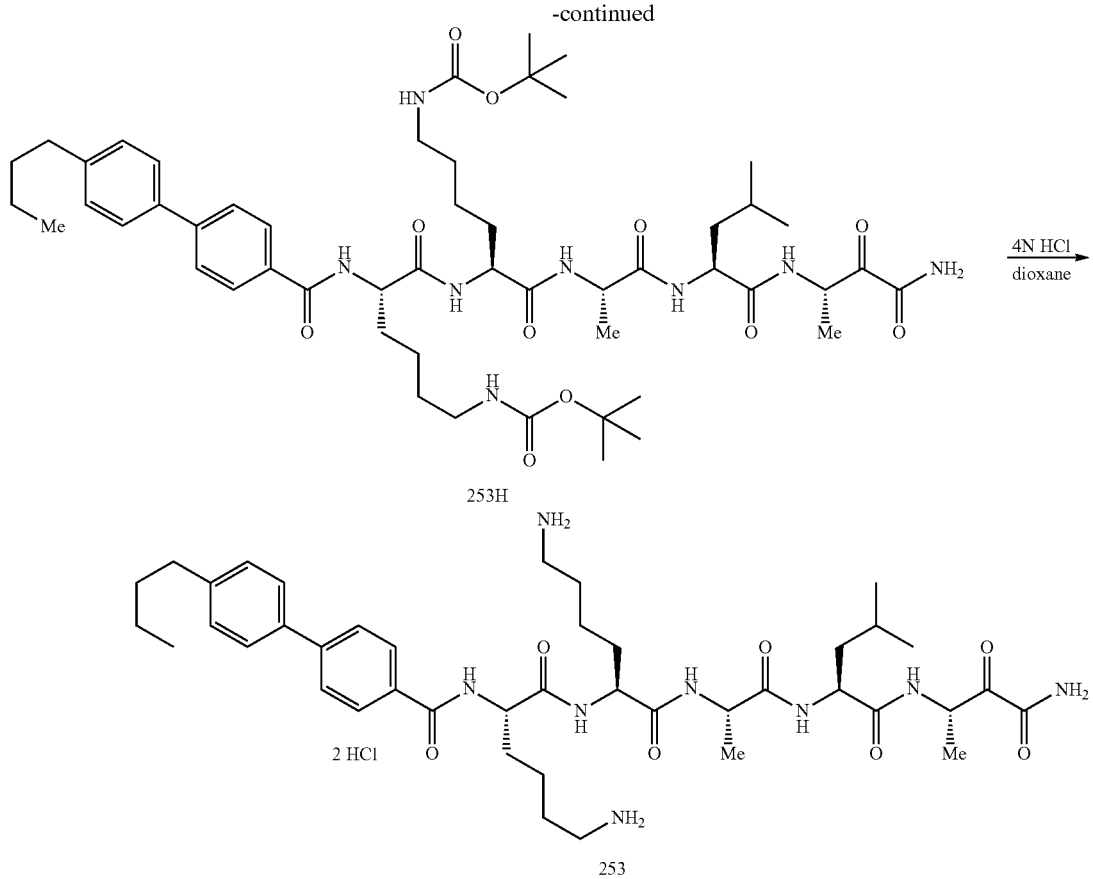

Compound 253: To a mixture of Boc-L-Ala-OH (50.0 g, 0.265 mol), Compound 253B (16.1 g, 0.265 mol), and DIEA (102.4 g, 0.794 mol) in DMF (600 mL) was added HOBt (39.3 g, 0.291 mol) and EDCI (66.0 g, 0.344 mol) at 0° C. The mixture was stirred overnight at 26° C. After LCMS showed the reaction was complete, the mixture was extracted with t-BuOMe and H$_2$O. The combined organic layers were washed with brine, dried over Na$_2$SO$_4$ and concentrated to give Compound 253A2 (50.0 g, yield: 81.5%).

A solution of LAH (2.16 g, 51.7 mmol) in dry THF (70 mL) agitated with an overhead stirrer was chilled to 15° C. A solution of Compound 253A2 (12.0 g, 51.7 mmol) in dry THF (80 mL) was added with cooling so as to keep the reaction temperature <5° C. The reaction mixture was stirred for 45 min quenched by slow addition of EA (20 mL) keeping the internal temperature <5° C. The combined organic layers were washed with sat. aq. NaHCO$_3$ and brine, dried with Na$_2$SO$_4$, filtered and concentrated to give Compound 253A3 (10.0 g, yield: >90%).

A solution of Compound 253A3 (10.0 g, 57.8 mmol) in dry DCM (100 mL) was added Et$_3$N (7.01 g, 69.4 mmol) and acetone cyanohydrin (9.83 g, 116 mmol) at 26° C. The reaction mixture was stirred overnight at 26° C. After TLC showed the reaction was complete, the reaction mixture was concentrated diluted with aqueous 1N HCl (30 mL) and extracted with DCM. The combined organic layers were washed with H$_2$O and brine, dried over Na$_2$SO$_4$, filtered and concentrated to give Compound 253A4 (4.00 g, yield: 34.6%).

A mixture of Compound 253A4 (3.00 g, 15.0 mmol) in HCl/MeOH (30 mL) was heated to reflux for 1 hour. After ELSD showed the reaction was complete, HCl/MeOH was evaporated to give Compound 253A5 (3.00 g, yield: >90%).

A mixture of Compound 253A5 (3.00 g, 17.7 mmol) in NH$_3$/THF (30 mL) in a sealed tube was heated to 100° C. overnight. After ELSD showed the reaction was complete, the mixture was evaporated to give Compound 253A6 (1.30 g, yield: 62.2%). MS (ESI) m/z 852.2 (M+H)$^+$.

To a solution of Compound 146F (18 mg, 0.02 mmol) in anhydrous DMF (1 mL) was added HATU (15 mg, 0.04 mmol), DIEA (8 µL, 0.06 mmol) and 253A (5 mg, 0.03 mmol). The mixture was stirred at room temperature overnight. After LCMS showed the reaction was complete, crushed ice was added to the reaction mixture and after standing for about an hour a white solid was precipitated. The solid was filtered and dried to afford Compound 253G. The solid was dissolved in anhydrous DCM (2 mL) and Dess Martin Periodinane (DMP, 5 eq, 0.1 mmol, 42 mg) was added. The reaction mixture was stirred for 24 h. After LCMS showed the reaction was complete, the reaction mixture was diluted with DCM-EtOAC(1:1), washed with saturated NaHCO$_3$ solution and brine, dried (Na$_2$SO$_4$) and concentrated. The residue was purified by ISCO column (DCM and 20% MeOH-DCM) to isolate 9 mg of Compound 253H as a white solid. To a solution of Compound 253H in dioxane (1 mL) was added 4N HCl in dioxane (0.3 mL) at 0° C. and the resulting solution was stirred at rt for 2 h while warming up the reaction temperature to rt. After LCMS showed the reaction was complete, the material was allowed stand for about 10 minutes. A gummy material formed and the supernatant dioxane was removed and dry ether was added and stirred for 5 min. White precipitate was formed. Ether layer was removed and the solid was dried to afford Compound 253, a white solid as the bis-HCl salt. MS (ESI) m/z 793.3 (M+H)$^+$.

Example 154
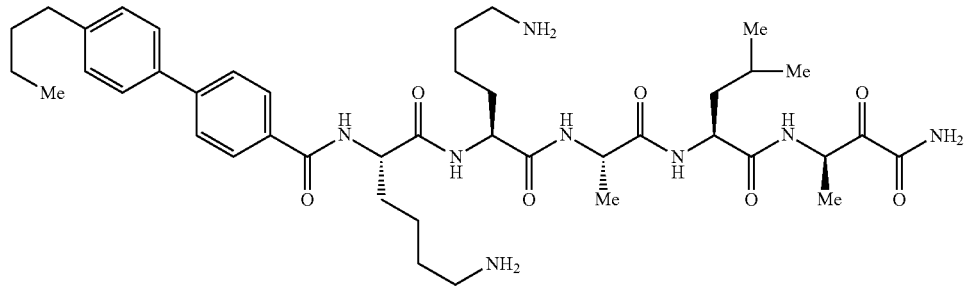
254
Compound 254: Compound 254A was prepared in a manner similar to Compound 253A using Boc-D-Ala-OH as the starting material. Compound 254 was prepared in a manner similar to that of Compound 253 from Compound 146F and Compound 254A. MS (ESI) m/z 793.4 (M+H)$^+$.
Example 155
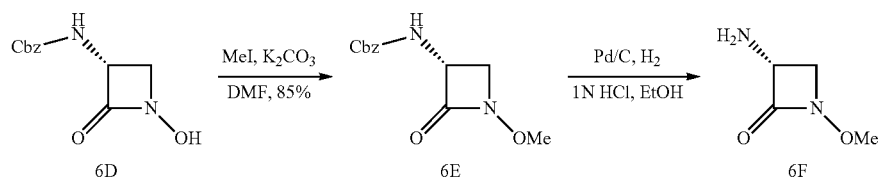
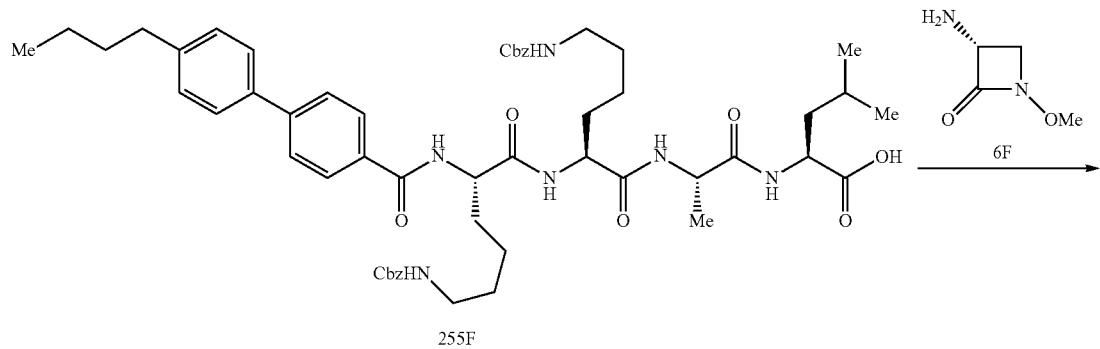
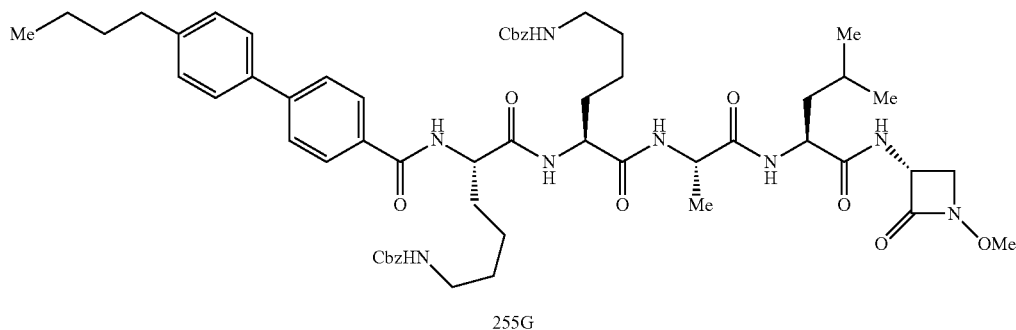

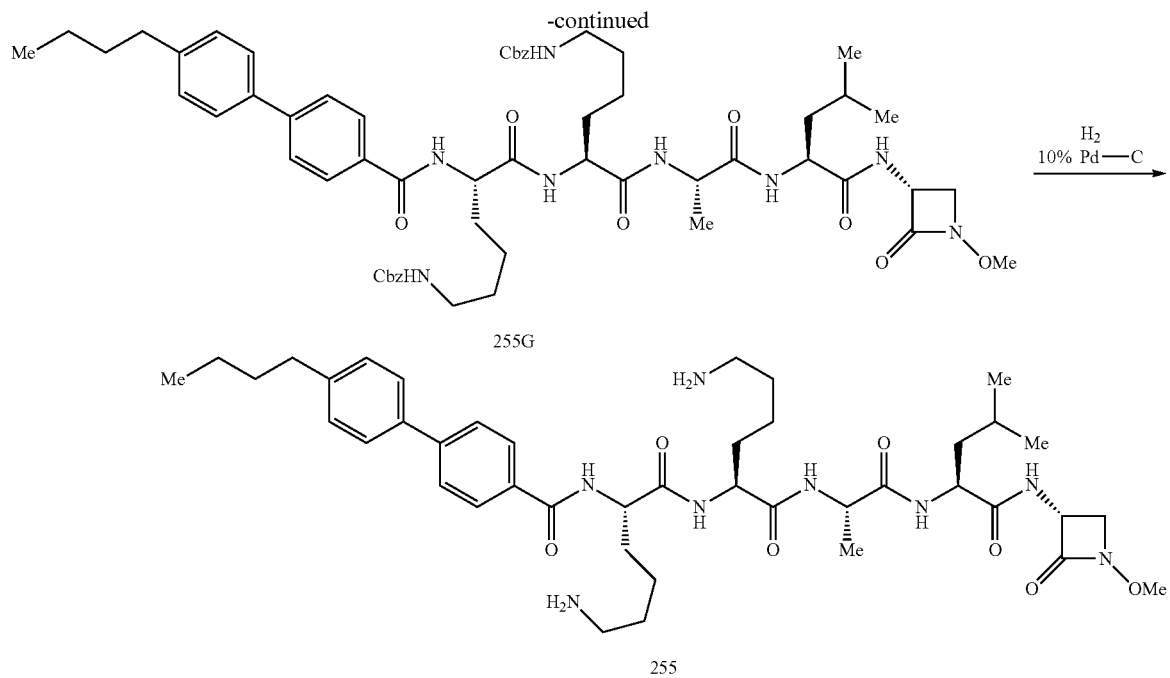

255G

255

Compound 255: Compound 6D (*Tetrahedron* (1983) vol 39, no. 15, 2571-2575) was dissolved in DMF and treated with $K_2CO_3$ (1.1 eq) and iodomethane (2.5 eq) and allowed to stir for 4 hrs. The reaction was then quenched by the addition of water and a small amount of brine and extracted 3× with EtOAc. The combined organic fractions were washed with 1% citric acid and brine then dried over sodium sulfate and concentrated. The crude material was purified by ISCO silica gel chromatography (0-50% EtOAc in Hex, compound eluted at 40% EtOAc) to give Compound 6E (75% yield). $^1$H NMR ($CDCl_3$) δ 7.35 (m, 5H), 5.41 (br s, 1H), 5.112 (s, 2H), 4.61 (m, 1H), 3.84 (m, 1H), 3.81 (s, 3H).

To a solution of Compound 6E in EtOH was added 1N HCl (2 eq). The solution was then put under nitrogen atmosphere and 10% Pd/C (50% by weight of starting material) was added. The solution was then put under an atmosphere of hydrogen and hydrogen was left to bubble through the solution. After 3 hrs the mixture was filtered through celite and concentrated to give crude Compound 6F.

Compound 255F was prepared according to General Methods 6-8. MS (ESI) m/z 963.2 (M+H)$^+$.

To a slightly cloudy solution of Compound 255F and Compound 6F (4 eq) in anhydrous DMF was added HATU (1.2 eq) and DIEA (5 eq). The reaction was complete as judged by LCMS after 10 min and water and DCM were added. The aqueous layer was extracted 3× with DCM then the combined organic fractions were washed with water (2×) then brine. The solution was then dried over sodium sulfate and concentrated. The crude material was then passed through a plug of silica to provide the Compound 255G (75% yield) (MS (ESI) for ($C_{57}H_{72}N_8O_{11}$): m/z 1067.5 (M+Na).

To a cloudy solution of Compound 255G in EtOH was added 1 N HCl (2 eq). The solution was put under nitrogen atmosphere then 10% Pd/C (100% by weight of the starting material) was added. The mixture was put under an atmosphere of hydrogen and stirred overnight. The mixture was then filtered over celite and evaporated to afford Compound 255 by LCMS. MS (ESI) for ($C_{42}H_{67}N_8O_7$): m/z 815.4 (M+Na).

Example 156

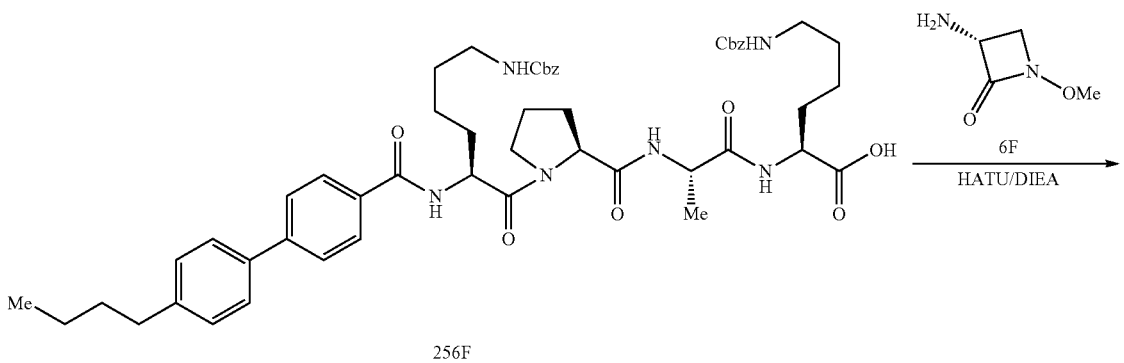

256F

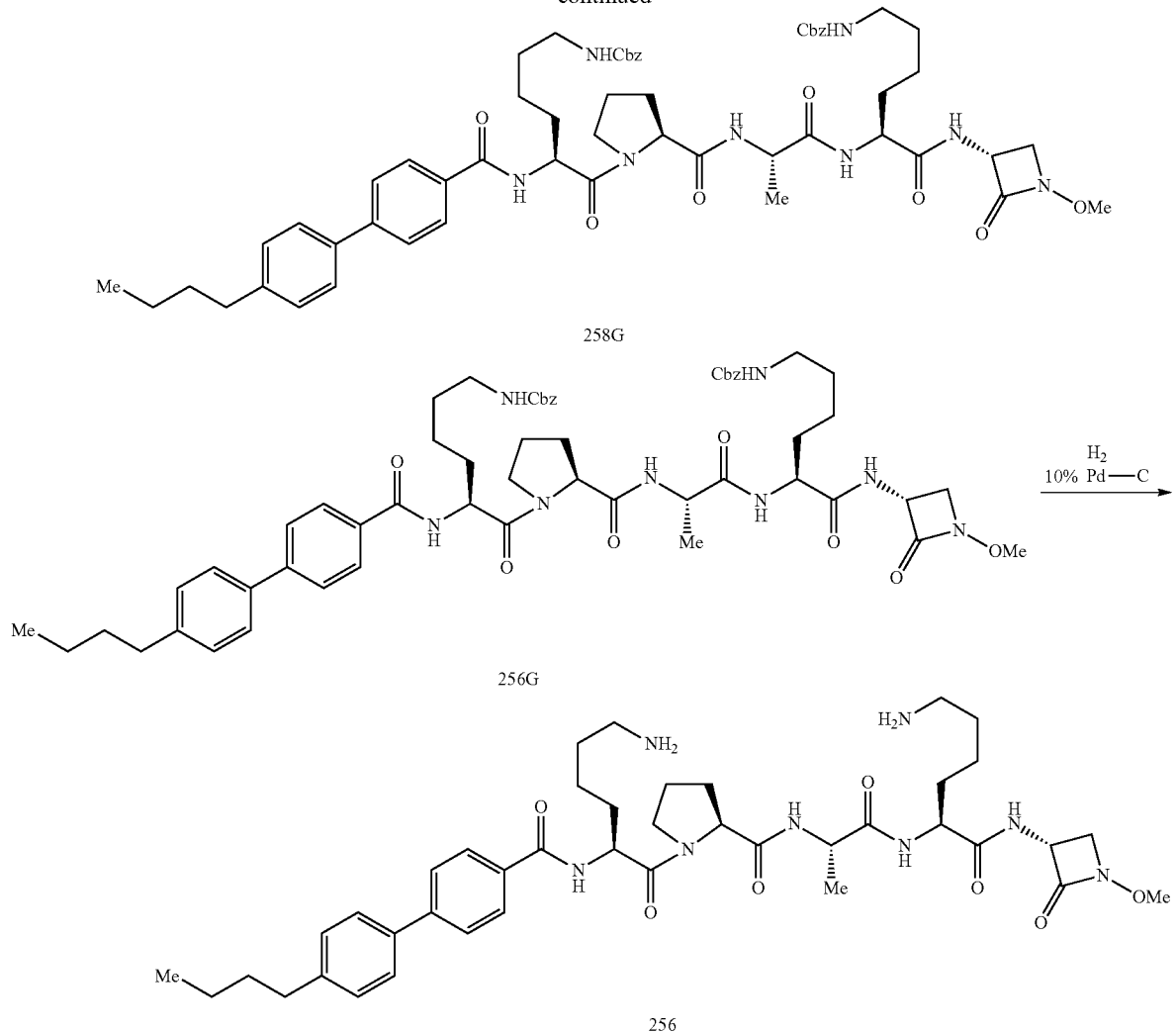

258G

256G

256

Compound 256: Compound 256F was prepared according to General Methods 6-8. MS (ESI) m/z 947.3 (M+H)+.

To a solution of Compound 256F and Compound 6F (4 eq) in anhydrous DMF was added HATU (1.2 eq) and DIEA (5 eq). The reaction was complete as judged by LCMS after 10 min and water, a small amount of brine and EtOAc were added. The aqueous layer was extracted 3× with EtOAc then the combined organic fractions were washed with dilute citric acid, water then brine. The solution was then dried over sodium sulfate and concentrated. The crude material was purified by ISCO silica gel chromatography to provide Compound 256G (41% yield). MS (ESI) for ($C_{57}H_{72}N_8O_{11}$): m/z 799.4 (M+Na).

To a solution of Compound 256G in EtOH was added 1 N HCl (1.9 eq). The solution was put under nitrogen atmosphere then 10% Pd/C (100% by weight of the starting material) was added. The mixture was then put under an atmosphere of hydrogen and stirred overnight. The mixture was filtered through celite then the dilute filtrate was checked by LCMS and found to give correct mass (MS (ESI) for ($C_{41}H_{60}N_8O_7$): m/z 799.4 (M+Na)).

Example 157

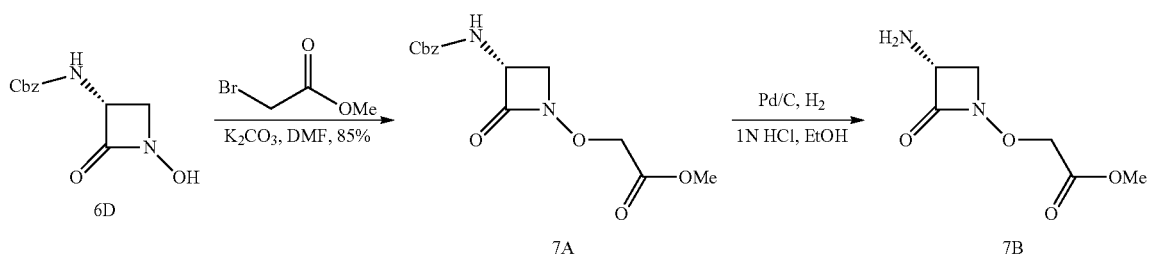

-continued

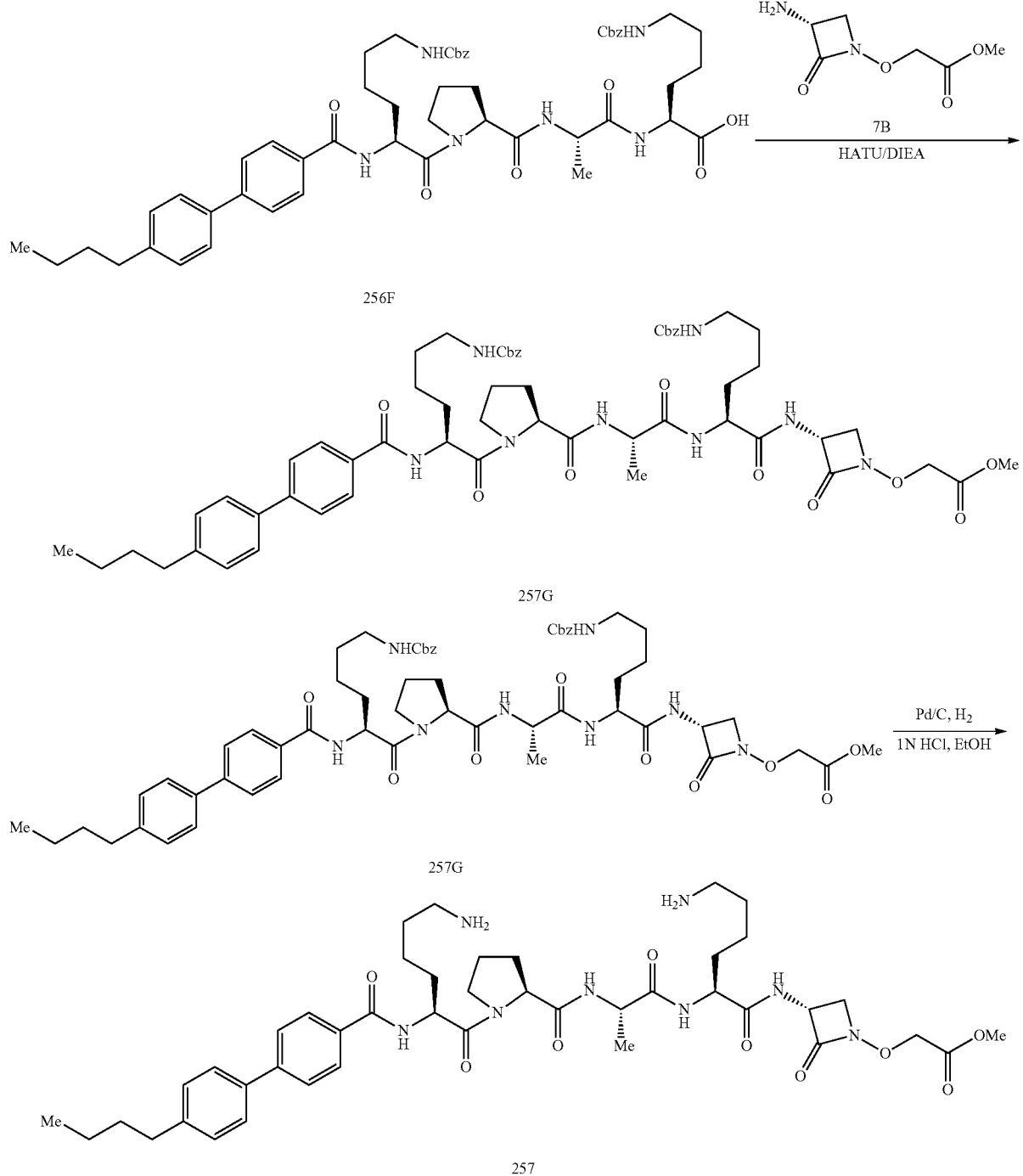

To a solution of Compound 6D in anhydrous DMF was added K$_2$CO$_3$ (1.1 eq) and methyl bromocetate (1.5 eq). The mixture was stirred at room temperature until TLC indicated complete consumption of the starting material after 2.5 hrs then dilute citric acid and EtOAc were added. The aqueous layer was extracted 3× with EtOAc then the combined organic layers were washed twice with water then brine. The combined organic solution were dried over sodium sulfate and concentrated to give crude product then purified by ISCO silica gel chromatography (0 to 65% EtOAc in Hexanes—product eluted at 60% EtOAc) to give Compound 7A (73% yield). $^1$H NMR (CDCl$_3$) δ 7.35 (m, 5H), 5.31 (br s, 1H), 5.11 (s, 2H), 4.62 (m, 1H), 4.55 (s, 2H), 3.99 (m, 1H), 3.79 (s, 3H), 3.67 (m, 1H).

To a solution of Compound 7A in EtOH was added 1N HCl (2 eq). The solution was put under nitrogen atmosphere and the 10% Pd/C (100% by weight of starting material) was added. The solution was then put under an atmosphere of hydrogen and hydrogen was left to bubble through the solution. After 2 hrs the mixture was filtered through celite and concentrated to give crude Compound 7B.

A solution of Compound 256F (10 eq) in anhydrous DMF was added to Compound 7B then HATU (1.2 eq) and DIEA (10 eq) were added. The reaction was stirred at room temperature for 4.5 hrs then water and EtOAc were added. The aqueous layer was extracted 2× with EtOAc then the combined organic layers were washed with water (2×), dilute citric acid, and brine then dried over sodium sulfate and concentrated. The crude material was then purified by filtration through a silica plug to give Compound 257G (56% yield) (MS (ESI) for ($C_{59}H_{74}N_8O_{13}$): m/z 1103.2 (M+H)).

To a solution of Compound 257G in EtOH was added 1 N HCl (1.9 eq). The solution was put under nitrogen atmosphere then 10% Pd/C (100% by weight of the starting material) was added. The mixture was then put under an atmosphere of hydrogen and stirred overnight. The mixture was filtered through celite then the dilute filtrate was checked by LCMS and found to give the correct product. MS (ESI) for ($C_{43}H_{62}N_8O_9$): m/z 857.4 (M+Na). The filtrate was then concentrated down to an 8 mg/mL solution in EtOH and checked again by LCMS which showed an identical mass spectrum to the diluted sample. Compound 257 was stored as an 8 mg/mL solution.

Example 158

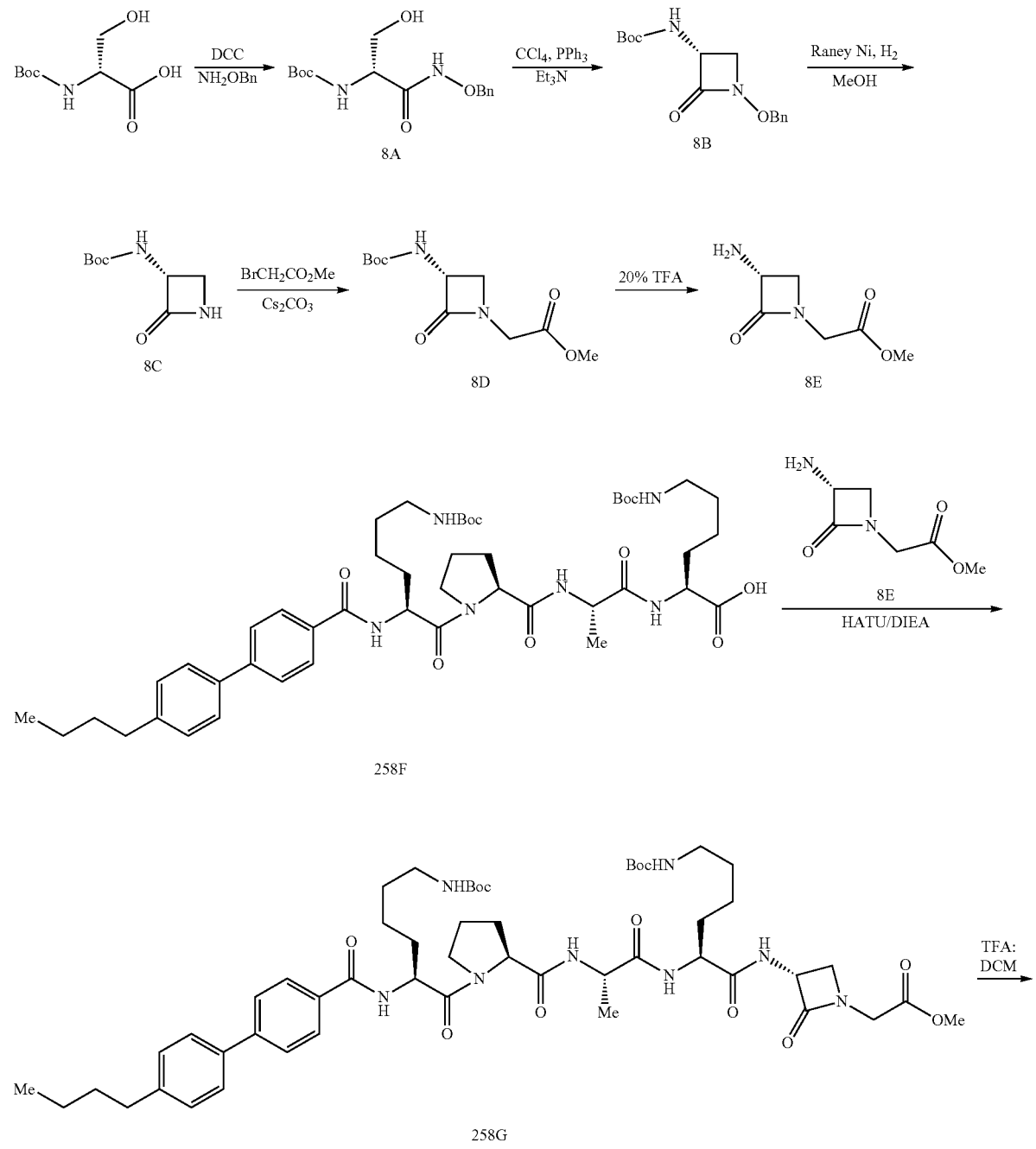

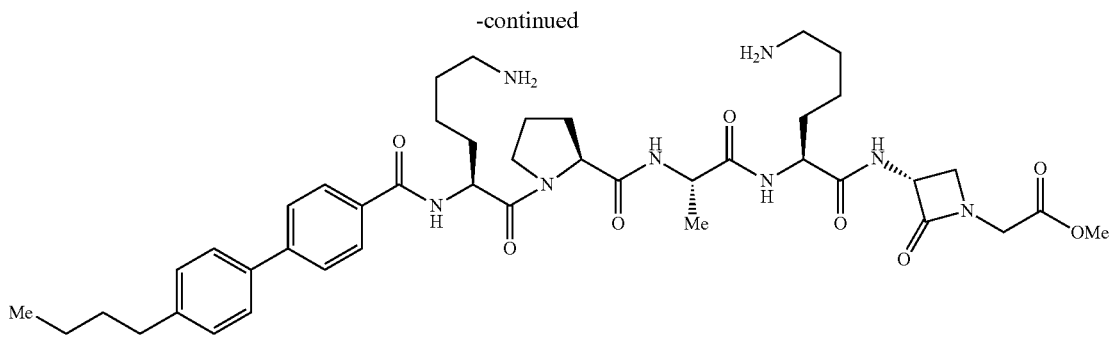

258

To a solution of Boc-D-Ser-OH (1.5 g, 1 eq) in THF (54 mL) was added a solution of O-benzylhydroxylamine (1.3 eq) in THF (3 mL), H₂O (30 mL), and a solution of DCC (1.3 eq) in THF (3 mL). The solution was stirred at room temperature until analysis by LCMS indicated the starting material had been consumed (1 hr), at which point the THF was evaporated by rotary evaporation. EtOAc and water were added to the residue and the aqueous layer was extracted 3× with EtOAc and the combined organic layers were evaporated. The crude residue was then taken up in a small amount of EtOAc and filtered. The filtrate was diluted with EtOAc, washed with 5% citric acid, saturated NaHCO₃ and brine then dried over sodium sulfate and concentrated. The crude residue was purified via ISCO silica gel chromatography (20% to 90% EtOAc in Hex, product eluted at ~90% EtOAc) to give pure Compound 8A (63% yield).

In a flame dried flask over activated 4 A molecular sieves under Ar, a solution of Compound 8A (1 eq) and triphenylphosphine (1.1 eq) in acetonitrile was treated with a solution of anhydrous CCl4 (10 eq) in anhydrous AcCN and a solution of triethylamine (1.2 eq) in anhydrous AcCN. The mixture was allowed to stir overnight, then was filtered through celite and concentrated. The crude material was purified by ISCO silica gel chromatography (0 to 3% MeOH in DCM, product eluted at 2.9%) to give Compound 8B (62% yield).

To a solution of Compound 8B (1 eq) in MeOH under Ar atmosphere was added Raney Ni slurry in water. The solution was then put under an atmosphere of H₂ and allowed to stir at room temperature for 7 hrs or until TLC indicated complete consumption of starting material. The mixture was then filtered through celite and the filtrate was concentrated. The crude material was purified via ISCO silica gel chromatography (0 to 6% MeOH in DCM, product eluted at ~1% MeOH) to give Compound 8C (79% yield).

In a flame dried flask under Ar, a solution of Compound 8C (1 eq) in AcCN was heated to 50° C. The solution was then treated with cesium carbonate (1.2 eq) and methyl bromoacetate (1.5 eq). The mixture was stirred at 50° C. until TLC indicated complete consumption of starting materials then the reaction was cooled and diluted with EtOAc and water. The aqueous layer was extracted 3× with EtOAc, then the combined organic layers were washed with brine and dried over sodium sulfate and concentrated. The crude material was purified via ISCO silica gel chromatography (0 to 10% MeOH in DCM, product eluted at 6.5% MeOH) to give Compound 8D (36% yield). ¹H NMR (CDCl₃) δ 7.35 (m, 5H), 5.41 (br s, 1H), 5.112 (s, 2H), 4.61 (m, 1H), 3.84 (m, 1H), 3.81 (s, 3H).

Compound 8D was treated with a 5:1 mixture of DCM: TFA on an ice bath. After 2 hrs TLC indicated the complete consumption of starting material and the solvents were evaporated. The crude was taken up in DCM and evaporated by rotary evaporation 3× to give crude Compound 8E which was used without further purification.

Compound 258F was prepared using the procedures described in General Methods 6-8 and Scheme XIX.

To a solution of Compound 8E (5 eq) and Compound 258F (1 eq) in DMF was added HATU (1.2 eq) and DIEA (8 eq) and the reaction mixture was stirred at room temperature. After 4 hrs, the mixture was diluted with water and EtOAc. The aqueous layer was extracted 3× with EtOAc then the combined organic layers were washed with water and brine, dried over sodium sulfate and concentrated. The crude material was purified via ISCO silica gel chromatography (0 to 12%, MeOH in DCM, product eluted at ~8% MeOH) to give pure Compound 258G (49% yield). MS (ESI) m/z 1087.1 (M+H)⁺.

To a solution of Compound 258G in EtOH under Ar was added 1 N HCl (1.9 eq) 10% Pd/C (100% w/w). The mixture was then put under an atmosphere of H₂ and allowed to stir for 4 hrs at which point TLC indicated complete consumption of starting material. The mixture was filtered through celite and concentrated to give the Compound 258 as a bis-hydrochloride salt. MS (ESI) m/z 819.3 (M+H)⁺.

Example 159

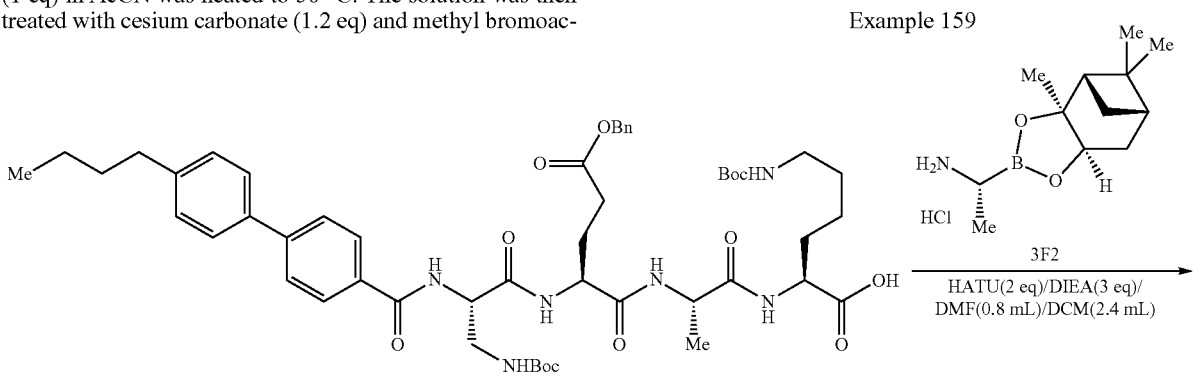

259F

-continued
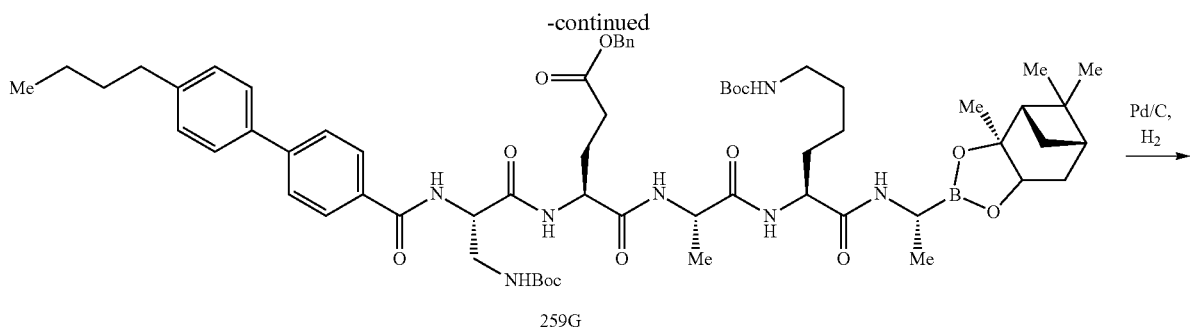
259G
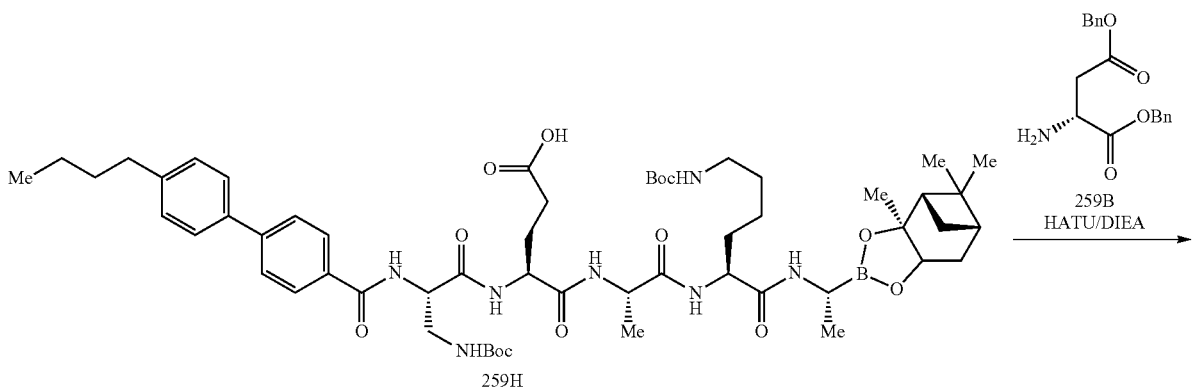
259H
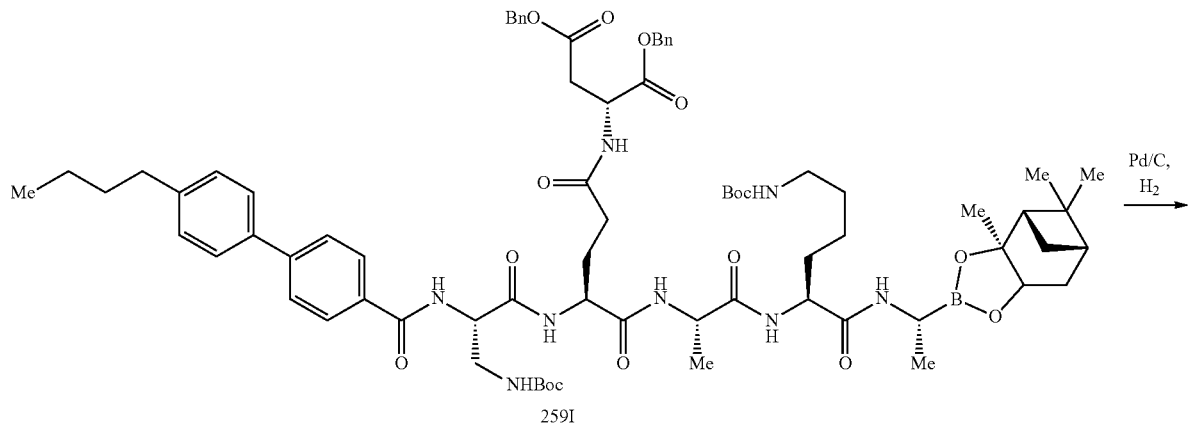
259I
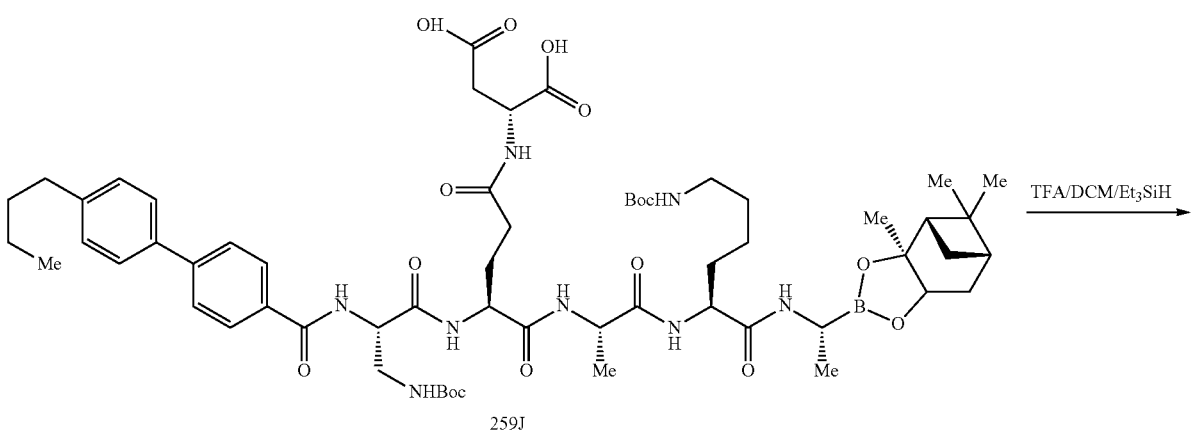
259J

-continued

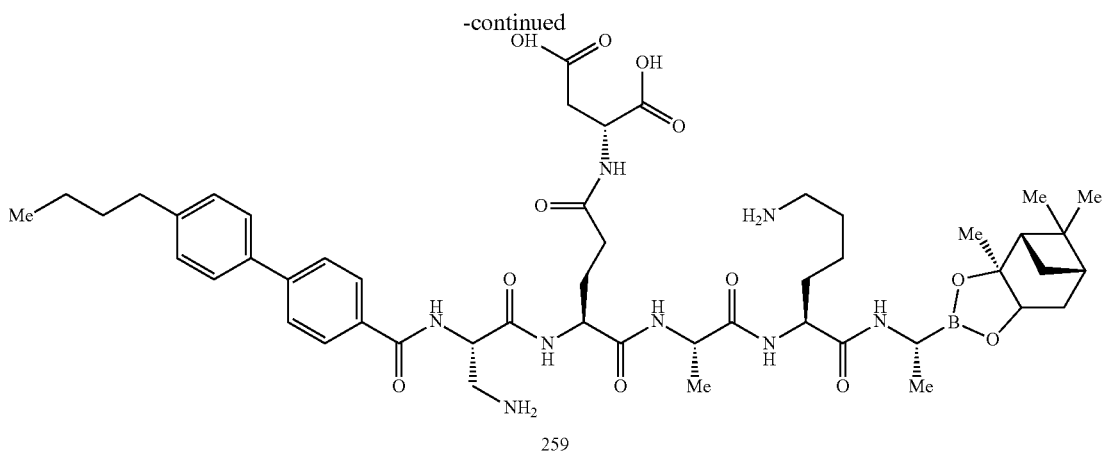

259

Compound 259F is prepared using the procedures described in General Methods 6-8. MS (ESI) m/z 959.2 (M+H)⁺.

To a solution of Compound 259F (100 mg, 0.104 mmol), HATU (79.0 mg, 0.208 mmol), and Compound 3F2 (40.4 mg, 0.156 mmol) in DCM (2.4 mL) and DMF (0.8 mL) at 0° C. was added DIEA (40.2 mg, 0.312 mmol). After 15-30 min the reaction was allowed to warm 25° C. and stirred at 25° C. for 30 min. After ELSD showed the reaction was complete, the mixture was extracted with DCM (10 mL) and water (5 mL). The resulting mixture was extracted with DCM (5 mL×2). The combined organic layers were washed with diluted HCl (<0.1 M), then NaHCO₃ solution, brine. The solvent was removed and the residue was extracted with EtOAc (30-50 mL):water (10-15 mL). The organic layers were washed water (10 mL), brine, dried over Na₂SO₄. The mixture was filtered and the filtrate was concentrated. The residue was crystallized from acetonitrile to give Compound 259G (90.0 mg, yield: 74.3%). MS (ESI) m/z 1165.0 (M+H)⁺.

To a mixture of Compound 259G (190 mg, 0.163 mmol) in THF (2 mL) was added Pd/C (50.0 mg) and CH₃COOH (0.5 mL) under H₂. The mixture was degassed with H₂ three times before stirring at 25° C. at 50 psi H₂. After 12 hrs, LC-MS showed the reaction was completed. The catalyst was filtered and the solvent was evaporated, the crude residue was purified by prep-HPLC to give Compound 259H (120 mg, yield: 68.5%).

To a solution of Compound 259H (50.0 mg, 0.0466 mmol), HATU (35.4 mg, 0.0932 mmol) and Compound 259B (29.2 mg, 0.0932 mmol) in DCM (0.5 mL) and DMF (0.5 mL) at 0° C. was added DIEA (18.1 mg, 0.140 mmol). The reaction was stirred 2 hrs at 0° C. After LCMS showed the reaction was complete, DCM was evaporated. The crude residue was taken up in DMF and purified by prep-HPLC to give Compound 259I (15.0 mg, yield: 23.4%).

To a mixture of Compound 259I (7.50 mg, 0.00548 mmol) in EtOAc (0.5 mL) was added Pd/C (10.0 mg) under H₂. The mixture was degassed with H₂ three times before stirring at 25° C. under 50 psi H₂. After 12 hrs, LC-MS showed the reaction was completed. Then the catalyst was filtered and the solvent was evaporated to give Compound 259J (5.0 mg, yield: 76.8%).

A solution of Compound 259J (5.00 mg, 0.00421 mmol) in TFA:DCM:TES (50:45:5) (1 mL) was stirred at 25° C. for 1 hr, then TFA was evaporated and ELSD showed the reaction was completed. The crude residue was taken up in DMSO and purified by prep-HPLC to give Compound 259 (3.0 mg, yield: 71%). MS (ESI) m/z 989.3 (M+H)⁺.

Example 160

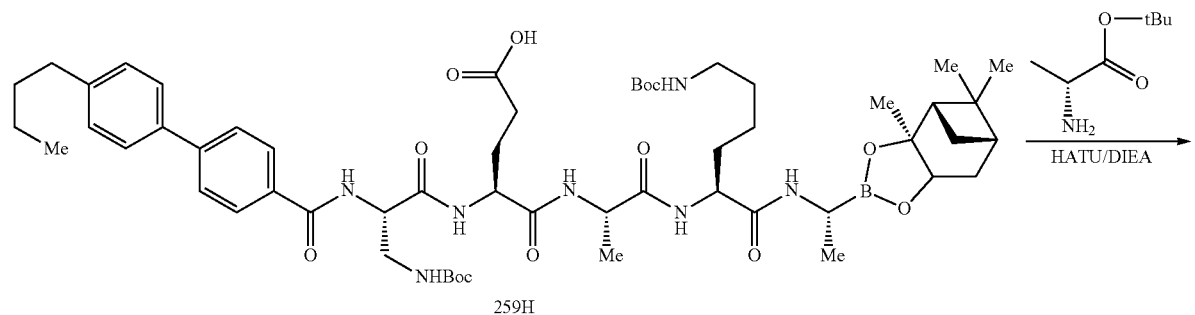

259H

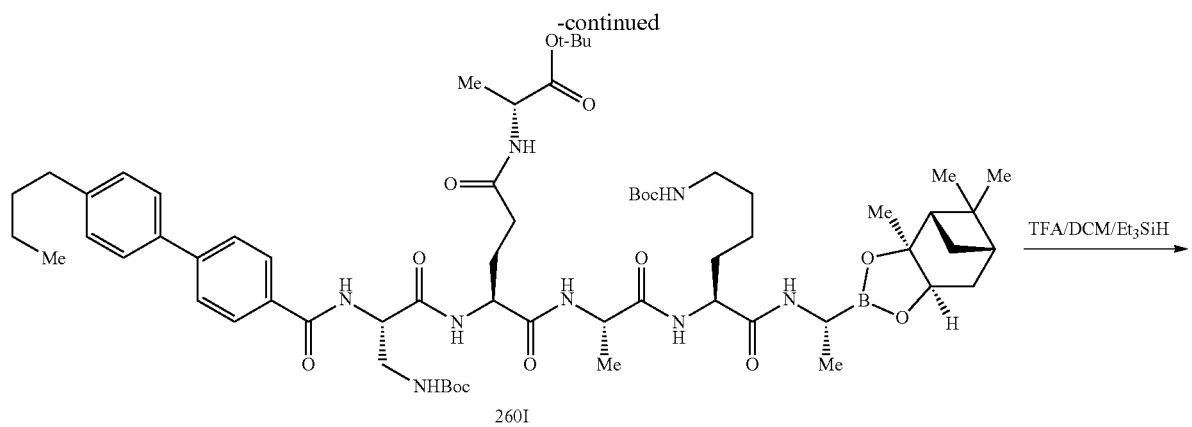

To a solution of Compound 259H (50.0 mg, 0.0466 mmol), HATU (35.4 mg, 0.0932 mmol), then D-Ala(O-tBu) (13.5 mg, 0.0932 mmol) in DCM (0.5 mL) and DMF (0.5 mL) at 0° C. was added DIEA (18.1 mg, 0.140 mmol). The reaction was stirred 2 hrs at 0° C. After LCMS showed the reaction was complete and DCM was evaporated. The crude residue was taken up in DMF and purified by prep-HPLC to give Compound 260I (40.0 mg, yield: 71.6%).

To a solution of Compound 260I (40.0 mg, 0.0333 mmol) in TFA:DCM:TES (50:45:5) (1 mL), was stirred at 25° C. for 1 hr, then TFA was evaporated and ELSD showed the reaction was completed. Then the crude residue was washed with petroleum ether to give Compound 260 (15.0 mg, yield: 47.6%). MS (ESI) m/z 945.6 (M+H)$^+$.

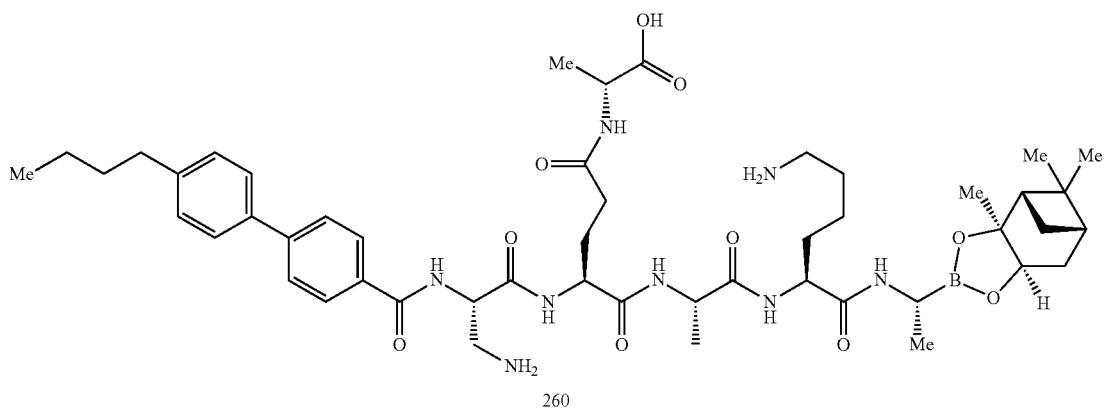

Example 161

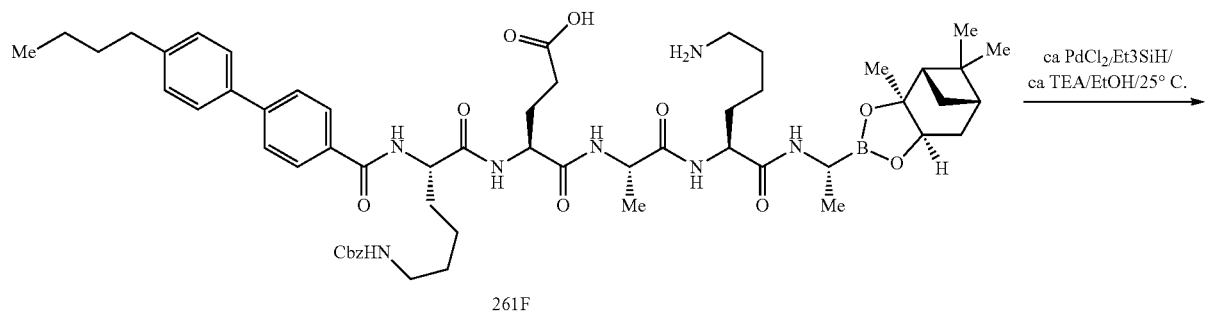

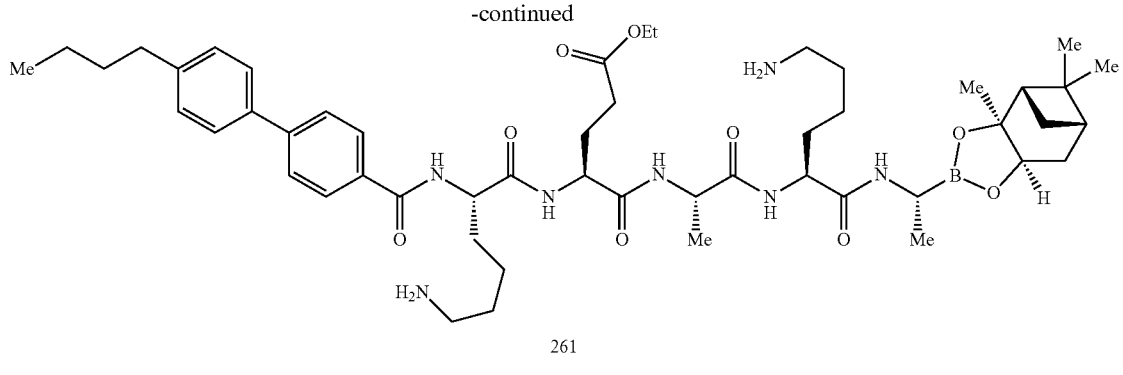
261
To a mixture of Compound 261F (10 mg, 0.00953 mmol) in EtOH (1.0 mL) was added PdCl$_2$ (0.2 mg,), Et$_3$N (0.1 mg, 0.000953 mmol), Et$_3$SiH (11.0 mg, 0.095 mmol) under N$_2$. The mixture was stirred overnight. After LCMS showed the reaction was complete, the solvent was removed and the crude residue was taken up in DMSO and purified by prep-HPLC to give Compound 261 (3.0 mg, yield: 33%). MS (ESI) m/z 945.5.
Example 162
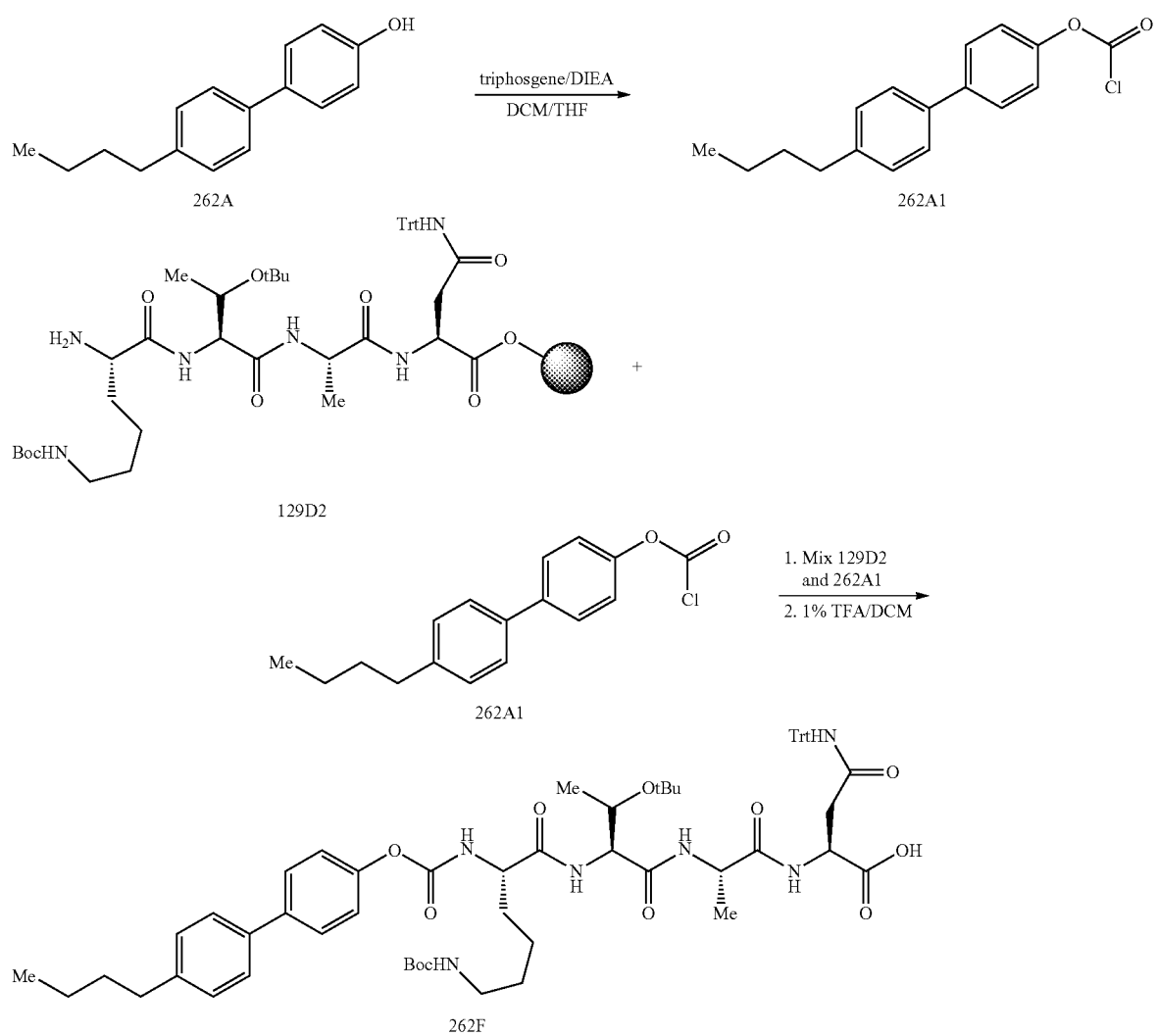

-continued

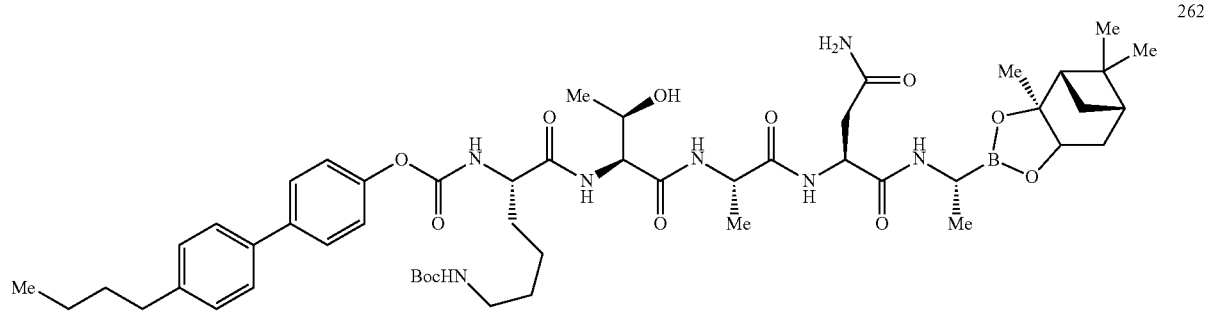

262

To a solution of triphosgene (47.7 mg, 0.162 mmol) in dry DCM (5.0 mL) was slowly added a solution of Compound 262A (110 mg, 0.487 mmol) and DIEA (0.503 g, 3.90 mmol) in THF (5.0 mL) at 0° C. The reaction mixture was allowed to stir at 20° C. for 25 min. The solution of Compound 262A1 was used to next step directly without purification.

Compound 129D2 was added to the solution of Compound 262A1 at 0° C. The reaction mixture was warmed to 20° C. and was shaken at 20° C. for 4 hrs. After ELSD showed the reaction was complete, the mixture was filtered. The filter cake was washed with THF (20.0 mL×3) and DCM (20.0 mL×3) separately, and then dried. TFA/DCM (1%, 5.0 mL) was added and the mixture was shaken at 20° C. for 5 min.

The mixture was filtered and the filtrate was treated with saturated NaHCO$_3$ solution until pH ~7-8. The aqueous layer was adjusted with citric acid until pH ~3-4. The mixture was extracted with DCM (20.0 mL×3). The combined organic layers were washed with brine, dried over Na$_2$SO$_4$ and concentrated to give a residue, which was purified by prep-HPLC to give Compound 262F (80.0 mg, yield: 61.6%). MS (ESI) m/z 1083.3 (M+H)$^+$.

Using the procedures described in General Methods 9 and 10, Compound 262 was prepared from Compound 262F. MS (ESI) m/z 890.4 (M+H)$^+$.

Example 163

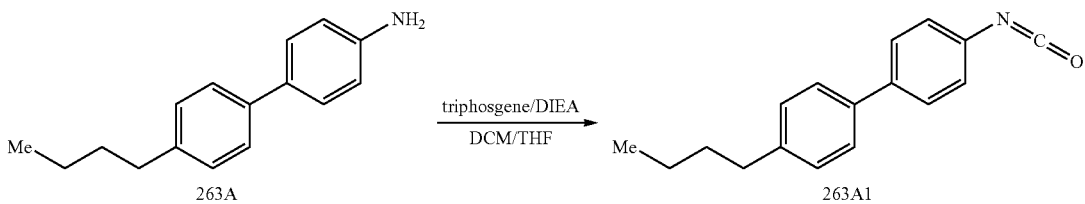

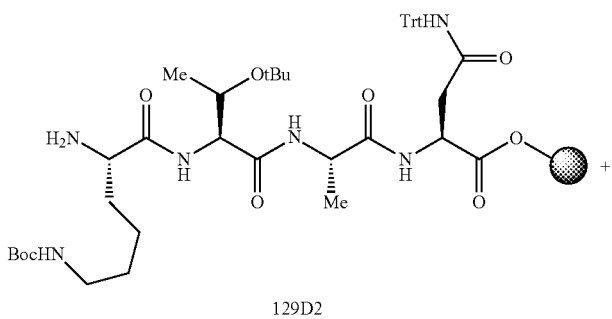

129D2

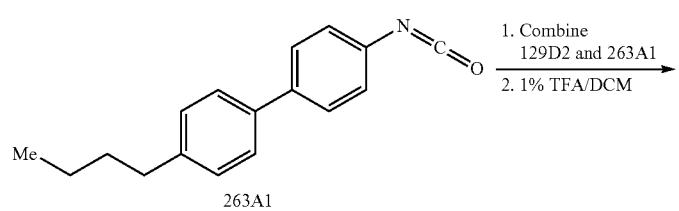

-continued

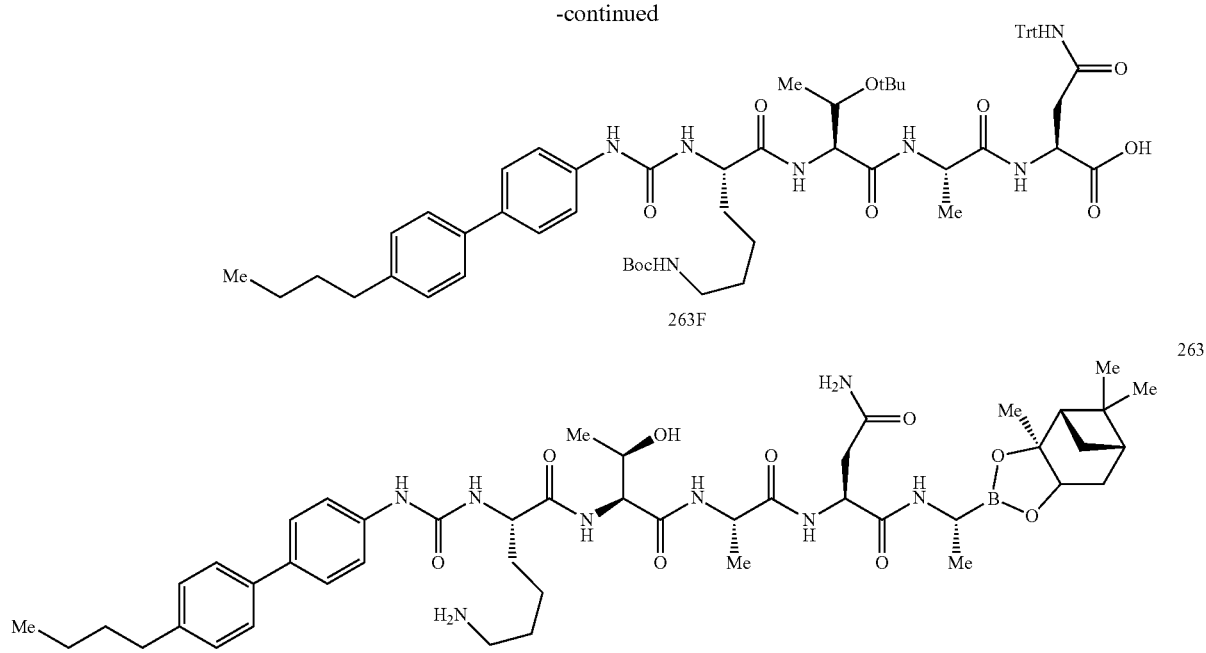

To a solution of triphosgene (47.7 mg, 0.162 mmol) in dry DCM (5 mL) was slowly added a solution of Compound 263A (110 mg, 0.487 mmol) and DIEA (0.500 g, 3.90 mmol) in THF (5 mL) at 0° C. The reaction mixture was allowed to stir at 20° C. for 25 min. The solution of Compound 263A1 was used directly in the next step without purification.

A solution of Compound 263A1 and Compound 129D2 was mixed at 0° C. in THF (5 mL). The reaction mixture was warmed to 20° C. and was shaken at 20° C. for 4 hrs. After ELSD showed the reaction was complete, the mixture was filtered. The filter cake was washed with THF (20 mL×3) and DCM (20 mL×3) sequentially, and then dried. TFA/DCM (1%, 5 mL) was added and the mixture was shaken at 20° C. for 5 min. Then the mixture was filtered and the filtrate was treated with saturated NaHCO₃ solution until pH ~7-8. The aqueous layer was adjusted with citric acid until pH ~3-4. The mixture was extracted with DCM (20 mL×3). The combined organic layers were washed with brine, dried over Na₂SO₄ and concentrated to give a residue, which was purified by prep-HPLC to give Compound 263F (80.0 mg, yield: 61.7%). MS (ESI) m/z 1082.4 (M+H)⁺.

Using the procedures described in General Methods 9 and 10, Compound 263 was prepared from Compound 263F. MS (ESI) m/z 889.4 (M+H)⁺.

Example 164

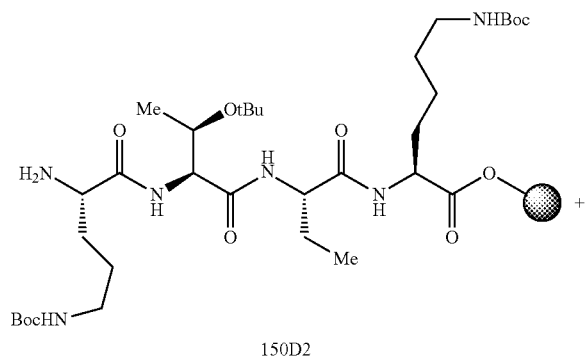

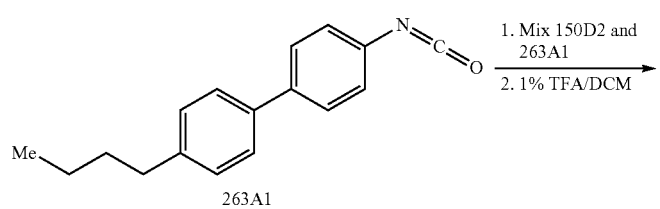

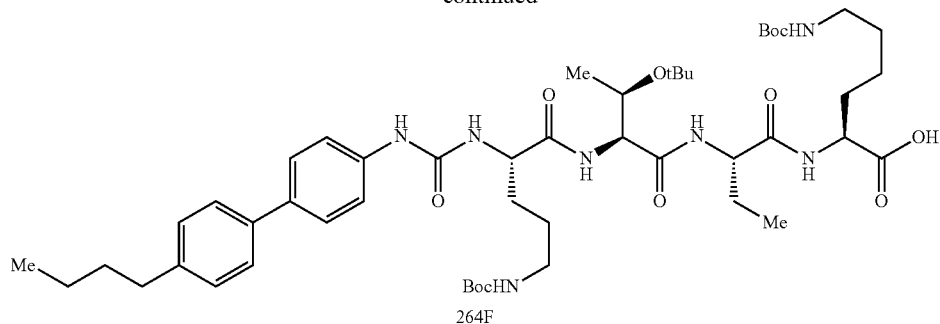

264F

A solution of Compound 263A1 (10.0 mL, approximately 0.480 mmol) and Compound 150D2 (prepared according to General Methods 5 and 6, 0.400 g, 0.200 mmol) was stirred at 0° C. The reaction mixture was warmed to 20° C. and was shaken at 20° C. for 4 hrs. After ELSD showed the reaction was completed, the mixture was filtered. The cake was washed with THF (20 mL×3) and DCM (20 mL×3) sequentially, and then dried. TFA/DCM (1%, 5 mL) was added and the mixture was shaken at 20° C. for 5 min. The mixture was filtered and the filtrate was treated with saturated NaHCO$_3$ solution until pH ~7-8. The aqueous layer was adjusted with citric acid until pH ~3-4. The mixture was extracted with DCM (20 mL×3). The combined organic layers were washed with brine, dried over Na$_2$SO$_4$ and concentrated to give a residue, which was purified by prep-HPLC to give Compound 264F (80.0 mg, yield: 42.0%). MS (ESI) m/z 954.5 (M+H)$^+$.

Using the procedures described in General Methods 9, 10 and 11, Compound 264 was prepared from Compound 264F.

Example 165

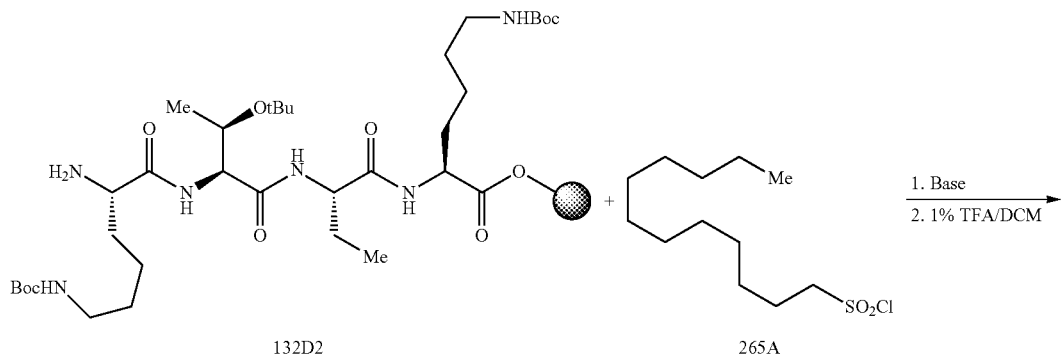

132D2      265A

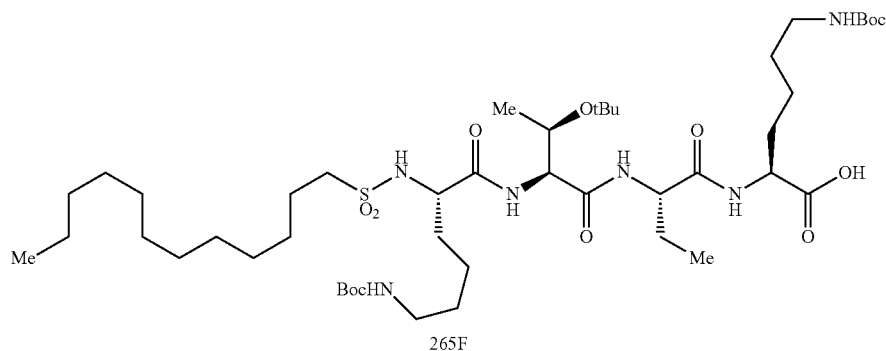

265F

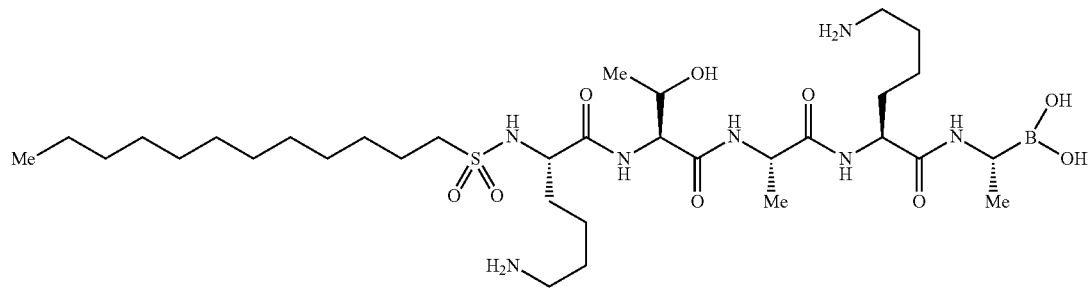
Using the procedures described in General Methods 9, 10 and 11, Compound 265 was prepared from Compound 265F. MS (ESI) m/z 732.4 (M−H$_2$O+H)$^+$.
Example 166
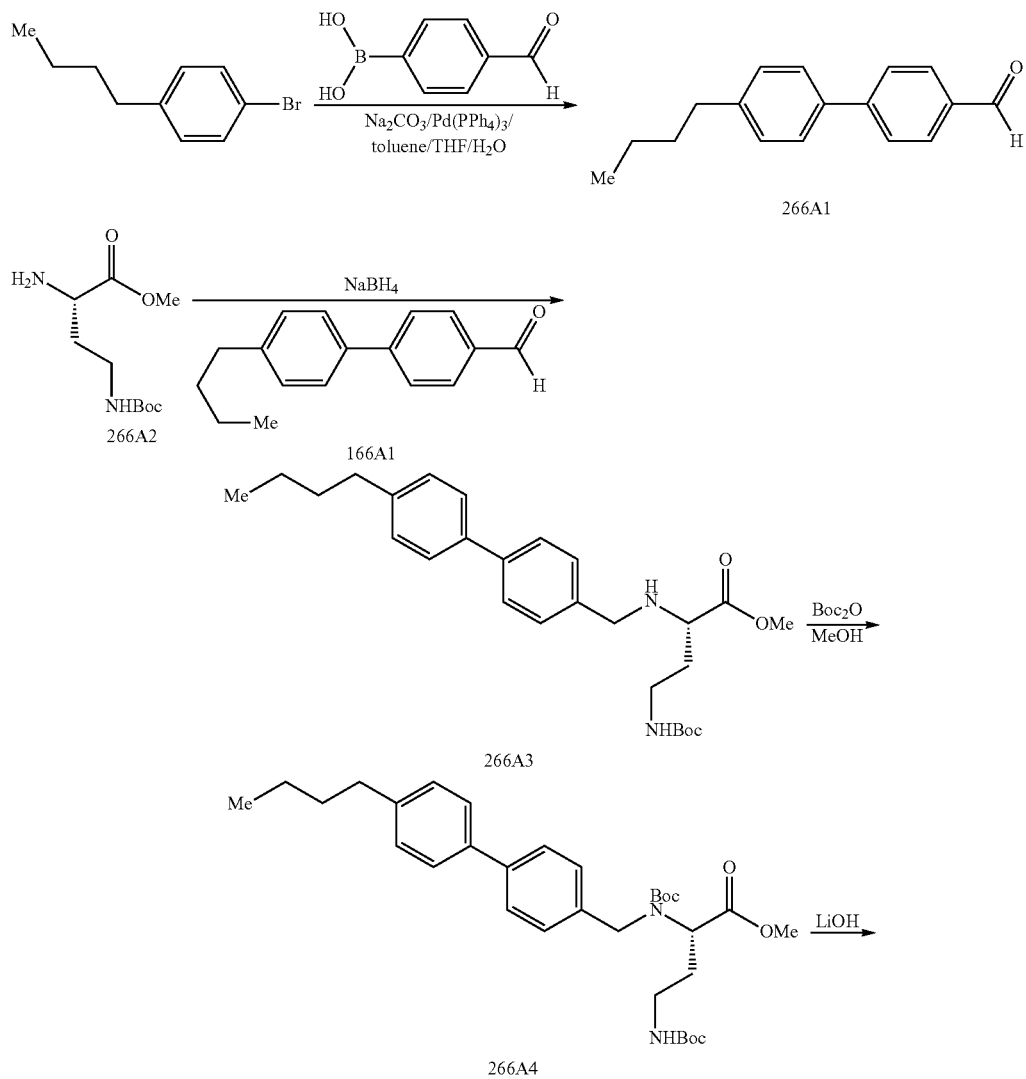

-continued

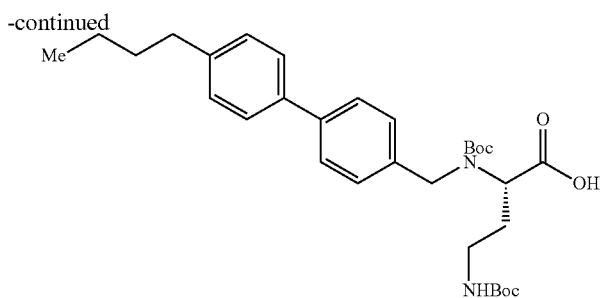

266A5

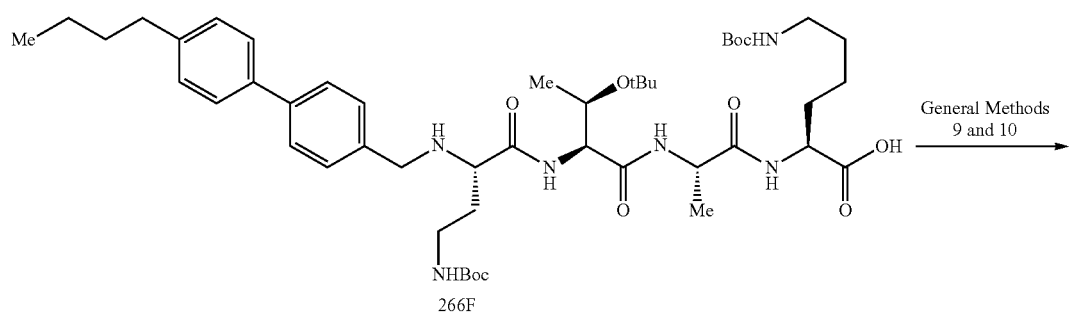

266F

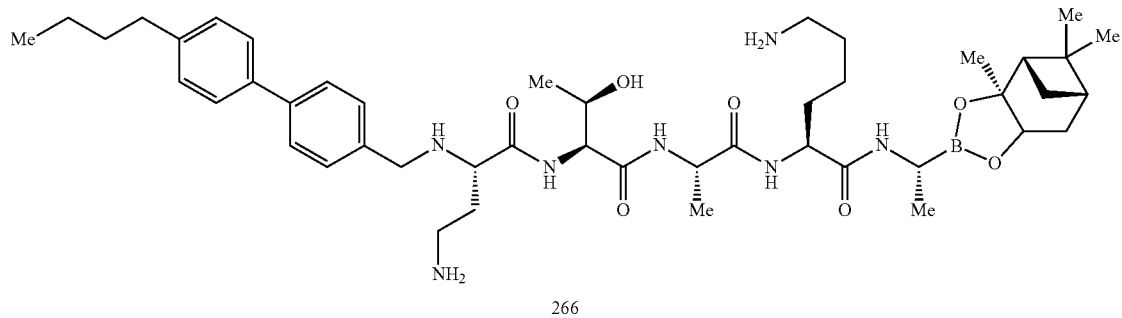

266

A solution of 1-bromo-4-butylbenzene (50.0 g, 0.333 mol), 4-formylphenylboronic acid (47.2 g, 0.222 mol), Na$_2$CO$_3$ (70.6 g, 0.666 mol) in toluene/THF/H$_2$O (200 mL/200 mL/200 mL) was degassed with N$_2$ three times, then Pd(PPh$_3$)$_4$ (12.8 g, 11.2 mmol) was added. The resulting mixture was degassed with N$_2$ three times and then heated to reflux for 5 hrs. After TLC showed the reaction was complete, toluene and THF was removed under vacuum. The residue was extracted with EA (30 mL×3). The combined organic layers were washed with brine, dried with Na$_2$SO$_4$. The solvent was removed to give the crude product. The crude product was purified by column chromatography on silica gel eluted with PE. The solvent was removed to give Compound 266A1 (20.0 g, yield: 37.8%), as a yellow oil.

To a mixture of Compound 266A2 (0.8 g, 3.45 mmol) and Compound 266A1 (0.862 g, 3.62 mmol) in DCM (2 mL) was added DIEA (0.31 g, 2.3 mmol) and Na$_2$SO$_4$. After stirring for 4 h, the mixture was filtered and the filtrate was concentrated to give a residue. The residue was dissolved in MeOH (5 ml) and NaBH$_4$ (144 mg, 3.79 mmol) was added at 0° C. The mixture was warmed to 26° C. After 2 h, TLC (PE/EA=1/1, R$_f$=0.1) showed the reaction was complete. The reaction was quenched with water (1 mL), concentrated and purified by column chromatography (PE/EA=1:1) give Compound 266A3 (2 g, crude). MS (ESI) m/z 455.1 (M+H)$^+$.

To a mixture of Compound 266A3 (1.60 g, crude) in MeOH (2 ml) was added Boc$_2$O (900 mg, 4.13 mmol). The mixture was stirred at 24° C. for 12 h. TLC (PE/EA=1/1, R$_f$=0.5) showed the reaction was completed. The solvent was concentrated to give a residue which was purified by column chromatography (PE/EA=1:1) to give Compound 266A4 (1.30 g, 66.7%) as colorless oil. MS (ESI) m/z 577.0 (M+Na)$^+$.

To a mixture of Compound 266A4 (1.30 g, 2.35 mmol) in THF (5 mL) was added LiOH (0.296 g, 7.04 mmol) in H$_2$O (5 ml). The reaction was stirred at 30° C. for 36 h. TLC (PE/EA=1/1, R$_f$=0.6) showed the reaction was completed. The solvent was acidified to pH ~3-4 with 1N HCl, extracted with DCM (20.0 ml×4). The organic layer were dried, filtered and concentrated to give Compound 266A5 (0.9 g, 70.9%) as yellow oil. MS (ESI) m/z 563.3 (M+Na)$^+$.

Using Compound 266A5 and the procedures described in General Methods 6-8 and Scheme XIX, Compound 266F was prepared. MS (ESI) m/z 997.6 (M+H)$^+$.

Using the procedures described in General Methods 9 and 10, Compound 266 was prepared from Compound 266F. MS (ESI) m/z 846.4 (M+H)$^+$.

Example 167
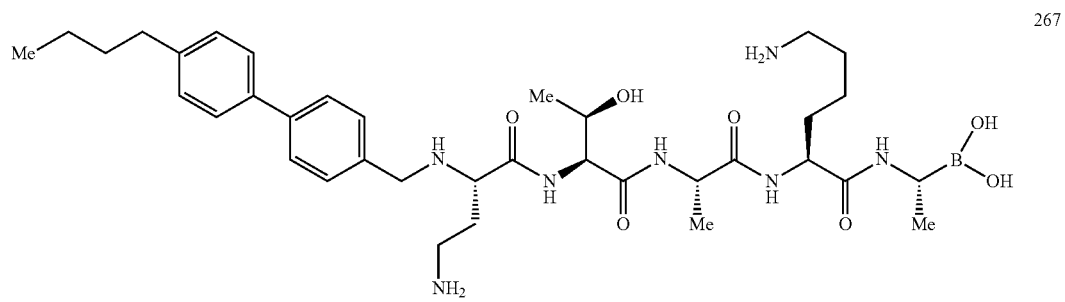 [SMILES: CCCCc1ccc(-c2ccc(CN[C@@H](CCN)C(=O)N[C@H](C(=O)N[C@@H](C)C(=O)N[C@@H](CCCCN)C(=O)N[C@@H](C)B(O)O)[C@@H](C)O)cc2)cc1]
Using the procedure described in General Procedure 11, Compound 267 was prepared from Compound 266. MS (ESI) m/z 694.3 (M–H$_2$O+H)$^+$.
Example 168
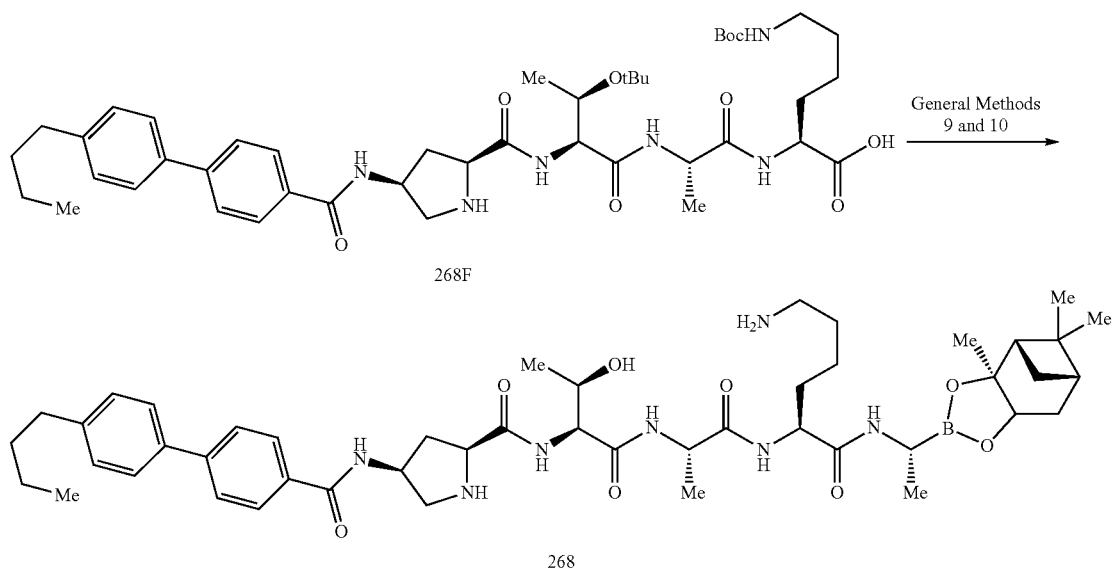
Using the procedures described in General Methods 6-8 and Scheme XIX, Compound 268F was prepared. MS (ESI) m/z 923.1 (M+H)$^+$. Using the procedures described in General Methods 9 and 10, Compound 268 was prepared from Compound 268F. MS (ESI) m/z 872.3 (M+H)$^+$.
Example 169
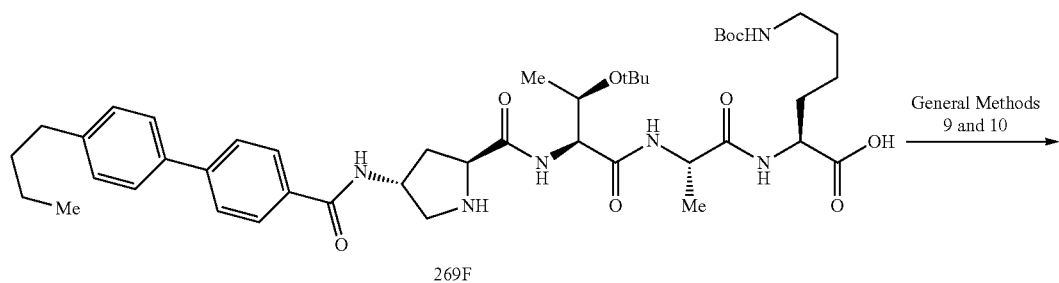

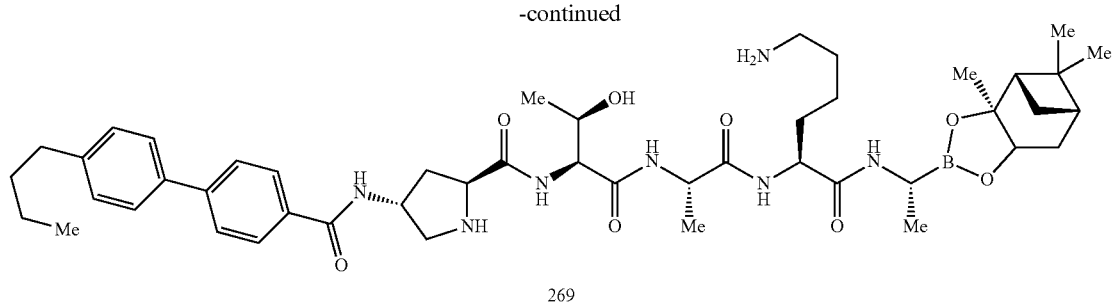
269
Using the procedures described in General Methods 6-8 and Scheme XIX, Compound 269F was prepared. MS (ESI) m/z 923.2 (M+H)⁺. MS (ESI) m/z 923.1 (M+H)⁺. Using the procedures described in General Methods 9 and 10, Compound 269 was prepared from Compound 269F. MS (ESI) m/z 872.1 (M+H)⁺.
Example 170
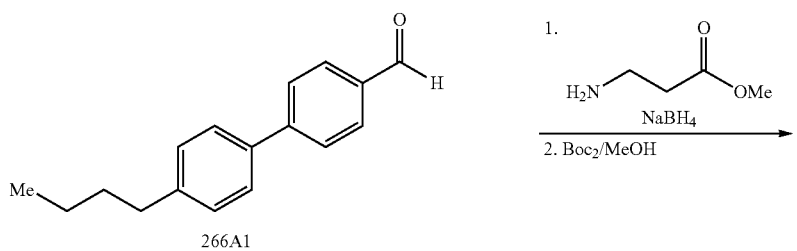
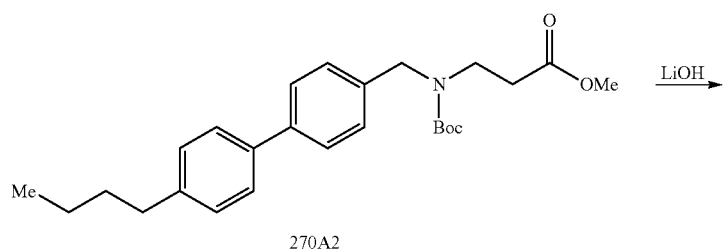
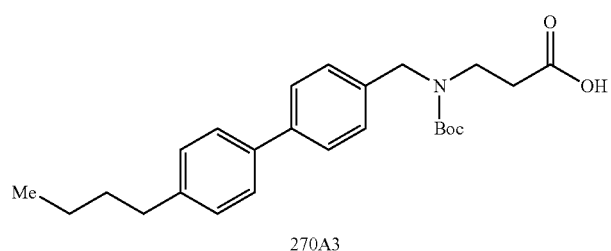

-continued

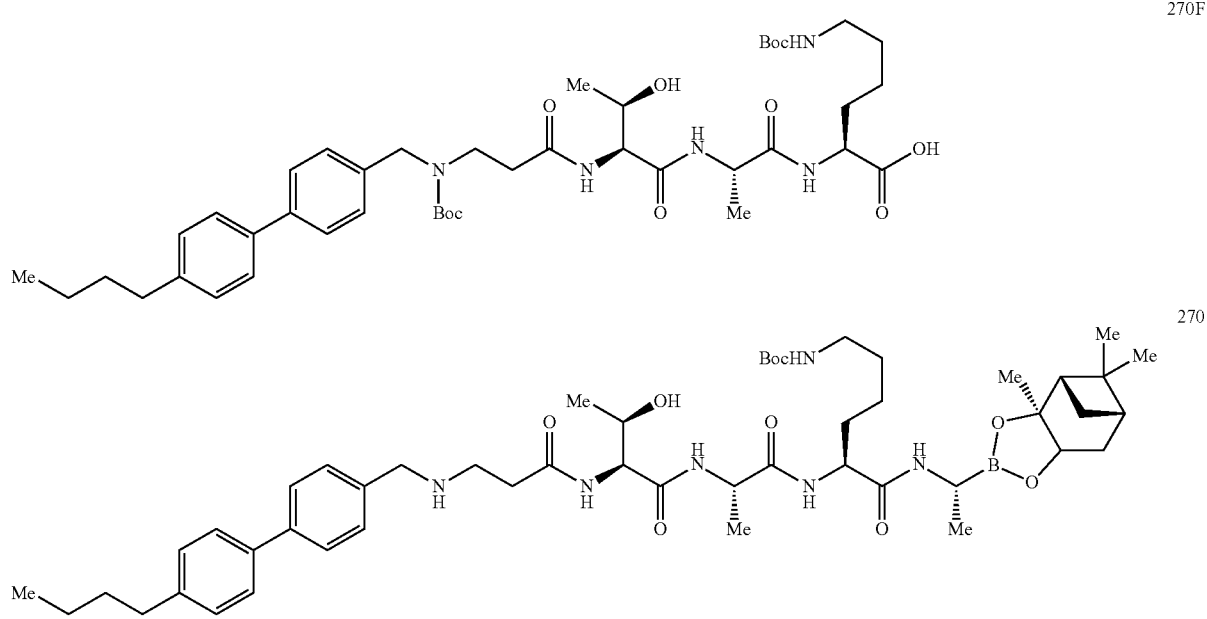

To a mixture of Compound 266A1 (0.5 g, 2 mmol) and methyl 3-aminopropanoate (0.3 g, 2.2 mmol) in DCM (2 ml) was added DIEA (0.3 g, 2.3 mmol) and Na$_2$SO$_4$. After stirring for 4 h, the mixture was filtered and the filtrate was concentrated. The residue was dissolved in MeOH (5 ml) and NaBH$_4$ (84 mg, 2.2 mmol) was added to the solution at 0° C. The mixture was warmed to room temperature. After 2 h, TLC (PE/EA=10/1, R$_f$=0.1) showed the reaction was complete. The reaction was quenched by water (1 mL), concentrated to give a solid (0.7 g, crude) used in the next step without further purification. This material was treated with Boc$_2$O (0.5 g, 2.3 mmol) in MeOH (5 mL) was stirred at 26° C. for 5 h. TLC (DCM/MeOH=10/1, R$_f$=0.7) showed the reaction was complete. The solvent was concentrated to get a residue, which purified by column chromatography (PE) to give Compound 270A2 (0.65 g, 73%) as a colorless oil. MS (ESI) m/z 448.2 (M+Na)$^+$.

To a mixture of Compound 270A2 (0.68 g, 2 mmol) in THF (5 ml) was added LiOH (96 mg, 2.3 mmol) in water (5 mL). The mixture was stirred at 26° C. for 2 h. TLC (PE/EA=5/1, R$_f$=0.1) showed the reaction was complete. Volatiles were removed in vacuo and the aqueous mixture was acidified to pH=3~4 with 0.3N HCl and extracted with DCM (20 ml×3). The organic layer were dried, filtered and concentrated to give Compound 270A3 (0.4 g, 84%) as a white solid.

Using the procedures described in General Methods 6-8 and Scheme XIX, Compound 270F was prepared from Compound 270A3. MS (ESI) m/z 890.5 (M+Na)$^+$. Using the procedures described in General Methods 9 and 10, Compound 270 was prepared from Compound 270F. MS (ESI) m/z 817.7 (M+H)$^+$.

Example 171

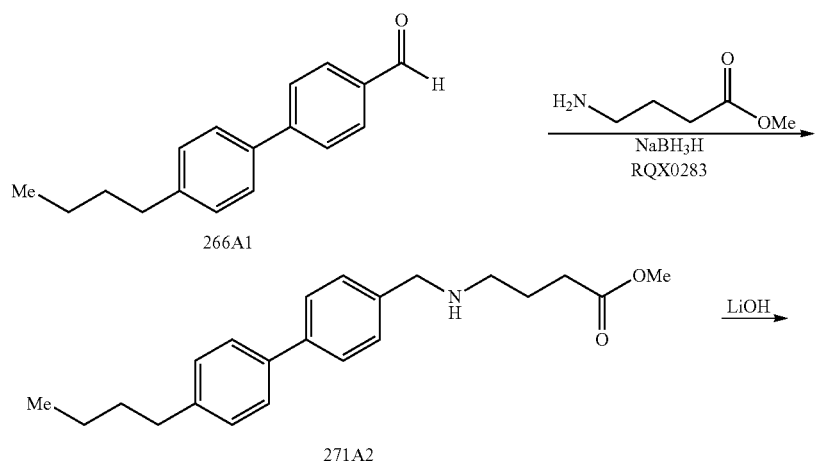

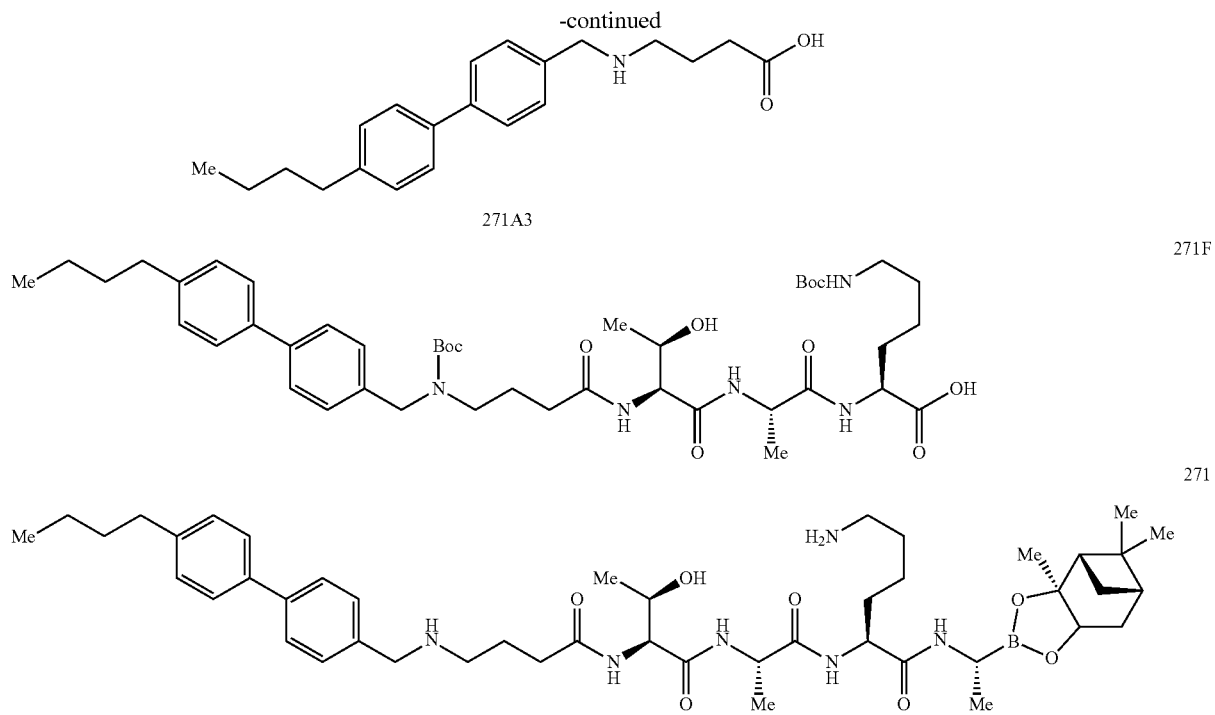

To a mixture of Compound 266A1 (0.5 g, 2 mmol) and methyl 3-aminobutanoate (0.34 g, 2.2 mmol) in DCM (2 ml) was added DIEA (0.31 g, 2.3 mmol) and $Na_2SO_4$. After stirring for 4 h, the mixture was filtered and the filtrate was concentrated to get a residue, which dissolved in MeOH (5 ml). $NaBH_4$ (84 mg, 2.2 mmol) was added to it at 0° C. Then the mixture was warmed to 26° C. After 2 h, TLC (PE/EA=10/1, $R_f$=0.1) showed the reaction was complete. The reaction was quenched by water (1 ml), concentrated to give a solid (0.7 g, crude) used in the next step without further purification. This material was treated with $Boc_2O$ (0.5 g, 2.3 mmol) in MeOH (5 ml) was stirred at room temperature for 5 h. TLC (DCM/MeOH=10/1, $R_f$=0.7) showed the reaction was complete. The solvent was concentrated to get a residue, which was purified by column chromatography (petroleum ether) to give Compound 271A2 (0.45 g, 73%) as a colorless oil. MS (ESI) m/z 462.1 $(M+Na)^+$.

To a mixture of Compound 270A2 (0.45 g, 2 mmol) in THF (5 ml) was added LiOH (96 mg, 2.3 mmol) in water (5 ml). The mixture was stirred room temperature for 2 h. TLC (PE/EA=5/1, $R_f$=0.1) showed the reaction was complete. Volatiles were removed in vacuo and the aqueous mixture was acidified to pH=3~4 with 0.3N HCl, extracted with DCM (20 ml×3). The organic layer was dried, filtered and concentrated to give Compound 271A3 (0.4 g, 84%) as white solid.

Using the procedures described in General Methods 6-8 and Scheme XIX, Compound 271F was prepared from Compound 271A3. MS (ESI) m/z 881.8 $(M+Na)^+$. Using the procedures described in General Methods 9 and 10, Compound 271 was prepared from Compound 271F. MS (ESI) m/z 831.8 $(M+H)^+$.

Example 172

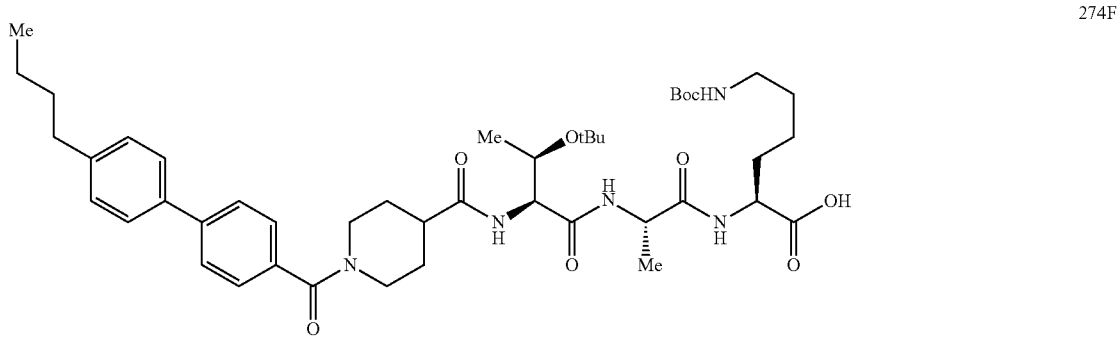

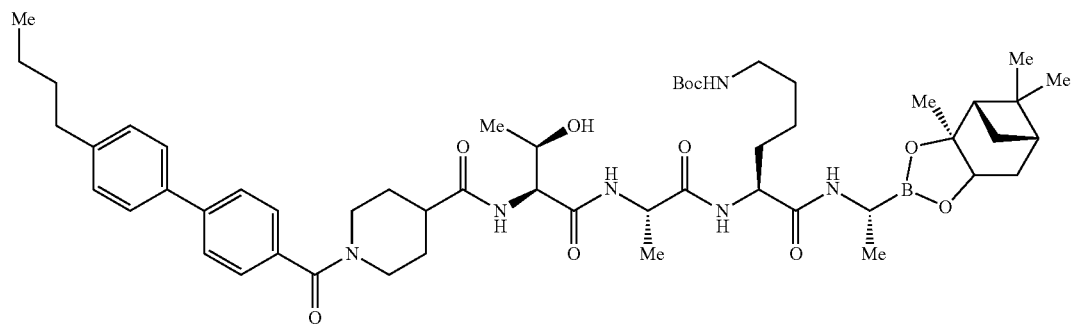
272
Compound 272F was prepared using the procedures described in General Methods 6-8 and Scheme XIX, Compound 272F. MS (ESI) m/z 822.5 (M+Na)⁺. Using the procedures described in General Methods 9 and 10, Compound 271 was prepared from Compound 271F. MS (ESI) m/z 831.8 (M+H)⁺.
Example 173
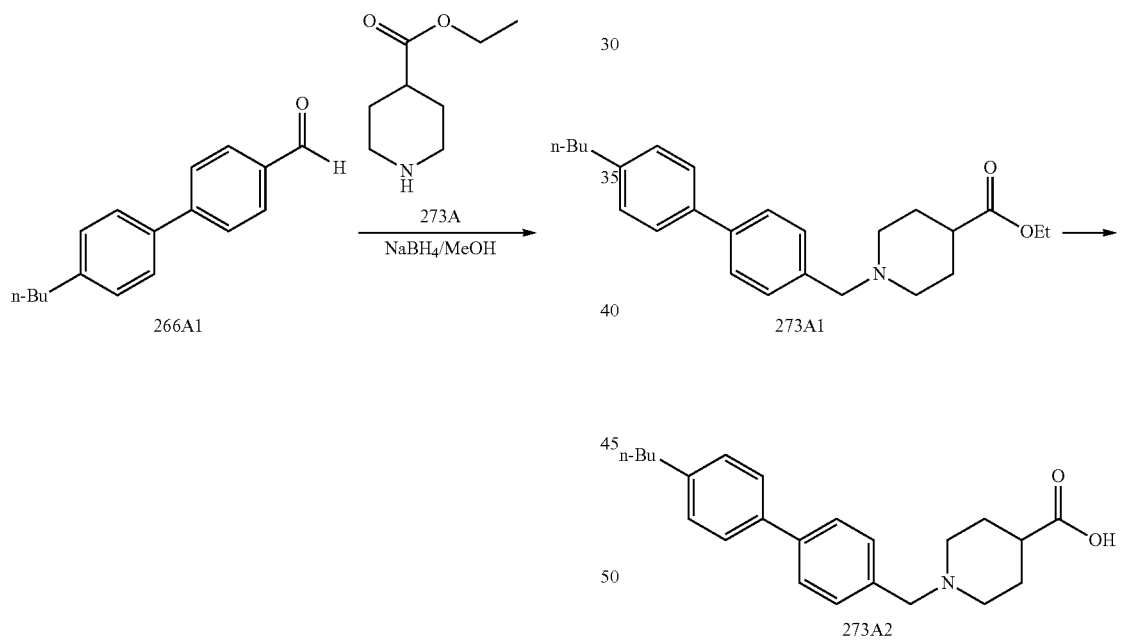
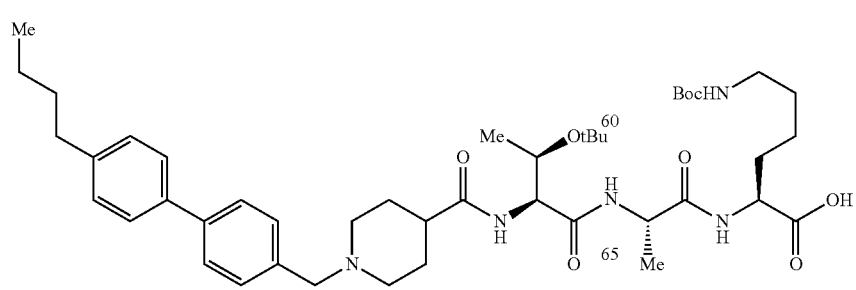
273F

273

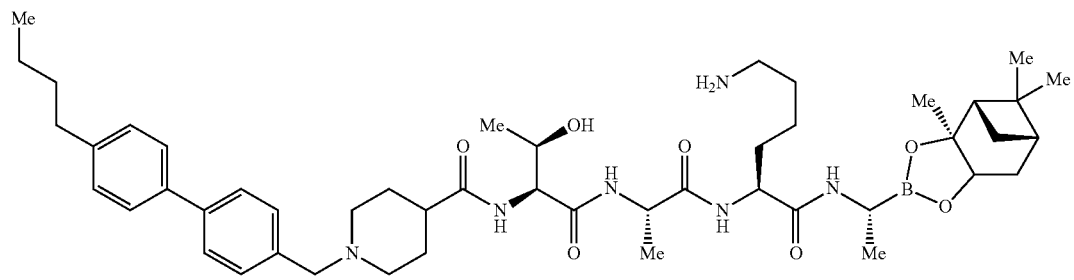

To a mixture of Compound 266A1 (1.10 g, 4.62 mmol) in dry DCM (20 mL) was added Compound 273A (0.762 g, 4.85 mmol), DIEA (0.686 g, 5.32 mmol) and Na$_2$SO$_4$ at 24° C. The mixture was stirred for 2 hrs at 24° C. The mixture was filtered and the filtrate was evaporated. The residue was dissolved in dry MeOH (10 mL), cooled to 0° C., and then NaBH$_4$ (184 mg, 4.85 mmol) was added portion-wise. The mixture was stirred at 24° C. for 2 hrs. After LCMS showed the reaction was complete, MeOH was evaporated. The crude product was purified by chromatography on gel silica, then the mixture was in EA/HCl for 3 mins and evaporated. The solid was washed with EA to give the pure product Compound 273A1 (450 mg, yield: 25.7%).

To a solution of Compound 273A1 (450 mg, 1.19 mmol) in THF/H$_2$O (10 mL/2 mL) was added LiOH.H$_2$O (100 mg, 2.37 mmol) at 21° C. The mixture was stirred overnight at 21° C. After TLC showed the reaction was complete, THF was evaporated and the mixture was extracted with EA. 1N HCl was added 1N HCl to the aqueous layer until pH to ~3-4. The mixture was extracted with EA, the organic layers were combined, dried with Na$_2$SO$_4$, filtered and concentrated to give the Compound 273A2 (260 mg, yield: 62.2%).

Using the procedures described in General Methods 6-8 and Scheme XIX, Compound 273F was prepared from Compound 273A2. MS (ESI) m/z 808.2 (M+Na)$^+$. Using the procedures described in General Methods 9 and 10, Compound 273 was prepared from Compound 273F. MS (ESI) m/z 857.3 (M+H)$^+$.

Example 174

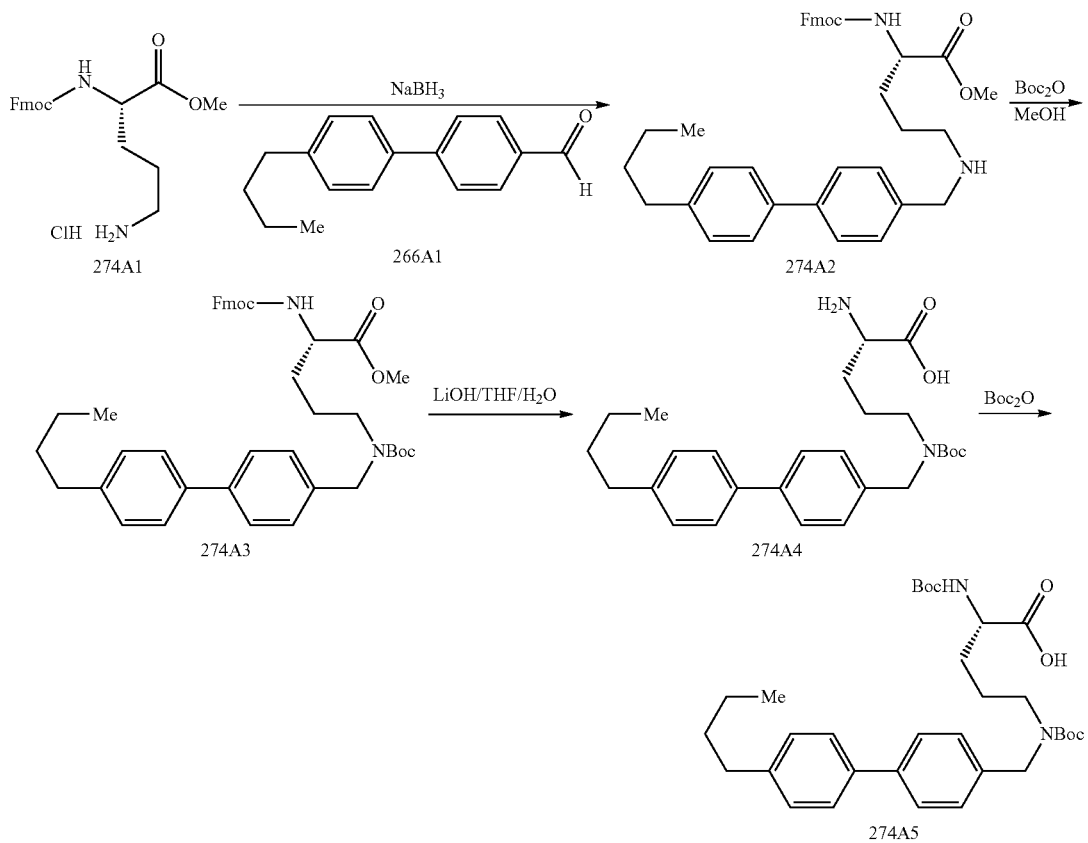

-continued

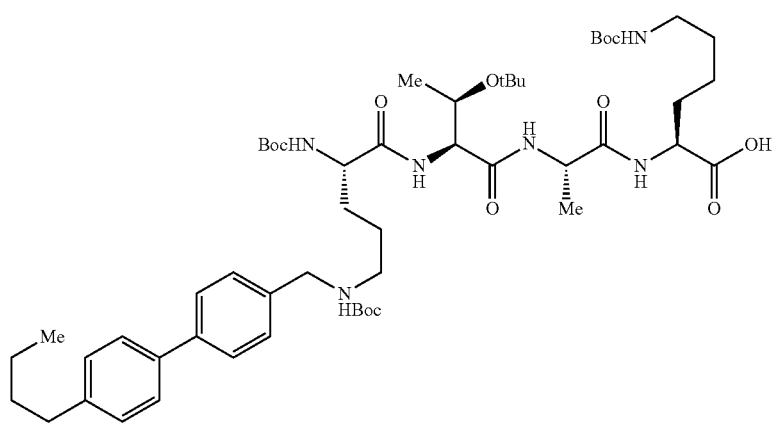

274F

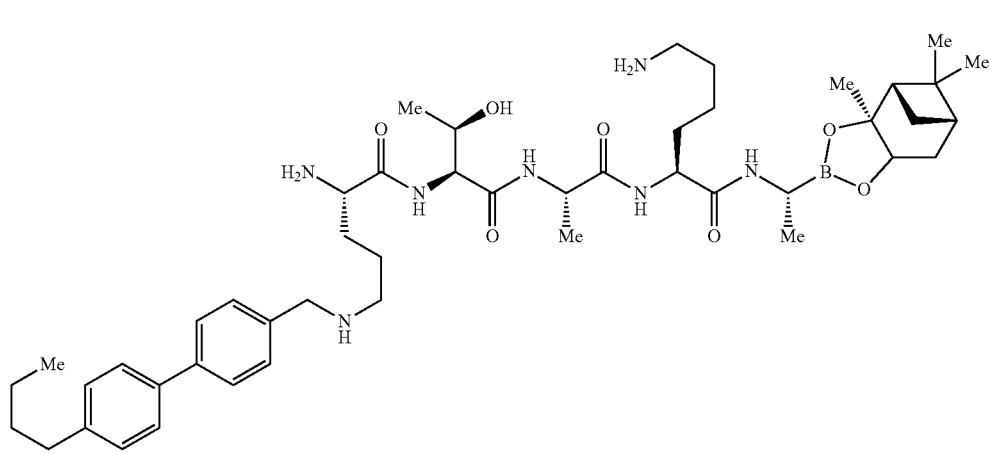

274

To a solution of Compound 274A1 (1.00 g, 2.47 mmol), Compound 266A1 (679 mg, 2.85 mmol) and DIEA (719 mg, 5.57 mmol) in dry DCM (50 mL) was added $Na_2SO_4$ (10 g). The mixture was stirred at 25° C. for 4 hrs, filtered and the filtrate was evaporated. To the residue was added dry MeOH (50 mL) and $NaBH_4$ (108 mg, 2.84 mmol) at 0° C. The reaction mixture was stirred at 25° C. for 30 mins. After LCMS showed the reaction was completed, 1 N HCl was added until pH to ~7. The solution was evaporated to give Compound 274A2 (1.00 g, yield: 68.4%) as light yellow solid. MS (ESI) m/z 591.9 (M+H)+.

To a solution of Compound 274A2 (1.00 g, 1.69 mmol) in dry MeOH (20 mL) was added 1N HCl until pH to ~6-7, followed by addition of DIEA until pH to ~7-8. To the mixture was added $Boc_2O$ (0.732 g, 3.39 mmol) at 24° C. The mixture was stirred overnight at 24° C. After LCMS showed the reaction was complete, MeOH was evaporated and the crude product was purified by chromatography on gel silica (PE: EA=15:1) to give Compound 274A3 (0.680 g, yield: 58.3%). MS (ESI) m/z 713.4 (M+Na)+.

To a solution of Compound 274A3 (0.680 g, 0.985 mmol) in $THF/H_2O$ (10 mL/3 mL) was added $LiOH.H_2O$ (0.166 g, 3.94 mmol) at 24° C. The mixture was stirred overnight at 24° C. After TLC showed the reaction was complete, THF was evaporated. The mixture was extracted with PE and $H_2O$. To the aqueous layer was added 1N HCl until the pH to ~4-5. The aqueous mixture was extracted with EA (10 mL×3). The organic layers were combined, dried with $Na_2SO_4$ and concentrated to give Compound 274A4 (0.400 g, yield: 89.3%).

To a solution of Compound 274A4 (0.400 g, 0.880 mmol) in DCM (15 mL) was added $Boc_2O$ (0.228 g, 1.06 mmol) and $Et_3N$ (0.267 g, 2.64 mmol) at 24° C. The mixture was stirred for 2 hrs at 24° C. After LCMS showed the reaction was complete, DCM was evaporated. The crude product was washed with PE. The PE layer was evaporated to give Compound 274A5 (380 mg, 77.9%).

Using the procedures described in General Methods 6-8 and Scheme XIX, Compound 274F was prepared from Compound 274A5. MS (ESI) m/z 1011.2 (M+Na)+. Using the procedures described in General Methods 9 and 10, Compound 274 was prepared from Compound 274F. MS (ESI) m/z 860.2 (M+H)+.

Example 175

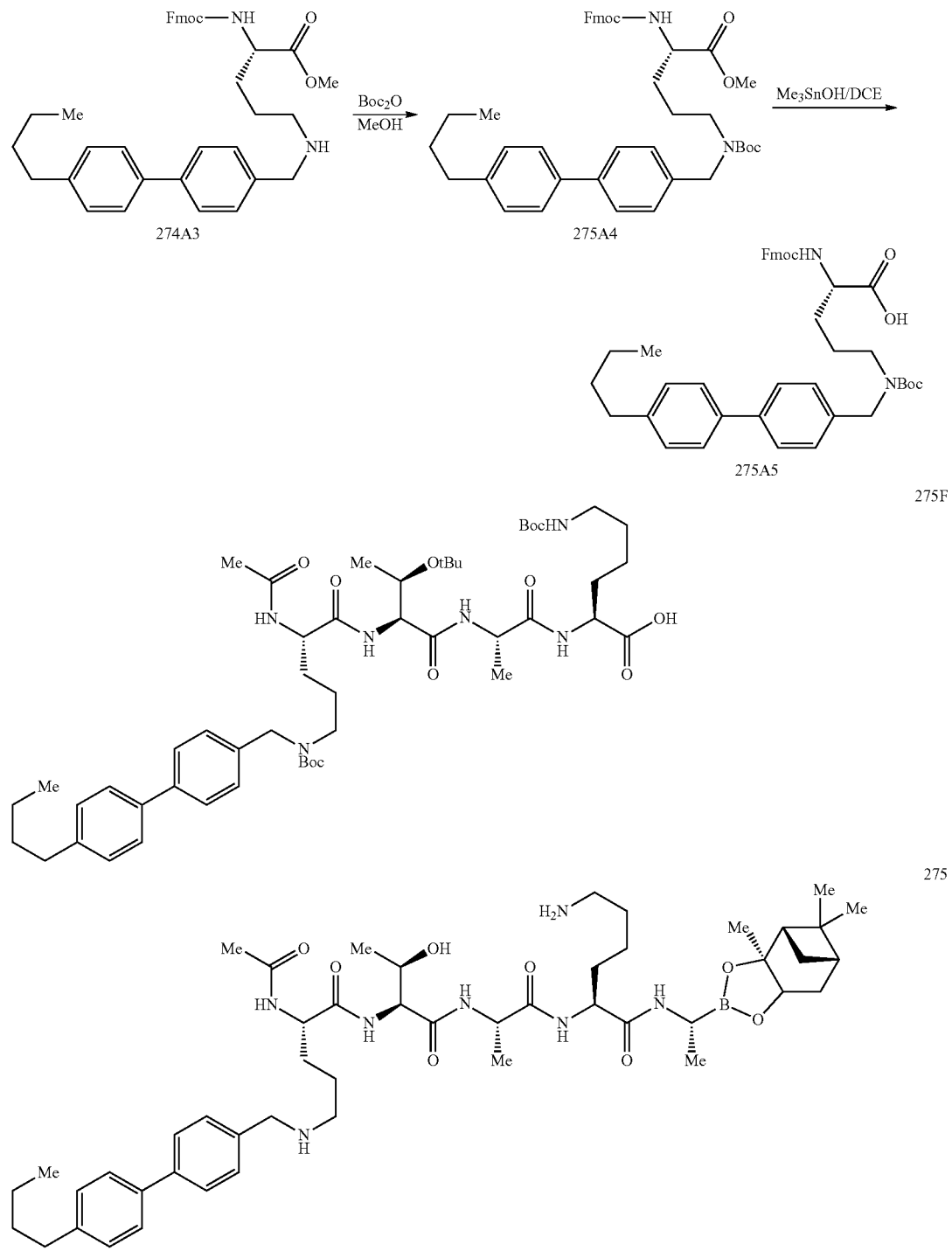

To a solution of Compound 274A3 (1.00 g, 1.69 mmol) in MeOH (50.0 mL) was added Boc$_2$O (527 mg, 2.44 mmol). The reaction was stirred at 25° C. for 4 hrs. After LCMS showed the reaction was completed, the solvent was evaporated and the residue purified by silica-gel column chromatography to give Compound 275A4 (0.580 g, yield: 49.7%) as a white solid.

To a solution of Compound 275A4 (0.580 g, 0.840 mmol) in DCE (20.0 mL) was added Me$_3$SnOH (1.18 g, 6.50 mmol). The reaction was stirred at 70° C. for 4 hrs. After LCMS showed the reaction was completed, the mixture was cooled to 0° C. and treated with 1 M NaH$_2$PO$_4$ (60.0 mL). The mixture was extracted with DCM (30.0 mL×2). The combined organic layers were washed with brine, dried over Na$_2$SO$_4$ and concentrated to give the crude product. The crude product was purified by silica-gel column chromatography to give Compound 275A5 (0.550 g, yield: 96.4%) as white solid. MS (ESI) m/z 699.0 (M+Na)⁺.

Using the procedures described in General Methods 6-8 and Scheme XIX, Compound 275F was prepared from Compound 275A5. MS (ESI) m/z 953.1 (M+Na)⁺. Using the procedures described in General Methods 9 and 10, Compound 275 was prepared from Compound 275F. MS (ESI) m/z 902.4 (M+H)⁺.

Example 176

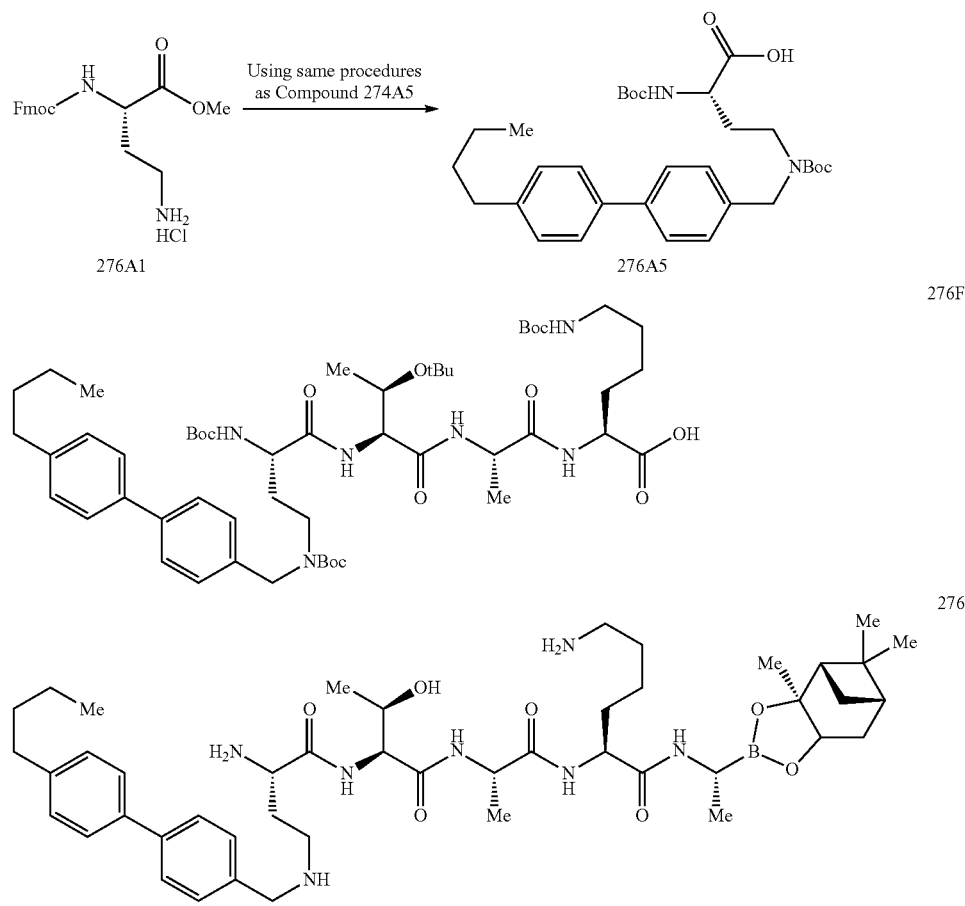

Using the procedures described in Example 174, Compound 276A5 was prepared from Compound 276A1. Using the procedures described in General Methods 6-8 and Scheme XIX, Compound 276F was prepared from Compound 276A5. MS (ESI) m/z 997.2 (M+Na)⁺. Using the procedures described in General Methods 9 and 10, Compound 276 was prepared from Compound 276F. MS (ESI) m/z 846.2 (M+H)⁺.

Example 177

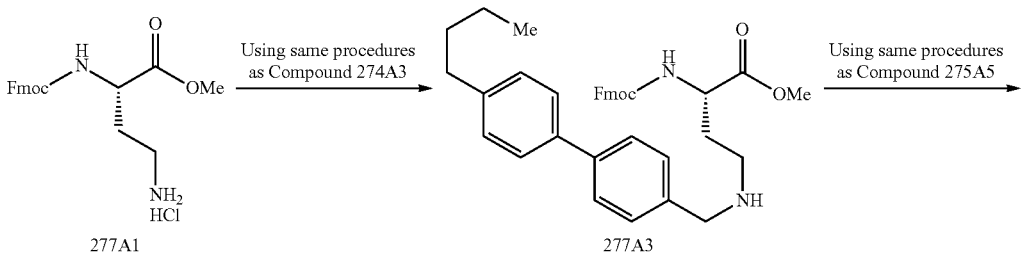

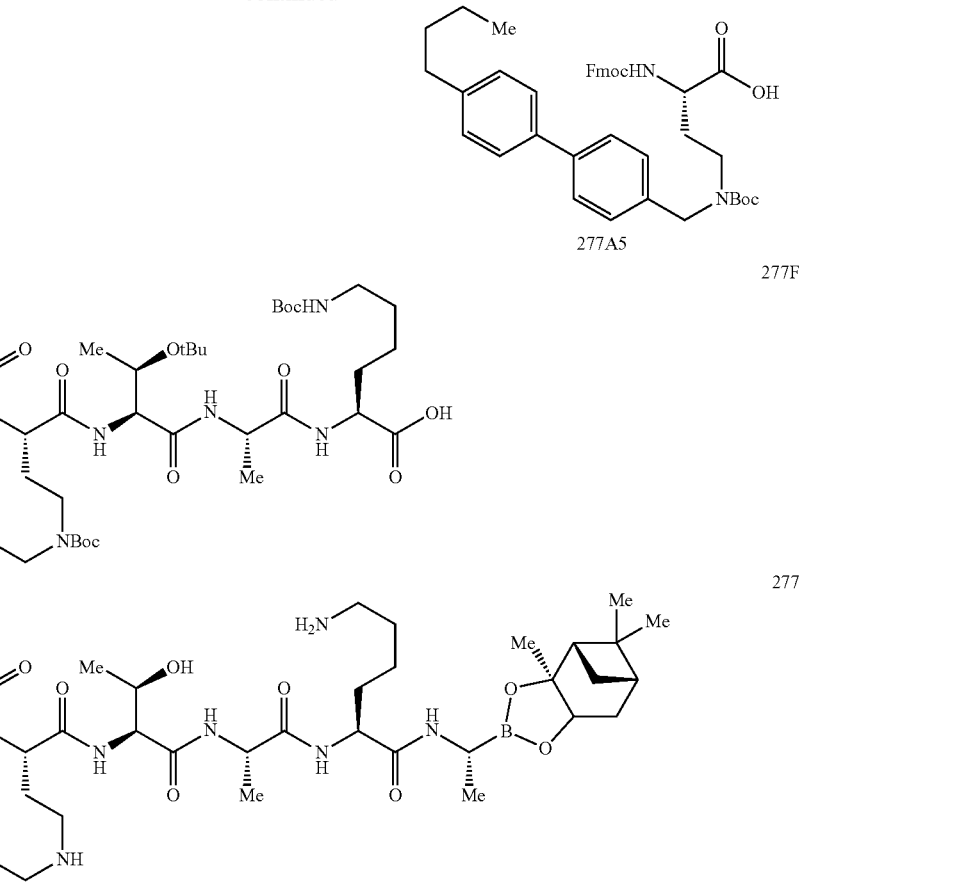
Using the procedures described in Examples 174 and 175, Compound 277A5 was prepared from Compound 277A1. MS (ESI) m/z 663.1 (M+H)⁺. Using the procedures described in General Methods 6-8 and Scheme XIX, Compound 277F was prepared from Compound 277A5. MS (ESI) m/z 939.5 (M+Na)⁺. Using the procedures described in General Methods 9 and 10, Compound 277 was prepared from Compound 277F. MS (ESI) m/z 888.2 (M+H)⁺.
Example 178
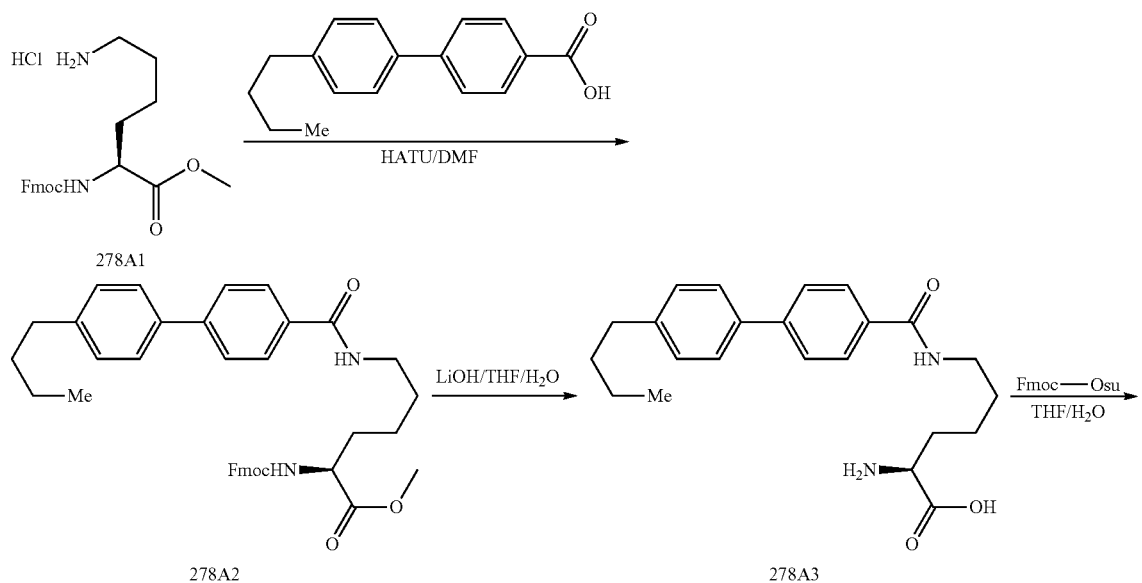

-continued
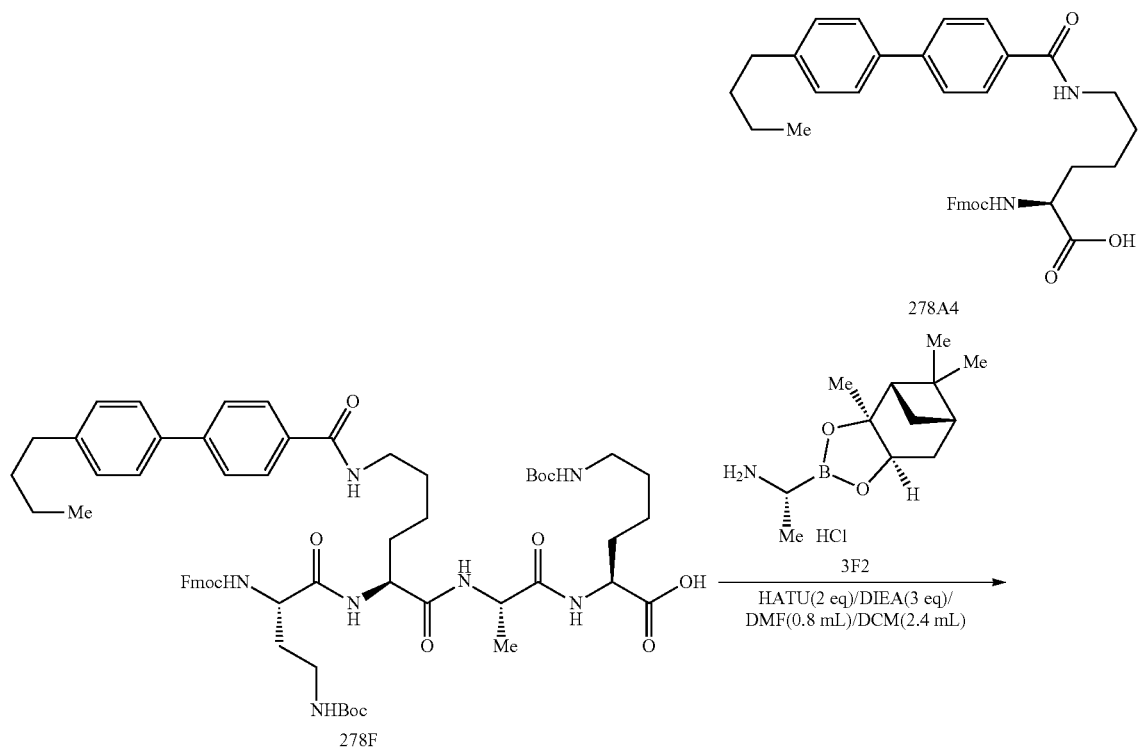
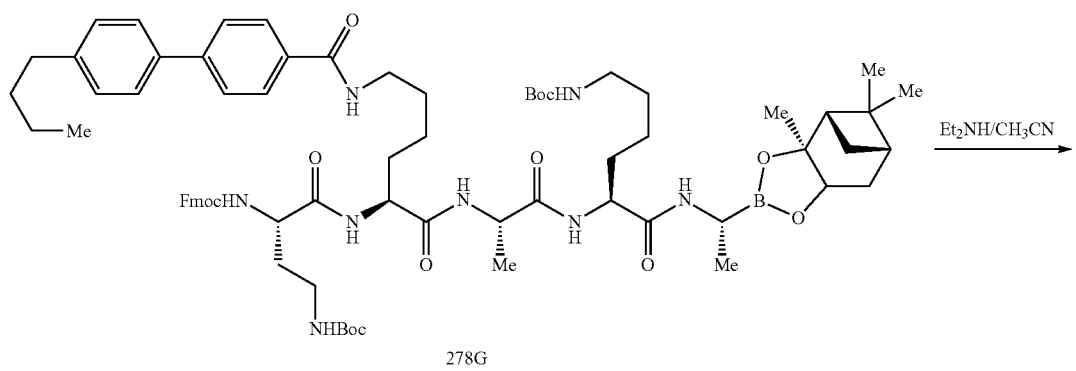
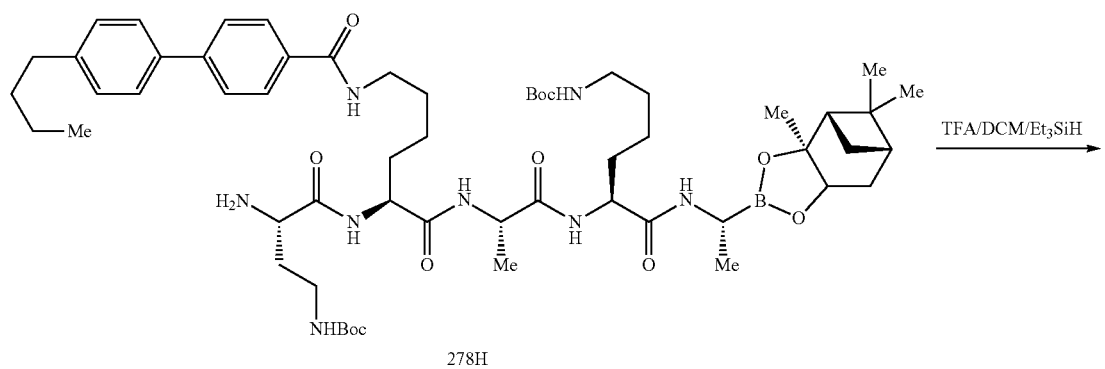

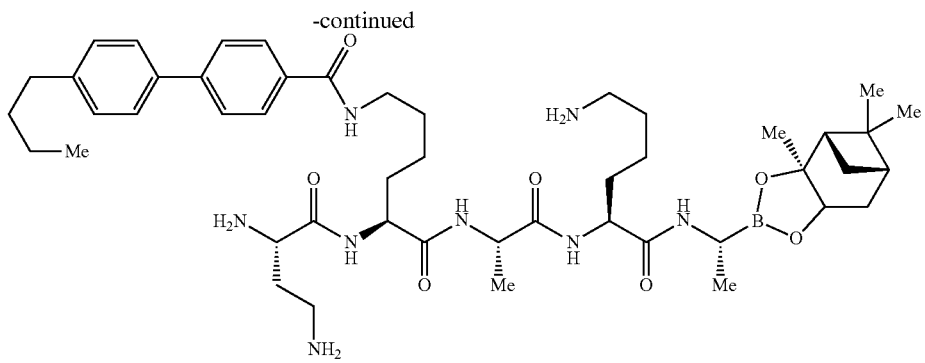

278

To a solution of Compound 278A1 (1.00 g, 2.39 mmol), 4-(4-butylphenyl)benzoic acid (0.728 g, 2.89 mmol) and NaHCO$_3$ (0.742 g, 8.84 mmol) in dry THF (30 mL) and DMF (30 mL) was added HATU (1.09 g, 2.89 mmol). The mixture was stirred at 25° C. until LCMS indicated the reaction was finished (5 hrs). THF was evaporated and the mixture was poured into water (100 mL) and extracted with DCM (80 mL×2). The combined organic layers were evaporated and purified by silica-gel column chromatography to give Compound 278A2 (800 mg, yield: 54.4%).

A mixture of Compound 278A2 (800 mg, 1.29 mmol) and LiOH (108 mg, 2.58 mmol) in THF/H$_2$O (30 mL/10 mL) was stirred at 10° C. LCMS showed the reaction was complete after 2 hrs, at which time the THF was evaporated. The mixture was extracted with PE (30 mL×3), the aqueous layers were adjusted to pH ~3-4 with 1 N HCl solution. The resulting mixture was filtered and the cake was washed with water and dried to give Compound 278A3 (400 mg, yield: 91.0%), as a white solid.

To a mixture of Compound 278A3 (400 mg, 1.05 mmol) in THF/H$_2$O (100 mL/100 mL) was added NaHCO$_3$ (176 mg, 2.10 mmol). The mixture was cooled to 0° C. and a solution of Fmoc-OSu (354 mg, 1.05 mmol) in THF (100 mL) was added dropwise over 8 hrs. After stirring for an additional 2 hrs at 10° C., LCMS showed the reaction was complete and the THF was evaporated. The mixture was extracted with PE (30 mL×3) and the aqueous layers were adjusted to pH ~4-5 with 1 N HCl solution. The resulting mixture was filtered and the filter cake was washed with water and dried to give Compound 278A4 (600 mg, yield: 94.9%), as a white solid. MS (ESI) m/z 605.1 (M+H)$^+$.

Using the procedures described in General Methods 6-8 and Scheme XIX, Compound 278F was prepared from Compound 278A4. MS (ESI) m/z 1104.1 (M+H)$^+$.

To a solution of Compound 278F (200 mg, 0.181 mmol), HATU (138 mg, 0.362 mmol), and 3F2 (70.3 mg, 0.272 mmol) in DCM (2.4 mL) and DMF (0.8 mL) was added DIEA (70.0 mg, 0.543 mmol). After 15-30 mins the reaction was allowed to warm to 15° C. and stirred for 30 mins. After LCMS showed the reaction was complete, water (1 mL) was added and the mixture was filtrated, the filter cake was washed with water and petrol ether to afford Compound 278G as a crude product (180 mg, yield: 75.9%).

To a mixture of Compound 278G (160 mg, 0.122 mmol) in CH$_3$CN (5 mL) was added Et$_2$NH (26.7 mg, 0.366 mmol). The mixture was stirred at 10° C. for 17 hrs. After LCMS showed the reaction was completed, CH$_3$CN was removed. The residue was dissolved in MeOH and purified by prep-HPLC to give Compound 278H (50.0 mg, yield: 37.7%).

A solution of Compound 278H (25.0 mg, 0.0230 mmol) in TFA:DCM:TES (50:45:5) (1 mL) was stirred at 10° C. for 20 mins, then TFA was evaporated and LCMS showed the reaction was completed. The crude residue was dissolved in MeOH and purified by prep-HPLC to give Compound 278 (5.60 mg, yield: 27.5%). MS (ESI) m/z 887.6 (M+H)$^+$.

Example 179

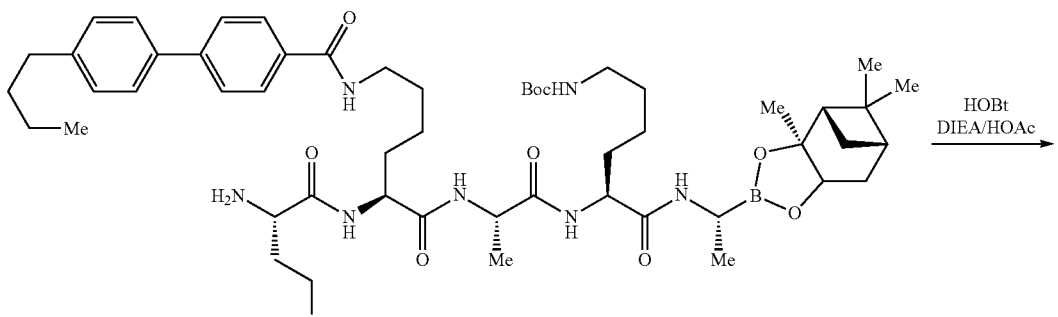

278H

-continued

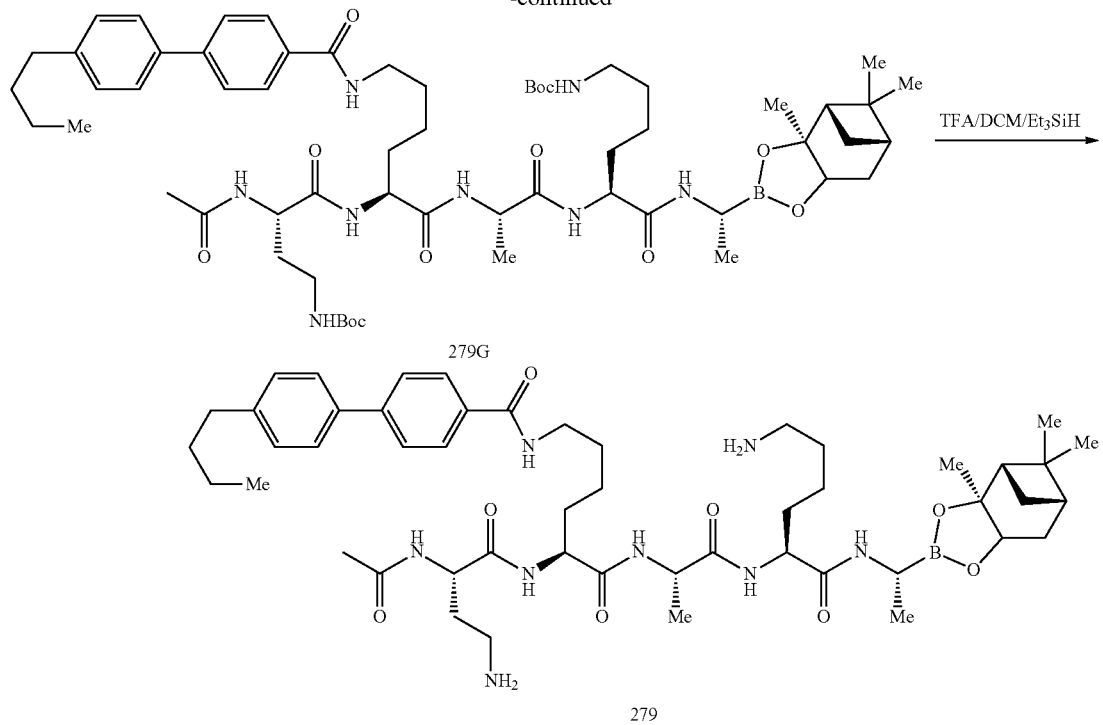

Using the procedure described in General Methods 10 for the preparation of the boronate esters, the boronate ester Compound 279 was prepared from Compound 279G (1.5 mg, yield: 18.3%). MS (ESI) m/z 929.2 (M+H)$^+$.

Biological Data

Example 180

Determination of Minimum Inhibitory Concentration—Method A

In vitro antimicrobial activity of each compound was determined by measuring minimal inhibitor concentrations (MICs) using the broth micro-dilution technique as approved by the Clinical and Laboratory Standards Institute (CLSI). Antibacterial activity was measure against two strains of bacteria: 1) Methicillin Resistant *Staphylococcus aureus* strain USA 300 (NRS384) and 2) a strain of *Escherichia coli* MC4100 IMP-4213 in which transcription of the SPase encoding gene has been placed under the control of a tetracycline inducible promoter in order to decrease SPase expression levels. Cells were inoculated onto Trypyticase Soy Agar or Luria Agar containing 16 ng/ml of anhydrotetracycline respectively and grown at 35° C. for 20 hours. Inocula suspensions were made by scraping cells into 1 mL of testing media (cation adjusted Mueller Hinton Broth supplemented with 0.002% v/v Tween-80) and diluting to a final $OD_{600nm}$ of 0.01.

Test compounds were prepared in DMSO at a concentration of 10 mg/ml. These compound stocks were diluted into testing media at a concentration of 64 µg/ml and 9 serial 1:2 dilutions were made in the same media, in 96-well U bottom microtiter dishes. Inocula suspensions were added to the two fold serial dilutions of test compounds to a final density of OD $OD_{600nm}$ of 0.0005 and incubated stationary at 35° C. for 22 hours, after which the plates were examined visually. The MICs were recorded as the lowest concentration of test compound that completely prevented bacterial growth. The results are listed in Table 1.

TABLE 1

Antimicrobial activities in whole cell bacterial assays

| Compound | MIC (µg/mL) E. coli | MIC (µg/mL) S. aureus |
|---|---|---|
| 108 | >64 | 64 |
| 103 | ND | >64 |
| 104 | ND | 8 |
| 105 | >64 | >64 |
| 110 | >64 | >64 |
| 123 | 25 | 64 |
| 109 | >64 | >64 |
| 128 | >64 | >64 |
| 111 | >64 | >64 |
| 122 | >64 | 40 |
| 112 | >64 | >64 |
| 124 | >64 | >64 |
| 102 | >64 | >64 |
| 101 | >64 | >64 |
| 113 | ND | ND |
| 125 | ND | ND |
| 114 | ND | ND |
| 117 | >64 | >64 |
| 116 | >64 | >64 |
| 115 | >64 | >64 |
| 118 | 11 | 0.71 |
| 127 | 1.6 | 16 |
| 126 | 1.4 | 16 |
| 119 | >64 | >64 |
| 120 | 32 | >64 |
| 121 | 0.5 | 0.25 |

ND = not determined

Determination of Minimum Inhibitory Concentration—Method B

In vitro antimicrobial activity of each compound was determined by measuring minimal inhibitor concentrations (MICs) using the broth micro-dilution technique as approved by the Clinical and Laboratory Standards Institute (CLSI). Antibacterial activity was measure against two strains of bacteria: 1) methicillin resistant *Staphylococcus aureus* (MRSA) strain USA300 (NRS384) and 2) *Escherichia coli* strain MC4100 IMP-4213, which harbors an LptD mutation. Bacterial inocula were prepared by scraping cells into 1 mL of testing media (cation adjusted Mueller Hinton Broth supplemented with 0.002% v/v Tween-80) and diluting to a final $OD_{600nm}$ of 0.01.

Test compounds were prepared in DMSO at a concentration of 10 mg/ml. These compound stocks were diluted into testing media at a concentration of 64 µg/ml and 9 serial 1:2 dilutions were made in the same media, in 96-well U bottom microtiter dishes. Bacterial inocula were added to the two fold serial dilutions of test compounds to a final density of OD $OD_{600nm}$ of 0.0005 and incubated stationarily at 35° C. for 22 hours, after which the plates were examined visually. The MICs were recorded as the lowest concentration of test compound that completely prevented bacterial growth. The results are listed in Table 2.

TABLE 2

Antimicrobial activities in whole cell bacterial assays

| Compound | MIC (µg/mL) E. coli | MIC (µg/mL) S. aureus | Compound | MIC (µg/mL) E. coli | MIC (µg/mL) S. aureus |
|---|---|---|---|---|---|
| 129 | 0.91 | 0.74 | 130 | 11 | 64 |
| 131 | 0.44 | 0.45 | 132 | 1 | 0.21 |
| 133 | 0.79 | 1.4 | 134 | 1.4 | 0.87 |
| 135 | 16 | 3.2 | 136 | 1 | 1.4 |
| 137 | 23 | 16 | 138 | >64 | 5 |
| 139 | 2 | 1 | 140 | 8 | 1 |
| 141 | 5.7 | 0.79 | 142 | 0.5 | 0.22 |
| 143 | 5.7 | 0.35 | 144 | 0.25 | 0.25 |
| 145 | 5 | 3.2 | 146 | 0.25 | 0.4 |
| 147 | 0.31 | 0.25 | 148 | 0.4 | 0.23 |
| 149 | 0.31 | 0.28 | 150 | 0.5 | 0.3 |
| 151 | 1.2 | 0.71 | 152 | 0.5 | 0.4 |
| 154 | 32 | 2.8 | 155 | ND | ND |
| 156 | 0.5 | 0.31 | 157 | 4 | 2 |
| 158 | 5 | 5.7 | 159 | 16 | 1 |
| 160 | 64 | 2.8 | 161 | 0.71 | 0.63 |
| 162 | 0.5 | 0.4 | 163 | >64 | 4 |
| 164 | 1 | 1.4 | 165 | 0.63 | 0.63 |
| 166 | 0.5 | 0.63 | 167 | 4 | 1.7 |
| 168 | 1 | 0.79 | 169 | 11 | 3.2 |
| 170 | 0.4 | 2 | 171 | 0.25 | 0.71 |
| 172 | 8 | 8 | 173 | 2 | 2 |
| 174 | 0.5 | 0.25 | 175 | 2 | 1.2 |
| 176 | 8 | 16 | 177 | 2 | 2 |
| 178 | 0.25 | 0.063 | 179 | 0.5 | 2 |
| 180 | 1 | 1 | 181 | 0.5 | 0.4 |
| 182 | 0.71 | 4 | 183 | 1 | 1 |
| 184 | 0.13 | 0.25 | 185 | 0.71 | 4 |
| 186 | 0.13 | 0.13 | 187 | 2.8 | 8 |
| 188 | 8 | 16 | 189 | 64 | >64 |
| 190 | >64 | 64 | 191 | 16 | 20 |
| 192 | 16 | 0.59 | 193 | 5 | 0.16 |
| 194 | 6.3 | 0.71 | 195 | 32 | 1.2 |
| 196 | 2.5 | 0.66 | 197 | 1 | 0.3 |
| 198 | 5 | 0.5 | 199 | >64 | 7 |
| 200 | 64 | >64 | 201 | 64 | 4.6 |
| 202 | 23 | 1.1 | 203 | 32 | 1.4 |
| 204 | 4.6 | 0.45 | 205 | 32 | 2 |
| 206 | 2 | 0.5 | 207 | 2 | 0.099 |
| 208 | 4 | 0.31 | 209 | 2.5 | 1 |
| 210 | 4 | 0.71 | 211 | 32 | 0.71 |

TABLE 2-continued

Antimicrobial activities in whole cell bacterial assays

| Compound | MIC (µg/mL) E. coli | MIC (µg/mL) S. aureus | Compound | MIC (µg/mL) E. coli | MIC (µg/mL) S. aureus |
|---|---|---|---|---|---|
| 212 | 5 | 0.84 | 213 | 1.3 | 0.22 |
| 214 | 5.7 | 0.35 | 215 | 4 | 0.5 |
| 216 | 4 | 0.21 | 217 | 1.6 | 0.35 |
| 218 | 1.3 | 0.5 | 219 | 64 | 5 |
| 220 | 4 | 0.5 | 221 | 8 | 1 |
| 222 | 2 | 1.4 | 223 | ND | ND |
| 224 | 2.8 | 0.13 | 225 | 2 | 0.57 |
| 226 | 25 | 2.8 | 227 | 13 | 8 |
| 228 | 2.8 | 5.7 | 229 | 32 | 64 |
| 230 | 20 | 2 | 231 | 0.5 | 0.5 |
| 232 | 0.25 | 0.31 | 233 | 1 | 0.5 |
| 234 | 0.5 | 0.4 | 235 | 0.5 | 0.25 |
| 236 | 8 | 2 | 237 | 2 | 0.71 |
| 238 | 0.35 | 0.35 | 239 | 2 | 0.71 |
| 240 | 4 | 0.71 | 241 | 0.18 | 0.25 |
| 242 | 11 | 1.4 | 243 | 2 | 0.5 |
| 244 | 64 | 45 | 245 | 0.5 | 0.35 |
| 246 | 64 | 23 | 247 | 0.5 | 0.5 |
| 248 | 0.25 | 0.25 | 249 | 1 | 0.35 |
| 250 | 0.71 | 0.35 | 251 | >64 | 3.4 |
| 252 | >64 | 5 | 253 | 11 | 8 |
| 254 | 11 | 8 | 255 | ND | ND |
| 256 | ND | ND | 257 | ND | ND |
| 258 | 23 | >64 | 259 | 4 | 11 |
| 260 | 1 | 4 | 261 | 0.79 | 0.71 |
| 262 | 8 | 2.8 | 263 | 2 | 0.71 |
| 264 | ND | ND | 265 | 4 | 0.13 |
| 266 | 1 | 0.5 | 267 | 0.25 | 0.13 |
| 268 | 16 | 1 | 269 | 8 | 0.5 |
| 270 | 8 | 0.5 | 271 | 11 | 0.5 |
| 272 | 32 | 0.71 | 273 | 8 | 0.088 |
| 274 | 16 | 0.13 | 275 | 32 | 1 |
| 276 | 16 | 0.5 | 277 | 32 | 0.5 |
| 278 | 16 | 4 | 279 | 8 | 11 |

ND = not determined

Enzyme Inhibition Assay

Full length His-tagged *E. coli* SPase proteins were expressed in *E. coli* BL21(DE3) containing the plasmid pET23-lepB. Briefly, saturated overnight cultures grown in 20 ml of Luria-Bertani medium supplemented with ampicillin were subcultures into 1.5 L of Luria-Bertani, and shaken at 37° C. until an optical density at 600 nm of 0.4-0.5 was achieved. Protein expression was induced with Isopropyl β-D-1-thiogalactopyranoside (ITPG) at a final concentration of 0.5 µM, and purified using nickel affinity chromatography.

Full length His-tagged *S. aureus* SPase protein was expressed similarly from *E. coli* BL21(DE3) containing the plasmid pCDF1-SaSpsB and purified similarly to the *E. coli* protein with the following exceptions. SPase protein was solubilized using 300 mM NaCl, 20 mM Tris pH 8.06, 5 mM Imidazole, 10% glycerol, 1% Triton X-100, prior to purification in Ni-NTA Superflow resin and resin bound protein was washed in a similar buffer containing 1% Elugent in place of Triton X-100 prior to protein eluted in wash buffer supplemented with 300 mM imidazole. Protein purity was judged to exceed 95% by visual inspection of SDS-PAGE followed by Comassie staining. All protein concentrations were determined by BCA assay.

Signal peptidase enzyme activity of the above proteins was measured using two fluorogenic peptide substrates (decanoyl-LS SPAYNO2A⇓ADKabzPD (SEQ ID NO:1) and decanyol-LTPTAYNO2A⇓ASKKabzDD) (SEQ ID NO:2), where abz is the fluorescence donor 2-aminobenzamide, YNO2 is the fluorescence acceptor 3-nitrotyrosine, and the cleavage site is indicated with an arrow. Enzyme mix solution was prepared by diluting 2.5 nM of *Escherichia coli* or *Staphylococcus aureus* SPase protein into reaction buffers consisting of 20 mM PO4 pH 7.4, 100 mM NaCl, and 1% Elugent™ or octyl phenoxypolyethoxylethanol detergent at a concentration of 0.25% or 0.0625%. Reactions were initiated by the addition of substrate to a final concentration of 20 µM. Reaction progress was monitored by measuring the increase in fluorescence signal (excitation at 314 nm, emission at 416 nm) using a SpectraMax M2 fluorescence microplate reader. To determine IC50 values of test compounds, compound stock solutions were prepared in DMSO at a concentration of 1 mM. Three-folder serial dilutions of test compounds, starting at 10 µM, were prepared in enzyme mix solution and incubated at room temperature for 10 minutes. Following this incubation, fluorogenic substrate was added to a final concentration of 20 µM and the increase in fluorescence, corresponding to substrate cleavage, was monitored continuously at room temperature for 1 hour. Initial reaction rates were calculated based on the rate of increase in fluorescence during the reaction. Reaction rates were plotted as a function of compound concentration, and $IC_{50}$ values are determined nonlinear regression analysis (SoftMaxPro 5.4, Molecular Devices™) of the sigmoidal dose-response curve. The results are listed in Table 3.

TABLE 3

Inhibitory activities (IC50) in biochemical SPase activity assays

| Compound | IC 50 (nM) E. coli | IC 50 (nM) S. aureus | Compound | IC 50 (nM) E. coli | IC 50 (nM) S. aureus |
|---|---|---|---|---|---|
| 101 | 11000 | 86 | 102 | 18000 | 9.7 |
| 103 | 11000 | 110 | 104 | 8900 | 18 |
| 105 | ND | ND | 108 | 20000 | 2100 |
| 109 | 50000 | 4900 | 110 | ND | 150 |
| 111 | 4900 | 18000 | 112 | 31000 | 3400 |
| 113 | 50000 | 470 | 114 | 50000 | 390 |
| 115 | 1000 | 170 | 116 | 310 | 38 |
| 117 | 300 | 350 | 118 | 1100 | 9.4 |
| 119 | 290 | 59 | 120 | 1600 | 100 |
| 121 | ND | ND | 122 | 1500 | 7.6 |
| 123 | 220 | 42 | 124 | 810 | 83 |
| 125 | 730 | 55 | 126 | 17 | 6 |
| 127 | 12 | 3.7 | 128 | 3000 | 670 |
| 129 | 14 | 140 | 130 | 1000 | 530 |
| 131 | 19 | 98 | 132 | 24 | 77 |
| 133 | 15 | 170 | 134 | 8.7 | 120 |
| 135 | 31 | 25 | 136 | 14 | 39 |
| 137 | 1200 | 26000 | 138 | 1000 | 1100 |
| 139 | 3.4 | 8.5 | 140 | 50 | 52 |
| 141 | 33 | 23 | 142 | 15 | 34 |
| 143 | 250 | 180 | 144 | 18 | 36 |
| 145 | 39 | 240 | 146 | 12 | 160 |
| 147 | 14 | 98 | 148 | 7.4 | 140 |
| 149 | 3.9 | 129 | 150 | 6 | 270 |
| 151 | 8.8 | 38 | 152 | 25 | 350 |
| 154 | 14 | 8.1 | 155 | 39 | 250 |
| 156 | 5.5 | 97 | 157 | 130 | 1000 |
| 158 | 33 | 400 | 159 | 240 | 86 |
| 160 | 2100 | 900 | 161 | 60 | 300 |
| 162 | 12 | 200 | 163 | 240 | 310 |
| 164 | 44 | 120 | 165 | 120 | 410 |
| 166 | 36 | 350 | 167 | 5.2 | 190 |
| 168 | 5.4 | 250 | 169 | 3.9 | 87 |
| 170 | 10 | 530 | 171 | 27 | 520 |
| 172 | 20 | 750 | 173 | 69 | 550 |
| 174 | 59 | 130 | 175 | 5.5 | 110 |
| 176 | 56 | 1200 | 177 | 70 | 640 |
| 178 | 3.1 | 58 | 179 | 22 | 570 |
| 180 | 11 | 280 | 181 | 5.4 | 18 |
| 182 | 35 | 1100 | 183 | 20 | 610 |
| 184 | 5.9 | 300 | 185 | 41 | 580 |
| 186 | 6.9 | 370 | 187 | 170 | 2100 |
| 188 | 120 | 2900 | 189 | 430 | 7700 |
| 190 | 1300 | 64000 | 191 | 38000 | 50000 |
| 192 | 27 | 12 | 193 | 15 | 3 |
| 194 | 16 | 4.7 | 195 | 19 | 2.6 |
| 196 | 8.8 | 5.7 | 197 | 11 | 6.2 |
| 198 | 42 | 8.9 | 199 | 4.5 | 1.4 |
| 200 | 5200 | 1200 | 201 | 8 | 1.9 |
| 202 | 7.1 | 3.5 | 203 | 130 | 21 |
| 204 | 33 | 13 | 205 | 210 | 20 |
| 206 | 6.3 | 5.2 | 207 | 87 | 13 |
| 208 | 20 | 5.7 | 209 | 12 | 15 |
| 210 | 56 | 16 | 211 | 50000 | 36 |
| 212 | 26 | 12 | 213 | 6.8 | 7.7 |
| 214 | 77 | 17 | 215 | 77 | 17 |
| 216 | 29 | 4.1 | 217 | 15 | 14 |
| 218 | 6.9 | 13 | 219 | 560 | 46 |
| 220 | 36 | 7 | 221 | 62 | 130 |
| 222 | 6.6 | 24 | 223 | ND | ND |
| 224 | 55 | 12 | 225 | 7.1 | 4 |
| 226 | 440 | 140 | 227 | 550 | 850 |
| 228 | 360 | 270 | 229 | 290 | 220 |
| 230 | 390 | 150 | 231 | 4.5 | 95 |
| 232 | 5 | 140 | 233 | 29 | 220 |
| 234 | 8.3 | 53 | 235 | 21 | 50 |
| 236 | 28 | 130 | 237 | 16 | 210 |
| 238 | 4.6 | 33 | 239 | 17 | 670 |
| 240 | 28 | 88 | 241 | 2.1 | 42 |
| 242 | 21 | 54 | 243 | 10 | 80 |
| 244 | 350 | 1100 | 245 | 8.7 | 130 |
| 246 | 55 | 290 | 247 | 17 | 110 |
| 248 | 11 | 170 | 249 | 17 | 160 |
| 250 | 8.4 | 110 | 251 | 9200 | 18 |
| 252 | 3000 | 8.7 | 253 | 4800 | 2100 |
| 254 | 1200 | 660 | 255 | ND | ND |
| 256 | ND | ND | 257 | ND | ND |
| 258 | 50000 | 50000 | 259 | 2.6 | 32 |
| 260 | 5.6 | 83 | 261 | 41 | 280 |
| 262 | 37 | 15 | 263 | 88 | 72 |
| 264 | ND | ND | 265 | 120 | 17 |
| 266 | 22 | 160 | 267 | 11 | 33 |
| 268 | 1600 | 81 | 269 | 1800 | 340 |
| 270 | 650 | 120 | 271 | 200 | 16 |
| 272 | 1300 | 50 | 273 | 470 | 9.8 |
| 274 | 1700 | 35 | 275 | 1500 | 110 |
| 276 | 2000 | 110 | 277 | 680 | 110 |
| 278 | 800 | 2300 | 279 | 530 | 7400 |

ND = not determined

Example 181

Clinical Trial of the Safety and Efficacy of Compounds of Formula (I), (I'), (II), (II'), (III), or (III') in Patients with *C. Difficile*-Associated Diarrhea Purpose:

This study aims to determine the safety and efficacy of compounds presented herein for the treatment of symptoms of *C. difficile*-associated diarrhea and lowering the risk of repeat episodes of diarrhea. The compounds are evaluated in comparison to current standard antibiotic treatment, so all patients will receive active medication. All study-related care is provided including doctor visits, physical exams, laboratory tests and study medication. Total length of participation is approximately 10 weeks.

Patients:

Eligible subjects will be men and women 18 years and older.

Criteria:

Inclusion Criteria:

Be at least 18 years old;

Have active mild to moderate *C. difficile*-Associated Diarrhea (CDAD);

Be able to tolerate oral medication;

Not be pregnant or breast-feeding; and

Sign and date an informed consent form.

Study Design:

This is a randomized, double-blind, active control study of the efficacy, safety, and tolerability of a compound of Formula (I), (I'), (II), (II'), (III), or (III') in patients with *C. difficile*-associated diarrhea.

Example 182

Clinical Trial Comparing a Compound of Formula (I), (I'), (II), (II'), (III), or (III') with Vancomycin for the Treatment of MRSA Osteomyleitis Purpose:

This study aims to determine the efficacy of compounds presented herein as compared to vancomycin for the treatment of methicillin-resistant *Staphylococcus aureus* (MRSA) osteomyelitis.

Patients:

Eligible subjects will be men and women 18 years and older.

Criteria:

Inclusion Criteria:

Culture-proven MRSA, obtained in operating room or sterile biopsy procedure from bone site. The infection and sampling site is either within the bone or a deep soft-tissue site that is contiguous with bone; OR radiographic abnormality consistent with osteomyelitis in conjunction with a positive blood culture for MRSA;

Surgical debridement of infection site, as needed;

Subject is capable of providing written informed consent; and

Subject capable of receiving outpatient parenteral therapy for 12 weeks.

Exclusion Criteria:

Hypersensitivity to a compound of Formula (I), (I'), (II), (II'), (III), or (III') or vancomycin;

*S. aureus* resistant to a compound of Formula (I), (I'), (II), (II'), (III), or (III') or vancomycin;

Osteomyelitis that develops directly from a chronic, open wound;

Polymicrobial culture (the only exception is if coagulase-negative *staphylococcus* is present in the culture and the clinical assessment is that it is a contaminant);

Subject has a positive pregnancy test at study enrollment;

Baseline renal or hepatic insufficiency that would preclude administration of study drugs;

Active injection drug use without safe conditions to administer intravenous antibiotics for 3 months; and Anticipated use of antibiotics for greater than 14 days for an infection other than osteomyelitis.

Study Design:

This is a randomized, open-label, active control, efficacy trial comparing vancomycin with a compound of Formula (I), (I'), (II), (II'), (III), or (III') for the treatment of MRSA Osteomyelitis.

Example 183

Clinical Trial Evaluating a Compound of Formula (I), (I'), (II), (II'), (III), or (III') in Selected Serious Infections Caused by Vancomycin-Resistant *Enterococcus* (VRE)

Purpose:

This study aims to determine the safety and efficacy of a compound of Formula (I), (I'), (II), (II'), (III), or (III') in the treatment of selected serious infections caused by VRE.

Patients:

Eligible subjects will be men and women 18 years and older.

Criteria:

Inclusion Criteria:

Isolation of one of the following multi-antibiotic resistant bacteria: vancomycin-resistant *Enterococcus faecium*, vancomycin-resistant *Enterococcus faecalis* alone or as part of a polymicrobial infection; and Have a confirmed diagnosis of a serious infection (eg, bacteremia [unless due to an excluded infection], complicated intra-abdominal infection, complicated skin and skin structure infection, or pneumonia) requiring administration of intravenous (IV) antibiotic therapy.

Exclusion Criteria:

Subjects with any concomitant condition or taking any concomitant medication that, in the opinion of the investigator, could preclude an evaluation of a response or make it unlikely that the contemplated course of therapy or follow-up assessment will be completed or that will substantially increase the risk associated with the subject's participation in this study. Anticipated length of antibiotic therapy less than 7 days Study Design:

This is a randomized, double-blind, safety and efficacy study of a compound of Formula (I), (I'), (II), (II'), (III), or (III') in the treatment of selected serious infections caused by VRE.

Pharmaceutical Compositions

Parenteral Composition

To prepare a parenteral pharmaceutical composition suitable for administration by injection, 100 mg of a compound of Formula (I), (I'), (II), (II'), (III), or (III') is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I), (I'), (II), (II'), (III), or (III') | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formula (I), (I'), (II), (II'), (III), or (III') is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I), (I'), (II), (II'), (III), or (III') | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I), (I'), (II), (II'), (III), or (III') | 200 |
| lactose, spray-dried | 148 |
| magnesium stearate | 2 |

In yet another embodiment, the following ingredients are mixed to form a solution/suspension for oral administration:

| Ingredient | Amount |
| --- | --- |
| Compound of Formula (I), (I'), (II), (II'), (III), or (III') | 1 g |
| Anhydrous Sodium Carbonate | 0.1 g |
| Ethanol (200 proof), USP | 10 mL |
| Purified Water, USP | 90 mL |
| Aspartame | 0.003 g |

Topical Gel Composition

To prepare a pharmaceutical topical gel composition, 100 mg of a compound of Formula (I), (I'), (II), (II'), (III), or (III') is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A compound having the structure of Formula (I):

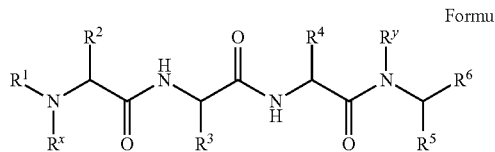

Formula (I)

wherein:

$R^1$ is selected from:

A)

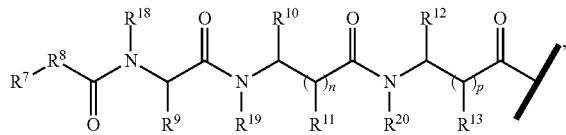

B)

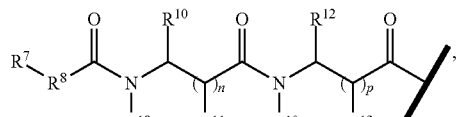

C)

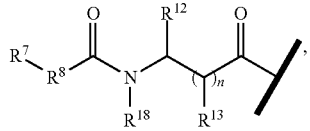

D)

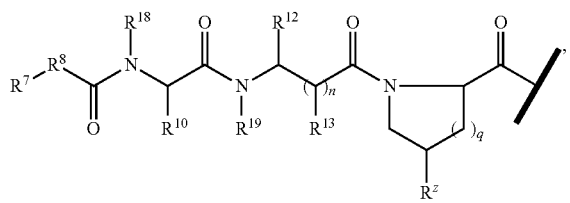

E)

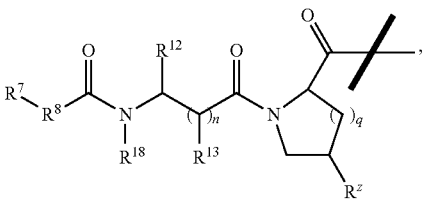

F)

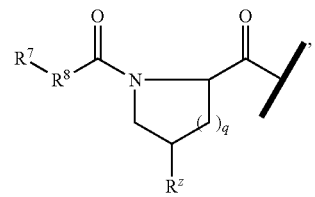

G)

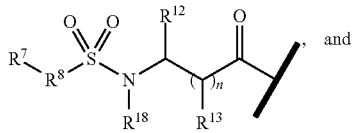

and

H)

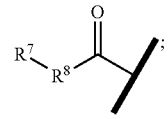

$R^2$, $R^4$, $R^{10}$, $R^{11}$, $R^{12}$, and $R^{13}$ are each independently —H, —CH$_3$, —CH(CH$_3$)$_2$, —C(CH$_3$)$_3$, —CH(CH$_3$)(CH$_2$CH$_3$), —CH$_2$CH(CH$_3$)$_2$, —CH$_2$OH, —CH(OH)(CH$_3$), —CH$_2$CF$_3$, —CH$_2$C(O)OH, —CH$_2$C(O)OR$^{25}$, —CH$_2$CH$_2$C(O)OH, —CH$_2$CH$_2$C(O)OR$^{25}$, —CH$_2$C(O)NH$_2$, —CH$_2$CH$_2$C(O)NH$_2$, —CH$_2$CH$_2$C(O)N(H)C(H)(CH$_3$)CO$_2$H, —CH$_2$CH$_2$C(O)N(H)C(H)(CO$_2$H)CH$_2$CO$_2$H, —CH$_2$NR$^{21}$R$^{22}$, —(CH$_2$)$_2$NR$^{21}$R$^{22}$, —(CH$_2$)$_3$NR$^{21}$R$^{22}$, —(CH$_2$)$_4$NR$^{21}$R$^{22}$, —(CH$_2$)$_4$N(R$^{25}$)$_3$, —(CH$_2$)$_4$N(H)C(O)(2,3-dihydroxybenzene), optionally substituted C$_1$-C$_8$alkyl, optionally substituted C$_1$-C$_8$heteroalkyl, optionally substituted C$_3$-C$_8$cycloalkyl, optionally substituted —CH$_2$—C$_3$-C$_8$cycloalkyl, optionally substituted heterocycloalkyl, optionally substituted aryl, optionally substituted heteroaryl,

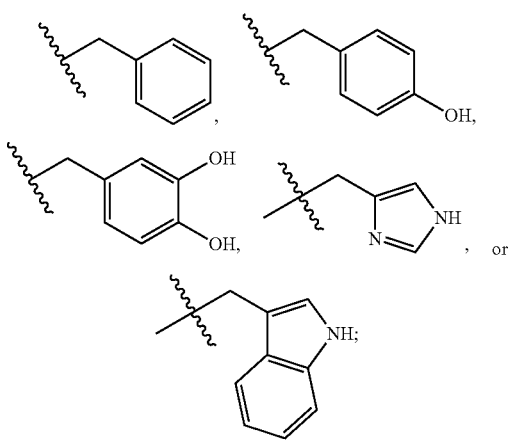

R³ is methyl, ethyl, isopropyl, or cyclopropyl;

R⁵ is H, methyl, ethyl, or —CH₂OH; or R⁵ and R²⁴ together with the boron atom form a 5- or 6-membered boron containing ring;

R⁶ is —CH₂C(=O)H, —B(OR²³)(OR²⁴), or

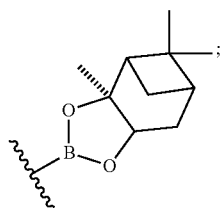 [SMILES: *B1OC2CC3CC(C3(C)C)[C@]2(C)O1]

or R⁵ and R⁶ together with the carbon atom form

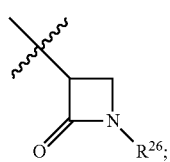

$R^x$ is H, optionally substituted $C_1$-$C_6$alkyl, optionally substituted $C_1$-$C_6$heteroalkyl, or optionally substituted $C_3$-$C_8$cycloalkyl; or $R^x$ and $R^2$ together with the nitrogen atom form an optionally substituted nitrogen containing ring;

$R^y$ is H or methyl; or $R^y$ and $R^5$ together with the nitrogen atom form an optionally substituted nitrogen containing ring;

$R^z$ is —NR¹⁵R¹⁶, —CH₂—NR¹⁵R¹⁶, or —(CH₂)₂—NR¹⁵R¹⁶;

R⁷ is optionally substituted aryl, optionally substituted heteroaryl, optionally substituted heterocycloalkyl, optionally substituted alkenyl, or a linear or branched alkyl chain of about 1-22 carbon atoms, optionally comprising within the alkyl chain or at an alkyl chain terminus an optionally substituted aryl, an optionally substituted heteroaryl, an optionally substituted heterocycloalkyl, or an optionally substituted

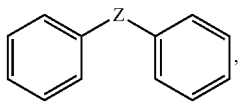

wherein Z is a bond, O, S, NH, CH₂, NHCH₂, or C≡C;

R⁸ is a bond, —O—, —N(R¹⁷)—, optionally substituted aryl, or optionally substituted heteroaryl;

R⁹ is —CH₂OH, —CH₂CH(CH₃)₂,

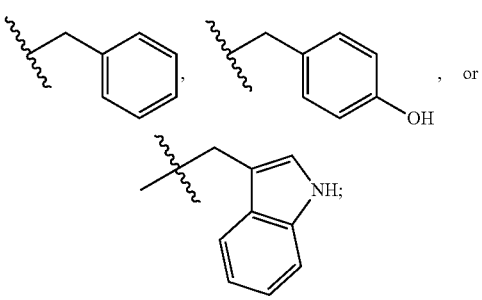

R¹⁵ and R¹⁶ are each independently H, or $C_1$-$C_4$alkyl;

R¹⁷ is H, methyl, ethyl, isopropyl, or cyclopropyl;

R¹⁸, R¹⁹, and R²⁰ are each independently H, or methyl;

each R²¹ is independently H, or $C_1$-$C_4$alkyl;

each R²² is independently H, $C_1$-$C_4$alkyl, —C(=NH)(NH₂), or —CH(=NH);

R²³ and R²⁴ are each independently H, or $C_1$-$C_4$alkyl; or R²³ and R²⁴ together with the boron atom form an optionally substituted 5- or 6-membered boron containing ring;

each R²⁵ is independently $C_1$-$C_6$alkyl;

R²⁶ is H, $C_1$-$C_4$alkyl, $C_1$-$C_4$alkoxy, —CH₂C(O)OR²⁵, or —OCH₂C(O)OR²⁵;

n is 0 or 1;

p is 0 or 1; and q is 0 or 1;

or a pharmaceutically acceptable salt, solvate, or prodrug thereof.

2. The compound of claim 1 wherein R¹ is

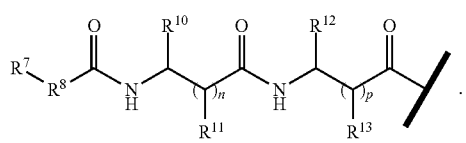

3. The compound of claim 2 wherein R⁸ is a bond.

4. The compound of claim 3 wherein R², R⁴, R¹⁰, R¹¹, R¹², and R¹³ are each independently —H, —CH₃, —CH(CH₃)₂, —C(CH₃)₃, —CH(CH₃)(CH₂CH₃), —CH₂CH(CH₃)₂, —CH₂OH, —CH(OH)(CH₃), —CH₂CF₃, —CH₂C(O)OH, —CH₂CH₂C(O)OH, —CH₂C(O)NH₂, —CH₂CH₂C(O)NH₂, —CH₂NH₂, —(CH₂)₂NH₂, —(CH₂)₃NH₂, —(CH₂)₄NH₂,

363

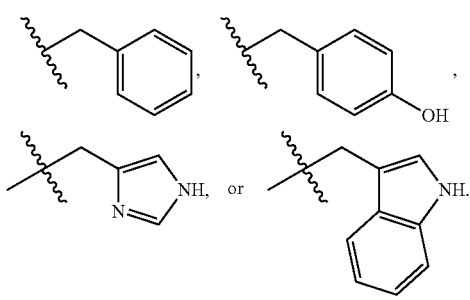

5. The compound of claim 4 wherein $R^2$, $R^4$, $R^{10}$, $R^{11}$, $R^{12}$, and $R^{13}$ are each independently —H, —$CH_3$, —$CH_2CH(CH_3)_2$, —$CH_2OH$, —$CH(OH)(CH_3)$, —$CH_2CH_2C(O)OH$, —$CH_2C(O)NH_2$, —$CH_2CH_2C(O)NH_2$, —$CH_2NH_2$, —$(CH_2)_2NH_2$, —$(CH_2)_3NH_2$, —$(CH_2)_4NH_2$, or

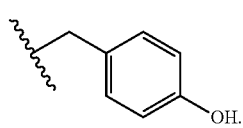

6. The compound of claim 5 wherein n is 1 and p is 0.

7. The compound of claim 6 having the structure of Formula (Ib):

Formula Ib

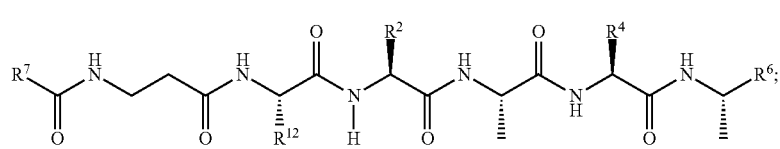

wherein $R^2$, $R^4$, and $R^{12}$ are each independently —$CH_2CH(CH_3)_2$, —$(CH_2)_3NH_2$, or —$(CH_2)_4NH_2$.

8. The compound of claim 1 wherein $R^1$ is

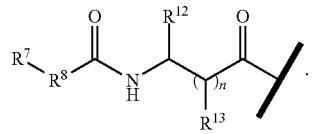

9. The compound of claim 8 wherein $R^2$, $R^4$, $R^{12}$, and $R^{13}$ are each independently —H, —$CH_3$, —$CH(CH_3)_2$, —$C(CH_3)_3$, —$CH(CH_3)(CH_2CH_3)$, —$CH_2CH(CH_3)_2$, —$CH_2OH$, —$CH(OH)(CH_3)$, —$CH_2CF_3$, —$CH_2C(O)OH$, —$CH_2CH_2C(O)OH$, —$CH_2C(O)NH_2$, —$CH_2CH_2C(O)NH_2$, —$CH_2NH_2$, —$(CH_2)_2NH_2$, —$(CH_2)_3NH_2$, —$(CH_2)_4NH_2$,

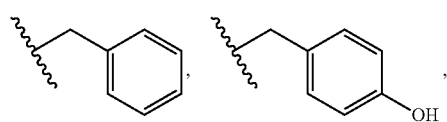

364
-continued

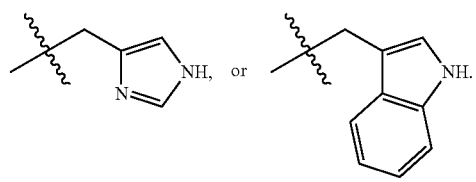

10. The compound of claim 9 wherein $R^2$, $R^4$, $R^{12}$, and $R^{13}$ are each independently —H, —$CH_3$, —$CH_2CH(CH_3)_2$, —$CH_2OH$, —$CH(OH)(CH_3)$, —$CH_2CH_2C(O)OH$, —$CH_2C(O)NH_2$, —$CH_2CH_2C(O)NH_2$, —$CH_2NH_2$, —$(CH_2)_2NH_2$, —$(CH_2)_3NH_2$, —$(CH_2)_4NH_2$,

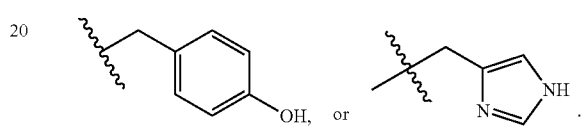

11. The compound of claim 10 wherein n is 0.

12. The compound of claim 11 wherein $R^8$ is a bond.

13. The compound of claim 12 having the structure of Formula (Ic):

Formula (Ic)

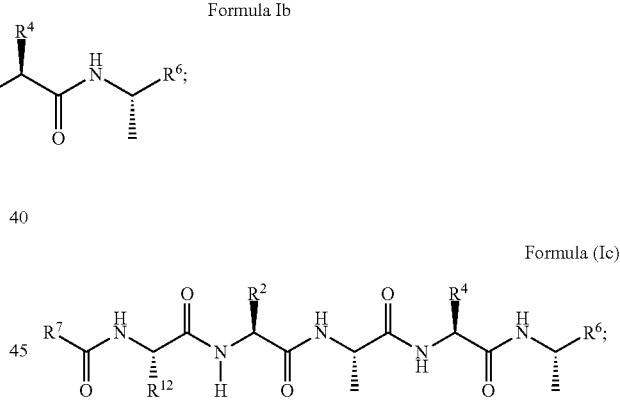

wherein $R^2$, $R^4$, and $R^{12}$ are each independently —$CH_2CH(CH_3)_2$, —$CH(OH)(CH_3)$, —$CH_2C(O)NH_2$, —$CH_2CH_2C(O)NH_2$, —$CH_2NH_2$, —$(CH_2)_2NH_2$, —$(CH_2)_3NH_2$, or —$(CH_2)_4NH_2$.

14. The compound of claim 1 wherein $R^1$ is

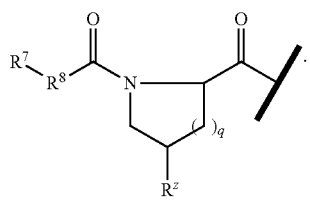

15. The compound of claim 14 wherein $R^2$ and $R^4$ are each independently —H, —$CH_3$, —$CH(CH_3)_2$, —$C(CH_3)_3$, —$CH(CH_3)(CH_2CH_3)$, —$CH_2CH(CH_3)_2$, —$CH_2OH$, —CH (OH)(CH$_3$), —CH$_2$CF$_3$, —CH$_2$C(O)OH, —CH$_2$CH$_2$C(O)OH, —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, —(CH$_2$)$_4$NH$_2$,

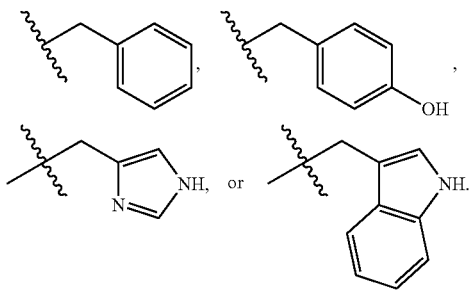

16. The compound of claim 15 wherein q is 1; and R$^8$ is a bond.

17. The compound of claim 16 having the structure of Formula (Id):

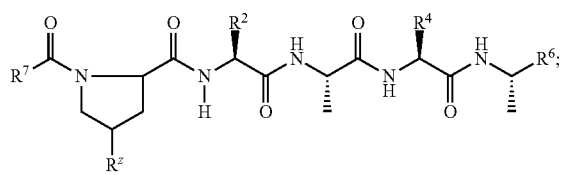

Formula (Id)

wherein R$^z$ is NH$_2$; and R$^2$ and R$^4$ are each independently —CH$_2$CH(CH$_3$)$_2$, —CH(OH)(CH$_3$), —CH$_2$C(O)NH$_2$, —CH$_2$CH$_2$C(O)NH$_2$, —CH$_2$NH$_2$, —(CH$_2$)$_2$NH$_2$, —(CH$_2$)$_3$NH$_2$, or —(CH$_2$)$_4$NH$_2$.

18. A pharmaceutical composition comprising a compound of claim 1 and a pharmaceutically acceptable excipient.

19. A method of treatment of a bacterial infection in a mammal, comprising administering an effective amount of a compound of claim 1 to the mammal at a frequency and for a duration sufficient to provide a beneficial effect to the mammal.

20. The method of claim 19, wherein the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

21. The method of claim 19 further comprising administering a second therapeutic agent.

22. The compound of claim 13 wherein R$^6$ is

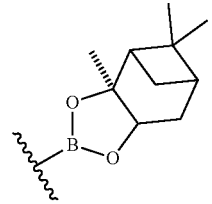

23. The compound of claim 13 wherein R$^6$ is B(OH)$_2$.

24. The compound of claim 22 or 23 wherein R$^7$ is

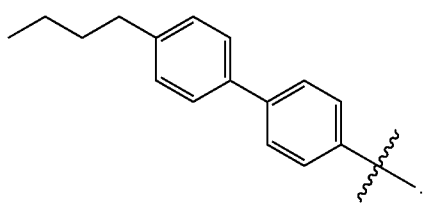 [SMILES: *c1ccc(-c2ccc(CCCC)cc2)cc1]

25. The compound of claim 22 or 23 wherein R$^7$ is

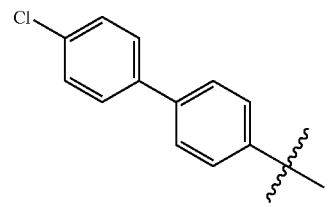

* * * * *